(12) United States Patent
Zou

(10) Patent No.: US 11,376,248 B2
(45) Date of Patent: Jul. 5, 2022

(54) TREATMENT OF ANEURYSMS

(71) Applicant: Georgia State University Research Foundation, Inc., Atlanta, GA (US)

(72) Inventor: Ming-Hui Zou, Atlanta, GA (US)

(73) Assignee: Georgia State University Research Foundation, Inc., Atlanta, GA (US)

(*) Notice: Subject to any disclaimer, the term of this patent is extended or adjusted under 35 U.S.C. 154(b) by 125 days.

(21) Appl. No.: 16/723,304

(22) Filed: Dec. 20, 2019

(65) Prior Publication Data

US 2020/0138810 A1  May 7, 2020

Related U.S. Application Data

(63) Continuation of application No. PCT/US2018/040422, filed on Jun. 29, 2018.

(60) Provisional application No. 62/680,488, filed on Jun. 4, 2018, provisional application No. 62/621,169, filed on Jan. 24, 2018, provisional application No. 62/527,418, filed on Jun. 30, 2017.

(51) Int. Cl.
| | |
|---|---|
| *A61K 31/4965* | (2006.01) |
| *A61K 31/197* | (2006.01) |
| *A61K 31/664* | (2006.01) |
| *A61P 9/00* | (2006.01) |
| *A61K 31/192* | (2006.01) |
| *A61K 31/426* | (2006.01) |
| *A61K 31/423* | (2006.01) |

(52) U.S. Cl.
CPC ........ *A61K 31/4965* (2013.01); *A61K 31/192* (2013.01); *A61K 31/197* (2013.01); *A61K 31/423* (2013.01); *A61K 31/426* (2013.01); *A61K 31/664* (2013.01); *A61P 9/00* (2018.01)

(58) Field of Classification Search
None
See application file for complete search history.

(56) References Cited

U.S. PATENT DOCUMENTS

| | | | |
|---|---|---|---|
| 6,569,190 B2 | 5/2003 | Whalen, II et al. | |
| 2012/0270884 A1* | 10/2012 | Wood | A61K 31/495 514/255.01 |
| 2014/0296567 A1 | 10/2014 | Hansson et al. | |

FOREIGN PATENT DOCUMENTS

| | | | | |
|---|---|---|---|---|
| WO | WO-03080068 A1 * | 10/2003 | | A61P 3/00 |

OTHER PUBLICATIONS

Song et al. "Abnormal kynurenine pathway of tryptophan catabolism in cardiovascular diseases" Cellular and Molecular Life Sciences Mar. 17, 2017 (Mar. 17, 2017) vol. 74, p. 2899-2916.
International Search Report for International Application No. PCT/US18/40422 dated Nov. 2, 2018.

* cited by examiner

*Primary Examiner* — My-Chau T. Tran
(74) *Attorney, Agent, or Firm* — Thomas | Horstemeyer, LLP

(57) ABSTRACT

The present invention provides methods for detecting and/or treating a subject having an aneurysm or at risk for developing an aneurysm. It has been discovered that a key metabolite of the kynurenine (Kyn) pathway, a major route for the metabolism of essential amino acid tryptophan (Trp) into nicotinamide adenine dinucleotide (NAD+), plays a critical role in the formation of aneurysms, for example abdominal aortic aneurysms. In particular, it has been discovered that 3-Hydroxyanthranilic acid (3-HAA), a product of kynureninase (KYNU), plays a causative role in the formation of aneurysms by, for example exerting pro-inflammatory effects on vascular smooth muscle cells. It has further been discovered that elevated levels of 3-HAA are indicative of the presence and/or progression of an aneurysm, and 3-HAA levels correlate with the size (aortic diameter) of the aneurysm.

19 Claims, 63 Drawing Sheets

TREATMENT OF ANEURYSMS

RELATED APPLICATIONS

This application is a continuation of International Application No. PCT/US2018/040422, filed in the International Patent Cooperation Treaty, U.S. Receiving Office on Jun. 29, 2018, which claims benefit of U.S. Provisional Application No. 62/680,488, filed Jun. 4, 2018, U.S. Provisional Application No. 62/621,169, filed Jan. 24, 2018, and U.S. Provisional Application No. 62/527,419, filed Jun. 30, 2017, the entirety of which are incorporated herein for all purposes.

GOVERNMENT INTEREST

The United States Government has rights in this invention by virtue of support under Grant No. HL089220, HL079584, HL080499, HL110488, HL128014, HL132500, AG047776, and CA213022 awarded by the National Institute of Health.

FIELD OF THE INVENTION

This invention provides methods for identifying and treating a subject having an aneurysm, including an abdominal aortic aneurysm, cerebral aneurysm, or thoracic aortic aneurysm, or is at risk of developing an aneurysm due to, for example, an underlying genetic disorder, for example Marfan syndrome and like disorders, which makes the subject prone to the development of an aneurysm.

BACKGROUND OF THE INVENTION

Aneurysms are excessive localized enlargements of an artery caused by a weakening of the artery wall. The balloon-like bulges have increasing risk of rupture as they increase in size, in addition to be being a potential site for thrombosis and the eventual formation of an embolism. Aneurysms may be the result of a hereditary condition or a later acquired disease. Three particularly lethal types of aneurysms upon rupture are abdominal aortic aneurysm (AAA), thoracic aortic aneurysm (TAA), and cerebral aneurysm (CA).

Aortic aneurysm formation is the result of a thinning medial layer and deterioration of the elastic lamina resulting in weakening of the tensile strength of the arterial wall. Aortic aneurysms are commonly identified in the thoracic and infrarenal aorta, with the latter referred to as abdominal aortic aneurysms (AAA). The pathogenesis of AAA includes endothelial cell (EC) apoptosis, inflammation, and vascular smooth muscle cell (VSMC) proliferation and migration.

Abdominal aortic aneurysm (AAA) is a permanent, localized dilation of the abdominal aorta. It occurs in up to 9% of adults older than 65 years of age, with about 15,000 annual deaths after rupture in the United States. See Weintraub N L. Understanding abdominal aortic aneurysm. N Engl J Med. (2009) 361:1114-6; Nordon et al., Pathophysiology and epidemiology of abdominal aortic aneurysms. Nature reviews Cardiology. (2011) 8:92-102. Pathologically, AAA is characterized by a dilatation of all layers of the arterial wall due to elastin loss, smooth muscle cell apoptosis, and compensatory collagen deposition. See Wang S, et al., Activation of AMP-activated protein kinase alpha2 by nicotine instigates formation of abdominal aortic aneurysms in mice in vivo. Nat Med. (2012) 18:902-10; Satoh K, et al., Cyclophilin A enhances vascular oxidative stress and the development of angiotensin II-induced aortic aneurysms. Nat Med. (2009) 15:649-56; Raaz U, et al., Segmental aortic stiffening contributes to experimental abdominal aortic aneurysm development. Circulation. (2015) 131:1783-95. The hallmarks of AAA include the formation of intraluminal thrombus (ILT), destructive remodeling of structural connective tissue, and chronic adventitial inflammation.

As most AAA's are asymptomatic, screening programs have been established to target at-risk groups, commonly men aged >60 years. Most, if not all, of these programs utilize ultrasound to identify AAA. Ultrasound is also commonly used to monitor disease progression, since the natural course of most AAAs is to gradually expand, thereby increasing the risk of rupture. Specifically, maximal AAA diameter as measured by ultrasound is the most commonly used surrogate marker of rupture risk.

Significant intra- and inter-observational variability in ultrasound measurement has been noted, risking inaccuracies in diagnosis and/or monitoring of disease progression (See Beales, L. et al., Reproducibility of ultrasound measurement of the abdominal aorta. Br J Surg. 2011; 98:1517-1525 and Gurtelschmid, M. et al., Br J Surg. 2014; 101: 633-636). While computed tomography (CT) and magnetic resonance imaging (MRI) would offer greater accuracy, both techniques are considerably more expensive than ultrasound- and prohibitively so with respect to screening programs. Although numerous circulating markers thought to be important for AAA formation and progression have been identified, none has been accepted in clinical practice as an alternative and/or supplement to imaging (See Wanhainen et al., Surrogate markers of abdominal aortic aneurysm progression. Arterioscler Thromb Vasc Biol. (2016) 36:236-244 and Golledge et al., Circulating markers of abdominal aortic aneurysm presence and progression. Circ. (2008) 118:2382-2392).

In addition, certain underlying genetic disorders relating to connective tissue impact the integrity of the aortic wall structure, resulting in a pathological alteration of the aorta which compromises its function. Such individuals with structural abnormalities of the aorta due to underlying genetic disorders are more susceptible to the development of AAA. One such disorder includes Marfan syndrome (MFS) (see Dietz et al., Recent progress towards a molecular understanding of Marfan syndrome. Am. J. Med. Genet Part C Semin Med Genet (2005) 139C; 4-9. Individuals with disorders related to Marfan syndrome such as Loeys-Dietz syndrome, Ehlers-Danlos syndrome, Familial Thoracic Aortic Aneurysm and Dissection, Mitral valve, myopia, Aorta, Skin and Skeletal (MASS) syndrome, are also prone to the development of AAA.

Currently, there is no recognized pharmacological treatment specific to AAA that has been found to be effective at decreasing the growth rate or rupture rate of asymptomatic AAAs. Rather, invasive approaches (either open or endovascular surgical repair) are utilized for large (>55 mm), rapidly growing (>10 mm/yr) or symptomatic AAAs, while standard of care for patients with small AAAs (<55 mm) is limited to monitoring for growth. In recent years, an increase in screening has led to an increase in the number of patients who are simply being monitored rather than treated for AAA, and typically, utilizing an imaging technique (ultrasound) subject to significant variability.

Several strategies for pharmacologic treatment have been proposed, including inhibition of proteolytic activity, inflammatory response and/or oxidative stress. Up-regulated synthesis of extracellular matrix proteins (ECM) has also been suggested. Agents that have been tested clinically for the treatment of AAA include statins, Angiotensin-converting enzyme (ACE) inhibitors, and anti-inflammatory agents.

(See Miyake et al., Pharmacological treatment of abdominal aortic aneurysm. Cardiovascular Research 2009; 83; 436-443). Matrix metalloproteinase inhibition has been one of the most extensively studied anti-aneurysm strategy thus far and has advanced to human clinical trials for its potential to treat small aneurysms (Lindeman, J. H., Abdul-Hussien, H., van Bockel, J. H., Wolterbeek, R. & Kleemann, R. Clinical trial of doxycycline for matrix metalloproteinase-9 inhibition in patients with an abdominal aneurysm: doxycycline selectively depletes aortic wall neutrophils and cytotoxic T cells. Circulation 119, 2209-2216 (2009); Meijer, C. A. et al. Doxycycline for stabilization of abdominal aortic aneurysms: a randomized trial. Annals of internal medicine 159, 815-823 (2013)). However, none has shown clinical success adequate to replace or modify the current standard of care (See Mosorin et al., Use of doxycycline to decrease the growth rate of abdominal aortic aneurysms: a randomized, double-blind, placebo-controlled pilot study, J. Vasc. Surg. 2001; 34:606-610, Baxter et al., Prolonged administration of doxycycline in patients with small asymptomatic abdominal aortic aneurysms: report of a prospective Phase II multi-center study, J. Vasc. Surg. 2002; 36:1-12, Meijer et al., Doxycycline for stabilization of abdominal aortic aneurysms: A randomized trial, Ann. Intern. Med. 2013; 159: 815-823). Some positive results have been reported in experimental models of AAA (see Wang, Q. et al., Inhibition of Receptor-interacting protein kinase 1 with necrostatin-1s ameliorate disease progression in elastase-induced mouse abdominal aortic aneurysm model, Sci. Rep. 7, 42159; doi:10.1038/srep42159 (2017)). Nonetheless, a pharmaceutical approach remains elusive despite the large and growing population of patients with AAA.

A thoracic aortic aneurysm (TAA) is an aortic aneurysm that presents primarily in the thorax. TAAs, which have an estimated annual incidence of 10.4 per 100,000 people, are typically clinically silent yet potentially fatal, as their natural history is to progressively expand until dissection or rupture occurs. Brownstein A J, Ziganshin B A, Kuivaniemi H, Body S C, Bale A E, Elefteriades J A. Genes Associated with Thoracic Aortic Aneurysm and Dissection: An Update and Clinical Implications. AORTA (Stamford). 2017; 5(1): 11-20. DOI: 10.12945/j.aorta.2017.17.003 Aneurysms in patients younger than 40 usually involve the ascending aorta due to a weakening of the aortic wall associated with connective tissue disorders like the Marfan and Ehler-Danlos syndromes or congenital bicuspid aortic valve. Other disorders associated with TAAs include Syndromes associated with thoracic aortic aneurysms include Marfan syndrome (MFS), Loeys-Dietz syndrome (LDS), Ehlers-Danlos syndrome (EDS), familial thoracic aortic aneurysms and dissections (TAAD), autosomal dominant polycystic kidney disease (ADPKD), bicuspid aortic valve (BAV), Meester-Loeys syndrome, cutis laxa, contractural arachnodactyly, periventricular nodular heterotpia, Shprintzen-Goldberg syndrome, arterial tortuosity syndrome, and neurofibromatosis type 1 (NF1).

Younger patients may develop aortic aneurysms of the thoracoabdominal aorta after an aortic dissection. Atherosclerosis is the principal cause of descending aortic aneurysms, while aneurysms of the aortic arch may be due to dissection, atherosclerosis or inflammation. The size cut off for aortic aneurysm is crucial to its treatment. A thoracic aorta greater than 4.5 cm is generally defined as aneurysmal, while a size greater than 6 cm is the distinction for treatment, which can be either endovascular or surgical, with the former reserved for pathology at the descending aorta. Indication for surgery may depend upon the size of the aneurysm. Aneurysms in the ascending aorta may require surgery at a smaller size than aneurysms in the descending aorta.

Cerebral aneurysms (CA) affect about 5 percent of the population and occur when the wall of a blood vessel in the brain becomes weakened and bulges or balloons out. Pre-rupture treatments are generally limited to surgical clipping or endovascular coiling or a flow diverter can be used to seal off an unruptured brain aneurysm and help prevent a future rupture. However, in some unruptured aneurysms, the known risks of the procedures may outweigh the potential benefit.

Cerebral aneurysms are usually found at the base of the brain just inside the skull, in an area called the subarachnoid space. Rupture of these cerebral aneurysms results in bleeding into the space around the brain and is often referred to as subarachnoid hemorrhage (SAH). This kind of hemorrhage can lead to a stroke, coma and/or death. The treatment for un-ruptured cerebral aneurysms has been a matter of debate for decades. In the largest study on the management of un-ruptured aneurysms "International study of unruptured intracranial aneurysms" (ISUIA), the five-year cumulative rupture rates for patients without a history of SAH and with aneurysms in anterior circulation were 0 percent, 2.6 percent, 14.5 percent and 40 percent for aneurysms <7 mm, 7-12 mm, 13-24 mm, and >25 mm, respectively. For posterior circulation and posterior communicating artery aneurysms these rates were higher: 2.5 percent; 14.5 percent, 18.4 percent and 50 percent for <7 mm, 7-12 mm, 13-24 mm, and >25 mm, respectively. Current non-surgical treatments include life-style changes and blood pressure control medications, such as anti-hypertensive medications. The exact mechanisms by which cerebral aneurysms develop, grow and rupture are unknown.

As such, there remains a need for improved, non-invasive strategies for diagnosing, monitoring and treating patients with aneurysms. There also remains a need for strategies to identify pharmaceutical agents likely to be successful in treating aneurysms.

SUMMARY OF THE INVENTION

The present invention provides methods for detecting and/or treating a subject having an aneurysm or at risk for developing an aneurysm. It has been discovered that a key metabolite of the kynurenine (Kyn) pathway, a major route for the metabolism of essential amino acid tryptophan (Trp) into nicotinamide adenine dinucleotide (NAD+), plays a critical role in the formation of aneurysms, for example abdominal aortic aneurysms. In particular, it has been discovered that 3-Hydroxyanthranilic acid (3-HAA), a product of kynureninase (KYNU) (see FIG. 25), plays a causative role in the formation of aneurysms by, for example exerting pro-inflammatory effects on vascular smooth muscle cells (see, for example, Example 5). It has further been discovered that elevated levels of 3-HAA are indicative of the presence and/or progression of an aneurysm (see, for example, Example 11 and FIGS. 16, 17, and 28), and 3-HAA levels correlate with the size (aortic diameter) of the aneurysm (see, for example, Example 14 and FIG. 29). This important discovery of 3-HAA's causative role in the formation and progression of aneurysms, and its established correlation with aneurysm size and progression, provides an effective biomarker for the diagnosis and monitoring of aneurysm formation using a simple blood test instead of costlier medical imaging, allowing for earlier intervention in treating the aneurysm and assisting in lowering the incidence of mortality associated with the development of aneurysms.

Furthermore, the identification of 3-HAA as a causative agent in the formation of aneurysms provides an attractive target in the treatment of aneurysms. Accordingly, the present invention provides methods for treating formed aneurysms by administering compounds that inhibit the formation of 3-HAA or alter the effects of excessive 3-HAA formation. In particular, it has been discovered that the administration of certain KYN pathway metabolism inhibitors effectively inhibits the formation of 3-HAA and reduces aneurysm formation. Importantly, such inhibitors are also effective at reducing or delaying the progression of aneurysms once formed (see, for example, Example 15). In particular, it has been discovered that inhibitors of KYNU are especially effective at inhibiting the formation of 3-HAA, as well as inhibiting the formation of and progression of aneurysms, compared to KYN pathway inhibitors that act further upstream in the KYN pathway (see, for example, Example 15 and FIGS. 30, 31A, 31B, 31C, and 32C). In has further been discovered that the administration of the compound 5-methylpyrazine-2-carboxylic acid-4-oxide (acipimox), which mitigates the effects of excessive levels of 3-HAA (see, for example, Example 17), significantly reduces aneurysm formation and reduces or delays aneurysm progression (see Examples 12 and 13). The discovery of effective treatments for reducing or delaying aneurysm progression provides a novel pharmaceutical approach to treating formed aneurysms, thus eliminating, diminishing, and/or delaying the requirement for more invasive surgical interventions. The combination of earlier detection via 3-HAA level determinations as well as more patient-friendly treatment methods may provide for improved outcomes in those at risk for developing or who have developed an aneurysm.

In a particular aspect of the present invention, it has been discovered that 3-HAA levels in a subject are indicative of the presence of an aneurysm, wherein subjects with an aneurysm have significantly elevated levels of 3-HAA compared to subjects without an aneurysm, and patients who have had a dissected aneurysm have further elevated plasma levels of 3-HAA compared to subjects with non-dissected aneurysms. By assessing the levels of 3-HAA in a sample from a subject, for example a blood, serum, or plasma sample, the presence of an aneurysm, including asymptomatic aneurysms, can be detected. Furthermore, increasing levels of 3-HAA over time in a subject with a formed aneurysm are associated with aneurysmal size progression (i.e., aneurysmal growth; see Example 14). By monitoring 3-HAA levels over time, aneurysmal growth can be monitored and assessed, and if necessary, appropriate intervention undertaken, for example the administration of a suitable pharmaceutical or surgical intervention.

In one aspect of the present invention, provided herein is a method of screening for the presence of an aneurysm in a subject comprising:
 i. determining the level of 3-HAA present in a sample from the subject; and
 ii. comparing the subject's level of 3-HAA to a range of standardized 3-HAA levels derived from individuals without an aneurysm ("normal range");
 wherein the presence of an aneurysm is suspected if the subject's 3-HAA level is greater than the normal range. In embodiments, the aneurysm is an AAA. In embodiments, the aneurysm is a TAA. In embodiments, the aneurysm is a CA. In embodiments, an aneurysm is suspected if the subject's 3-HAA level is greater than about 1.5 times (1.5×) the mean of the normal range. In embodiments, an aneurysm is suspected if the subject's 3-HAA level is greater than about 1.75× the mean of the normal range. In embodiments, an aneurysm is suspected if the subject's 3-HAA level is greater than about 2.0× the mean of the normal range. In embodiments, an aneurysm is suspected if the subject's 3-HAA level is greater than about 2.25× the mean of the normal range. In embodiments, an aneurysm is suspected if the subject's 3-HAA level is greater than about 2.5× the mean of the normal range. In embodiments, the method further includes performing a medical imaging technique on the subject if the subject's 3-HAA plasma level is greater than the normal range in order to verify or exclude the presence of an aneurysm. In embodiments, if the subject's 3-HAA level is determined to be greater than the normal range, the subject undergoes a medical intervention, for example, the administration of a compound or composition capable of inhibiting, delaying, or reducing aneurysmal progression or growth or capable of stabilizing the aneurysm, for example a compound described herein. Alternatively, the subject undergoes surgical intervention to repair the aneurysm.

In one aspect of the present invention, provided herein is a method of screening for the presence of an aneurysm in a subject comprising:
 i. determining the level of 3-HAA present in a sample from the subject; and
 ii. comparing the subject's level of 3-HAA to a range of standardized 3-HAA levels derived from individuals with an aneurysm ("aneurysmal range");
 wherein the presence of an aneurysm is suspected if the subject's 3-HAA level falls within the aneurysmal range. In embodiments, the aneurysm is an AAA. In embodiments, the aneurysm is a TAA. In embodiments, the aneurysm is a CA. In embodiments, the subject's level of 3-HAA is compared to a range of standardized 3-HAA levels derived from individuals with a verified AAA ("AAA range"). In embodiments, the subject's level of 3-HAA is compared to a range of standardized 3-HAA levels derived from individuals with a verified TAA ("TAA range"). In embodiments, the subject's level of 3-HAA is compared to a range of standardized 3-HAA levels derived from individuals with a verified CA ("CA range"). In embodiments, the method further includes performing a medical imaging technique on a subject with a 3-HAA plasma level within the aneurysmal range in order to verify the presence of an aneurysm. In embodiments, if the subject's 3-HAA level is determined to be within the aneurysmal range, the subject undergoes a medical intervention, for example, the administration of a compound or composition capable of inhibiting, delaying, or reducing aneurysmal progression or growth, or capable of stabilizing the aneurysm. Alternatively, the subject undergoes surgical intervention to repair the aneurysm.

In one aspect of the present invention, provided herein is a method of determining whether an aneurysm in a subject is at risk for dissection comprising:
 i. determining the level of 3-HAA present in a sample from the subject; and
 ii. comparing the subject's level of 3-HAA to a range of standardized 3-HAA levels derived from individuals having a dissected aneurysm ("dissected aneurysmal range");
 wherein the risk of the aneurysm dissecting is elevated if the subject's 3-HAA level falls within the dissected aneurysmal range. In embodiments, the aneurysm is an AAA. In embodiments, the aneurysm is a TAA. In embodiments, the aneurysm is a CA. In embodiments, the subject's level of 3-HAA is compared to a range of standardized 3-HAA levels derived from individuals having a dissected AAA ("dissected AAA range"). In embodiments, the subject's level of 3-HAA is compared to a range of standardized 3-HAA levels derived from individuals having a dissected TAA ("dissected TAA range"). In embodiments, the subject's level of 3-HAA is compared to a range of standardized 3-HAA levels derived from individuals having a dissected CA ("dissected CA range"). In embodiments, the method further includes performing a medical imaging technique on a subject with a 3-HAA plasma level within the dissected aneurysmal range in order to verify the presence of an aneurysm. In embodiments, if the subject's 3-HAA level is determined to be within the dissected aneurysmal range, the subject undergoes a medical intervention, for example, the administration of a compound or composition capable of inhibiting, delaying, or reducing aneurysmal progression or growth, or capable of stabilizing the aneurysm. Alternatively, the subject undergoes surgical intervention to repair the aneurysm, for example an open surgical or endovascular aneurysm repair is performed to repair the AAA, TAA, or CA.

In one aspect of the present invention, provided herein is a method of detecting arterial diameter expansion in an aneurysm in a subject comprising:

i. determining a first level of 3-HAA present in a first sample from the subject, wherein the first sample is taken at a first point in time;

ii. determining a second level of 3-HAA present in a second sample from the subject, wherein the second sample is taken at a second point in time, wherein the second point in time is after the first point in time; and, iii. comparing the subject's first level of 3-HAA to the subject's second level of 3-HAA;

wherein arterial diameter expansion of the aneurysm exists if the second level of 3-HAA is greater than the first level of 3-HAA. In embodiments, the aneurysm is an AAA. In embodiments, the aneurysm is a TAA. In embodiments, the aneurysm is a CA. In embodiments, the arterial diameter expansion of an AAA or TAA is an expansion of the diameter of the aorta at the site of the aneurysm ("aortic diameter expansion"). In embodiments, the arterial diameter expansion of a CA is an expansion of the diameter of the anterior communicating artery, posterior communicating artery, anterior cerebral artery, middle cerebral artery, posterior cerebral artery, internal carotid artery, or the tip of the basilar artery at the site of the aneurysm. In embodiments, the method further includes performing a medical imaging technique on a subject with a second level of 3-HAA greater than the first level of 3-HAA in order to verify the presence of arterial diameter expansion in the aneurysm. In embodiments, if the subject's second level of 3-HAA is greater than the first level of 3-HAA, an open surgical or endovascular aneurysm repair is performed to repair the aneurysm. In embodiments, if the subject's second level of 3-HAA is greater than the first level of 3-HAA, the subject undergoes a medical intervention, for example, the administration of a compound or composition capable of inhibiting, delaying, or reducing aneurysmal progression or growth, or capable of stabilizing the aneurysm. Alternatively, the subject undergoes surgical intervention to repair the aneurysm, for example an open surgical or endovascular aneurysm repair is performed to repair the AAA, TAA, or CA.

As described above, a subject determined to have 3-HAA levels indicative of the formation or expansion of an aneurysm, or whose 3-HAA levels indicate a risk for dissection, may further undergo a medical intervention to treat the aneurysm, for example the administration of a suitable compound or composition or a surgical intervention.

Accordingly, provided herein is a method of treating a subject determined to have 3-HAA levels indicative of the formation or expansion of an aneurysm, or whose 3-HAA levels indicate a risk for dissection, comprising administering to the subject a compound or composition capable of inhibiting, delaying, or reducing aneurysmal progression or growth, or capable of stabilizing the aneurysm. Alternatively, the subject is treated for the aneurysm by undergoing a surgical intervention, for example open surgical or endovascular aneurysm repair. In one embodiment, the subject is administered an effective amount of a KYNU inhibitor as a monotherapy, or in combination with another agent. In one embodiment, the subject is administered an effective amount of a KMO inhibitor as a monotherapy, or alternatively in combination with another agent. In an alternative embodiment, the subject is administered an effective amount of a KYN pathway inhibitor selected from an indoleamine 2,3-dioxygenase 1 (IDO1) inhibitor, a tryptophan 2,3-dioxygenase (TDO2) inhibitor, a dual IDO1/TDO2 inhibitor, or a combination thereof. In an alternative embodiment, the subject is administered an effective amount of acipimox. In one embodiment, acipimox is administered as a monotherapy. In one embodiment, acipimox is administered in combination with another agent. In one embodiment, acipimox is administered in combination with a KMO inhibitor. In one embodiment, acipimox is administered in combination with a KYNU inhibitor. In one embodiment, the subject is administered an effective amount of a 3-HAO up-regulator. In an alternative embodiment, the subject with a determined elevated 3-HAA level as described herein is administered a compound selected from fenofibrate, telmisartan, 5-((7-Cl-1H-indol-3-yl)methyl)-3-methylimidazolidine-2,4-dione) (7-Cl—O-Nec-1), a β-blocker, angiotensin converting enzyme inhibitor (ACEI), angiotensin II type I receptor (AGTR1) blocker (ARBs), statin, tetracycline/macrolide, ERK inhibitor, losartan, pravastatin, β-blocker atenolol, the ACEI perindopril, the calcium channel blocker (CCB) verapamil, roxithromycin, ethinyl estradiol, nebivolol, and doxycycline.

Further provided herein is a method of treating a subject having a formed aneurysm comprising administering to the subject an effective amount of a compound described herein. In embodiments, the subject is administered an effective amount of a KYNU inhibitor. In some embodiments, the KYNU inhibitor is administered as a monotherapy. In some embodiments, the KYNU inhibitor is administered in combination with another compound, for example an IDO1 inhibitor, a TDO2 inhibitor, a dual IDO1/TDO2 inhibitor, a KMO inhibitor, acipimox, another agent, or a combination thereof. In an alternative embodiment, the subject is administered an effective amount of a KMO inhibitor. In some embodiments, the KMO inhibitor is administered in combination with another compound, for example an IDO1 inhibitor, a TDO2 inhibitor, a dual IDO1/TDO2 inhibitor, a KMO inhibitor, acipimox, another agent, or a combination thereof. In an alternative embodiment, the subject is administered an effective amount of acipimox. In some embodiments, acipimox is administered as a monotherapy. In some embodiments, acipimox is administered in combination with an IDO1 inhibitor, a TDO2 inhibitor, a dual IDO1/TDO2 inhibitor, a KMO inhibitor, a KYNU inhibitor, or a combination thereof. In one embodiment, the subject is administered an effective amount of a 3-HAO up-regulator. In an alternative embodiment, the subject is administered an IDO1 inhibitor, a TDO2 inhibitor, a dual IDO1/TDO2 inhibitor, or a combination thereof. In some embodiments, the aneurysm is an AAA. In some embodiments, the aneurysm is a TAA.

In some embodiments, the aneurysm is a CA. In some embodiments, the subject is at risk for developing a dissected aneurysm, for example a dissected AAA, dissected TAA, or dissected CA. In some embodiments, the subject has an AAA or TAA with an aortic diameter of less than or equal to about 3 cm. In some embodiments, the subject has an AAA or TAA with an aortic diameter of less than or equal to about 5 cm. In some embodiments, the subject has an AAA or TAA with an aortic diameter of greater than or equal to about 5 cm. In some embodiments, the subject has an AAA or TAA with an aortic diameter of greater than or equal to about 7 cm. In some embodiments, the subject has a CA with an arterial diameter of less than or equal to about 5 mm. In some embodiments, the subject has a CA with an arterial diameter of greater than or equal to about 5 mm. In some embodiments, the subject has a CA with an arterial diameter of greater than or equal to about 10 mm. In some embodiments, the subject has a CA with an arterial diameter of greater than or equal to about 25 mm.

In one aspect of the present invention, provided herein is a method of prophylactically inhibiting the formation of an aneurysm in a subject predisposed to the development of an aneurysm by administering to the subject a compound described herein. In embodiments, the subject is administered an effective amount of a KYNU inhibitor. In some embodiments, the KYNU inhibitor is administered as a monotherapy. In some embodiments, the subject is administered an effective amount of a KYNU inhibitor. In some embodiments, the KYNU inhibitor is administered as a monotherapy. In some embodiments, the KYNU inhibitor is administered in combination with another compound, for example an IDO1 inhibitor, a TDO2 inhibitor, a dual IDO1/TDO2 inhibitor, a KMO inhibitor, acipimox, another agent, or a combination thereof. In an alternative embodiment, the subject is administered an effective amount of a KMO inhibitor. In some embodiments, the KMO inhibitor is administered in combination with another compound, for example an IDO1 inhibitor, a TDO2 inhibitor, a dual IDO1/TDO2 inhibitor, a KMO inhibitor, acipimox, another agent, or a combination thereof. In an alternative embodiment, the subject is administered an effective amount of acipimox. In some embodiments, acipimox is administered as a monotherapy. In some embodiments, acipimox is administered in combination with an IDO1 inhibitor, a TDO2 inhibitor, a dual IDO1/TDO2 inhibitor, a KMO inhibitor, a KYNU inhibitor, or a combination thereof. In one embodiment, the subject is administered an effective amount of a 3-HAO up-regulator. In an alternative embodiment, the subject is administered an IDO1 inhibitor, a TDO2 inhibitor, a dual IDO1/TDO2 inhibitor, or a combination thereof. In some embodiments the aneurysm is an AAA. In some embodiments, the aneurysm is a TAA. In some embodiments, the subject has a genetic disorder associated with an increased risk of aneurysm development. In some embodiments, the subject has a genetic disorder selected from Marfan syndrome, Loeys-Dietz syndrome, Ehlers-Danlos syndrome, Familial Thoracic Aortic Aneurysm and Dissection, Mitral valve, myopia, Aorta, Skin and Skeletal (MASS) syndrome, Beals syndrome, aneurysms-osteoarthritis syndrome, Shprintzen-Goldberg syndrome, cutis laxa syndrome, aortic valve disease, arterial tortuosity syndrome, X-linked Alport syndrome, Turner syndrome, and Bicuspid Aortic Valve syndrome. In some embodiments, the subject has a mutation in a gene selected from COL1A1, COL1A2, MED12, PLOD3, ENG, ACVRL1 or NF1, or a combination thereof.

In one aspect of the present invention, provided herein is a method of reducing the risk of aneurysmal rupture in a subject predisposed to the development of an aneurysm by administering to the subject a compound described herein. In embodiments, the subject is administered an effective amount of a KYNU inhibitor. In some embodiments, the KYNU inhibitor is administered as a monotherapy. In some embodiments, the KYNU inhibitor is administered in combination with another compound, for example an IDO1 inhibitor, a TDO2 inhibitor, a dual IDO1/TDO2 inhibitor, a KMO inhibitor, acipimox, another agent, or a combination thereof. In an alternative embodiment, the subject is administered an effective amount of a KMO inhibitor. In some embodiments, the KMO inhibitor is administered in combination with another compound, for example an IDO1 inhibitor, a TDO2 inhibitor, a dual IDO1/TDO2 inhibitor, a KMO inhibitor, acipimox, another agent, or a combination thereof. In an alternative embodiment, the subject is administered an effective amount of acipimox. In some embodiments, acipimox is administered as a monotherapy. In some embodiments, acipimox is administered in combination with an IDO1 inhibitor, a TDO2 inhibitor, a dual IDO1/TDO2 inhibitor, a KMO inhibitor, a KYNU inhibitor, or a combination thereof. In one embodiment, the subject is administered an effective amount of a 3-HAO up-regulator. In an alternative embodiment, the subject is administered an IDO1 inhibitor, a TDO2 inhibitor, a dual IDO1/TDO2 inhibitor, or a combination thereof. In one embodiment, the subject is predisposed to the development of an AAA or TAA. In one embodiment, the subject is predisposed to the development of a CA. In one embodiment, the subject has a genetic disorder associated with an increased risk of AAA or TAA development. In one embodiment, the subject has a genetic disorder selected from Marfan syndrome, Loeys-Dietz syndrome, Ehlers-Danlos syndrome, Familial Thoracic Aortic Aneurysm and Dissection, Mitral valve, myopia, Aorta, Skin and Skeletal (MASS) syndrome, Beals syndrome, aneurysms-osteoarthritis syndrome, Shprintzen-Goldberg syndrome, cutis laxa syndrome, aortic valve disease, arterial tortuosity syndrome, X-linked Alport syndrome, Turner syndrome, and Bicuspid Aortic Valve syndrome. In some embodiments, the subject has a mutation in a gene selected from COL1A1, COL1A2, MED12, PLOD3, ENG, ACVRL1 or NF1, or a combination thereof.

In any of the above embodiments wherein a KYNU inhibitor is administered, the KYNU inhibitor may be selected from 2-Amino-4-[3'-hydroxyphenyl]-4-hydroxybutanoic acid,

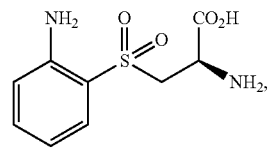 [SMILES: Nc1ccccc1S(=O)(=O)C[C@H](N)C(=O)O]

(4R)-dihydro-L-kynurenine, (4S)-dihydro-L-kynurenine,

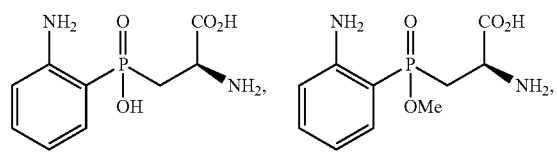

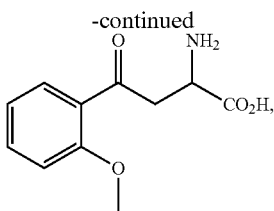

benserazide, o-Methoxybenzoylalanine (OMBA), and (m-Nitrobenzoyl)alanine (NBA).

In any of the above embodiments wherein a KMO inhibitor is administered, the KMO inhibitor may be selected from GSK180, (R)-3-(5-chloro-6-(1-phenylethoxy)benzo[d]isoxazol-3-yl)propanoic acid, CHDI-340246, des-amino FCE 28833, UPF 648, and Ro-61-8048.

In any of the above embodiments wherein an IDO1 inhibitor is administered, the IDO1 inhibitor may be selected from 1-methyl-D-tryptophan, navoximod, NLG802, epacadostat, BMS-986205, PF-06840003,

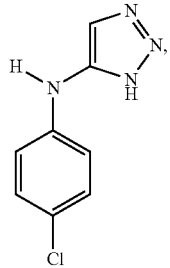

SHR9146, IOM2983, RG-70099/CRD1152, and Necrostatin-1.

In one aspect of the present invention, provided herein is a kit for analyzing the level of 3-HAA in a subject. In one embodiment, the kit includes at least one antibody directed to 3-HAA. In one embodiment, the kit further includes a control protein or molecule in an amount useful in normalizing or standardizing levels of 3-HAA.

DETAILED DESCRIPTION OF THE INVENTION

Terminology

Figure 1A:
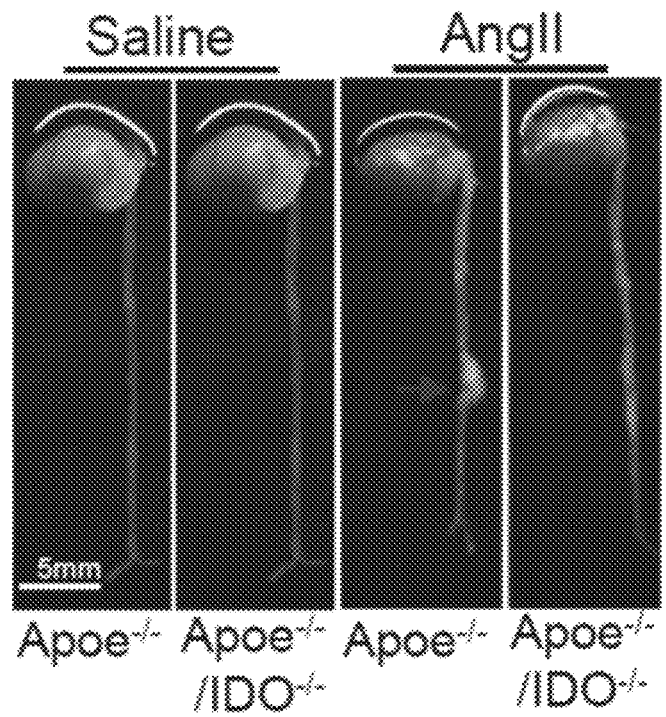
FIG. 1A depicts representative photographs showing the macroscopic features of AngII-induced aneurysms in ApoE$^{-/-}$ and ApoE$^{-/-}$/IDO$^{-/-}$ mice administered with saline or AngII (100 ng/min per kg) for 4 weeks. The arrow indicates typical abdominal aortic aneurysm (AAA).

The terms "a" and "an" do not denote a limitation of quantity, but rather denote the presence of at least one of the referenced items. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as," "for example," etc.), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

Kynurenine (Kyn) pathway enzymes and/or metabolites refers to the enzymes and metabolites associated with the degradation of tryptophan in the kynurenine pathway.

"Kynurenine (Kyn) pathway enzymes and/or metabolites" include indoleamine-2,3-dioxygenase-1 (IDO1), indoleamine-2,3-dioxygenase-2 (IDO2), tryptophan 2,3-dioxygenase (TDO), N-formylkynurenine, formamidase, kynurenine (Kyn), kynurenine amino-transferase (KAT), kynureninase (KYNU), kynurenic acid (KA), anthranilic acid (AA), kynurenine-3-monooxygenase (KMO), 3-hydroxykynurenine (3-HK), 3-hydroxyanthranilic acid (3-HAA), xanthurenic acid (XA), 2-amino-3-carboxymuconate semialdehyde, 2-aminomuconic acid semialdehyde, picolinic acid (PA), quinolinic acid (QA), NAD+, 3-hydroxyanthranilate 3,4-dioxygenase (3-HAO), 2-amino-3-carboxy-muconate semialdehyde decarboxylase (ACMSD), and quinolinate phosphoribosyltransferase (QPRT). See also FIG. 25.

A "patient" or "host" or "subject" is a human or non-human animal in need of detection and/or treatment of an aneurysm, for example an abdominal aortic aneurysm (AAA), a thoracic aortic aneurysm (TAA), or a cerebral aneurysm (CA). Typically, the subject is a human. A "patient" or "host" or "subject" also refers to for example, a mammal, primate (e.g., human), cows, sheep, goat, horse, dog, cat, rabbit, rat, mice, fish, bird and the like.

The term "sample" can include any bodily fluid or tissue sample that may contain a metabolite, RNA, or a protein associated with the Kyn pathway to be analyzed as described herein. The term "sample" or "sample from the subject" can be used generally to refer to a sample or any type which contains products that are to be evaluated by the present method, including but not limited to, a sample of isolated cells, a tissue sample, and/or a bodily fluid sample. In some embodiments, the sample may comprise blood, plasma, or serum.

An "effective amount" of a compound or combination of this invention means an amount effective, when administered to a host, to provide a therapeutic benefit such as an amelioration of symptoms or prevention, reduction, or diminution of the disease itself.

The term "pharmaceutically acceptable salt" as used herein refers to those salts which are, within the scope of sound medical judgment, suitable for use in contact with subjects (e.g., human subjects) without undue toxicity, irritation, allergic response, and the like, commensurate with a reasonable benefit/risk ratio, and effective for their intended use, as well as the zwitterionic forms, where possible, of the compounds of the presently disclosed subject matter.

Thus, the term "salt" refers to the relatively non-toxic, inorganic and organic acid addition salts of compounds of the presently disclosed subject matter. These salts can be prepared in situ during the final isolation and purification of the compounds or by separately reacting the purified compound in its free base form with a suitable organic or inorganic acid and isolating the salt thus formed. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

"Pharmaceutical compositions" are compositions comprising at least one active agent, and at least one other substance, such as a pharmaceutically acceptable carrier or pharmaceutically acceptable excipient.

A "pharmaceutically acceptable excipient" means an excipient that is useful in preparing a pharmaceutical composition that is generally safe, non-toxic and neither biologically nor otherwise inappropriate for administration to a host, typically a human. In one embodiment, an excipient is used that is acceptable for veterinary use.

As used herein, the term "prodrug" means a compound which when administered to a host in vivo is converted into the parent drug. As used herein, the term "parent drug"

means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

Throughout the specification and claims, a given chemical formula or name shall encompass all optical and stereoisomers, as well as racemic mixtures where such isomers and mixtures exist, unless otherwise noted.

In one embodiment, acipimox includes desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2$H) and tritium ($^3$H) may be used anywhere in described structures. Alternatively, or in addition, isotopes of carbon, e.g., $^{13}$C and $^{14}$C, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect).

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1$H), deuterium ($^2$H) and tritium ($^3$H). Thus, reference herein to a compound encompasses all potential isotopic forms unless the context clearly dictates otherwise.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90%, 95%, or 99% or more enriched in an isotope at any location of interest. In some embodiments, it is deuterium that is 90%, 95%, or 99% enriched at a desired location.

In the description above, below, and herein generally, whenever any of the terms referring to specific compounds, for example acipimox or 5-methylpyrazine-2-carboxylic acid-4-oxide, are used, it should be understood that pharmaceutically acceptable salts, prodrugs or compositions are considered included, unless otherwise stated or inconsistent with the text.

As contemplated herein and for purposes of the disclosed ranges herein, all ranges described herein include any and all numerical values occurring within the identified ranges. For example, a range of 1 to 10, or between 1 and 10, as contemplated herein, would include the numerical values 1, 2, 3, 4, 5, 6, 7, 8, 9, 10, as well as fractions thereof.

Abdominal Aortic Aneurysm (AAA)

Methods of detecting abdominal aortic aneurysm (AAA) and treating AAA are provided herein. AAA is characterized in most cases by the formation of intraluminal thrombus (ILT), destructive remodeling of structural connective tissue, and chronic adventitial inflammation. Michael J B et al., Topological determinants and consequences of adventitial responses to arterial wall injury. Arterioscler Thromb Vasc Biol. (2007) 27:1259-68. Abdominal aortic aneurysms often grow slowly and usually without symptoms, making them difficult to detect. Abdominal aortic aneurysm risk factors include:

Age: Abdominal aortic aneurysms occur most often in people age 65 and older;

Tobacco use: Tobacco use is a strong risk factor for the development of an abdominal aortic aneurysm and a higher risk of rupture. The longer one has used tobacco, the greater the risk;

Gender: Men develop abdominal aortic aneurysms much more often than women do;

Race: Caucasians are at higher risk of abdominal aortic aneurysms;

Family history: People who have a family history of abdominal aortic aneurysms are at increased risk of having the condition;

Atherosclerosis: Atherosclerosis—the buildup of fat and other substances that can damage the lining of a blood vessel—increases the risk of an AAA;

Other aneurysms: People who have an aneurysm in another large blood vessel, such as the artery behind the knee or the thoracic aorta in the chest, may have a higher risk of developing an abdominal aortic aneurysm; and, High blood pressure: High blood pressure may increase your risk of developing an abdominal aortic aneurysm.

Tears in one or more of the layers of the wall of the aorta (aortic dissection) or a ruptured aortic aneurysm are the main complications of abdominal aortic aneurysms. A ruptured aortic aneurysm can lead to life-threatening internal bleeding. In general, the larger the aneurysm and the faster the aneurysm grows, the greater the risk of rupture.

The natural course of many AAAs is to gradually expand and eventually rupture. Monitoring the disease progression is essential to their management. Traditional AAA screening, evaluation, and surveillance programs employ the use of medical imaging techniques, including for example, but not limited to, CT angiogram (CTA), ultrasound sonography (US), and magnetic resonance imaging (MRI). Despite the proven efficacy of these imaging techniques, the cost associated with such programs can incur significant financial burdens to the health care systems.

In addition to the risk factors described above, individuals with underlying genetic conditions that affect connective tissue, collagen, elastin, and/or fibrillin are prone to the development of AAA. Because connective tissue, collagen, elastin, and fibrillin are involved in the formation of blood vessels and the structural integrity of functioning blood vessels, including the aorta, individuals with connective tissue collagen, elastin, and/or fibrillin disorders often suffer from structural abnormalities to the aorta, resulting in a predisposition to the development of AAA.

Genetic causes of aortic aneurysms include Marfan syndrome (MFS; caused by FBN1 mutations), Loeys-Dietz syndrome (LDS; associated with mutations in the genes TGFBR1, TGFBR2, TGFB2, and SMAD3), aneurysms-osteoarthritis syndrome (AOS; caused by SMAD3 mutations), Ehlers-Danlos syndrome, including vascular Ehlers-Danlos syndrome (EDS IV; caused by COL3A1 mutations), familial thoracic aortic aneurysm/dissection (FTAAD; associated with ACTA2, MYH11, and MYLK mutations), Shprintzen-Goldberg syndrome, cutis laxa syndrome (CL; associated with ELN and EFEMP2 mutations), aortic valve disease (AOVD1; caused by NOTCH1 mutations), arterial tortuosity syndrome (ATS; caused by SLC2A10 mutations), X-linked Alport syndrome (XLAS; caused by COL4A5 mutations), and Turner syndrome (45,X) as well as other congenital heart malformations. AAA has also been associated with mutations in the genes COL1A1, COL1A2, MED12 or SMAD4 as well as medium-sized AAAs with mutations in the genes PLOD3, ENG, ACVRL1 or NF1.

Thoracic Aortic Aneurysm (TAA)

Methods of detecting thoracic aortic aneurysm (TAA) and treating TAA are provided for herein. A thoracic aortic aneurysm is a weakened area in the upper part of the aorta. The aorta is the major blood vessel that feeds blood to the body. A thoracic aortic aneurysm may also be called thoracic aneurysm and aortic dissection (TAAD) because an aneurysm can lead to a tear in the artery wall (dissection) that can cause life-threatening bleeding. Small and slow-growing thoracic aortic aneurysms may not ever rupture, but large, fast-growing aneurysms may rupture. Depending on the size and growth rate of the thoracic aortic aneurysm, treatment may vary from monitoring size and progression over time to emergency surgery. Thoracic aortic aneurysms often grow slowly and usually without symptoms, making them difficult to detect. Some aneurysms will never rupture. Many start small and stay small, although many expand over time. How quickly an aortic aneurysm may grow is difficult to predict. As a thoracic aortic aneurysm grows, symptoms include: tenderness or pain in the chest, back pain, hoarseness, cough, and/or shortness of breath. Thoracic aortic aneurysm risk factors include:

Age: Thoracic aortic aneurysms occur most often in people age 65 and older;

Tobacco use: Tobacco use is a strong risk factor for the development of a thoracic aortic aneurysm and a higher risk of rupture. The longer one has used tobacco, the greater the risk;

Gender: Men develop thoracic aortic aneurysms much more often than women do;

Race: Caucasians are at higher risk of thoracic aortic aneurysms;

Family history: People who have a family history of thoracic aortic aneurysms are at increased risk of having the condition;

Atherosclerosis: increases the risk of TAA;

Other aneurysms: People who have an aneurysm in another large blood vessel, such as the artery behind the knee or the abdominal aorta in the chest, may have a higher risk of developing a thoracic aortic aneurysm; and, High blood pressure: High blood pressure may increase your risk of developing a thoracic aortic aneurysm.

Tears in one or more of the layers of the wall of the aorta (aortic dissection) or a ruptured aortic aneurysm are the main complications of thoracic aortic aneurysms. A ruptured aortic aneurysm can lead to life-threatening internal bleeding. In general, the larger the aneurysm and the faster the aneurysm grows, the greater the risk of rupture.

The natural course of many TAAs is to gradually expand and eventually rupture. Monitoring the disease progression is essential to their management. Traditional TAA screening, evaluation, and surveillance programs employ the use of medical imaging techniques, including for example, but not limited to, chest x-ray, echocardiogram (ECG), transesophageal echocardiogram, CT angiogram (CTA), ultrasound sonography (US), magnetic resonance imaging (MRI), and magnetic resonance angiography (MRA). Despite the proven efficacy of these imaging techniques, the cost associated with such programs can incur significant financial burdens to the health care systems.

In addition to the risk factors described above, individuals with underlying genetic conditions that affect connective tissue, collagen, elastin, and/or fibrillin are prone to the development of TAA. Because connective tissue, collagen, elastin, and fibrillin are involved in the formation of blood vessels and the structural integrity of functioning blood vessels, including the aorta, individuals with connective tissue collagen, elastin, and/or fibrillin disorders often suffer from structural abnormalities to the aorta, resulting in a predisposition to the development of TAA.

Genetic causes of aortic aneurysms include Marfan syndrome (MFS; caused by FBN1 mutations), Loeys-Dietz syndrome (LDS; associated with mutations in the genes TGFBR1, TGFBR2, TGFB2, and SMAD3), aneurysms-osteoarthritis syndrome (AOS; caused by SMAD3 mutations), Ehlers-Danlos syndrome, including vascular Ehlers-Danlos syndrome (EDS IV; caused by COL3A1 mutations), familial thoracic aortic aneurysm/dissection (FTAAD; associated with ACTA2, MYH11, and MYLK mutations), Shprintzen-Goldberg syndrome, cutis laxa syndrome (CL; associated with ELN and EFEMP2 mutations), aortic valve disease (AOVD1; caused by NOTCH1 mutations), arterial tortuosity syndrome (ATS; caused by SLC2A10 mutations), X-linked Alport syndrome (XLAS; caused by COL4A5 mutations), and Turner syndrome (45,X) as well as other congenital heart malformations. TAA has also been associated with mutations in the genes COL1A1, COL1A2, MED12 or SMAD4 as well as medium-sized TAAs with mutations in the genes PLOD3, ENG, ACVRL1 or NF1.

Cerebral Aneurysm (CA)

Methods of detecting and/or treating cerebral aneurysm (CA) are provided herein. A cerebral aneurysm is a bulge or ballooning in a blood vessel in the brain. Cerebral aneurysms most commonly occur in the anterior communicating artery, posterior communicating artery, anterior cerebral artery, middle cerebral artery, posterior cerebral artery, internal carotid artery, or the tip of the basilar artery. A brain aneurysm can leak or rupture, causing bleeding into the brain (hemorrhagic stroke). Most often a ruptured brain aneurysm occurs in the space between the brain and the thin tissues covering the brain. This type of hemorrhagic stroke is called a subarachnoid hemorrhage. A ruptured aneurysm quickly becomes life-threatening and requires prompt medical treatment. Most brain aneurysms, however, don't rupture, create health problems, or cause symptoms. Such aneurysms are often detected during tests for other conditions.

Common signs and symptoms of a ruptured aneurysm include: sudden, extremely severe headache, nausea and vomiting, stiff neck, blurred or double vision, sensitivity to light, seizure, a drooping eyelid, loss of consciousness, and/or confusion.

A number of factors can contribute to weakness in an artery wall and increase the risk of a brain aneurysm or aneurysm rupture. Brain aneurysms are more common in adults than in children and more common in women than in men. Some of these risk factors develop over time; others are present at birth. Risk factors that develop over time include: older age, cigarette smoking, high blood pressure (hypertension), drug abuse, particularly the use of cocaine, and heavy alcohol consumption. Some types of aneurysms may occur after a head injury (dissecting aneurysm) or from certain blood infections (mycotic aneurysm).

Diagnostic tests for CA include: computerized tomography (CT), CT angiography, cerebrospinal fluid test, magnetic resonance imaging (MRI) angiography, or a cerebral angiogram.

The Kynurenine Pathway

As described herein, it has been discovered that the Kyn pathway metabolite 3-HAA plays a fundamental role in the development of aneurysms, and the presence of excess levels of 3-HAA, indicates the presence of an aneurysm.

Figure 25:
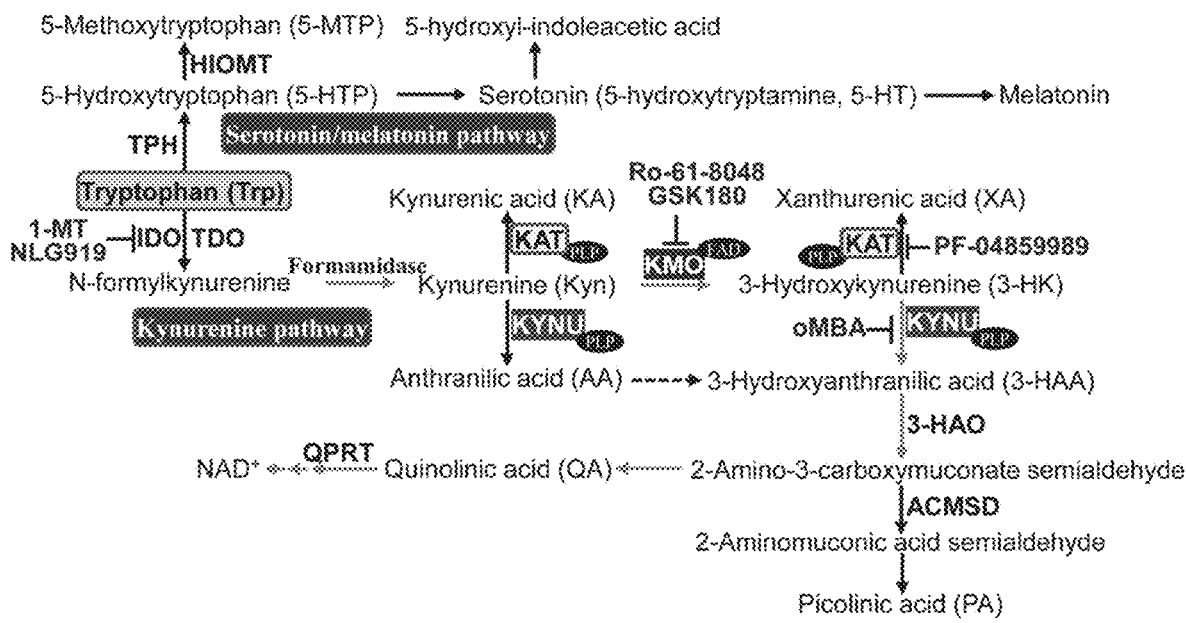
FIG. 25 is a schematic drawing depicting the major enzymes and catabolites in tryptophan metabolism. Tryptophan is metabolized via two major pathways: the kynurenine pathway and the serotonin/melatonin pathway.
Figure 26A:
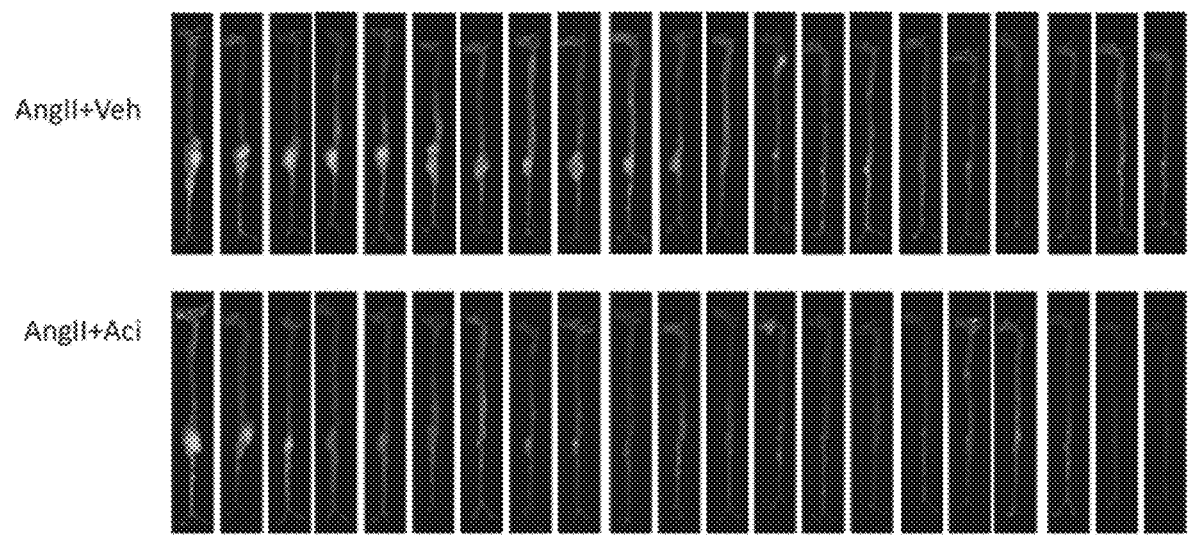
FIG. 26A shows representative images of abdominal aorta from four groups of ApoE$^{-/-}$ mice who were infused with AngII (1.44 mg/kg/day) for 14 days, followed by infusion with vehicle or 0.1% acipimox for 6 weeks. N=21.
Figure 26B:
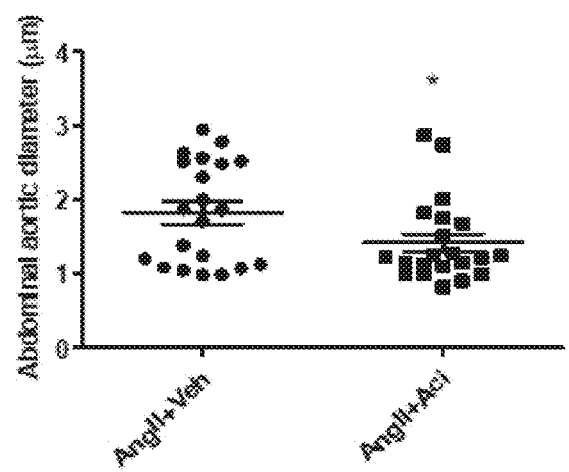
FIG. 26B is a scatter plot that shows the abdominal aortic diameter of mice treated with AngII (1.44 mg/kg/day) for 14 days, followed by infusion with vehicle or 0.1% acipomox for 6 weeks. The x-axis shows the treatment, and the y-axis shows the abdominal aortic diameter in millimeters. N=21. *P<0.01 versus vehicle. The error bars are standard error of the mean.
Figure 26C:
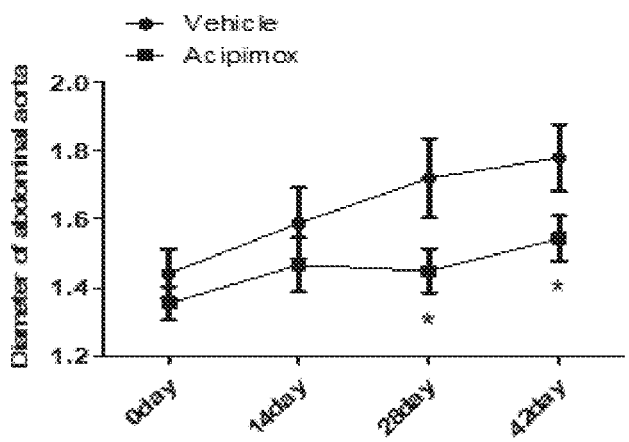
FIG. 26C is a line graph that shows the change over time in abdominal aortic diameter in mice treated with AngII (1.44 mg/kg/day) for 14 days, followed by infusion with vehicle or 0.1% acipimox for 6 weeks. The x-axis shows time in days, and the y-axis shows the abdominal aortic diameter in millimeters. The error bars are standard error of the mean.

The Kyn pathway is the major route for the metabolism of the essential amino acid tryptophan (Trp). Enzymes and metabolites associated with the Kyn pathway include indoleamine-2,3-dioxygenase-1 (IDO1), indoleamine-2,3-dioxygenase-2 (IDO2), tryptophan 2,3-dioxygenase (TDO), N-formylkynurenine, formamidase, kynurenine (Kyn), kynurenine amino-transferase (KAT), kynureninase (KYNU), kynurenic acid (KA), anthranilic acid (AA), kynurenine-3-monooxygenase (KMO), 3-hydroxykynurenine (3-HK), 3-hydroxyanthranilic acid (3-HAA), xanthurenic acid (XA), 2-amino-3-carboxymuconate semialdehyde, 2-aminomuconic acid semialdehyde, picolinic acid (PA), quinolinic acid (QA), NAD+, 3-hydroxyanthranilate 3,4-dioxygenase (3-HAO), 2-amino-3-carboxy-muconate semialdehyde decarboxylase (ACMSD), and quinolinate phosphoribosyltransferase (QPRT). A schematic of the Kyn pathway is depicted in FIG. 25.

Trp is constitutively oxidized by tryptophan 2,3-dioxygenase in liver cells. In other cell types, Trp is catalyzed by an alternative inducible indoleamine-pyrrole 2,3-dioxygenase-1 (IDO1) under certain pathophysiological conditions. See Wang Q, et al., Tryptophan-kynurenine pathway is dysregulated in inflammation, and immune activation. Frontiers in bioscience (Landmark edition). (2015) 20:1116-43. The first stable intermediate from the Kyn pathway is kynurenine (Kyn). Subsequently, in eukaryotes, kynureninase (KYNU) directly catalyzes the hydrolysis of Kyn or 3-hydroxykynurenine (3-HK) to form anthranilic acid (AA) or 3-hydroxyanthranilic acid (3-HAA), respectively (FIG. 25). Catabolites in the Kyn pathway of tryptophan metabolism play critical roles in vascular physiology and pathology (Wang Y, et al., Kynurenine is an endothelium-derived relaxing factor produced during inflammation. Nat Med. (2010) 16:279-85; Wang Q, et al., Activation of NAD(P)H Oxidase by Tryptophan-Derived 3-Hydroxykynurenine Accelerates Endothelial Apoptosis and Dysfunction In Vivo. Circ Res. (2014) 114:480-92), in addition to regulating the immune system (Jones S P, et al., Expression of the Kynurenine Pathway in Human Peripheral Blood Mononuclear Cells: Implications for Inflammatory and Neurodegenerative Disease. PLoS One. (2015) 10: e0131389; Platten M, et al., Cancer Immunotherapy by Targeting IDO1/TDO and Their Downstream Effectors. Front Immunol. (2014) 5:673) and inflammation (Wang Q, et al., Tryptophan-kynurenine pathway is dysregulated in inflammation, and immune activation. Frontiers in Bioscience (Landmark edition). 2015; 20:1116-43; Campbell B M, et al., Kynurenines in CNS disease: regulation by inflammatory cytokines. Front Neurosci. (2014) 8:12). Moreover, IDO1 is a potential novel contributor to vessel relaxation in systemic infections (Hofmann F. Ido brings down the pressure in systemic inflammation. Nat Med. (2010) 16:265-7; Changsirivathanathamrong D, et al., Tryptophan metabolism to kynurenine is a potential novel contributor to hypotension in human sepsis. Crit Care Med. (2011) 39:2678-83), which are also activated in acute severe heart attacks (Ristagno G et al., Early kynurenine pathway activation following cardiac arrest in rats, pigs, and humans. Resuscitation. 2013; 84:1604-10). Recently, IDO1 was reported to play a critical role in atherogenesis in mice (Cole J E, et al., Indoleamine 2,3-dioxygenase-1 is protective in atherosclerosis and its metabolites provide new opportunities for drug development. Proc Natl Acad Sci USA. (2015) 112:13033-8; Metghalchi S, et al., Indoleamine 2,3-Dioxygenase Fine-Tunes Immune Homeostasis in Atherosclerosis and Colitis through Repression of Interleukin-10 Production. Cell Metab. (2015) 22:460-71).

Kynurenine Pathway Inhibitors

In mammalian cells, the essential amino acid tryptophan is degraded primarily by the kynurenine pathway, a cascade of enzymatic steps containing several biologically active compounds. Metabolites of this pathway, collectively termed 'kynurenines', have been shown to be involved in many diverse physiological and pathological processes. Kynurenine pathway inhibitors for use in the methods described herein include, but are not limited to, indoleamine 2,3-dioxygenase-1 (IDO1) inhibitors, tryptophan 2,3, dioxygenase (TDO1) inhibitors, dual IDO1/TDO1 inhibitors, kynurenine 3-monooxygenase (KMO) inhibitors, and kynureninase (KYNU) inhibitors.

Alternatively, methods for degrading excessive 3-HAA are provided herein. In one aspect, a subject determined to have an excessive 3-HAA level, or a subject with a formed aneurysm, or at risk for forming an aneurysm, is administered an 3-HAO up-regulator, which induces the expression of 3-HAO, providing a mechanism for the degradation of formed 3-HAA.

As described further below, it has been found that, in particular, the inhibition of KNYU provides a particular effective method of inhibiting the formation of 3-HAA. Accordingly, in certain embodiments, the KYN pathway inhibitor administered to a subject to inhibit the formation of or delay the progression of an aneurysm is a KNYU inhibitor. In an alternative embodiment, the KYN inhibitor for administration is a KMO. In still another alternative embodiment, the KYN inhibitor is an IDO1 inhibitor. In certain aspects, the KYN inhibitor administered is not an IDO1 inhibitor. In one embodiment, the subject is administered an effective amount of a 3-HAO up-regulator.

Kynurenine pathway inhibitors are known in the art and include, but are not limited to, those described further below.

Kynureninase (KYNU) Inhibitors

In one aspect, a kynureninase (KYNU) inhibitor is administered to a subject having a formed aneurysm or at risk for developing an aneurysm. In an alternative embodiment, a KYNU inhibitor is administered to a subject with an elevated 3-HAA level as determined by the methods described herein. As shown herein, KYNU inhibitors have shown a more efficient inhibition of 3-HAA formation and, accordingly, aneurysm formation and progression than upstream KYN inhibitors such as IDO1 and KMO inhibitors. KYNU inhibitors are known in the art and include, but are not limited to, those described further below.

2-Amino-4-[3'-hydroxyphenyl]-4-hydroxybutanoic acid is a KYNU inhibitor having the chemical formula:

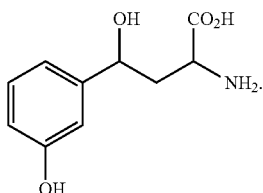

This compound is described in Walsh, H. A. et al. "2-Amino-4-[3'-hydroxyphenyl]-4-hydroxybutanoic acid; A potent inhibitor of rate and recombinant human kynureninase" Bioorg. Med. Chem. Lett. 2002, 12:361-363, incorporated herein by reference.

A series of KYNU inhibitors are described in Dua, R. K. et al. "S-Aryl-L-cystein S,S-Dioxides: Design, Synthesis, and Evaluation of a New Class of Inhibitors of Kynureninase" J. Am. Chem. Soc. 1993, 115:1264-1270, incorporated herein by reference. A particularly useful KYNU inhibitor of the series is the compound having the chemical formula:

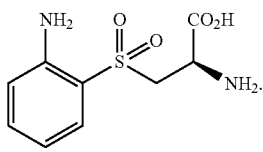 [SMILES: Nc1ccccc1S(=O)(=O)C[C@H](N)C(=O)O]

A series or related KYNU inhibitors are described in U.S. Pat. Nos. 5,442,104; 5,254,725; 5,495,044; and 5,516,936, incorporated herein by reference, all assigned to the University of Georgia Research Foundation, Inc.

Both (4R)-dihydro-L-kynurenine and (4S)-dihydro-L-kynurenine are KYNU inhibitors having the chemical formulas:

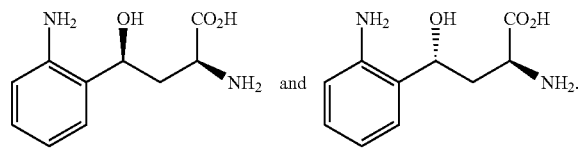 [SMILES: Nc1ccccc1[C@@H](O)C[C@H](N)C(=O)O ; "and" ; Nc1ccccc1[C@H](O)C[C@H](N)C(=O)O]

These compounds are described in Phillips, R. S. and Dua, R. K. "Stereochemistry and Mechanism of Aldol Reactions Catalyzed by Kynureninase" J. Am. Chem. Soc. 1991, 113:7385-7388, incorporated herein by reference.

A series of KYNU inhibitors are described in Ross, F. C. and Botting, N. P. "Synthesis of Phosphinic Acid Transition State Analogues for the Reaction Catalysed by Kynureninase" Bioorg. Med. Chem. Lett. 1996, 6:2643-2646 (incorporated herein by reference), having the chemical formulas:

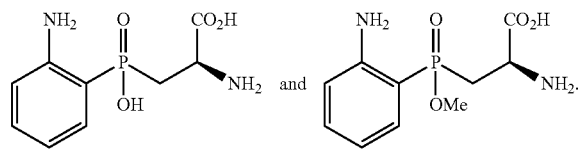 [SMILES: Nc1ccccc1P(=O)(O)C[C@H](N)C(=O)O ; "and" ; COP(=O)(C[C@H](N)C(=O)O)c1ccccc1N]

A series of KYNU inhibitors, for example a compound of the chemical formula

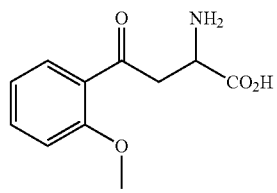 [SMILES: COc1ccccc1C(=O)CC(N)C(=O)O]

are described in U.S. Patent Publication No. 2001/0008947 titled "2-Amino-4-phenyl-4-oxo-butyric acid derivatives," incorporated herein by reference.

Benserazide is a KYNU inhibitor and aromatic L-amino acid decarboxylase/DOPA decarboxylase inhibitor having the chemical formula:

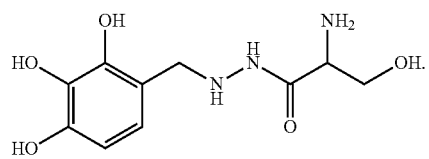 [SMILES: NC(CO)C(=O)NNCc1ccc(O)c(O)c1O]

o-Methoxybenzoylalanine (OMBA) is a KYNU inhibitor having the chemical formula:

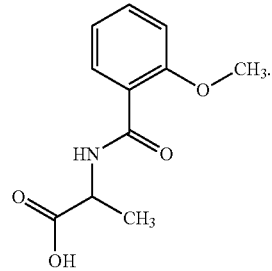 [SMILES: COc1ccccc1C(=O)NC(C)C(=O)O]

(m-Nitrobenzoyl)alanine (NBA) is an inhibitor of kyurenine-3-monooxygenase (KMO) with the chemical formula:

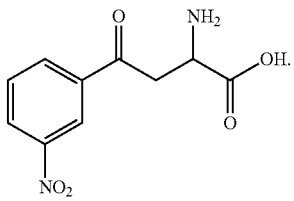 [SMILES: NC(CC(=O)c1cccc([N+](=O)[O-])c1)C(=O)O]

KYNU can also be inhibited by the administration of, for example, an siRNA, for example kynureninase siRNA (Invitrogen, 4457308).

Kynurenine-3-monooxygenase (KMO) Inhibitors

In one aspect, a kynurenine-3-monooxygenase (KMO) inhibitor is administered to a subject having a formed aneurysm or at risk for developing an aneurysm. In an alternative embodiment, a KMO inhibitor is administered to a subject with an elevated 3-HAA level as determined by the methods described herein. KMO inhibitors are known in the art and include, but are not limited to, those described further below.

GSK180 (oxazolidinone) is a potent, selective and competitive inhibitor of kynurenine-3-monooxygenase (KMO) with the chemical formula:

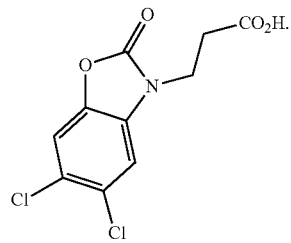 [SMILES: O=C(O)CCn1c(=O)oc2cc(Cl)c(Cl)cc21]

GSK180 is described in U.S. Patent App. No. US20170349577 entitled "3-(6-Alkoxy-5-chlorobenzo[D]isoxazol-3-yl)propanoic acid useful as kynurenine monooxygenase inhibitors," incorporated herein by reference.

A series of kyurenine-3-monooxygenase (KMO) inhibitors are described by GlaxoSmithKline in Walker, A. L. et al. J. Med. Chem. 2017, 60(8):3383-3404, incorporated herein by reference in its entirety. One representative KMO inhibitor described therein is (R)-3-(5-chloro-6-(1-phenylethoxy) benzo[d]isoxazol-3-yl)propanoic acid having the chemical formula:

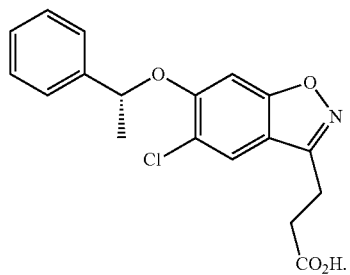 [SMILES: C[C@@H](Oc1cc2onc(CCC(=O)O)c2cc1Cl)c1ccccc1]

CHDI-340246 is a potent and selective inhibitor of kynurenine 3-monooxygenase (KMO) with the chemical formula:

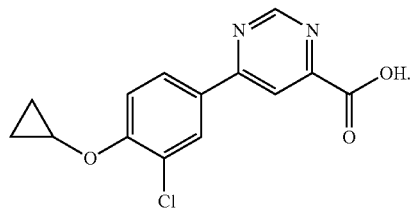 [SMILES: O=C(O)c1cc(-c2ccc(OC3CC3)c(Cl)c2)ncn1]

CHDI-340246 is described in Beaumont, V. et al. "The novel KMO inhibitor CHDI-340246 leads to restoration of electrophysiological alterations in mouse models of Huntington's disease" Exp. Neurol. 2016, 282:99-118, the entirety of which is incorporated herein by reference.

Des-amino FCE 28833 is an inhibitor of kynurenine 3-monooxygenase (KMO) with the chemical formula:

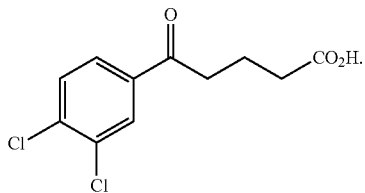 [SMILES: O=C(O)CCCC(=O)c1ccc(Cl)c(Cl)c1]

Des-amino FCE 28833 is described in Speciale, C. et al. "Kynurenic Acid-Enhancing and Anti-ischemic Effects of the Potent Kynurenine 3-Hydroxylase Inhibitor FCE 28833 in Rodents" Adv. Exp. Med. Biol. 1996, 398:221-227, the entirety of which is incorporated herein by reference.

UPF 648 is a kynurenine 3-monooxygenase (KMO) inhibitor with the chemical formula:

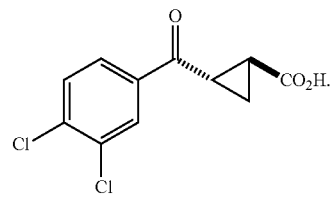

UPF 648 is described in Amori, L. et al. "On the Relationship between the Two Branches of the Kynurenine Pathway in the Rat Brain In Vivo" J. Neurochem. 2009, 109:316-325, the entirety of which is incorporated herein by reference.

Ro-61-8048 is an inhibitor of kynurenine 3-monooxygenase with the chemical formula:

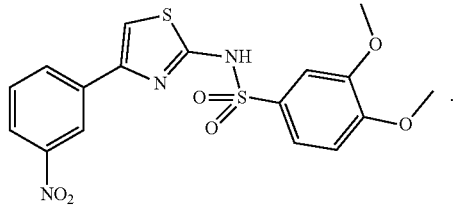 [SMILES: COc1ccc(S(=O)(=O)Nc2nc(-c3cccc([N+](=O)[O-])c3)cs2)cc1OC]

Ro-61-8048 and structurally related KMO inhibitors are described in Rover, S. et al. "Synthesis and Biochemical Evaluation of N-(4-phenylthiazol-2-yl)benzenesulfonamides as High Affinity Inhibitors of Kynurenine 3-Hydroxylase" J. Med. Chem. 1997, 40:4378-4385, the entirety of which is incorporated herein by reference.

Indoleamine 2,3-dioxygenase-1 (IDO1) Inhibitors

In one aspect, a indoleamine 2,3-dioxygenase-1 (IDO1) inhibitor is administered to a subject with an elevated 3-HAA level as determined by the methods described herein. IDO1 inhibitors are known in the art and include, but are not limited to, those described further below.

Indoximod (1-methyl-D-tryptophan) is an orally available small molecule targeting Indoleamine 2,3-dioxygenase-1 (IDO1) having the chemical formula:

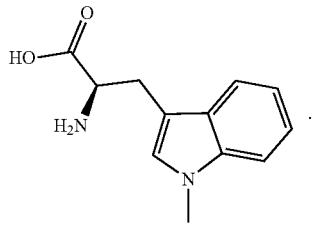 [SMILES: Cn1cc(C[C@@H](N)C(=O)O)c2ccccc21]

The structure of indoximod is found in U.S. Pat. No. 8,232,313 entitled "Pharmaceutical compositions containing 1-methyl-D-tryptophan" and U.S. Pat. No. 9,732,035 entitled "Salts and prodrugs of 1-methyl-d-tryptophan," incorporated herein by reference.

NLG919 (Navoximod), is an orally available inhibitor of indoleamine 2,3-dioxygenase 1 (IDO1) having the chemical formula:

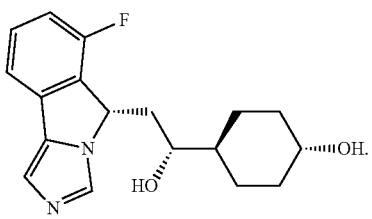 [SMILES: O[C@H](C[C@H]1c2c(F)cccc2-c2cncn21)[C@H]1CC[C@H](O)CC1]

The structure of navoximod is found in U.S. Pat. No. 9,260,434 entitled "Fused imidazole derivatives useful as IDO inhibitors," incorporated herein by reference.

NLG802 (NewLink Genetics Corporation) is an orally available prodrug of indoximod, a small molecule targeting the IDO1 Pathway.

Epacadostat, (1,2,5-Oxadiazole-3-carboximidamide, 4-((2-((Aminosulfonyl)amino) ethyl) amino)-N-(3-bromo-4-fluorophenyl)-N'-hydroxy-, (C(Z))—), is an orally available hydroxyamidine and inhibitor of indoleamine 2,3-dioxygenase (IDO1) with the chemical formula:

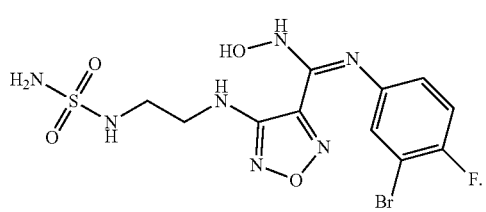 [SMILES: NS(=O)(=O)NCCNc1nonc1/C(=N\c1ccc(F)c(Br)c1)NO]

The structure of Epacadostat is found in U.S. Pat. No. 8,088,803 entitled "1,2,5-Oxadiazoles as inhibitors of indoleamine 2,3,-dioxygenase," incorporated herein by reference.

BMS-986205 (F-001287) is an orally available inhibitor of indoleamine 2,3-dioxygenase (IDO1) with the chemical formula:

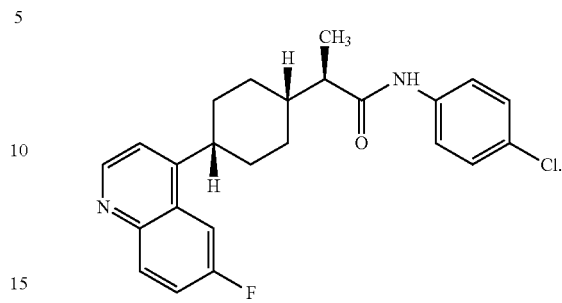

The structure of BMS-986205 is found in U.S. Pat. No. 9,598,422 entitled "Immunoregulatory Agents," incorporated herein by reference.

PF-06840003 is a highly selective orally bioavailable IDO-1 inhibitor with the chemical formula:

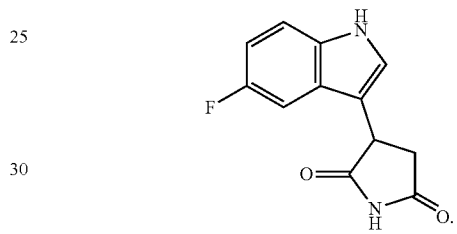

The structure of PF-06840003 is found in U.S. Pat. No. 9,603,836 entitled "Pyrrolidine-2,5-Dione Derivatives, Pharmaceutical Compositions and Methods for use as IDO1 inhibitors," incorporated herein by reference.

Other small molecule inhibitors of indoleamine 2,3-dioxygenase (IDO1), for example the compound of the chemical formula

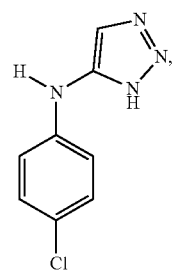

are disclosed in WO2014/081689 (Vertex) entitled "Compounds Useful as Inhibitors of Indoleamine 2,3-dioxygenase (IDO)," incorporated herein by reference.

HTI-1090 (SHR9146) is an orally bioavailable, highly potent, novel small-molecule IDO1/TDO dual inhibitor. HTI-1090 is disclosed in WO2016/169421 entitled "Imidazo Isoindole Derivative, Preparation Method Therefore and Medical Use Thereof," incorporated herein by reference.

Additional dual IDO/TDO inhibitors include IOM2983 (Merck) and related compounds disclosed in US2014/0221354, US20160367564, US20170107178, US20170267668, and WO/2017/189386A1, all incorporated herein by reference.

RG-70099/CRD1152 (Roche/Curadev) is an orally bioavailable small molecule dual indoleamine 2,3-dioxygenase 1 (IDO1) and tryptophan 2,3-dioxygenase (IDO:TDO) inhibitor described in U.S. Pat. No. 9,815,811 entitled "Inhibitors of the kynurenine pathway," incorporated herein by reference.

3-Hydroxyanthranilate-3,4-dioxygenase (3-HAO) Upregulator

In one aspect, a 3-Hydroxyanthranilate-3,4-dioxygenase (3-HAO) upregulator is administered to a subject having a formed aneurysm or at risk for developing an aneurysm. In an alternative embodiment, a 3-HAO upregulator is administered to a subject with an elevated 3-HAA level as determined by the methods described herein. 3-HAO is a non-heme extradiol dioxygenase belonging to the cupin superfamily of proteins and is dependent upon $Fe^{2+}$ for activity. Thus, any agent that increases $Fe^{2+}$ status, for example lipid peroxides or ascorbic acid, will increase the activity of this enzyme. In one embodiment, the 3-HAO upregulator is selected from an iron supplement, ascorbic acid, and a combination thereof.

5-methylpyrazine-2-carboxylic acid-4-oxide (Acipimox)

In one aspect, acipimox is administered to a subject having a formed aneurysm or at risk for developing an aneurysm. In an alternative embodiment, acipimox is administered to a subject with an elevated 3-HAA level as determined by the methods described herein. Acipimox is a niacin derivative and nicotinic acid analog with activity as a hypolipidemic agent having the chemical formula:

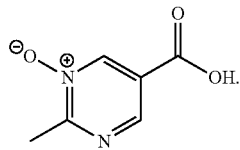

Other Active Agents

In one aspect, provided herein is a method of treating an aneurysm in a subject with an elevated 3-HAA level as determined by the methods described herein comprising administering to the subject a compound selected from fenofibrate, telmisartan, 5-((7-Cl-1H-indol-3-yl)methyl)-3-methylimidazolidine-2,4-dione) (7-Cl—O-Nec-1), a β-blocker, angiotensin converting enzyme inhibitor (ACEI), angiotensin II type I receptor (AGTR1) blocker (ARBs), statin, tetracycline/macrolide, ERK inhibitor, losartan, pravastatin, β-blocker atenolol, the ACEI perindopril, the calcium channel blocker (CCB) verapamil, roxithromycin, ethinyl estradiol, nebivolol, and doxycycline.

In one aspect, provided herein is a method of treating a subject with a formed aneurysm, or who is at risk of developing an aneurysm, comprising administering a KNYU inhibitor, a KMO inhibitor, or acipimox in combination with an additional agent. In one embodiment, the additional agent is selected from fenofibrate, telmisartan, 5-((7-Cl-1H-indol-3-yl)methyl)-3-methylimidazolidine-2,4-dione) (7-Cl—O-Nec-1), a β-blocker, angiotensin converting enzyme inhibitor (ACEI), angiotensin II type I receptor (AGTR1) blocker (ARBs), statin, tetracycline/macrolide, ERK inhibitor, losartan, pravastatin, β-blocker atenolol, the ACEI perindopril, the calcium channel blocker (CCB) verapamil, roxithromycin, ethinyl estradiol, nebivolol, and doxycycline.

Detection of Aneurysms by Assessing Levels of Kyn Pathway Enzymes and/or Metabolites Provided herein are methods for detecting the presence of and/or monitoring the progression of an aneurysm in a subject, for example an abdominal aortic aneurysm (AAA), a thoracic aortic aneurysm (TAA), or a cerebral aneurysm (CA). As described herein, the presence or expansion of an aneurysm in a subject can be determined, for example, by analyzing the level of one or more Kyn Pathway enzymes and/or metabolites in a sample from a subject and comparing the subject's level of one or more Kyn enzymes and/or metabolites to a range of standardized Kyn enzyme and/or metabolite levels derived from subjects without an aneurysm, subjects with an aneurysm, and/or subjects with a dissected aneurysm.

In one aspect of the present invention, provided herein is a method of screening for the presence of an aneurysm in a subject comprising:
 i. determining the level of one or more kynurenine (Kyn) pathway enzymes and/or metabolites present in a sample from the subject; and
 ii. comparing the subject's level of one or more kynurenine (Kyn) pathway enzymes and/or metabolites to a range of standardized levels of Kyn pathway enzymes and/or metabolites derived from individuals:
  a. without an aneurysm ("normal range"), or;
  b. with an aneurysm ("aneurysm range);
 wherein the presence of an aneurysm is suspected if the subject's levels of Kyn pathway enzymes and/or metabolites is either a) greater than the normal range or b) falls within the aneurysm range. In one embodiment, the one or more Kyn pathway enzymes and/or metabolites is selected from kynurenine (KYN), kynurenine acid (KYNA), 3-hydroxykynurenine (3-HK), xanthurenic acid (XA), anthranilic acid (AA), picolinic acid (PIC), quinolinic acid (QUIN), 3-hydroxyanthranilic acid (3-HAA), nicotinic acid (NA), nicotinamide (NAM), N1-methylnicotinamide (mNAM), kynuruenine-3-monooxygenase (KMO), kynurenine aminotransferase (KAT), tryptophan 2,3 dioxygenase (TDO), indoleamine 2,3-dioxygenase (DO), and kynureninase (KYNU), or a combination thereof. In one embodiment, the Kyn pathway enzyme or metabolite is 3-HAA. In one embodiment, the one or more Kyn pathway enzymes and/or metabolites includes at least 3-HAA. In one embodiment, the one or more Kyn pathway enzymes and/or metabolites includes 3-HAA and one or more of KYN, 3-HK, XA, AA, KYNA, PIC, NA, NAM, mNAM, KAT, KMO, IDO, TDO, and QUIN. In one embodiment, the aneurysm is an AAA. In one embodiment, the aneurysm is a TAA. In one embodiment, the aneurysm is a CA. In one embodiment, the sample from the subject is blood, plasma, or serum. In one embodiment, the method further comprises confirming the presence of an aneurysm through the use of a medical imaging technique, for example through for example, but not limited to, chest x-ray, echocardiogram (ECG), transesophageal echocardiogram, CT angiogram (CTA), ultrasound sonograph, magnetic resonance imaging (MRI), computerized tomography (CT), CT angiography, cerebrospinal fluid test, or a cerebral angiogram. In one embodiment, if the subject's level of one or more Kyn pathway enzymes and/or metabolites is greater than the normal range, the subject is administered an effective amount of pharmaceutical composition capable of delaying or inhibiting the progression of the growth of the aneurysm, for example, a compound described herein.

In one embodiment, a Kyn pathway metabolite, for example, kynurenine (KYN), kynurenic acid (KYNA), 3-hydroxykynurenine (3-HK), xanthurenic acid (XA), anthranilic acid (AA), picolinic acid (PIC), quinolinic acid (QUIN), 3-hydroxyanthranilic acid (3-HAA), nicotinic acid (NA), nicotinamide (NAM), or N1-methylnicotinamide (mNAM), is analyzed to determine the presence of an aneurysm. In one embodiment, the metabolite 3-HAA is analyzed, as described herein, to determine the presence of an aneurysm. In one embodiment, the metabolite 3-HAA is analyzed, as described herein, in addition to one or more additional Kyn metabolites selected from kynurenine (KYN), kynurenic acid (KYNA), 3-hydroxykynurenine (3-HK), xanthurenic acid (XA), anthranilic acid (AA), picolinic acid (PIC), quinolinic acid (QUIN), nicotinic acid (NA), nicotinamide (NAM), or N1-methylnicotinamide (mNAM), to determine the presence of an aneurysm. In one embodiment, one or more Kyn pathway metabolites are analyzed to determine the presence of AAA. In one embodiment, one or more Kyn pathway metabolites are analyzed to determine the presence of TAA. In one embodiment, one or more Kyn pathway metabolites are analyzed to determine the presence of CA.

In one embodiment, the Kyn enzyme and/or metabolite is selected from IDO-1, TDO, kynurenine 3-monooxygenase (KMO), kynureninase (KYNU), and 3-HAA, or a combination thereof. In one embodiment, the one or more Kyn enzymes and/or metabolites includes at least 3-HAA. In one embodiment, the Kyn enzyme and/or metabolite is 3-HAA. In one embodiment, the Kyn enzyme and/or metabolite analyzed is 3-HAA and IDO-1. In one embodiment, the Kyn enzyme and/or metabolite analyzed is 3-HAA and TDO. In one embodiment, the Kyn enzyme and/or metabolite analyzed is 3-HAA and KMO. In one embodiment, the Kyn enzyme and/or metabolite analyzed is 3-HAA and KYNU. In one embodiment, the Kyn enzyme and/or metabolite analyzed is 3-HAA, IDO-1, TDO, KMO and KYNU.

Methods to measure expression levels of Kyn pathway enzymes and metabolites are generally known in the art, and generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), liquid chromatography-mass spec (LC-MS), HPLC methods with UV detection or coulometric detection, LC-MS/MS, and flow cytometry, as well as assays based on a property of the enzyme or metabolite including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, Anal. Biochem. 212:457; Schuster et al., 1993, Nature 365:343). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR). Methods for determining the concentration of Kyn metabolites in plasma or serum have previously been described, for example, in Midttun O, Hustad S, Ueland P M., Quantitative profiling of biomarkers related to B-vitamin status, tryptophan metabolism and inflammation in human plasma by liquid chromatography/tandem mass spectrometry. Rapid Commun Mass Spectrom RCM. 2009; 23(9):1371-9 and Huang et al., A simple LC-MS/MS method for determination of kynurenine and tryptophan concentrations in human plasma from HIV-infected patients. Bioanalysis. 2013 June; 5(11): 10.4155/bio.13.74, both incorporated herein in their entirety.

In one embodiment, the Kyn pathway metabolite analyzed is 3-HAA. Direct measurements of 3-HAA can be measured using techniques for measuring 3-HAA concentrations known in the field as described above. For example, the level of 3-HAA in a sample can be measured with various techniques including metabolite isolation, separation, and analysis by chromatographic, electrophoretic, and immunochemical techniques, for example ELISA, Western Blot, and/or PAGE gel. In one embodiment, 3-HAA is measured using an anti-conjugated 3-HAA antibody, for example, a polyclonal antibody against Conjugated 3-HAA (Eagle BioSciences, IS1008). For example, Western blots may be performed as described previously in Wang Q, et al., Activation of NAD(P)H Oxidase by Tryptophan-Derived 3-Hydroxykynurenine Accelerates Endothelial Apoptosis and Dysfunction In Vivo. Circ Res. (2014) 114:480-92.

In one embodiment, 3-HAA concentrations in a sample can be determined by reference to a standard curve consisting of known concentrations of a purified reference protein or metabolite. As contemplated herein, the 3-HAA level in a subject having, or suspected of having, an aneurysm, for example AAA, TAA, or CA, is derived and compared against a standardized 3-HAA level. In one embodiment, the standardized 3-HAA level is derived from a pool of samples, for example human plasma, blood, or serum, that is reflective of a 3-HAA level from a data set of individuals that do not have an aneurysm. In one embodiment, the standardized 3-HAA level represents a range of 3-HAA levels from a data set of individuals that do not have an aneurysm ("normal range"). In one embodiment, the normal range includes a mean. In one embodiment, the subject's 3-HAA level is compared to the mean of the normal range. In one embodiment, an aneurysm is suspected if the subject's 3-HAA level is greater than the normal range.

In one embodiment, an aneurysm, for example an AAA, TAA, or CA, is suspected if the subject's 3-HAA level is greater than about 1.5 times (1.5×) the mean of the normal range. In one embodiment, an aneurysm is suspected if the subject's 3-HAA level is greater than about 1.75× the mean of the normal range. In one embodiment, an aneurysm is suspected if the subject's 3-HAA level is greater than about 2.0× the mean of the normal range. In one embodiment, an aneurysm is suspected if the subject's 3-HAA level is greater than about 2.25× the mean of the normal range. In one embodiment, an aneurysm is suspected if the subject's 3-HAA level is greater than about 2.5× the mean of the normal range.

Alternatively, the standardized 3-HAA level is derived from a pool of samples, for example human plasma, blood, or serum, that is reflective of a 3-HAA level from a data set of individuals having an aneurysm, for example an AAA, TAA, or CA. In one embodiment, the standardized 3-HAA level comprises a range of 3-HAA levels from a data set of individuals that have AAA ("AAA range"), TAA ("TAA range"), or CA ("CA range"). In one embodiment, AAA is suspected if the subject's 3-HAA level falls within the AAA range. In one embodiment, TAA is suspected if the subject's 3-HAA level falls within the TAA range. In one embodiment, CA is suspected if the subject's 3-HAA level falls within the CA range.

In one embodiment, the standardized 3-HAA level comprises a set of ranges of 3-HAA levels, wherein each set is derived from a data set of individuals that have an aneurysm with an arterial diameter of a defined size ("aneurysmal range set"). In one embodiment, the standardized 3-HAA level comprises a set of ranges of 3-HAA levels, wherein each set is derived from a data set of individuals that have an AAA or TAA with an aortal diameter of a defined size, for example less than about 5 cm, from about 5 cm to about 6 cm, greater than about 6 cm, etc. ("AAA or TAA range set"). In one embodiment, the 3-HAA level from the subject having, or suspected of having, AAA or TAA is compared to the AAA or TAA range set, wherein a 3-HAA level that falls within a particular AAA or TAA range set, for example a 3-HAA level corresponding to the AAA or TAA range set of a defined size, for example greater than about 6 cm, is indicative of the presence in the subject of an AAA or TAA having that defined diameter size. In one embodiment, the standardized 3-HAA level comprises a set of ranges of 3-HAA levels, wherein each set is derived from a data set of individuals that have a CA with an arterial diameter of a defined size ("CA range set").

Alternatively, the standardized 3-HAA level is derived from a pool of samples, for example human plasma, that is reflective of a 3-HAA level from a data set of individuals having a dissected aneurysm ("dissected aneurysmal range"). In one embodiment, the standardized 3-HAA level is derived from a pool of samples that is reflective of a 3-HAA level from a data set of individuals having a dissected AAA or TAA ("dissected AAA range"). In one embodiment, the standardized 3-HAA level is derived from a pool of samples that is reflective of a 3-HAA level from a data set of individuals having a dissected CA ("dissected CA range"). In one embodiment, a subject with a 3-HAA level within the dissected AAA or TAA range indicates the presence of an AAA or TAA at risk of dissecting. In one embodiment, a subject with a 3-HAA level within the dissected CA range indicates the presence of a CA at risk of dissecting.

In one aspect of the present invention, provided herein is a method of determining whether an aneurysm in a subject is at risk for dissection comprising determining the level of 3-HAA present in a sample from the subject, and comparing the subject's level of 3-HAA to a range of standardized 3-HAA levels derived from individuals having a dissected aneurysm ("dissected aneurysmal range"), wherein the risk of the aneurysm dissecting is elevated if the subject's one or more 3-HAA levels fall within the dissected aneurysmal range. In one embodiment, the aneurysm is an AAA, TAA, or CA.

In one aspect of the present invention, provided herein is a method of screening for the presence of an aneurysm in a subject comprising:
i. determining the level of 3-HAA present in a sample from the subject; and
ii. comparing the subject's level of 3-HAA to a range of standardized 3-HAA levels derived from individuals without an aneurysm ("normal range");
wherein the presence of an aneurysm is suspected if the subject's 3-HAA level is greater than the normal range. In embodiments, the aneurysm is an AAA. In embodiments, the aneurysm is a TAA. In embodiments, the aneurysm is a CA. In embodiments, an aneurysm is suspected if the subject's 3-HAA level is greater than about 1.5 times (1.5×) the mean of the normal range. In embodiments, an aneurysm is suspected if the subject's 3-HAA level is greater than about 1.75× the mean of the normal range. In embodiments, an aneurysm is suspected if the subject's 3-HAA level is greater than about 2.0× the mean of the normal range. In embodiments, an aneurysm is suspected if the subject's 3-HAA level is greater than about 2.25× the mean of the normal range. In embodiments, an aneurysm is suspected if the subject's 3-HAA level is greater than about 2.5× the mean of the normal range. In embodiments, the method further includes performing a medical imaging technique on the subject if the subject's 3-HAA plasma level is greater than the normal range in order to verify or exclude the presence of an aneurysm. In embodiments, if the subject's 3-HAA level is determined to be greater than the normal range, the subject undergoes a medical intervention, for example, the administration of a compound or composition capable of inhibiting, delaying, or reducing aneurysmal progression or growth or capable of stabilizing the aneurysm, for example a compound described herein. Alternatively, the subject undergoes surgical intervention to repair the aneurysm.

In one aspect of the present invention, provided herein is a method of screening for the presence of an aneurysm in a subject comprising:
i. determining the level of 3-HAA present in a sample from the subject; and
ii. comparing the subject's level of 3-HAA to a range of standardized 3-HAA levels derived from individuals with an aneurysm ("aneurysmal range");
wherein the presence of an aneurysm is suspected if the subject's 3-HAA level falls within the aneurysmal range. In embodiments, the aneurysm is an AAA. In In embodiments, the aneurysm is a TAA. In embodiments, the aneurysm is a CA. In embodiments, the subject's level of 3-HAA is compared to a range of standardized 3-HAA levels derived from individuals with a verified AAA ("AAA range"). In embodiments, the subject's level of 3-HAA is compared to a range of standardized 3-HAA levels derived from individuals with a verified TAA ("TAA range"). In embodiments, the subject's level of 3-HAA is compared to a range of standardized 3-HAA levels derived from individuals with a verified CA ("CA range"). In embodiments, the method further includes performing a medical imaging technique on a subject with a 3-HAA plasma level within the aneurysmal range in order to verify the presence of an aneurysm. In embodiments, if the subject's 3-HAA level is determined to be within the aneurysmal range, the subject undergoes a medical intervention, for example, the administration of a compound or composition capable of inhibiting, delaying, or reducing aneurysmal progression or growth, or capable of stabilizing the aneurysm. Alternatively, the subject undergoes surgical intervention to repair the aneurysm.

In one aspect of the present invention, provided herein is a method of determining whether an aneurysm in a subject is at risk for dissection comprising:
i. determining the level of 3-HAA present in a sample from the subject; and
ii. comparing the subject's level of 3-HAA to a range of standardized 3-HAA levels derived from individuals having a dissected aneurysm ("dissected aneurysmal range");
wherein the risk of the aneurysm dissecting is elevated if the subject's 3-HAA level falls within the dissected aneurysmal range. In embodiments, the aneurysm is an AAA. In embodiments, the aneurysm is a TAA. In embodiments, the aneurysm is a CA. In embodiments, the subject's level of 3-HAA is compared to a range of standardized 3-HAA levels derived from individuals having a dissected AAA ("dissected AAA range"). In embodiments, the subject's level of 3-HAA is compared to a range of standardized 3-HAA levels derived from individuals having a dissected TAA ("dissected TAA range"). In embodiments, the subject's level of 3-HAA is compared to a range of standardized 3-HAA levels derived from individuals having a dissected CA ("dissected CA range"). In embodiments, the method further includes performing a medical imaging technique on a subject with a 3-HAA plasma level within the dissected aneurysmal range in order to verify the presence of an aneurysm. In embodiments, if the subject's 3-HAA level is determined to be within the dissected aneurysmal range, the subject undergoes a medical intervention, for example, the administration of a compound or composition capable of inhibiting, delaying, or reducing aneurysmal progression or growth, or capable of stabilizing the aneurysm. Alternatively, the subject undergoes surgical intervention to repair the aneurysm, for example an open surgical or endovascular aneurysm repair is performed to repair the AAA, TAA, or CA.

In one aspect of the present invention, provided herein is a method of detecting arterial diameter expansion in an aneurysm in a subject comprising:

i. determining a first level of 3-HAA present in a first sample from the subject, wherein the first sample is taken at a first point in time;

ii. determining a second level of 3-HAA present in a second sample from the subject, wherein the second sample is taken at a second point in time, wherein the second point in time is after the first point in time; and, iii. comparing the subject's first level of 3-HAA to the subject's second level of 3-HAA;

wherein arterial diameter expansion of the aneurysm exists if the second level of 3-HAA is greater than the first level of 3-HAA. In embodiments, the aneurysm is an AAA. In embodiments, the aneurysm is a TAA. In embodiments, the aneurysm is a CA. In embodiments, the arterial diameter expansion of an AAA or TAA is an expansion of the diameter of the aorta at the site of the aneurysm ("aortic diameter expansion"). In embodiments, the arterial diameter expansion of a CA is an expansion of the diameter of the anterior communicating artery, posterior communicating artery, anterior cerebral artery, middle cerebral artery, posterior cerebral artery, internal carotid artery, or the tip of the basilar artery at the site of the aneurysm. In embodiments, the method further includes performing a medical imaging technique on a subject with a second level of 3-HAA greater than the first level of 3-HAA in order to verify the presence of arterial diameter expansion in the aneurysm. In embodiments, if the subject's second level of 3-HAA is greater than the first level of 3-HAA, an open surgical or endovascular aneurysm repair is performed to repair the aneurysm. In embodiments, if the subject's second level of 3-HAA is greater than the first level of 3-HAA, the subject undergoes a medical intervention, for example, the administration of a compound or composition capable of inhibiting, delaying, or reducing aneurysmal progression or growth, or capable of stabilizing the aneurysm. Alternatively, the subject undergoes surgical intervention to repair the aneurysm, for example an open surgical or endovascular aneurysm repair is performed to repair the AAA, TAA, or CA.

Figure 17:
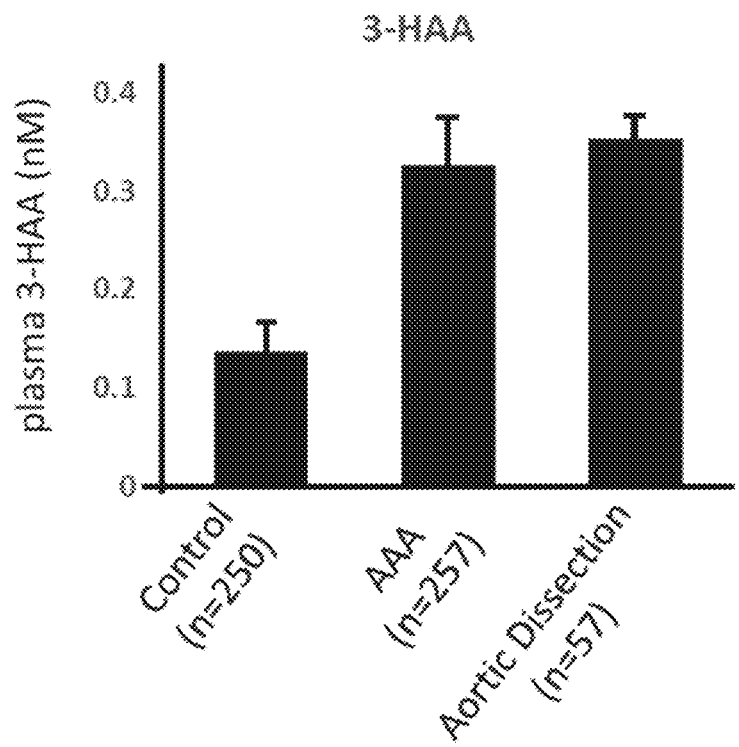
FIG. 17 is a bar graph that shows the association of plasma 3-HAA in patients with AAA (N=257) or aortic dissection (N=57) against a control (N=250). The x-axis shows the analyzed group, and the y-axis shows the micromolar plasma concentration of 3-HAA. Human AAA samples exhibited higher concentrations of plasma 3-HAAA than those in non-AAA patients. The error bars are standard error of the mean.

While the use of varying techniques may result in a range of "normal range," "aneurysmal range," and "dissected aneurysmal range" 3-HAA levels, as provided herein, the sample tested is compared to standardized ranges derived using the same technique, thus accounting for potential differences and sensitivity levels across differing measuring techniques. Additionally, the sample detected may be compared to standardized ranges derived from one type of aneurysm, for example AAA, TAA, or CA, even though there may be overlap between the ranges for different types of aneurysms. Kyn pathway metabolite levels in human populations have been previously described, see for example, Midttun et al., Circulating concentrations of biomarkers and metabolites related to vitamin status, one-carbon and the kynurenine pathways in US, Nordic, Asian, and Australian populations. Am J Clin Nutr 2017; 105:1314-26. For example, as described in the examples below and FIG. 17, the mean normal range of 3-HAA in a plasma sample of 250 subjects as measured by HPLC-LC-MS was about 0.14 µm/L. Comparatively, subjects (n=257) having AAA had a mean 3-HAA plasma level of about 0.32 m/L, while subjects (n=57) with a dissected AAA had a mean 3-HAA plasma level of about 0.36 m/L.

In one embodiment of any of the aspects above, the method further includes determining the level of one or more additional markers selected from a marker related to thrombus remodeling, a marker associated with the extracellular matrix, a proteolytic enzyme, a lipid, and inflammation, or a combination thereof. In one embodiment, the additional marker is selected from ETS domain-containing protein Elk-1 (ELK-1), phosphorylated ELK-1 (p-ELK-1), matrix metalloproteinase-1 (MMP-1), matrix metalloproteinase-2 (MMP-2), matrix metalloproteinase-3 (MMP-3), matrix metalloproteinase-9 (MMP-9), D-dimer, prostatic acid phosphatase (PAP), C-reactive protein (CRP), cystatin C, procollagen III N-terminal propeptide (PIIINP), Tissue plasminogen activator (tPA), Paired related homeobox 1 (PRX-1), TNF-related weak inducer of apoptosis (TWEAK), alpha 1-antitrypsin (a1-AT), P-elastase, osteopontin (OPN), and osteoprotegerin (OPG), carboxyterminal propeptide of type I procollagen (PICP), tenascin-C(TN-C), neutrophil gelatinase-associated lipocalin (NGAL), insulin-like growth factor I (IGF-I) and II (IGF-II), insulin-like growth factor binding protein I (IGFBP-I), cathepsin S, Ficolin-3, or a combination thereof.

Methods of Treatment

A subject determined to have 3-HAA levels indicative of the formation or expansion of an aneurysm, or whose 3-HAA levels indicate a risk for dissection, may further undergo a medical intervention to treat the aneurysm, for example the administration of a suitable compound or composition or a surgical intervention.

Accordingly, provided herein is a method of treating a subject determined to have 3-HAA levels indicative of the formation or expansion of an aneurysm, or whose 3-HAA levels indicate a risk for dissection, comprising administering to the subject a compound or composition capable of inhibiting, delaying, or reducing aneurysmal progression or growth, or capable of stabilizing the aneurysm. Alternatively, the subject is treated for the aneurysm by undergoing a surgical intervention, for example open surgical or endovascular aneurysm repair.

In one embodiment, a method of treating a subject determined to have 3-HAA levels indicative of the formation or expansion of an aneurysm, or whose 3-HAA levels indicate a risk for dissection, is provided comprising administering an effective amount of a KYNU inhibitor as a monotherapy, or in combination with another agent. In one embodiment, the KYNU inhibitor is 2-amino-4-[3'-hydroxyphenyl]-4-hydroxybutanoic acid. In one embodiment, the KYNU inhibitor is dihydro-L-kynurenine. In one embodiment, the KYNU inhibitor is benserazide. In one embodiment, the KYNU inhibitor is OMBA. In one embodiment, the subject is administered a KYNU inhibitor in combination with an IDO1 inhibitor. In one embodiment, the subject is administered a KYNU inhibitor in combination with a TDO2 inhibitor. In one embodiment, the subject is administered a KYNU inhibitor in combination with a dual IDO1/TDO2 inhibitor. In one embodiment, the subject is administered a KYNU inhibitor in combination with a KMO inhibitor. In one embodiment, the subject is administered a KYNU inhibitor in combination with acipimox. In one embodiment, the subject is administered a KYNU inhibitor in combination with fenofibrate. In one embodiment, the subject is administered a KYNU inhibitor in combination with telmisartan. In one embodiment, the subject is administered a KYNU inhibitor in combination with 7-Cl—O-Nec-1. In one embodiment, the subject is administered a KYNU inhibitor in combination with a β-blocker. In one embodiment, the subject is administered a KYNU inhibitor in combination with an angiotensin converting enzyme inhibitor (ACEI). In one embodiment, the subject is administered a KYNU inhibitor in combination with an angiotensin II type 1 receptor (AGTR1) blocker (ARBs). In one embodiment, the subject is administered a KYNU inhibitor in combination with a statin. In one embodiment, the subject is administered a KYNU inhibitor in combination with tetracycline/macrolide. In one embodiment, the subject is administered a KYNU inhibitor in combination with a ERK inhibitor. In one embodiment, the subject is administered a KYNU inhibitor in combination with losartan. In one embodiment, the subject is administered a KYNU inhibitor in combination with pravastatin. In one embodiment, the subject is administered a KYNU inhibitor in combination with atenolol. In one embodiment, the subject is administered a KYNU inhibitor in combination with perindopril. In one embodiment, the subject is administered a KYNU inhibitor in combination with verapamil. In one embodiment, the subject is administered a KYNU inhibitor in combination with roxithromycin. In one embodiment, the subject is administered a KYNU inhibitor in combination with ethinyl estradiol. In one embodiment, the subject is administered a KYNU inhibitor in combination with nebivolol. In one embodiment, the subject is administered a KYNU inhibitor in combination with doxycycline.

In one embodiment, a method of treating a subject determined to have 3-HAA levels indicative of the formation or expansion of an aneurysm, or whose 3-HAA levels indicate a risk for dissection, is provided comprising administering an effective amount of a KMO inhibitor as a monotherapy, or in combination with another agent. In one embodiment, the KMO inhibitor is NBA. In one embodiment, the KMO inhibitor is GSK180. In one embodiment, the KMO inhibitor is (R)-3-(5-chloro-6-(1-phenylethoxy)benzo[d]isoxazol-3-yl)propanoic acid. In one embodiment, the KMO inhibitor is CHDI-340246. In one embodiment, the KMO inhibitor is des-amino FCE 28833. In one embodiment, the KMO inhibitor is UPF 648. In one embodiment, the KMO inhibitor is Ro-61-8048. In one embodiment, the subject is administered a KMO inhibitor in combination with an IDO1 inhibitor. In one embodiment, the subject is administered a KMO inhibitor in combination with a TDO2 inhibitor. In one embodiment, the subject is administered a KMO inhibitor in combination with a dual IDO1/TDO2 inhibitor. In one embodiment, the subject is administered a KMO inhibitor in combination with a KYNU inhibitor. In one embodiment, the subject is administered a KMO inhibitor in combination with acipimox. In one embodiment, the subject is administered a KMO inhibitor in combination with fenofibrate. In one embodiment, the subject is administered a KMO inhibitor in combination with telmisartan. In one embodiment, the subject is administered a KMO inhibitor in combination with 7-Cl—O-Nec-1. In one embodiment, the subject is administered a KMO inhibitor in combination with a β-blocker. In one embodiment, the subject is administered a KMO inhibitor in combination with an angiotensin converting enzyme inhibitor (ACEI). In one embodiment, the subject is administered a KMO inhibitor in combination with an angiotensin II type 1 receptor (AGTR1) blocker (ARBs). In one embodiment, the subject is administered a KMO inhibitor in combination with a statin. In one embodiment, the subject is administered a KMO inhibitor in combination with tetracycline/macrolide. In one embodiment, the subject is administered a KMO inhibitor in combination with a ERK inhibitor. In one embodiment, the subject is administered a KMO inhibitor in combination with losartan. In one embodiment, the subject is administered a KMO inhibitor in combination with pravastatin. In one embodiment, the subject is administered a KMO inhibitor in combination with atenolol. In one embodiment, the subject is administered a KMO inhibitor in combination with perindopril. In one embodiment, the subject is administered a KMO inhibitor in combination with verapamil. In one embodiment, the subject is administered a KMO inhibitor in combination with roxithromycin. In one embodiment, the subject is administered a KMO inhibitor in combination with ethinyl estradiol. In one embodiment, the subject is administered a KMO inhibitor in combination with nebivolol. In one embodiment, the subject is administered a KMO inhibitor in combination with doxycycline.

In one embodiment, a method of treating a subject determined to have 3-HAA levels indicative of the formation or expansion of an aneurysm, or whose 3-HAA levels indicate a risk for dissection, is provided comprising administering an effective amount of an IDO1 inhibitor, a TDO2 inhibitor, a dual IDO1/TDO2 inhibitor, or a combination thereof either as monotherapy or in combination with another agent. In one embodiment, the IDO1 inhibitor is indoximod. In one embodiment, the IDO1 inhibitor is navoximod. In one embodiment, the IDO1 inhibitor is NLG802. In one embodiment, the IDO1 inhibitor is epacadostat. In one embodiment, the IDO1 inhibitor is BMS-986205. In one embodiment, the IDO1 inhibitor is PF-0684003. In one embodiment, the dual IDO1/TDO2 inhibitor is HTI-1090. In one embodiment, the dual IDO1/TDO2 inhibitor is RG-70099. In one embodiment, the IDO1 inhibitor is necrostatin-1. In one embodiment, the subject is administered an IDO1 inhibitor, a TDO2 inhibitor, a dual IDO1/TDO2 inhibitor, or a combination thereof in combination with a KMO inhibitor In one embodiment, the subject is administered an IDO1 inhibitor, a TDO2 inhibitor, a dual IDO1/TDO2 inhibitor, or a combination thereof in combination with a KYNU inhibitor. In one embodiment, the subject is administered an IDO1 inhibitor, a TDO2 inhibitor, a dual IDO1/TDO2 inhibitor, or a combination thereof in combination with acipimox. In one embodiment, the subject is administered an IDO1 inhibitor, a TDO2 inhibitor, a dual IDO1/TDO2 inhibitor, or a combination thereof in combination with fenofibrate. In one embodiment, the subject is administered an IDO1 inhibitor, a TDO2 inhibitor, a dual IDO1/TDO2 inhibitor, or a combination thereof in combination with telmisartan. In one embodiment, the subject is administered an IDO1 inhibitor, a TDO2 inhibitor, a dual IDO1/TDO2 inhibitor, or a combination thereof in combination with 7-Cl—O-Nec-1. In one embodiment, the subject is administered an IDO1 inhibitor, a TDO2 inhibitor, a dual IDO1/TDO2 inhibitor, or a combination thereof in combination with a β-blocker. In one embodiment, the subject is administered an IDO1 inhibitor, a TDO2 inhibitor, a dual IDO1/TDO2 inhibitor, or a combination thereof in combination with an angiotensin converting enzyme inhibitor (ACEI). In one embodiment, the subject is administered an IDO1 inhibitor, a TDO2 inhibitor, a dual IDO1/TDO2 inhibitor, or a combination thereof in combination with an angiotensin II type 1 receptor (AGTR1) blocker (ARBs). In one embodiment, the subject is administered an IDO1 inhibitor, a TDO2 inhibitor, a dual IDO1/TDO2 inhibitor, or a combination thereof in combination with a statin. In one embodiment, the subject is administered an IDO1 inhibitor, a TDO2 inhibitor, a dual IDO1/TDO2 inhibitor, or a combination thereof in combination with tetracycline/macrolide. In one embodiment, the subject is administered an IDO1 inhibitor, a TDO2 inhibitor, a dual IDO1/TDO2 inhibitor, or a combination thereof in combination with a ERK inhibitor. In one embodiment, the subject is administered an IDO1 inhibitor, a TDO2 inhibitor, a dual IDO1/TDO2 inhibitor, or a combination thereof in combination with losartan. In one embodiment, the subject is administered an IDO1 inhibitor, a TDO2 inhibitor, a dual IDO1/TDO2 inhibitor, or a combination thereof in combination with pravastatin. In one embodiment, the subject is administered an IDO1 inhibitor, a TDO2 inhibitor, a dual IDO1/TDO2 inhibitor, or a combination thereof in combination with atenolol. In one embodiment, the subject is administered an IDO1 inhibitor, a TDO2 inhibitor, a dual IDO1/TDO2 inhibitor, or a combination thereof in combination with perindopril. In one embodiment, the subject is administered an IDO1 inhibitor, a TDO2 inhibitor, a dual IDO1/TDO2 inhibitor, or a combination thereof in combination with verapamil. In one embodiment, the subject is administered an IDO1 inhibitor, a TDO2 inhibitor, a dual IDO1/TDO2 inhibitor, or a combination thereof in combination with roxithromycin. In one embodiment, the subject is administered an IDO1 inhibitor, a TDO2 inhibitor, a dual IDO1/TDO2 inhibitor, or a combination thereof in combination with ethinyl estradiol. In one embodiment, the subject is administered an IDO1 inhibitor, a TDO2 inhibitor, a dual IDO1/TDO2 inhibitor, or a combination thereof in combination with nebivolol. In one embodiment, the subject is administered an IDO1 inhibitor, a TDO2 inhibitor, a dual IDO1/TDO2 inhibitor, or a combination thereof in combination with doxycycline.

In one embodiment, a method of treating a subject determined to have 3-HAA levels indicative of the formation or expansion of an aneurysm, or whose 3-HAA levels indicate a risk for dissection, is provided comprising administering an effective amount of acipimox as a monotherapy, or in combination with another agent. In one embodiment, the subject is administered acipimox in combination with a KMO inhibitor. In one embodiment, the subject is administered acipimox in combination with an IDO1 inhibitor. In one embodiment, the subject is administered acipimox in combination with a TDO2 inhibitor. In one embodiment, the subject is administered acipimox in combination with a dual IDO1/TDO2 inhibitor. In one embodiment, the subject is administered acipimox in combination with a KYNU inhibitor. In one embodiment, the subject is administered acipimox in combination with acipimox. In one embodiment, the subject is administered acipimox in combination with fenofibrate. In one embodiment, the subject is administered acipimox in combination with telmisartan. In one embodiment, the subject is administered acipimox in combination with 7-Cl—O-Nec-1. In one embodiment, the subject is administered acipimox in combination with a β-blocker. In one embodiment, the subject is administered acipimox in combination with an angiotensin converting enzyme inhibitor (ACEI). In one embodiment, the subject is administered acipimox in combination with an angiotensin II type 1 receptor (AGTR1) blocker (ARBs). In one embodiment, the subject is administered acipimox in combination with a statin. In one embodiment, the subject is administered acipimox in combination with tetracycline/macrolide. In one embodiment, the subject is administered acipimox in combination with a ERK inhibitor. In one embodiment, the subject is administered acipimox in combination with losartan. In one embodiment, the subject is administered acipimox in combination with pravastatin. In one embodiment, the subject is administered acipimox in combination with atenolol. In one embodiment, the subject is acipimox in combination with perindopril. In one embodiment, the subject is administered acipimox in combination with verapamil. In one embodiment, the subject is administered acipimox in combination with roxithromycin. In one embodiment, the subject is administered acipimox in combination with ethinyl estradiol. In one embodiment, the subject is administered acipimox in combination with nebivolol. In one embodiment, the subject is administered acipimox in combination with doxycycline.

In one embodiment, a method of treating a subject determined to have 3-HAA levels indicative of the formation or expansion of an aneurysm, or whose 3-HAA levels indicate a risk for dissection, is provided comprising administering an effective amount of fenofibrate. In one embodiment, a method of treating a subject determined to have 3-HAA levels indicative of the formation or expansion of an aneurysm, or whose 3-HAA levels indicate a risk for dissection, is provided comprising administering an effective amount of telmisartan. In one embodiment, a method of treating a subject determined to have 3-HAA levels indicative of the formation or expansion of an aneurysm, or whose 3-HAA levels indicate a risk for dissection, is provided comprising administering an effective amount of 7-Cl—O-Nec-1. In one embodiment, a method of treating a subject determined to have 3-HAA levels indicative of the formation or expansion of an aneurysm, or whose 3-HAA levels indicate a risk for dissection, is provided comprising administering an effective amount of a β-blocker. In one embodiment, a method of treating a subject determined to have 3-HAA levels indicative of the formation or expansion of an aneurysm, or whose 3-HAA levels indicate a risk for dissection, is provided comprising administering an effective amount of an angiotensin converting enzyme inhibitor (ACEI). In one embodiment, a method of treating a subject determined to have 3-HAA levels indicative of the formation or expansion of an aneurysm, or whose 3-HAA levels indicate a risk for dissection, is provided comprising administering an effective amount of an angiotensin II type 1 receptor (AGTR1) blocker (ARBs). In one embodiment, a method of treating a subject determined to have 3-HAA levels indicative of the formation or expansion of an aneurysm, or whose 3-HAA levels indicate a risk for dissection, is provided comprising administering an effective amount of a statin. In one embodiment, a method of treating a subject determined to have 3-HAA levels indicative of the formation or expansion of an aneurysm, or whose 3-HAA levels indicate a risk for dissection, is provided comprising administering an effective amount of tetracycline/macrolide In one embodiment, a method of treating a subject determined to have 3-HAA levels indicative of the formation or expansion of an aneurysm, or whose 3-HAA levels indicate a risk for dissection, is provided comprising administering an effective amount of a ERK inhibitor. In one embodiment, a method of treating a subject determined to have 3-HAA levels indicative of the formation or expansion of an aneurysm, or whose 3-HAA levels indicate a risk for dissection, is provided comprising administering an effective amount of losartan. In one embodiment, a method of treating a subject determined to have 3-HAA levels indicative of the formation or expansion of an aneurysm, or whose 3-HAA levels indicate a risk for dissection, is provided comprising administering an effective amount of pravastatin In one embodiment, a method of treating a subject determined to have 3-HAA levels indicative of the formation or expansion of an aneurysm, or whose 3-HAA levels indicate a risk for dissection, is provided comprising administering an effective amount of atenolol In one embodiment, a method of treating a subject determined to have 3-HAA levels indicative of the formation or expansion of an aneurysm, or whose 3-HAA levels indicate a risk for dissection, is provided comprising administering an effective amount of perindopril. In one embodiment, a method of treating a subject determined to have 3-HAA levels indicative of the formation or expansion of an aneurysm, or whose 3-HAA levels indicate a risk for dissection, is provided comprising administering an effective amount of verapamil In one embodiment, a method of treating a subject determined to have 3-HAA levels indicative of the formation or expansion of an aneurysm, or whose 3-HAA levels indicate a risk for dissection, is provided comprising administering an effective amount of roxithromycin. In one embodiment, a method of treating a subject determined to have 3-HAA levels indicative of the formation or expansion of an aneurysm, or whose 3-HAA levels indicate a risk for dissection, is provided comprising administering an effective amount of ethinyl estradiol. In one embodiment, a method of treating a subject determined to have 3-HAA levels indicative of the formation or expansion of an aneurysm, or whose 3-HAA levels indicate a risk for dissection, is provided comprising administering an effective amount of nebivolol. In one embodiment, a method of treating a subject determined to have 3-HAA levels indicative of the formation or expansion of an aneurysm, or whose 3-HAA levels indicate a risk for dissection, is provided comprising administering an effective amount of doxycycline.

Further provided herein is a method of treating a subject having a formed aneurysm comprising administering to the subject an effective amount of a compound described herein.

In one embodiment, a method of treating a subject having a formed aneurysm is provided comprising administering to the subject an effective amount of a KYNU inhibitor. In one embodiment, the KYNU inhibitor is 2-amino-4-[3'-hydroxyphenyl]-4-hydroxybutanoic acid. In one embodiment, the KYNU inhibitor is dihydro-L-kynurenine. In one embodiment, the KYNU inhibitor is benserazide. In one embodiment, the KYNU inhibitor is OMBA. In one embodiment, the subject is administered a KYNU inhibitor in combination with an IDO1 inhibitor. In one embodiment, the subject is administered a KYNU inhibitor in combination with a TDO2 inhibitor. In one embodiment, the subject is administered a KYNU inhibitor in combination with a dual IDO1/TDO2 inhibitor. In one embodiment, the subject is administered a KYNU inhibitor in combination with a KMO inhibitor. In one embodiment, the subject is administered a KYNU inhibitor in combination with acipimox. In one embodiment, the subject is administered a KYNU inhibitor in combination with fenofibrate. In one embodiment, the subject is administered a KYNU inhibitor in combination with telmisartan. In one embodiment, the subject is administered a KYNU inhibitor in combination with 7-Cl—O—Nec-1. In one embodiment, the subject is administered a KYNU inhibitor in combination with a β-blocker. In one embodiment, the subject is administered a KYNU inhibitor in combination with an angiotensin converting enzyme inhibitor (ACEI). In one embodiment, the subject is administered a KYNU inhibitor in combination with an angiotensin II type 1 receptor (AGTR1) blocker (ARBs). In one embodiment, the subject is administered a KYNU inhibitor in combination with a statin. In one embodiment, the subject is administered a KYNU inhibitor in combination with tetracycline/macrolide. In one embodiment, the subject is administered a KYNU inhibitor in combination with a ERK inhibitor. In one embodiment, the subject is administered a KYNU inhibitor in combination with losartan. In one embodiment, the subject is administered a KYNU inhibitor in combination with pravastatin. In one embodiment, the subject is administered a KYNU inhibitor in combination with atenolol. In one embodiment, the subject is administered a KYNU inhibitor in combination with perindopril. In one embodiment, the subject is administered a KYNU inhibitor in combination with verapamil. In one embodiment, the subject is administered a KYNU inhibitor in combination with roxithromycin. In one embodiment, the subject is administered a KYNU inhibitor in combination with ethinyl estradiol. In one embodiment, the subject is administered a KYNU inhibitor in combination with nebivolol. In one embodiment, the subject is administered a KYNU inhibitor in combination with doxycycline. In some embodiments, the aneurysm is an AAA. In some embodiments, the aneurysm is a TAA. In some embodiments, the aneurysm is a CA. In some embodiments, the subject is at risk for developing a dissected aneurysm, for example a dissected AAA, dissected TAA, or dissected CA. In some embodiments, the subject has an AAA or TAA with an aortic diameter of less than or equal to about 3 cm. In some embodiments, the subject has an AAA or TAA with an aortic diameter of less than or equal to about 5 cm. In some embodiments, the subject has an AAA or TAA with an aortic diameter of greater than or equal to about 5 cm. In some embodiments, the subject has an AAA or TAA with an aortic diameter of greater than or equal to about 7 cm. In some embodiments, the subject has a CA with an arterial diameter of less than or equal to about 5 mm. In some embodiments, the subject has a CA with an arterial diameter of greater than or equal to about 5 mm. In some embodiments, the subject has a CA with an arterial diameter of greater than or equal to about 10 mm. In some embodiments, the subject has a CA with an arterial diameter of greater than or equal to about 25 mm.

In one embodiment, a method of treating a subject having a formed aneurysm is provided comprising administering to the subject an effective amount of a KMO inhibitor. In one embodiment, the KMO inhibitor is NBA. In one embodiment, the KMO inhibitor is GSK180. In one embodiment, the KMO inhibitor is (R)-3-(5-chloro-6-(1-phenylethoxy)benzo[d]isoxazol-3-yl)propanoic acid. In one embodiment, the KMO inhibitor is CHDI-340246. In one embodiment, the KMO inhibitor is des-amino FCE 28833. In one embodiment, the KMO inhibitor is UPF 648. In one embodiment, the KMO inhibitor is Ro-61-8048. In one embodiment, the subject is administered a KMO inhibitor in combination with an IDO1 inhibitor. In one embodiment, the subject is administered a KMO inhibitor in combination with a TDO2 inhibitor. In one embodiment, the subject is administered a KMO inhibitor in combination with a dual IDO1/TDO2 inhibitor. In one embodiment, the subject is administered a KMO inhibitor in combination with a KYNU inhibitor. In one embodiment, the subject is administered a KMO inhibitor in combination with acipimox. In one embodiment, the subject is administered a KMO inhibitor in combination with fenofibrate. In one embodiment, the subject is administered a KMO inhibitor in combination with telmisartan. In one embodiment, the subject is administered a KMO inhibitor in combination with 7-Cl—O-Nec-1. In one embodiment, the subject is administered a KMO inhibitor in combination with a β-blocker. In one embodiment, the subject is administered a KMO inhibitor in combination with an angiotensin converting enzyme inhibitor (ACEI). In one embodiment, the subject is administered a KMO inhibitor in combination with an angiotensin II type 1 receptor (AGTR1) blocker (ARBs). In one embodiment, the subject is administered a KMO inhibitor in combination with a statin. In one embodiment, the subject is administered a KMO inhibitor in combination with tetracycline/macrolide. In one embodiment, the subject is administered a KMO inhibitor in combination with a ERK inhibitor. In one embodiment, the subject is administered a KMO inhibitor in combination with losartan. In one embodiment, the subject is administered a KMO inhibitor in combination with pravastatin. In one embodiment, the subject is administered a KMO inhibitor in combination with atenolol. In one embodiment, the subject is administered a KMO inhibitor in combination with perindopril. In one embodiment, the subject is administered a KMO inhibitor in combination with verapamil. In one embodiment, the subject is administered a KMO inhibitor in combination with roxithromycin. In one embodiment, the subject is administered a KMO inhibitor in combination with ethinyl estradiol. In one embodiment, the subject is administered a KMO inhibitor in combination with nebivolol. In one embodiment, the subject is administered a KMO inhibitor in combination with doxycycline. In some embodiments, the aneurysm is an AAA. In some embodiments, the aneurysm is a TAA. In some embodiments, the aneurysm is a CA. In some embodiments, the subject is at risk for developing a dissected aneurysm, for example a dissected AAA, dissected TAA, or dissected CA. In some embodiments, the subject has an AAA or TAA with an aortic diameter of less than or equal to about 3 cm. In some embodiments, the subject has an AAA or TAA with an aortic diameter of less than or equal to about 5 cm. In some embodiments, the subject has an AAA or TAA with an aortic diameter of greater than or equal to about 5 cm. In some embodiments, the subject has an AAA or TAA with an aortic diameter of greater than or equal to about 7 cm. In some embodiments, the subject has a CA with an arterial diameter of less than or equal to about 5 mm. In some embodiments, the subject has a CA with an arterial diameter of greater than or equal to about 5 mm. In some embodiments, the subject has a CA with an arterial diameter of greater than or equal to about 10 mm. In some embodiments, the subject has a CA with an arterial diameter of greater than or equal to about 25 mm.

In an alternative embodiment, a method of treating a subject having a formed aneurysm is provided comprising administering an effective amount of an IDO1 inhibitor, a TDO2 inhibitor, a dual IDO1/TDO2 inhibitor, or a combination thereof either as monotherapy or in combination with another agent. In one embodiment, the IDO1 inhibitor is indoximod. In one embodiment, the IDO11 inhibitor is navoximod. In one embodiment, the IDO1 inhibitor is NLG802. In one embodiment, the IDO1 inhibitor is epacadostat. In one embodiment, the IDO1 inhibitor is BMS-986205. In one embodiment, the IDO1 inhibitor is PF-0684003. In one embodiment, the dual IDO1/TDO2 inhibitor is HTI-1090. In one embodiment, the dual IDO1/TDO2 inhibitor is RG-70099. In one embodiment, the IDO1 inhibitor is necrostatin-1. In one embodiment, the subject is administered an IDO1 inhibitor is not necrostatin-1. In one embodiment, the subject is administered an IDO1 inhibitor, a TDO2 inhibitor, a dual IDO1/TDO2 inhibitor, or a combination thereof in combination with a KMO inhibitor In one embodiment, the subject is administered an IDO1 inhibitor, a TDO2 inhibitor, a dual IDO1/TDO2 inhibitor, or a combination thereof in combination with a KYNU inhibitor. In one embodiment, the subject is administered an IDO1 inhibitor, a TDO2 inhibitor, a dual IDO1/TDO2 inhibitor, or a combination thereof in combination with acipimox. In one embodiment, the subject is administered an IDO1 inhibitor, a TDO2 inhibitor, a dual IDO1/TDO2 inhibitor, or a combination thereof in combination with fenofibrate. In one embodiment, the subject is administered an IDO1 inhibitor, a TDO2 inhibitor, a dual IDO1/TDO2 inhibitor, or a combination thereof in combination with telmisartan. In one embodiment, the subject is administered an IDO1 inhibitor, a TDO2 inhibitor, a dual IDO1/TDO2 inhibitor, or a combination thereof in combination with 7-Cl—O-Nec-1. In one embodiment, the subject is administered an IDO1 inhibitor, a TDO2 inhibitor, a dual IDO1/TDO2 inhibitor, or a combination thereof in combination with a β-blocker. In one embodiment, the subject is administered an IDO1 inhibitor, a TDO2 inhibitor, a dual IDO1/TDO2 inhibitor, or a combination thereof in combination with an angiotensin converting enzyme inhibitor (ACEI). In one embodiment, the subject is administered an IDO1 inhibitor, a TDO2 inhibitor, a dual IDO1/TDO2 inhibitor, or a combination thereof in combination with an angiotensin II type 1 receptor (AGTR1) blocker (ARBs). In one embodiment, the subject is administered an IDO1 inhibitor, a TDO2 inhibitor, a dual IDO1/TDO2 inhibitor, or a combination thereof in combination with a statin. In one embodiment, the subject is administered an IDO1 inhibitor, a TDO2 inhibitor, a dual IDO1/TDO2 inhibitor, or a combination thereof in combination with tetracycline/macrolide. In one embodiment, the subject is administered an IDO1 inhibitor, a TDO2 inhibitor, a dual IDO1/TDO2 inhibitor, or a combination thereof in combination with a ERK inhibitor. In one embodiment, the subject is administered an IDO1 inhibitor, a TDO2 inhibitor, a dual IDO1/TDO2 inhibitor, or a combination thereof in combination with losartan. In one embodiment, the subject is administered an IDO1 inhibitor, a TDO2 inhibitor, a dual IDO1/TDO2 inhibitor, or a combination thereof in combination with pravastatin. In one embodiment, the subject is administered an IDO1 inhibitor, a TDO2 inhibitor, a dual IDO1/TDO2 inhibitor, or a combination thereof in combination with atenolol. In one embodiment, the subject is administered an IDO1 inhibitor, a TDO2 inhibitor, a dual IDO1/TDO2 inhibitor, or a combination thereof in combination with perindopril. In one embodiment, the subject is administered an IDO1 inhibitor, a TDO2 inhibitor, a dual IDO1/TDO2 inhibitor, or a combination thereof in combination with verapamil. In one embodiment, the subject is administered an IDO1 inhibitor, a TDO2 inhibitor, a dual IDO1/TDO2 inhibitor, or a combination thereof in combination with roxithromycin. In one embodiment, the subject is administered an IDO1 inhibitor, a TDO2 inhibitor, a dual IDO1/TDO2 inhibitor, or a combination thereof in combination with ethinyl estradiol. In one embodiment, the subject is administered an IDO1 inhibitor, a TDO2 inhibitor, a dual IDO1/TDO2 inhibitor, or a combination thereof in combination with nebivolol. In one embodiment, the subject is administered an IDO1 inhibitor, a TDO2 inhibitor, a dual IDO1/TDO2 inhibitor, or a combination thereof in combination with doxycycline.

In one embodiment, a method of treating a subject having a formed aneurysm is provided comprising administering to the subject an effective amount of acipimox. In one embodiment, the subject is administered acipimox in combination with a KMO inhibitor. In one embodiment, the subject is administered acipimox in combination with an IDO1 inhibitor. In one embodiment, the subject is administered acipimox in combination with a TDO2 inhibitor. In one embodiment, the subject is administered acipimox in combination with a dual IDO1/TDO2 inhibitor. In one embodiment, the subject is administered acipimox in combination with a KYNU inhibitor. In one embodiment, the subject is administered acipimox in combination with acipimox. In one embodiment, the subject is administered acipimox in combination with fenofibrate. In one embodiment, the subject is administered acipimox in combination with telmisartan. In one embodiment, the subject is administered acipimox in combination with 7-Cl—O-Nec-1. In one embodiment, the subject is administered acipimox in combination with a β-blocker. In one embodiment, the subject is administered acipimox in combination with an angiotensin converting enzyme inhibitor (ACEI). In one embodiment, the subject is administered acipimox in combination with an angiotensin II type 1 receptor (AGTR1) blocker (ARBs). In one embodiment, the subject is administered acipimox in combination with a statin. In one embodiment, the subject is administered acipimox in combination with tetracycline/macrolide. In one embodiment, the subject is administered acipimox in combination with a ERK inhibitor. In one embodiment, the subject is administered acipimox in combination with losartan. In one embodiment, the subject is administered acipimox in combination with pravastatin. In one embodiment, the subject is administered acipimox in combination with atenolol. In one embodiment, the subject is acipimox in combination with perindopril. In one embodiment, the subject is administered acipimox in combination with verapamil. In one embodiment, the subject is administered acipimox in combination with roxithromycin. In one embodiment, the subject is administered acipimox in combination with ethinyl estradiol. In one embodiment, the subject is administered acipimox in combination with nebivolol. In one embodiment, the subject is administered acipimox in combination with doxycycline. In some embodiments, the aneurysm is an AAA. In some embodiments, the aneurysm is a TAA. In some embodiments, the aneurysm is a CA. In some embodiments, the subject is at risk for developing a dissected aneurysm, for example a dissected AAA, dissected TAA, or dissected CA. In some embodiments, the subject has an AAA or TAA with an aortic diameter of less than or equal to about 3 cm. In some embodiments, the subject has an AAA or TAA with an aortic diameter of less than or equal to about 5 cm. In some embodiments, the subject has an AAA or TAA with an aortic diameter of greater than or equal to about 5 cm. In some embodiments, the subject has an AAA or TAA with an aortic diameter of greater than or equal to about 7 cm. In some embodiments, the subject has a CA with an arterial diameter of less than or equal to about 5 mm. In some embodiments, the subject has a CA with an arterial diameter of greater than or equal to about 5 mm. In some embodiments, the subject has a CA with an arterial diameter of greater than or equal to about 10 mm. In some embodiments, the subject has a CA with an arterial diameter of greater than or equal to about 25 mm.

In some embodiments, provided herein is a method of prophylactically inhibiting the formation of an aneurysm in a subject predisposed to the development of an aneurysm by administering to the subject a compound described herein.

In one embodiment, a method for the prophylactic inhibition of the formation of an aneurysm in a subject predisposed to the development of an aneurysm is provided comprising administering an effective amount of a KYNU inhibitor. In one embodiment, the KYNU inhibitor is 2-amino-4-[3'-hydroxyphenyl]-4-hydroxybutanoic acid. In one embodiment, the KYNU inhibitor is dihydro-L-kynurenine. In one embodiment, the KYNU inhibitor is benserazide. In one embodiment, the KYNU inhibitor is OMBA. In one embodiment, the subject is administered a KYNU inhibitor in combination with an IDO1 inhibitor. In one embodiment, the subject is administered a KYNU inhibitor in combination with a TDO2 inhibitor. In one embodiment, the subject is administered a KYNU inhibitor in combination with a dual IDO1/TDO2 inhibitor. In one embodiment, the subject is administered a KYNU inhibitor in combination with a KMO inhibitor. In one embodiment, the subject is administered a KYNU inhibitor in combination with acipimox. In one embodiment, the subject is administered a KYNU inhibitor in combination with fenofibrate. In one embodiment, the subject is administered a KYNU inhibitor in combination with telmisartan. In one embodiment, the subject is administered a KYNU inhibitor in combination with 7-Cl—O-Nec-1. In one embodiment, the subject is administered a KYNU inhibitor in combination with a β-blocker. In one embodiment, the subject is administered a KYNU inhibitor in combination with an angiotensin converting enzyme inhibitor (ACEI). In one embodiment, the subject is administered a KYNU inhibitor in combination with an angiotensin II type 1 receptor (AGTR1) blocker (ARBs). In one embodiment, the subject is administered a KYNU inhibitor in combination with a statin. In one embodiment, the subject is administered a KYNU inhibitor in combination with tetracycline/macrolide. In one embodiment, the subject is administered a KYNU inhibitor in combination with a ERK inhibitor. In one embodiment, the subject is administered a KYNU inhibitor in combination with losartan. In one embodiment, the subject is administered a KYNU inhibitor in combination with pravastatin. In one embodiment, the subject is administered a KYNU inhibitor in combination with atenolol. In one embodiment, the subject is administered a KYNU inhibitor in combination with perindopril. In one embodiment, the subject is administered a KYNU inhibitor in combination with verapamil. In one embodiment, the subject is administered a KYNU inhibitor in combination with roxithromycin. In one embodiment, the subject is administered a KYNU inhibitor in combination with ethinyl estradiol. In one embodiment, the subject is administered a KYNU inhibitor in combination with nebivolol. In one embodiment, the subject is administered a KYNU inhibitor in combination with doxycycline. In one embodiment, the subject is predisposed to development of AAA. In one embodiment, the subject is predisposed to development of TAA. In one embodiment, the subject is predisposed to development of CA. In one embodiment, the genetic disorder is Marfan syndrome, or a disorder related to Marfan syndrome. In one embodiment, the disorder is Loeys-Dietz syndrome. In one embodiment, the disorder is aneurysms-osteoarthritis syndrome. In one embodiment, the disorder is Ehlers-Danlos syndrome. In one embodiment, the disorder is vascular Ehlers-Danlos syndrome. In one embodiment, the disorder is familial thoracic aortic aneurysm/dissection. In one embodiment, the disorder is Shprintzen-Goldberg syndrome. In one embodiment, the disorder is cutis laxa syndrome. In one embodiment, the disorder is aortic valve disease. In one embodiment, the disorder is arterial tortuosity syndrome. In one embodiment, the disorder is X-linked Alport syndrome. In one embodiment, the disorder is Turner syndrome. In one embodiment, the disorder is Mitral valve, myopia, Aorta, Skin and Skeletal (MASS) syndrome. In one embodiment, the disorder is Beals syndrome. In one embodiment, the disorder is Bicuspid Aortic Valve syndrome. In one embodiment, the disorder is a congenital heart malformation. In one embodiment, the disorder is a mutation in the gene COL1A1. In one embodiment, the disorder is a mutation in the gene COL1A2. In one embodiment, the disorder is a mutation in the gene MED12. In one embodiment, the disorder is a mutation in the gene, SMAD4. In one embodiment, the disorder is a mutation in the gene PLOD3. In one embodiment, the disorder is a mutation in the gene ENG. In one embodiment, the disorder is a mutation in the gene ACVRL1. In one embodiment, the disorder is a mutation in the gene NF1.

In one embodiment, a method for the prophylactic inhibition of the formation of an aneurysm in a subject predisposed to the development of an aneurysm is provided comprising administering an effective amount of a KMO inhibitor. In one embodiment, the KMO inhibitor is NBA. In one embodiment, the KMO inhibitor is GSK180. In one embodiment, the KMO inhibitor is (R)-3-(5-chloro-6-(1-phenylethoxy)benzo[d]isoxazol-3-yl)propanoic acid. In one embodiment, the KMO inhibitor is CHDI-340246. In one embodiment, the KMO inhibitor is des-amino FCE 28833. In one embodiment, the KMO inhibitor is UPF 648. In one embodiment, the KMO inhibitor is Ro-61-8048. In one embodiment, the subject is administered a KMO inhibitor in combination with an IDO1 inhibitor. In one embodiment, the subject is administered a KMO inhibitor in combination with a TDO2 inhibitor. In one embodiment, the subject is administered a KMO inhibitor in combination with a dual IDO1/TDO2 inhibitor. In one embodiment, the subject is administered a KMO inhibitor in combination with a KYNU inhibitor. In one embodiment, the subject is administered a KMO inhibitor in combination with acipimox. In one embodiment, the subject is administered a KMO inhibitor in combination with fenofibrate. In one embodiment, the subject is administered a KMO inhibitor in combination with telmisartan. In one embodiment, the subject is administered a KMO inhibitor in combination with 7-Cl—O-Nec-1. In one embodiment, the subject is administered a KMO inhibitor in combination with a β-blocker. In one embodiment, the subject is administered a KMO inhibitor in combination with an angiotensin converting enzyme inhibitor (ACEI). In one embodiment, the subject is administered a KMO inhibitor in combination with an angiotensin II type 1 receptor (AGTR1) blocker (ARBs). In one embodiment, the subject is administered a KMO inhibitor in combination with a statin. In one embodiment, the subject is administered a KMO inhibitor in combination with tetracycline/macrolide. In one embodiment, the subject is administered a KMO inhibitor in combination with a ERK inhibitor. In one embodiment, the subject is administered a KMO inhibitor in combination with losartan. In one embodiment, the subject is administered a KMO inhibitor in combination with pravastatin. In one embodiment, the subject is administered a KMO inhibitor in combination with atenolol. In one embodiment, the subject is administered a KMO inhibitor in combination with perindopril. In one embodiment, the subject is administered a KMO inhibitor in combination with verapamil. In one embodiment, the subject is administered a KMO inhibitor in combination with roxithromycin. In one embodiment, the subject is administered a KMO inhibitor in combination with ethinyl estradiol. In one embodiment, the subject is administered a KMO inhibitor in combination with nebivolol. In one embodiment, the subject is administered a KMO inhibitor in combination with doxycycline. In one embodiment, the subject is predisposed to development of AAA. In one embodiment, the subject is predisposed to development of TAA. In one embodiment, the subject is predisposed to development of CA. In one embodiment, the genetic disorder is Marfan syndrome, or a disorder related to Marfan syndrome. In one embodiment, the disorder is Loeys-Dietz syndrome. In one embodiment, the disorder is aneurysms-osteoarthritis syndrome. In one embodiment, the disorder is Ehlers-Danlos syndrome. In one embodiment, the disorder is vascular Ehlers-Danlos syndrome. In one embodiment, the disorder is familial thoracic aortic aneurysm/dissection. In one embodiment, the disorder is Shprintzen-Goldberg syndrome. In one embodiment, the disorder is cutis laxa syndrome. In one embodiment, the disorder is aortic valve disease. In one embodiment, the disorder is arterial tortuosity syndrome. In one embodiment, the disorder is X-linked Alport syndrome. In one embodiment, the disorder is Turner syndrome. In one embodiment, the disorder is Mitral valve, myopia, Aorta, Skin and Skeletal (MASS) syndrome. In one embodiment, the disorder is Beals syndrome. In one embodiment, the disorder is Bicuspid Aortic Valve syndrome. In one embodiment, the disorder is a congenital heart malformation. In one embodiment, the disorder is a mutation in the gene COL1A1. In one embodiment, the disorder is a mutation in the gene COL1A2. In one embodiment, the disorder is a mutation in the gene MED12. In one embodiment, the disorder is a mutation in the gene, SMAD4. In one embodiment, the disorder is a mutation in the gene PLOD3. In one embodiment, the disorder is a mutation in the gene ENG. In one embodiment, the disorder is a mutation in the gene ACVRL1. In one embodiment, the disorder is a mutation in the gene NF1.

In one embodiment, a method for the prophylactic inhibition of the formation of an aneurysm in a subject predisposed to the development of an aneurysm is provided comprising administering an effective amount of an IDO1 inhibitor, a TDO2 inhibitor, a dual IDO1/TDO2 inhibitor, or a combination thereof. In one embodiment, the IDO1 inhibitor is indoximod. In one embodiment, the IDO1 inhibitor is navoximod. In one embodiment, the IDO1 inhibitor is NLG802. In one embodiment, the IDO1 inhibitor is epacadostat. In one embodiment, the IDO1 inhibitor is BMS-986205. In one embodiment, the IDO1 inhibitor is PF-0684003. In one embodiment, the dual IDO1/TDO2 inhibitor is HTI-1090. In one embodiment, the dual IDO1/TDO2 inhibitor is RG-70099. In one embodiment, the IDO1 inhibitor is necrostatin-1. In one embodiment, the subject is administered an IDO1 inhibitor that is not necrostatin-1. In one embodiment, the subject is administered an IDO1 inhibitor, a TDO2 inhibitor, a dual IDO1/TDO2 inhibitor, or a combination thereof in combination with a KMO inhibitor In one embodiment, the subject is administered an IDO1 inhibitor, a TDO2 inhibitor, a dual IDO1/TDO2 inhibitor, or a combination thereof in combination with a KYNU inhibitor. In one embodiment, the subject is administered an IDO1 inhibitor, a TDO2 inhibitor, a dual IDO1/TDO2 inhibitor, or a combination thereof in combination with acipimox. In one embodiment, the subject is administered an IDO1 inhibitor, a TDO2 inhibitor, a dual IDO1/TDO2 inhibitor, or a combination thereof in combination with fenofibrate. In one embodiment, the subject is administered an IDO1 inhibitor, a TDO2 inhibitor, a dual IDO1/TDO2 inhibitor, or a combination thereof in combination with telmisartan. In one embodiment, the subject is administered an IDO1 inhibitor, a TDO2 inhibitor, a dual IDO1/TDO2 inhibitor, or a combination thereof in combination with 7-Cl—O-Nec-1. In one embodiment, the subject is administered an IDO1 inhibitor, a TDO2 inhibitor, a dual IDO1/TDO2 inhibitor, or a combination thereof in combination with a β-blocker. In one embodiment, the subject is administered an IDO1 inhibitor, a TDO2 inhibitor, a dual IDO1/TDO2 inhibitor, or a combination thereof in combination with an angiotensin converting enzyme inhibitor (ACEI). In one embodiment, the subject is administered an IDO1 inhibitor, a TDO2 inhibitor, a dual IDO1/TDO2 inhibitor, or a combination thereof in combination with an angiotensin II type 1 receptor (AGTR1) blocker (ARBs). In one embodiment, the subject is administered an IDO1 inhibitor, a TDO2 inhibitor, a dual IDO1/TDO2 inhibitor, or a combination thereof in combination with a statin. In one embodiment, the subject is administered an IDO1 inhibitor, a TDO2 inhibitor, a dual IDO1/TDO2 inhibitor, or a combination thereof in combination with tetracycline/macrolide. In one embodiment, the subject is administered an IDO1 inhibitor, a TDO2 inhibitor, a dual IDO1/TDO2 inhibitor, or a combination thereof in combination with a ERK inhibitor. In one embodiment, the subject is administered an IDO1 inhibitor, a TDO2 inhibitor, a dual IDO1/TDO2 inhibitor, or a combination thereof in combination with losartan. In one embodiment, the subject is administered an IDO1 inhibitor, a TDO2 inhibitor, a dual IDO1/TDO2 inhibitor, or a combination thereof in combination with pravastatin. In one embodiment, the subject is administered an IDO1 inhibitor, a TDO2 inhibitor, a dual IDO1/TDO2 inhibitor, or a combination thereof in combination with atenolol. In one embodiment, the subject is administered an IDO1 inhibitor, a TDO2 inhibitor, a dual IDO1/TDO2 inhibitor, or a combination thereof in combination with perindopril. In one embodiment, the subject is administered an IDO1 inhibitor, a TDO2 inhibitor, a dual IDO1/TDO2 inhibitor, or a combination thereof in combination with verapamil. In one embodiment, the subject is administered an IDO1 inhibitor, a TDO2 inhibitor, a dual IDO1/TDO2 inhibitor, or a combination thereof in combination with roxithromycin. In one embodiment, the subject is administered an IDO1 inhibitor, a TDO2 inhibitor, a dual IDO1/TDO2 inhibitor, or a combination thereof in combination with ethinyl estradiol. In one embodiment, the subject is administered an IDO1 inhibitor, a TDO2 inhibitor, a dual IDO1/TDO2 inhibitor, or a combination thereof in combination with nebivolol. In one embodiment, the subject is administered an IDO1 inhibitor, a TDO2 inhibitor, a dual IDO1/TDO2 inhibitor, or a combination thereof in combination with doxycycline. In one embodiment, the subject is predisposed to development of AAA. In one embodiment, the subject is predisposed to development of TAA. In one embodiment, the subject is predisposed to development of CA. In one embodiment, the genetic disorder is Marfan syndrome, or a disorder related to Marfan syndrome. In one embodiment, the disorder is Loeys-Dietz syndrome. In one embodiment, the disorder is aneurysms-osteoarthritis syndrome. In one embodiment, the disorder is Ehlers-Danlos syndrome. In one embodiment, the disorder is vascular Ehlers-Danlos syndrome. In one embodiment, the disorder is familial thoracic aortic aneurysm/dissection. In one embodiment, the disorder is Shprintzen-Goldberg syndrome. In one embodiment, the disorder is cutis laxa syndrome. In one embodiment, the disorder is aortic valve disease. In one embodiment, the disorder is arterial tortuosity syndrome. In one embodiment, the disorder is X-linked Alport syndrome. In one embodiment, the disorder is Turner syndrome. In one embodiment, the disorder is Mitral valve, myopia, Aorta, Skin and Skeletal (MASS) syndrome. In one embodiment, the disorder is Beals syndrome. In one embodiment, the disorder is Bicuspid Aortic Valve syndrome. In one embodiment, the disorder is a congenital heart malformation. In one embodiment, the disorder is a mutation in the gene COL1A1. In one embodiment, the disorder is a mutation in the gene COL1A2. In one embodiment, the disorder is a mutation in the gene MED12. In one embodiment, the disorder is a mutation in the gene, SMAD4. In one embodiment, the disorder is a mutation in the gene PLOD3. In one embodiment, the disorder is a mutation in the gene ENG. In one embodiment, the disorder is a mutation in the gene ACVRL1. In one embodiment, the disorder is a mutation in the gene NF1.

In one embodiment, a method for the prophylactic inhibition of the formation of an aneurysm in a subject predisposed to the development of an aneurysm is provided comprising administering an effective amount of acipimox. In one embodiment, the subject is administered acipimox in combination with a KMO inhibitor. In one embodiment, the subject is administered acipimox in combination with an IDO1 inhibitor. In one embodiment, the subject is administered acipimox in combination with a TDO2 inhibitor. In one embodiment, the subject is administered acipimox in combination with a dual IDO1/TDO2 inhibitor. In one embodiment, the subject is administered acipimox in combination with a KYNU inhibitor. In one embodiment, the subject is administered acipimox in combination with acipimox. In one embodiment, the subject is administered acipimox in combination with fenofibrate. In one embodiment, the subject is administered acipimox in combination with telmisartan. In one embodiment, the subject is administered acipimox in combination with 7-Cl—O-Nec-1. In one embodiment, the subject is administered acipimox in combination with a β-blocker. In one embodiment, the subject is administered acipimox in combination with an angiotensin converting enzyme inhibitor (ACEI). In one embodiment, the subject is administered acipimox in combination with an angiotensin II type 1 receptor (AGTR1) blocker (ARBs). In one embodiment, the subject is administered acipimox in combination with a statin. In one embodiment, the subject is administered acipimox in combination with tetracycline/macrolide. In one embodiment, the subject is administered acipimox in combination with a ERK inhibitor. In one embodiment, the subject is administered acipimox in combination with losartan. In one embodiment, the subject is administered acipimox in combination with pravastatin. In one embodiment, the subject is administered acipimox in combination with atenolol. In one embodiment, the subject is acipimox in combination with perindopril. In one embodiment, the subject is administered acipimox in combination with verapamil. In one embodiment, the subject is administered acipimox in combination with roxithromycin. In one embodiment, the subject is administered acipimox in combination with ethinyl estradiol. In one embodiment, the subject is administered acipimox in combination with nebivolol. In one embodiment, the subject is administered acipimox in combination with doxycycline. In one embodiment, the subject is predisposed to development of AAA. In one embodiment, the subject is predisposed to development of TAA. In one embodiment, the subject is predisposed to development of CA. In one embodiment, the genetic disorder is Marfan syndrome, or a disorder related to Marfan syndrome. In one embodiment, the disorder is Loeys-Dietz syndrome. In one embodiment, the disorder is aneurysms-osteoarthritis syndrome. In one embodiment, the disorder is Ehlers-Danlos syndrome. In one embodiment, the disorder is vascular Ehlers-Danlos syndrome. In one embodiment, the disorder is familial thoracic aortic aneurysm/dissection. In one embodiment, the disorder is Shprintzen-Goldberg syndrome. In one embodiment, the disorder is cutis laxa syndrome. In one embodiment, the disorder is aortic valve disease. In one embodiment, the disorder is arterial tortuosity syndrome. In one embodiment, the disorder is X-linked Alport syndrome. In one embodiment, the disorder is Turner syndrome. In one embodiment, the disorder is Mitral valve, myopia, Aorta, Skin and Skeletal (MASS) syndrome. In one embodiment, the disorder is Beals syndrome. In one embodiment, the disorder is Bicuspid Aortic Valve syndrome. In one embodiment, the disorder is a congenital heart malformation. In one embodiment, the disorder is a mutation in the gene COL1A1. In one embodiment, the disorder is a mutation in the gene COL1A2. In one embodiment, the disorder is a mutation in the gene MED12. In one embodiment, the disorder is a mutation in the gene, SMAD4. In one embodiment, the disorder is a mutation in the gene PLOD3. In one embodiment, the disorder is a mutation in the gene ENG. In one embodiment, the disorder is a mutation in the gene ACVRL1. In one embodiment, the disorder is a mutation in the gene NF1.

In some embodiments, provided herein is a method of reducing the risk of aneurysmal rupture in a subject predisposed to the development of an aneurysm by administering to the subject a compound described herein.

In one embodiment, a method for reducing the risk of aneurysmal rupture in a subject predisposed to the development of an aneurysm is provided comprising administering an effective amount of a KYNU inhibitor. In one embodiment, the KYNU inhibitor is 2-amino-4-[3'-hydroxyphenyl]-4-hydroxybutanoic acid. In one embodiment, the KYNU inhibitor is dihydro-L-kynurenine. In one embodiment, the KYNU inhibitor is benserazide. In one embodiment, the KYNU inhibitor is OMBA. In one embodiment, the subject is administered a KYNU inhibitor in combination with an IDO1 inhibitor. In one embodiment, the subject is administered a KYNU inhibitor in combination with a TDO2 inhibitor. In one embodiment, the subject is administered a KYNU inhibitor in combination with a dual IDO1/TDO2 inhibitor. In one embodiment, the subject is administered a KYNU inhibitor in combination with a KMO inhibitor. In one embodiment, the subject is administered a KYNU inhibitor in combination with acipimox. In one embodiment, the subject is administered a KYNU inhibitor in combination with fenofibrate. In one embodiment, the subject is administered a KYNU inhibitor in combination with telmisartan. In one embodiment, the subject is administered a KYNU inhibitor in combination with 7-Cl—O—Nec-1. In one embodiment, the subject is administered a KYNU inhibitor in combination with a β-blocker. In one embodiment, the subject is administered a KYNU inhibitor in combination with an angiotensin converting enzyme inhibitor (ACEI). In one embodiment, the subject is administered a KYNU inhibitor in combination with an angiotensin II type 1 receptor (AGTR1) blocker (ARBs). In one embodiment, the subject is administered a KYNU inhibitor in combination with a statin. In one embodiment, the subject is administered a KYNU inhibitor in combination with tetracycline/macrolide. In one embodiment, the subject is administered a KYNU inhibitor in combination with a ERK inhibitor. In one embodiment, the subject is administered a KYNU inhibitor in combination with losartan. In one embodiment, the subject is administered a KYNU inhibitor in combination with pravastatin. In one embodiment, the subject is administered a KYNU inhibitor in combination with atenolol. In one embodiment, the subject is administered a KYNU inhibitor in combination with perindopril. In one embodiment, the subject is administered a KYNU inhibitor in combination with verapamil. In one embodiment, the subject is administered a KYNU inhibitor in combination with roxithromycin. In one embodiment, the subject is administered a KYNU inhibitor in combination with ethinyl estradiol. In one embodiment, the subject is administered a KYNU inhibitor in combination with nebivolol. In one embodiment, the subject is administered a KYNU inhibitor in combination with doxycycline. In one embodiment, the subject is predisposed to development of AAA. In one embodiment, the subject is predisposed to development of TAA. In one embodiment, the subject is predisposed to development of CA. In one embodiment, the genetic disorder is Marfan syndrome, or a disorder related to Marfan syndrome. In one embodiment, the disorder is Loeys-Dietz syndrome. In one embodiment, the disorder is aneurysms-osteoarthritis syndrome. In one embodiment, the disorder is Ehlers-Danlos syndrome. In one embodiment, the disorder is vascular Ehlers-Danlos syndrome. In one embodiment, the disorder is familial thoracic aortic aneurysm/dissection. In one embodiment, the disorder is Shprintzen-Goldberg syndrome. In one embodiment, the disorder is cutis laxa syndrome. In one embodiment, the disorder is aortic valve disease. In one embodiment, the disorder is arterial tortuosity syndrome. In one embodiment, the disorder is X-linked Alport syndrome. In one embodiment, the disorder is Turner syndrome. In one embodiment, the disorder is Mitral valve, myopia, Aorta, Skin and Skeletal (MASS) syndrome. In one embodiment, the disorder is Beals syndrome. In one embodiment, the disorder is Bicuspid Aortic Valve syndrome. In one embodiment, the disorder is a congenital heart malformation. In one embodiment, the disorder is a mutation in the gene COL1A1. In one embodiment, the disorder is a mutation in the gene COL1A2. In one embodiment, the disorder is a mutation in the gene MED12. In one embodiment, the disorder is a mutation in the gene, SMAD4. In one embodiment, the disorder is a mutation in the gene PLOD3. In one embodiment, the disorder is a mutation in the gene ENG. In one embodiment, the disorder is a mutation in the gene ACVRL1. In one embodiment, the disorder is a mutation in the gene NF1.

In one embodiment, a method for reducing the risk of aneurysmal rupture in a subject predisposed to the development of an aneurysm is provided comprising administering an effective amount of a KMO inhibitor. In one embodiment, the KMO inhibitor is NBA. In one embodiment, the KMO inhibitor is GSK180. In one embodiment, the KMO inhibitor is (R)-3-(5-chloro-6-(1-phenylethoxy)benzo[d]isoxazol-3-yl)propanoic acid. In one embodiment, the KMO inhibitor is CHDI-340246. In one embodiment, the KMO inhibitor is des-amino FCE 28833. In one embodiment, the KMO inhibitor is UPF 648. In one embodiment, the KMO inhibitor is Ro-61-8048. In one embodiment, the subject is administered a KMO inhibitor in combination with an IDO11 inhibitor. In one embodiment, the subject is administered a KMO inhibitor in combination with a TDO2 inhibitor. In one embodiment, the subject is administered a KMO inhibitor in combination with a dual IDO1/TDO2 inhibitor. In one embodiment, the subject is administered a KMO inhibitor in combination with a KYNU inhibitor. In one embodiment, the subject is administered a KMO inhibitor in combination with acipimox. In one embodiment, the subject is administered a KMO inhibitor in combination with fenofibrate. In one embodiment, the subject is administered a KMO inhibitor in combination with telmisartan. In one embodiment, the subject is administered a KMO inhibitor in combination with 7-Cl—O-Nec-1. In one embodiment, the subject is administered a KMO inhibitor in combination with a β-blocker. In one embodiment, the subject is administered a KMO inhibitor in combination with an angiotensin converting enzyme inhibitor (ACEI). In one embodiment, the subject is administered a KMO inhibitor in combination with an angiotensin II type 1 receptor (AGTR1) blocker (ARBs). In one embodiment, the subject is administered a KMO inhibitor in combination with a statin. In one embodiment, the subject is administered a KMO inhibitor in combination with tetracycline/macrolide. In one embodiment, the subject is administered a KMO inhibitor in combination with a ERK inhibitor. In one embodiment, the subject is administered a KMO inhibitor in combination with losartan. In one embodiment, the subject is administered a KMO inhibitor in combination with pravastatin. In one embodiment, the subject is administered a KMO inhibitor in combination with atenolol. In one embodiment, the subject is administered a KMO inhibitor in combination with perindopril. In one embodiment, the subject is administered a KMO inhibitor in combination with verapamil. In one embodiment, the subject is administered a KMO inhibitor in combination with roxithromycin. In one embodiment, the subject is administered a KMO inhibitor in combination with ethinyl estradiol. In one embodiment, the subject is administered a KMO inhibitor in combination with nebivolol. In one embodiment, the subject is administered a KMO inhibitor in combination with doxycycline. In one embodiment, the subject is predisposed to development of AAA. In one embodiment, the subject is predisposed to development of TAA. In one embodiment, the subject is predisposed to development of CA. In one embodiment, the genetic disorder is Marfan syndrome, or a disorder related to Marfan syndrome. In one embodiment, the disorder is Loeys-Dietz syndrome. In one embodiment, the disorder is aneurysms-osteoarthritis syndrome. In one embodiment, the disorder is Ehlers-Danlos syndrome. In one embodiment, the disorder is vascular Ehlers-Danlos syndrome. In one embodiment, the disorder is familial thoracic aortic aneurysm/dissection. In one embodiment, the disorder is Shprintzen-Goldberg syndrome. In one embodiment, the disorder is cutis laxa syndrome. In one embodiment, the disorder is aortic valve disease. In one embodiment, the disorder is arterial tortuosity syndrome. In one embodiment, the disorder is X-linked Alport syndrome. In one embodiment, the disorder is Turner syndrome. In one embodiment, the disorder is Mitral valve, myopia, Aorta, Skin and Skeletal (MASS) syndrome. In one embodiment, the disorder is Beals syndrome. In one embodiment, the disorder is Bicuspid Aortic Valve syndrome. In one embodiment, the disorder is a congenital heart malformation. In one embodiment, the disorder is a mutation in the gene COL1A1. In one embodiment, the disorder is a mutation in the gene COL1A2. In one embodiment, the disorder is a mutation in the gene MED12. In one embodiment, the disorder is a mutation in the gene, SMAD4. In one embodiment, the disorder is a mutation in the gene PLOD3. In one embodiment, the disorder is a mutation in the gene ENG. In one embodiment, the disorder is a mutation in the gene ACVRL1. In one embodiment, the disorder is a mutation in the gene NF1.

In one embodiment, a method for reducing the risk of aneurysmal rupture in a subject predisposed to the development of an aneurysm is provided comprising administering an effective amount of an IDO1 inhibitor, a TDO2 inhibitor, a dual IDO1/TDO2 inhibitor, or a combination thereof. In one embodiment, the IDO1 inhibitor is indoximod. In one embodiment, the IDO1 inhibitor is navoximod. In one embodiment, the IDO1 inhibitor is NLG802. In one embodiment, the IDO1 inhibitor is epacadostat. In one embodiment, the IDO1 inhibitor is BMS-986205. In one embodiment, the IDO1 inhibitor is PF-0684003. In one embodiment, the dual IDO1/TDO2 inhibitor is HTI-1090. In one embodiment, the dual IDO1/TDO2 inhibitor is RG-70099. In one embodiment, the IDO1 inhibitor is necrostatin-1. In one embodiment, the subject is administered an IDO1 inhibitor that is not necrostatin-1. In one embodiment, the subject is administered an IDO11 inhibitor, a TDO2 inhibitor, a dual IDO1/TDO2 inhibitor, or a combination thereof in combination with a KMO inhibitor In one embodiment, the subject is administered an IDO1 inhibitor, a TDO2 inhibitor, a dual IDO1/TDO2 inhibitor, or a combination thereof in combination with a KYNU inhibitor. In one embodiment, the subject is administered an IDO1 inhibitor, a TDO2 inhibitor, a dual IDO1/TDO2 inhibitor, or a combination thereof in combination with acipimox. In one embodiment, the subject is administered an IDO1 inhibitor, a TDO2 inhibitor, a dual IDO1/TDO2 inhibitor, or a combination thereof in combination with fenofibrate. In one embodiment, the subject is administered an IDO1 inhibitor, a TDO2 inhibitor, a dual IDO1/TDO2 inhibitor, or a combination thereof in combination with telmisartan. In one embodiment, the subject is administered an IDO1 inhibitor, a TDO2 inhibitor, a dual IDO1/TDO2 inhibitor, or a combination thereof in combination with 7-Cl—O-Nec-1. In one embodiment, the subject is administered an IDO1 inhibitor, a TDO2 inhibitor, a dual IDO1/TDO2 inhibitor, or a combination thereof in combination with a β-blocker. In one embodiment, the subject is administered an IDO1 inhibitor, a TDO2 inhibitor, a dual IDO1/TDO2 inhibitor, or a combination thereof in combination with an angiotensin converting enzyme inhibitor (ACEI). In one embodiment, the subject is administered an IDO1 inhibitor, a TDO2 inhibitor, a dual IDO1/TDO2 inhibitor, or a combination thereof in combination with an angiotensin II type 1 receptor (AGTR1) blocker (ARBs). In one embodiment, the subject is administered an IDO1 inhibitor, a TDO2 inhibitor, a dual IDO1/TDO2 inhibitor, or a combination thereof in combination with a statin. In one embodiment, the subject is administered an IDO1 inhibitor, a TDO2 inhibitor, a dual IDO1/TDO2 inhibitor, or a combination thereof in combination with tetracycline/macrolide. In one embodiment, the subject is administered an IDO1 inhibitor, a TDO2 inhibitor, a dual IDO1/TDO2 inhibitor, or a combination thereof in combination with a ERK inhibitor. In one embodiment, the subject is administered an IDO1 inhibitor, a TDO2 inhibitor, a dual IDO1/TDO2 inhibitor, or a combination thereof in combination with losartan. In one embodiment, the subject is administered an IDO1 inhibitor, a TDO2 inhibitor, a dual IDO1/TDO2 inhibitor, or a combination thereof in combination with pravastatin. In one embodiment, the subject is administered an IDO1 inhibitor, a TDO2 inhibitor, a dual IDO1/TDO2 inhibitor, or a combination thereof in combination with atenolol. In one embodiment, the subject is administered an IDO1 inhibitor, a TDO2 inhibitor, a dual IDO1/TDO2 inhibitor, or a combination thereof in combination with perindopril. In one embodiment, the subject is administered an IDO1 inhibitor, a TDO2 inhibitor, a dual IDO1/TDO2 inhibitor, or a combination thereof in combination with verapamil. In one embodiment, the subject is administered an IDO1 inhibitor, a TDO2 inhibitor, a dual IDO1/TDO2 inhibitor, or a combination thereof in combination with roxithromycin. In one embodiment, the subject is administered an IDO1 inhibitor, a TDO2 inhibitor, a dual IDO1/TDO2 inhibitor, or a combination thereof in combination with ethinyl estradiol. In one embodiment, the subject is administered an IDO1 inhibitor, a TDO2 inhibitor, a dual IDO1/TDO2 inhibitor, or a combination thereof in combination with nebivolol. In one embodiment, the subject is administered an IDO1 inhibitor, a TDO2 inhibitor, a dual IDO1/TDO2 inhibitor, or a combination thereof in combination with doxycycline. In one embodiment, the subject is predisposed to development of AAA. In one embodiment, the subject is predisposed to development of TAA. In one embodiment, the subject is predisposed to development of CA. In one embodiment, the genetic disorder is Marfan syndrome, or a disorder related to Marfan syndrome. In one embodiment, the disorder is Loeys-Dietz syndrome. In one embodiment, the disorder is aneurysms-osteoarthritis syndrome. In one embodiment, the disorder is Ehlers-Danlos syndrome. In one embodiment, the disorder is vascular Ehlers-Danlos syndrome. In one embodiment, the disorder is familial thoracic aortic aneurysm/dissection. In one embodiment, the disorder is Shprintzen-Goldberg syndrome. In one embodiment, the disorder is cutis laxa syndrome. In one embodiment, the disorder is aortic valve disease. In one embodiment, the disorder is arterial tortuosity syndrome. In one embodiment, the disorder is X-linked Alport syndrome. In one embodiment, the disorder is Turner syndrome. In one embodiment, the disorder is Mitral valve, myopia, Aorta, Skin and Skeletal (MASS) syndrome. In one embodiment, the disorder is Beals syndrome. In one embodiment, the disorder is Bicuspid Aortic Valve syndrome. In one embodiment, the disorder is a congenital heart malformation. In one embodiment, the disorder is a mutation in the gene COL1A1. In one embodiment, the disorder is a mutation in the gene COL1A2. In one embodiment, the disorder is a mutation in the gene MED12. In one embodiment, the disorder is a mutation in the gene, SMAD4. In one embodiment, the disorder is a mutation in the gene PLOD3. In one embodiment, the disorder is a mutation in the gene ENG. In one embodiment, the disorder is a mutation in the gene ACVRL1. In one embodiment, the disorder is a mutation in the gene NF1.

In one embodiment, a method for reducing the risk of aneurysmal rupture in a subject predisposed to the development of an aneurysm is provided comprising administering an effective amount of acipimox. In one embodiment, the subject is administered acipimox in combination with a KMO inhibitor. In one embodiment, the subject is administered acipimox in combination with an IDO1 inhibitor. In one embodiment, the subject is administered acipimox in combination with a TDO2 inhibitor. In one embodiment, the subject is administered acipimox in combination with a dual IDO1/TDO2 inhibitor. In one embodiment, the subject is administered acipimox in combination with a KYNU inhibitor. In one embodiment, the subject is administered acipimox in combination with acipimox. In one embodiment, the subject is administered acipimox in combination with fenofibrate. In one embodiment, the subject is administered acipimox in combination with telmisartan. In one embodiment, the subject is administered acipimox in combination with 7-Cl—O-Nec-1. In one embodiment, the subject is administered acipimox in combination with a β-blocker. In one embodiment, the subject is administered acipimox in combination with an angiotensin converting enzyme inhibitor (ACEI). In one embodiment, the subject is administered acipimox in combination with an angiotensin II type 1 receptor (AGTR1) blocker (ARBs). In one embodiment, the subject is administered acipimox in combination with a statin. In one embodiment, the subject is administered acipimox in combination with tetracycline/macrolide. In one embodiment, the subject is administered acipimox in combination with a ERK inhibitor. In one embodiment, the subject is administered acipimox in combination with losartan. In one embodiment, the subject is administered acipimox in combination with pravastatin. In one embodiment, the subject is administered acipimox in combination with atenolol. In one embodiment, the subject is acipimox in combination with perindopril. In one embodiment, the subject is administered acipimox in combination with verapamil. In one embodiment, the subject is administered acipimox in combination with roxithromycin. In one embodiment, the subject is administered acipimox in combination with ethinyl estradiol. In one embodiment, the subject is administered acipimox in combination with nebivolol. In one embodiment, the subject is administered acipimox in combination with doxycycline. In one embodiment, the subject is predisposed to development of AAA. In one embodiment, the subject is predisposed to development of TAA. In one embodiment, the subject is predisposed to development of CA. In one embodiment, the genetic disorder is Marfan syndrome, or a disorder related to Marfan syndrome. In one embodiment, the disorder is Loeys-Dietz syndrome. In one embodiment, the disorder is aneurysms-osteoarthritis syndrome. In one embodiment, the disorder is Ehlers-Danlos syndrome. In one embodiment, the disorder is vascular Ehlers-Danlos syndrome. In one embodiment, the disorder is familial thoracic aortic aneurysm/dissection. In one embodiment, the disorder is Shprintzen-Goldberg syndrome. In one embodiment, the disorder is cutis laxa syndrome. In one embodiment, the disorder is aortic valve disease. In one embodiment, the disorder is arterial tortuosity syndrome. In one embodiment, the disorder is X-linked Alport syndrome. In one embodiment, the disorder is Turner syndrome. In one embodiment, the disorder is Mitral valve, myopia, Aorta, Skin and Skeletal (MASS) syndrome. In one embodiment, the disorder is Beals syndrome. In one embodiment, the disorder is Bicuspid Aortic Valve syndrome. In one embodiment, the disorder is a congenital heart malformation. In one embodiment, the disorder is a mutation in the gene COL1A1. In one embodiment, the disorder is a mutation in the gene COL1A2. In one embodiment, the disorder is a mutation in the gene MED12. In one embodiment, the disorder is a mutation in the gene, SMAD4. In one embodiment, the disorder is a mutation in the gene PLOD3. In one embodiment, the disorder is a mutation in the gene ENG. In one embodiment, the disorder is a mutation in the gene ACVRL1. In one embodiment, the disorder is a mutation in the gene NF1.

Examples

Materials

Antibodies to MMP2 (ab37150) and alpha smooth muscle Actin (ab5694) were from Abcam. An antibody against IFN-γ (AMC4834) was from Invitrogen. Antibodies to phospho-Elk1 (Ser383, 9181), Elk1 (9182), and all secondary antibodies were from Cell Signaling Technology. Antibodies to human kynureninase (sc-390360), β3-actin (sc-47778) and GAPDH (sc-166545) were from Santa Cruz Biotechnology. An antibody to locate 100 (MAB5412) was from Millipore. An antibody against mouse kynureninase (MAB7389) was from R&D System. A goat anti-mouse 1gG conjugated to Alexa488 green (A-11001) was purchased from invitrogen. All primary antibodies were used in a 1:1,000 dilution for Western blot and a 1:100 dilution for immunocytochemistry and immunohistochemistry. IFN-γ Recombinant Human Protein (PHC4031) was obtained from GIBCO. Recombinant human pro-MMP2 protein (PF037) was purchased from Millipore. 3-Hydroxy-DL-kynurenine (H1771), anthranilic acid (A89855), and Angiotensin II (Ang II, A9525) were from Sigma. Kynurenic acid (sc-202683), Xanthurenic acid (sc-258335), and Quinolinic acid (sc-203226) were purchased from Santa Cruz Biotechnology. Control siRNA (sc-37007) and siRNAs targeting 100 (sc-45939), kynureninase (sc-95023) were from Santa Cruz Biotechnology. The transfection reagents for siRNA (Lipofectamine RNAiMax, 13778150) were from Invitrogen.

Animals $IDO^{-/-}$ and $ApoE^{-/-}$ mice were obtained from Jackson laboratory (Bar Harbor, Me.) in a C57BL/6 background. $IDO^{-/-}$ mice were crossed with $ApoE^{-/-}$ mice to generate $ApoE^{-/-}/IDO^{-/-}$ mice. Mice were housed in temperature-controlled cages under a 12-hour light/dark cycle and given free access to water and normal chow. All procedures involving animals were approved by the Institutional Animal Care and Use Committee at the University of Oklahoma Health Sciences Center. Experimental mice ($ApoE^{-/-}$ and $ApoE^{-/-}/IDO^{-/-}$ mice) at age 8 weeks or 4 weeks after bone marrow transplantation on a chow diet were infused with AngII (1,000 ng/kg/min) or physiological saline (0.9% sodium chloride) by Alzet osmotic pumps (OURECT Corp, Model 2004) as described previously in Wang et al., Activation of NAD(P)H Oxidase by Tryptophan-Derived 3-Hydroxykynurenine Accelerates Endothelial Apoptosis and Dysfunction In Vivo. Circ Res. (2014) 114:480-92.

$ApoE^{-/-}$ and $ApoE^{-/-}/IDO^{-/-}$ mice at age 8 weeks on a chow diet were intraperitoneally injected with 3-HAA (200 mg/kg. d) or vehicle for 6 weeks. 3-HAA was dissolved in OMSO and further diluted in Captisol (Captisol Technology).

In Vivo siRNA Delivery

The Ambion® in vivo pre-designed siRNA delivery was carried out according to Invitrogen's in vivo RNAi protocol. 0.875 mg/ml complex of control siRNA (Invitrogen, 4457289) or kynureninase siRNA (Invitrogen, 4457308) with Invivofectamine® 2.0 Reagent (Invitrogen, 1377-505) were Prepared in PBS using a Float-A-Lyzer® G2 cassette (Spectrum labs, G235031) freshly before every injection. 200 μI of siRNA (7 mg/Kg) complex was delivered into an $ApoE^{-/-}$ mouse by tail vein injection every five days which started on the first day of AngII infusion.

Bone Marrow Transplantation

Bone marrow transplantation was performed as described previously (Lukasova M, et al., Nicotinic acid inhibits progression of atherosclerosis in mice through its receptor GPR109A expressed by immune cells. J Clin Invest. (2011) 121:1163-73; Duran-Struuck R and Dysko R C. Principles of bone marrow transplantation (BMT): providing optimal veterinary and husbandry care to irradiated mice in BMT studies. J Am Assoc Lab Anim Sci. (2009) 48:11-22). Bone marrow was obtained aseptically from femora and tibiae of $ApoE^{-/-}$ or $ApoE^{-/-}/IDO^{-/-}$ mice. Cells ($5 \times 10^6$/mouse) were resuspended in sterile PBS and transplanted by intravenous infusion into lethally irradiated (10 Gy) $ApoE^{-/-}$ or $ApoE^{-/-}/IDO^{-/-}$ mice recipients 6 hours after irradiation at the age of 8 weeks.

Analysis and Quantitation of AAA

To quantify AAA incidence and size, the maximum width of abdominal aorta was measure with Image Pro Plus software (Media Cybernetics). We quantified aneurysm incidence based on a definition of aneurysm as an external width of the suprarenal aorta that was increased by 50% or greater compared with aortas from saline-infused mice, as described previously (Sparks A R, et al., Imaging of abdominal aortic aneurysms. Am Fam Physician. (2002) 65:1565-70). The average diameter of the normal suprarenal aorta in control mice is 0.8 mm. We therefore set a threshold of 1.22 mm as evidence of aneurysm formation.

Histological Analysis

After hemodynamic measurements, the mice were killed. For morphological analyses, aortas were perfused with saline and fixed with 10% formalin in PBS for 5 minutes. Whole aortas were harvested, fixed and embedded in paraffin, and cross-sections (5 μm) were prepared. Paraffin sections were stained with H&E (IHC World, IW-3100), Van Giesen elastic stain (Sigma, HT25A), Masson trichrome stain (Sigma, HT15), or were used for immunostaining (DAKO, K4065). The collagen deposition areas were calculated by Image J. In terms of the determination of elastin degradation, we used a standard for the grades of elastin degradation, as described previously in Satoh K, et al., Cyclophilin A enhances vascular oxidative stress and the development of angiotensin II-induced aortic aneurysms. Nat Med. (2009) 15:649-56. The grades were defined as follows: grade 1, no degradation; grade 2, mild elastin degradation; grade 3, severe elastin degradation; and grade 4, aortic rupture. Semiquantitative analysis of tissue immunoreactivity was done by 4 observers blinded to the identity of the samples using an arbitrary grading system from score 1 to 4 (score 1: 0-25% positive staining in medium; score 2: 26-50% positive staining in medium; score 3: 51-75% positive staining in medium; score 4: 76-100% positive staining in medium) to estimate the degree of positive staining for each individual marker.

Blood Pressure Measurement

Blood pressure was determined by a left carotid catheter method before sacrificing the mice as described previously in Wang Q, et al., Activation of NAD(P)H Oxidase by Tryptophan-Derived 3-Hydroxykynurenine Accelerates Endothelial Apoptosis and Dysfunction In Vivo. Circ Res. (2014) 114:480-92.

Cell Culture

Human aortic smooth muscle cells (HASMC) (GIBCO, C0075C) were grown in M231 medium (Gibco, M231500) containing 10% fetal bovine serum (FBS), penicillin (100 U/ml), streptomycin (100 μg/ml), and Smooth Muscle Growth Supplement (SMGS, Gibco, S00725). All cells were incubated at 37° C. in a humidified atmosphere of 5% $CO_2$. Cells were used between passages 3 and 8, and in all experiments, were grown to 70-80% confluence before being treated with different agents.

Determination of Tryptophan (Trp), Kynurenine (Kyn), and 3-Hydroxyanthranilic Acid (3-HAA)

The culture medium was centrifuged to pellet the cells to avoid contamination from the cells, and the supernatant was filtered (0.2 μM) before use. Sample preparation for plasma was operated as described previously (Becerra A, et al., Increased activity of indoleamine 2,3-dioxygenase in serum from acutely infected dengue patients linked to gamma interferon antiviral function. J Gen Virol. (2009) 90:810-7; Holmes E W. Determination of serum kynurenine and hepatic tryptophan dioxygenase activity by high-performance liquid chromatography. Anal Biochem. (1988) 172: 518-25). 200 μL of plasma was mixed by vortex in a small polyethylene conical tube with 1/10 volume of ice cold 2.4 mol/L perchloric acid. The cloudy suspension was chilled on ice for 15 min and then centrifuged at 10,000 g for 2 min. The clear protein-free supernatant was analyzed directly.

Kyn and Trp were measured by HPLC as described previously in Wang Q, et al., Activation of NAD(P)H Oxidase by Tryptophan-Derived 3-Hydroxykynurenine Accelerates Endothelial Apoptosis and Dysfunction In Vivo. Circ Res. (2014) 114:480-92. Kyn content was estimated along with standards ranging from 0.5-20 µM L-kynurenine (Sigma, K8625), and Trp level was assessed along standards ranging from 1-25 µM DL-Tryptophan (Sigma, 162698), using a GraceVydac C18 column (250×4.6 mm, 5.0 µM). The mobile phase was 20 mM sodium acetate at pH=4.5. The flow rate was 1 ml/min. The column effluent was monitored at 360 nm (Kyn) and 280 nm (Trp) by a UV detector.

3-HAA was measured by HPLC as described previously in Forrest C M, et al., Kynurenine pathway metabolism in patients with osteoporosis after 2 years of drug treatment. Clin Exp Pharmacol Physiol. (2006) 33:1078-87. 3-HAA content was estimated along with standards ranging from 1-200 nM 3-Hydroxyanthranilic acid (Santa Cruz, sc-216460), using a GraceVydac C18 column (250×4.6 mm, 5.0 µM). The mobile phase consisted of 25 mM sodium acetate (pH=5.5) and methanol (90:10 v/v) was pumped at a flow rate of 1 ml/min. Fluorescent detection at excitation 320 nm and emission 420 was used.

Western Blot Analysis

Western blots were performed as described previously in Wang Q, et al., Activation of NAD(P)H Oxidase by Tryptophan-Derived 3-Hydroxykynurenine Accelerates Endothelial Apoptosis and Dysfunction In Vivo. Circ Res. (2014) 114:480-92.

Immunocytochemistry

Immuno-cytochemistry was performed as described previously in Wang Q, et al., Activation of NAD(P)H Oxidase by Tryptophan-Derived 3-Hydroxykynurenine Accelerates Endothelial Apoptosis and Dysfunction In Vivo. Circ Res. (2014) 114:480-92, with a polyclonal antibody against Conjugated 3-HAA (Eagle BioSciences, IS1008).

Transfection of siRNA into Cells

Transient transfection of siRNA in culture cells was carried out according to Santa Cruz's protocol.

MMP Activity

The evaluation of MMP activities in cells and aortas was performed as described previously in: Satoh K, et al., Cyclophilin A enhances vascular oxidative stress and the development of angiotensin II-induced aortic aneurysms. Nat Med. (2009) 15:649-56; Becerra A, et al., Increased activity of indoleamine 2,3-dioxygenase in serum from acutely infected dengue patients linked to gamma interferon antiviral function. J Gen Virol. (2009) 90:810-7; Holmes E W. Determination of serum kynurenine and hepatic tryptophan dioxygenase activity by high-performance liquid chromatography. Anal Biochem. (1988) 172:518-25; Forrest C M, et al., Kynurenine pathway metabolism in patients with osteoporosis after 2 years of drug treatment. Clin Exp Pharmacol Physiol. (2006) 33:1078-87; Wang S, et al., Activation of AMP-activated protein kinase alpha2 by nicotine instigates formation of abdominal aortic aneurysms in mice in vivo. Nat Med. (2012) 18:902-10. 10 µg of protein in culture medium or tissue homogenates was electrophoresed in SOS-PAGE gels containing 1 mg/ml gelatin. Gels were washed in 2.5% Triton x-100 and incubated overnight in zymography developing buffer at 37° C. Subsequently, the gels were stained with Coomassie brilliant blue.

Statistical Analysis

Quantitative results are reported as means±standard errors of the means. The comparisons of AAA incidence were made by $\chi^2$ test. An unpaired Student's t-test was applied to detect significant differences between two groups. A one-way analysis of variance followed by Bonferroni's multiple comparison tests, as applicable, was used to compare differences among more than two groups. A value of p<0.05 was considered statistically significant.

Example 1. IDO Deletion Abrogates AngII-Induced AAA Formation

AngII-induced mouse AAA formation in the atherosclerotic-susceptible strain (ApoE$^{-/-}$) has become the most widely used model. See Qin Z, et al., Angiotensin II-induced TLR4 mediated abdominal aortic aneurysm in apolipoprotein E knockout mice is dependent on STAT3. J Mol Cell Cardiol. (2015) 87:160-70; Rateri D L, et al., Prolonged infusion of angiotensin II in ApoE (−/−) mice promotes macrophage recruitment with continued expansion of abdominal aortic aneurysm. Am J Pathol. (2011) 179:1542-8; Cassis L A, et al., ANG II infusion promotes abdominal aortic aneurysms independent of increased blood pressure in hypercholesterolemic mice. Am J Physiol Heart Circ Physiol. (2009) 296:H1660-5; Daugherty A and Cassis L A. Mouse models of abdominal aortic aneurysms. Arterioscler Thromb Vasc Biol. (2004) 24:429-34; Owens A P, 3rd, Rateri D L, Howatt D A, Moore K J, Tobias P S, Curtiss L K, Lu H, Cassis L A and Daugherty A. MyD88 deficiency attenuates angiotensin II-induced abdominal aortic aneurysm formation independent of signaling through Toll-like receptors 2 and 4. Arterioscler Thromb Vasc Biol. (2011) 31:2813-9. To unravel the role of the Trp-Kyn pathway in AAA formation ApoE$^{-/-}$/IDO$^{-/-}$ (double-knockout) mice were generated and the outcome of a 4-week AngII infusion (1000 ng/min/kg) in ApoE$^{-/-}$ and ApoE$^{-/-}$/IDO$^{-/-}$ mice was determined. As depicted in Table 1 and 2, AngII infusion increased blood pressure without affecting the heart rate or any metabolic parameters.

TABLE 1

Blood pressure and heart rate AngII-infused mice.

| Groups | Saline | | AngII | |
|---|---|---|---|---|
| | Apoe−/− | Apoe−/−/IDO−/− | Apoe−/− | Apoe−/−/IDO−/− |
| sBP (mm Hg) | 102.6 ± 12.7 | 107.4 ± 11.3 | 149.1 ± 19.5* | 155.6 ± 18.4* |
| Dbp (mmHg) | 81.5 ± 9.1 | 79.2 ± 10.3 | 112.7 ± 17.3* | 119.1 ± 14.9* |
| HR (Beats/min) | 486 ± 41 | 439 ± 37 | 471 ± 42 | 453 ± 43 |

N is 6-10 in each group. Data are expressed by mean ± s.e.m.
*P < 0.05 compared to saline Apoe−/− mice.

TABLE 2

Serum lipid and glucose level in AngII-infused mice.

| Groups | Saline | | AngII | |
|---|---|---|---|---|
| | Apoe-/- | Apoe-/-/IDO-/- | Apoe-/- | Apoe-/-/IDO-/- |
| Cholesterol (mg/dl) | 509 ± 37.1 | 498.6 ± 31.4 | 496.1 ± 22.0 | 497.9 ± 24.2 |
| Triglyceride (mg/dl) | 104.9 ± 6.9 | 122.5 ± 21.3 | 125 ± 12.6 | 108.3±19 |
| BG (mg/dll) | 149 ± 31 | 138 ± 23 | 151 ± 27 | 142 ± 19 |

N is 6-10 in each group. Data are expressed by mean ± s.e.m.

Figure 1B:
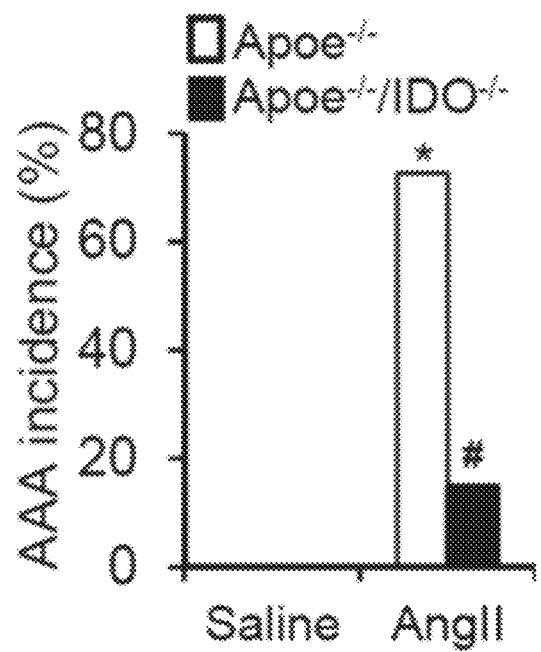
FIG. 1B is a bar graph that shows the incidence of AngII-induced AAA in ApoE$^{-/-}$ and ApoE$^{-/-}$/IDO$^{-/-}$ mice administered saline or AngII (1000 ng/min per kg) for 4 weeks. The x-axis shows the administration of saline, and the y-axis shows AAA incidence in percent. *P<0.01 vs. saline-infused ApoE$^{-/-}$ mice, #P<0.01 vs. AngII-infused ApoE$^{-/-}$ mice. N=8 in each group of ApoE$^{-/-}$ and ApoE$^{-/-}$/IDO$^{-/-}$ mice infused with saline. N=15 for AngII-infused ApoE$^{-/-}$ mice. N=12 for AngII-infused ApoE$^{-/-}$/IDO$^{-/-}$ mice.
Figure 1C:
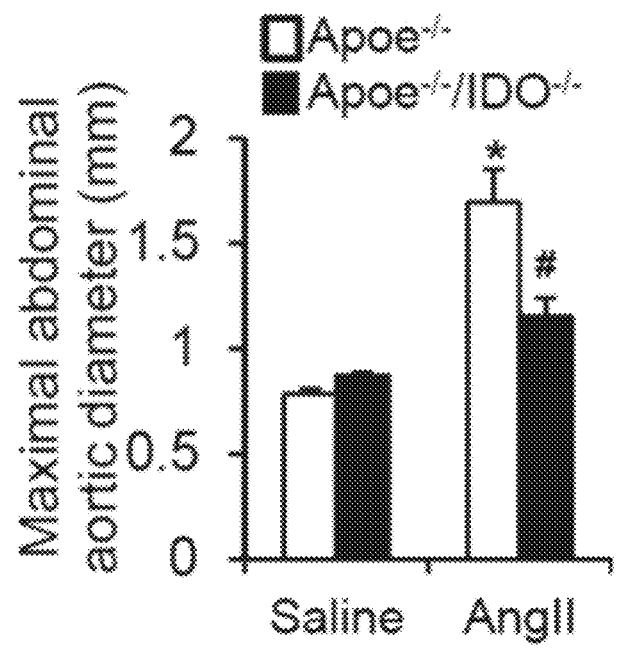
FIG. 1C is a bar graph that shows the maximum abdominal aortic diameter in ApoE$^{-/-}$ and ApoE$^{-/-}$/IDO$^{-/-}$ mice administered saline or AngII (1000 ng/min per kg) for 4 weeks. The x-axis shows the administration of saline or AngII, and the y-axis shows maximal abdominal aortic diameter in millimeters. P values were obtained by a $\chi^2$ test in band by a one-way analysis of variance (ANOVA) with a post hoc analysis using Bonferroni's multiple comparisons test. The error bars represent the standard error of the mean. *P<0.01 vs. saline-infused ApoE$^{-/-}$ mice, #P<0.01 vs. AngII-infused ApoE$^{-/-}$ mice. N=8 in each group of ApoE$^{-/-}$ and ApoE$^{-/-}$/IDO$^{-/-}$ mice infused with saline. N=15 for AngII-infused ApoE$^{-/-}$ mice. N=12 for AngII-infused ApoE$^{-/-}$/IDO$^{-/-}$ mice.
Figure 1D:
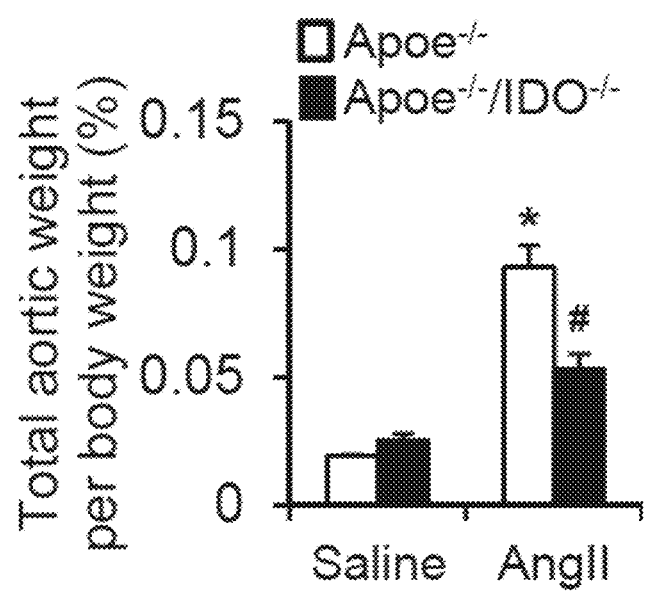
FIG. 1D is a bar graph that shows the total aortic weight in ApoE$^{-/-}$ and ApoE$^{-/-}$/IDO$^{-/-}$ mice administered saline or AngII (1000 ng/min per kg) for 4 weeks. The x-axis shows the administration of saline or AngII, and the y-axis shows the total aortic weight per body weight in percent. P values were obtained by a $\chi^2$ test in band by a one-way analysis of variance (ANOVA) with a post hoc analysis using Bonferroni's multiple comparisons test. The error bars represent the standard error of the mean. *P<0.01 vs. saline-infused ApoE$^{-/-}$ mice, #P<0.01 vs. AngII-infused ApoE$^{-/-}$ mice. N=8 in each group of ApoE$^{-/-}$ and ApoE$^{-/-}$/IDO$^{-/-}$ mice infused with saline. N=15 for AngII-infused ApoE$^{-/-}$ mice. N=12 for AngII-infused ApoE$^{-/-}$/IDO$^{-/-}$ mice.
Figure 1E:
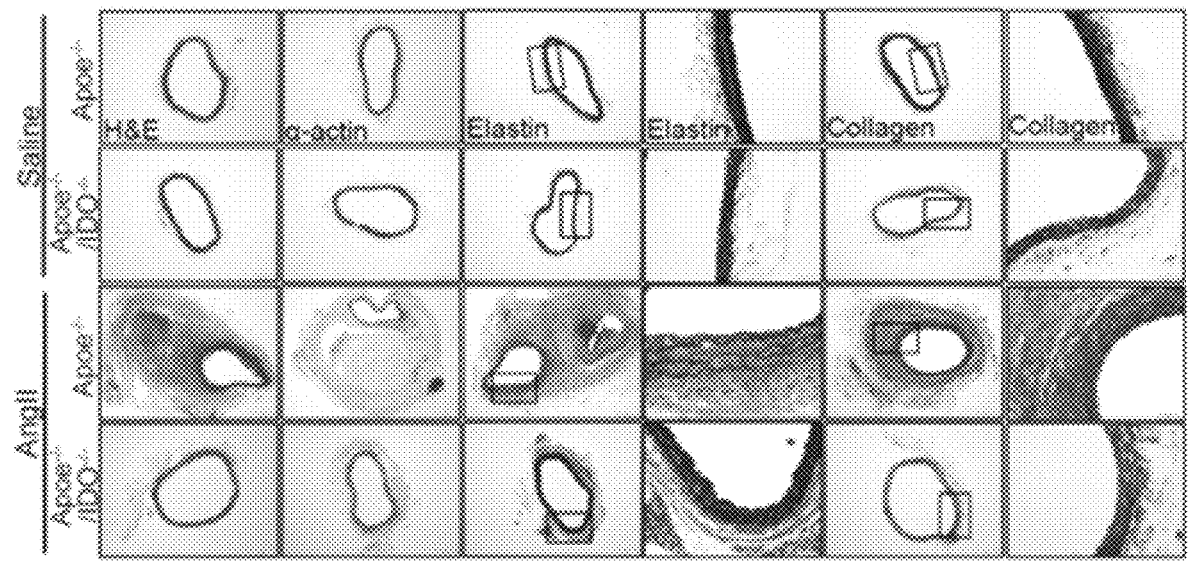
FIG. 1E shows representative staining with hematoxylin and eosin (H&E), α-actin, Van Gieson's (elastin), and Masson's Trichrome (collagen) in the suprarenal aortas of ApoE$^{-/-}$ and ApoE$^{-/-}$/IDO$^{-/-}$ mice after administration of saline or AngII (1000 ng/min per kg) for 4 weeks.
Figure 1F:
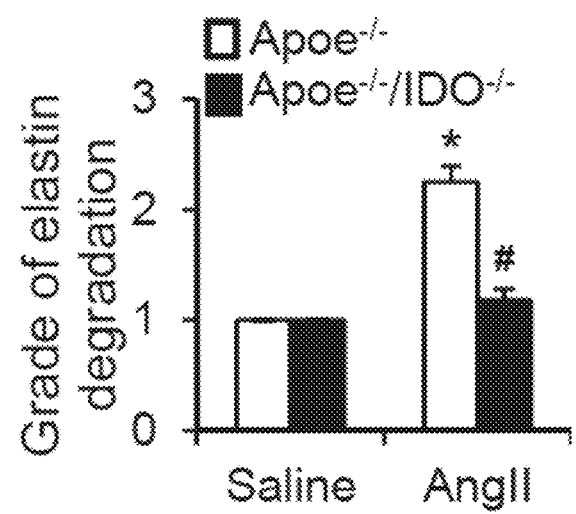
FIG. 1F is a bar graph that shows the grade of elastin degradation in ApoE$^{-/-}$ and ApoE$^{-/-}$/IDO$^{-/-}$ mice administered saline or AngII (1000 ng/min per kg) for 4 weeks. The x-axis shows the administration of saline or AngII, and the y-axis shows the grade of elastin degradation. P values were obtained by a $\chi^2$ test in band by a one-way analysis of variance (ANOVA) with a post hoc analysis using Bonferroni's multiple comparisons test. The error bars represent the standard error of the mean. *P<0.01 vs. saline-infused ApoE$^{-/-}$ mice, #P<0.01 vs. AngII-infused ApoE$^{-/-}$ mice. N=8 in each group of ApoE$^{-/-}$ and ApoE$^{-/-}$/IDO$^{-/-}$ mice infused with saline. n=15 for AngII-infused ApoE$^{-/-}$ mice. n=12 for AngII-infused ApoE$^{-/-}$/IDO$^{-/-}$ mice.
Figure 1G:
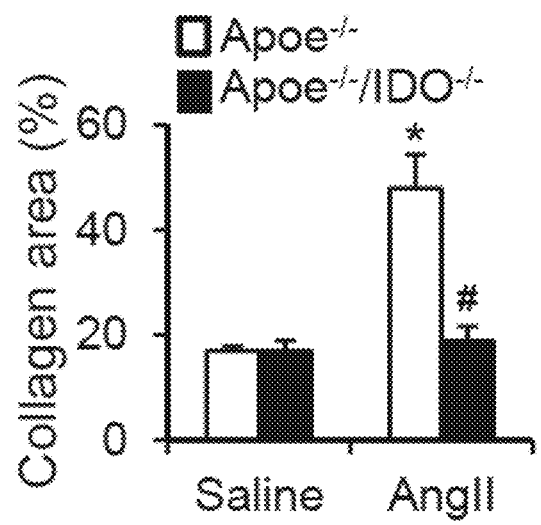
FIG. 1G is a bar graph that shows the amount of collagen deposition in ApoE$^{-/-}$ and ApoE$^{-/-}$/IDO$^{-/-}$ mice administered saline or AngII (1000 ng/min per kg) for 4 weeks. The x-axis shows the administration of saline or AngII, and the y-axis shows the collagen area in percent. P values were obtained by a $\chi^2$ test in band by a one-way analysis of variance (ANOVA) with a post hoc analysis using Bonferroni's multiple comparisons test. The error bars represent the standard error of the mean. *P<0.01 vs. saline-infused ApoE$^{-/-}$ mice, #P<0.01 vs. AngII-infused ApoE$^{-/-}$ mice. N=8 in each group of ApoE$^{-/-}$ and ApoE$^{-/-}$/IDO$^{-/-}$ mice infused with saline. n=15 for AngII-infused ApoE$^{-/-}$ mice. n=12 for AngII-infused ApoE$^{-/-}$/IDO$^{-/-}$ mice.

Morphologically, the aortas of saline-infused ApoE$^{-/-}$/IDO$^{-/-}$ mice did not differ from those of saline-infused control ApoE$^{-/-}$ mice (FIG. 1A). In line with previous reports (see Wang S, et al., Activation of AMP-activated protein kinase alpha2 by nicotine instigates formation of abdominal aortic aneurysms in mice in vivo. Nat Med. (2012) 18:902-10; Satoh K, et al., Cyclophilin A enhances vascular oxidative stress and the development of angiotensin II-induced aortic aneurysms. Nat Med. (2009) 15:649-56; Qin Z, et al., Angiotensin II-induced TLR4 mediated abdominal aortic aneurysm in apolipoprotein E knockout mice is dependent on STAT3. J Mol Cell Cardiol. (2015) 87:160-70), the incidence of AngII-induced AAA in ApoE$^{-/-}$ mice was 73% (FIGS. 1A and 1B). Both the maximal abdominal aortic diameter (FIG. 1C) and total aortic weight (FIG. 1D) were significantly higher in AngII-infused ApoE$^{-/-}$ mice than in saline-infused mice. Furthermore, the frequent disruption and increased degradation of elastic laminas were observed in AngII-infused ApoE$^{-/-}$ mice but not in saline-infused mice (FIGS. 1E and 1F). Markedly increased collagen deposition was also observed in AngII-infused ApoE$^{-/-}$ mice (FIGS. 1E and 1G).

In contrast, only 15% of AngII-infused ApoE$^{-/-}$/IDO$^{-/-}$ mice developed AAA (FIGS. 1A and 1B). The maximal abdominal aortic diameter (FIG. 1C) and total aortic weight (FIG. 1D) were remarkably reduced in AngII-treated ApoE$^{-/-}$/IDO$^{-/-}$ mice compared with AngII-treated ApoE$^{-/-}$ mice. Neither the aortic expansion nor the increased aortic thickness was observed in AngII-infused ApoE$^{-/-}$/IDO$^{-/-}$ mice (FIG. 1E). Moreover, AngII infusion in ApoE$^{-/-}$/IDO$^{-/-}$ mice did not cause aortic elastic lamina degradation or collagen deposition (FIGS. 1F and 1G). These results suggest that IDO deletion confers protection from AngII-induced AAA formation in ApoE$^{-/-}$ mice in vivo.

Example 2. IDO Deficiency Mitigates MMP2 Upregulation in AAA Mice

Figure 2A:
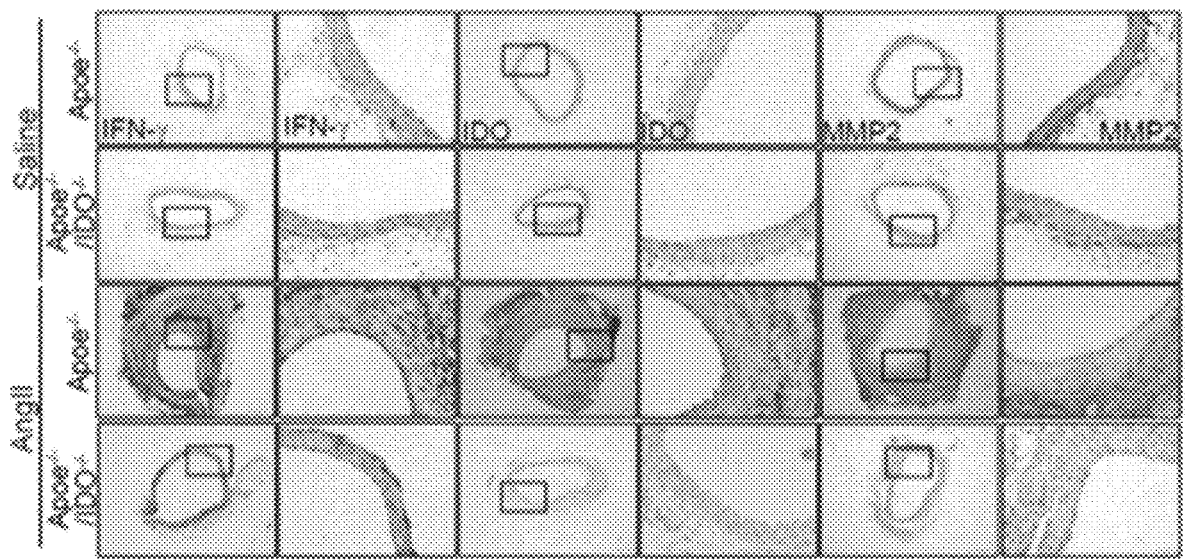
FIG. 2A shows representative immunohistochemical staining for interferon (IFN)-γ, IDO, and MMP2 in the suprarenal aortas of ApoE$^{-/-}$ and ApoE$^{-/-}$/IDO$^{-/-}$ mice administered saline or AngII (1000 ng/min per kg) for 4 weeks.
Figure 2B:
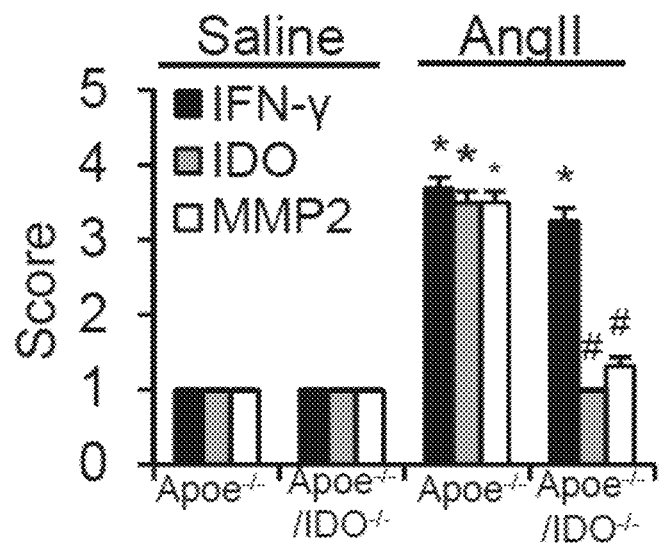
FIG. 2B is a bar graph that shows quantification of interferon (IFN)-γ, IDO, and MMP2 in the suprarenal aortas of ApoE$^{-/-}$ and ApoE$^{-/-}$/IDO$^{-/-}$ mice administered saline or AngII (1000 ng/min per kg) for 4 weeks. The x-axis shows the mouse genotype, and the y-axis shows the quantification score. *P<0.01 vs. saline-infused ApoE$^{-/-}$ mice, #P<0.01 vs. AngII-infused ApoE$^{-/-}$ mice. All results were obtained from 6-10 mice in each group. P values were obtained by a one-way ANOVA with a post hoc analysis using Bonferroni's multiple comparisons test. The error bars are standard error of the mean.
Figure 2C:
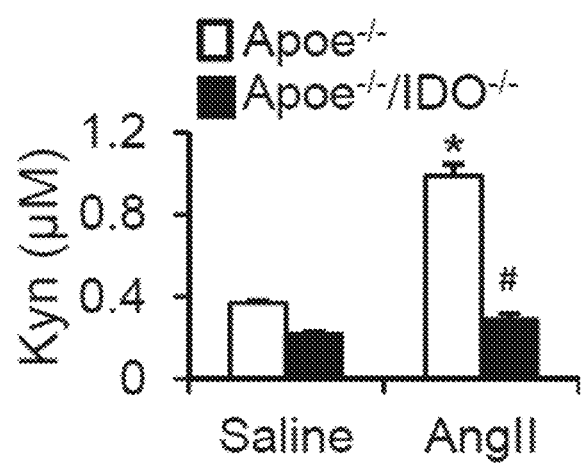
FIG. 2C is a bar graph that shows the serum concentration of Kyn detected in ApoE$^{-/-}$ and ApoE$^{-/-}$/IDO$^{-/-}$ mice administered saline or AngII (1000 ng/min per kg) for 4 weeks. The x-axis shows the administration of saline or AngII, and the y-axis shows micromolar Kyn concentration. *P<0.01 vs. saline-infused ApoE$^{-/-}$ mice, #P<0.01 vs. AngII-infused ApoE$^{-/-}$ mice. All results were obtained from 6-10 mice in each group. P values were obtained by a one-way ANOVA with a post hoc analysis using Bonferroni's multiple comparisons test. The error bars are standard error of the mean.
Figure 2D:
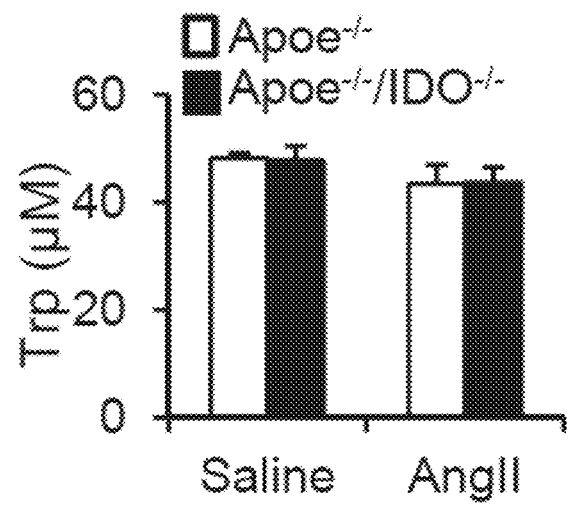
FIG. 2D is a bar graph that shows the serum concentration of tryptophan (Trp) detected in ApoE$^{-/-}$ and ApoE$^{-/-}$/IDO$^{-/-}$ mice administered saline or AngII (1000 ng/min per kg) for 4 weeks. The x-axis shows the administration of saline or AngII, and the y-axis shows micromolar Trp concentration. *P<0.01 vs. saline-infused ApoE$^{-/-}$ mice, #P<0.01 vs. AngII-infused ApoE$^{-/-}$ mice. All results were obtained from 6-10 mice in each group. P values were obtained by a one-way ANOVA with a post hoc analysis using Bonferroni's multiple comparisons test. The error bars are standard error of the mean.
Figure 2E:
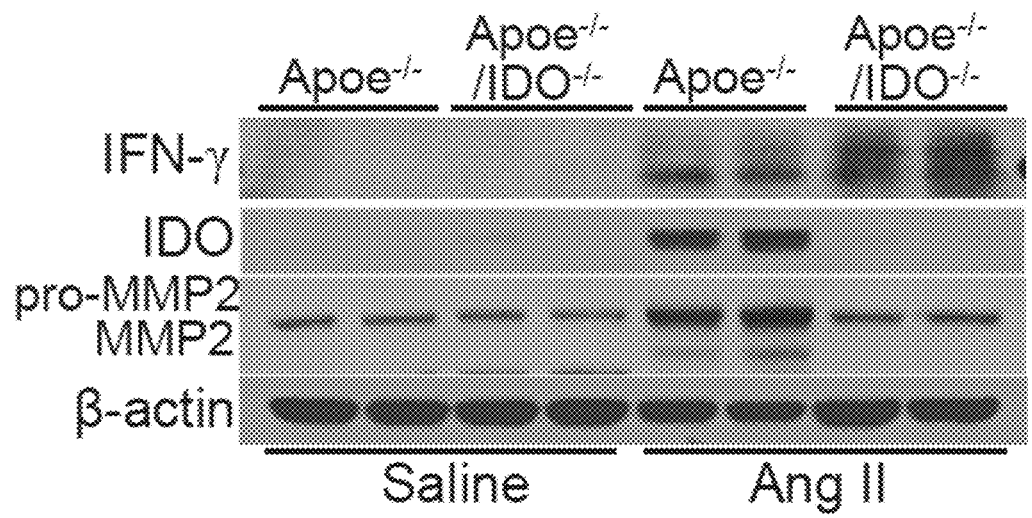
FIG. 2E shows protein expression of IFN-γ, IDO, and MMP2 in the suprarenal aortas of ApoE$^{-/-}$ and ApoE$^{-/-}$/IDO$^{-/-}$ mice administered saline or AngII (1000 ng/min per kg) for 4 weeks. Beta-actin was used as a loading control.

AngII infusion is intensely associated with vascular inflammation, which is considered a key mediator of AngII-induced AAA formation. See Qin Z, et al., Angiotensin II-induced TLR4 mediated abdominal aortic aneurysm in apolipoprotein E knockout mice is dependent on STAT3. J Mol Cell Cardiol. (2015) 87:160-70; Owens A P, et al., MyD88 deficiency attenuates angiotensin II-induced abdominal aortic aneurysm formation independent of signaling through Toll-like receptors 2 and 4. Arterioscler Thromb Vasc Biol. (2011) 31:2813-9. As shown in Table 3, serum concentrations of inflammatory cytokines, including interferon (IFN)-γ, tumor necrosis factor-α, interleukin-6, and cyclophilin A, are elevated in both AngII-infused ApoE$^{-/-}$ and ApoE$^{-/-}$/IDO-mice. These data indicate that IDO deletion does not alter AngII-induced inflammation. Previous studies demonstrated that IFN-γ mediates AngII-induced Kyn pathway activation in vivo. See Wang Q, et al., Activation of NAD(P)H Oxidase by Tryptophan-Derived 3-Hydroxykynurenine Accelerates Endothelial Apoptosis and Dysfunction In Vivo. Circ Res. (2014) 114:480-92. Similarly, an increase in IFN-γ expression was evident in the aortas of AngII-treated ApoE$^{-/-}$ and ApoE$^{-/-}$/IDO$^{-/-}$ mice. The consequent induction of IDO expression in the aortas of AngII-infused ApoE$^{-/-}$ mice was also observed (FIGS. 2A, 2B, and 2E). Accordingly, plasma levels of Kyn were significantly raised in AngII-infused ApoE$^{-/-}$ mice but not in IDO$^{-/-}$ mice (FIG. 2C), whereas AngII infusion did not alter plasma Trp levels in any mouse genotype (FIG. 2D). This may be due to the high content of Trp in mouse diets.

TABLE 3

Serum cytokine in AngII-infused mice.

| Groups | Saline | | AngII | |
|---|---|---|---|---|
| | Apoe-/- | Apoe-/-/IDO-/- | Apoe-/- | Apoe-/-/IDO-/- |
| IL-6 (pg/ml) | 6.38 ± 1.35 | 6.83 ± 1.13 | 20.07 ± 3.25* | 22.25 ± 5.45* |
| TNF-a (pg/ml) | 78.4 ± 8.6 | 83.1 ± 7.5 | 123.7 ± 18.2* | 118.5 ± 16.1* |
| CyPA (pM) | 486.7 ± 74.0 | 506.6 ± 72.0 | 771.8 ± 36.8* | 572.2 ± 42.7 |
| IFN-y (pg/ml) | 11.49 ± 2.23 | 11.24 ± 2.02 | 24.91 ± 1.75* | 28.32 ± 2.73* |

Figure 2F:
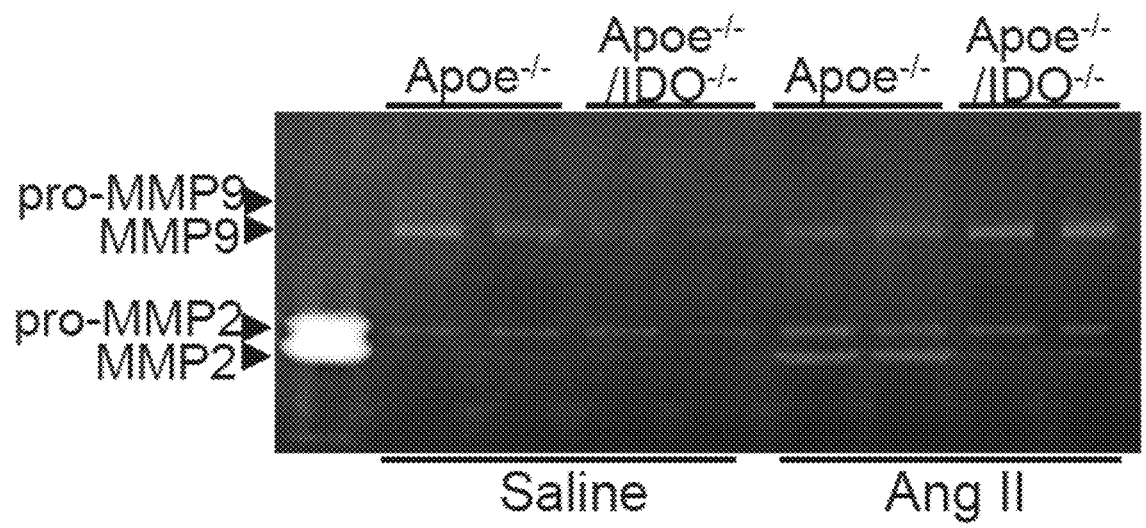
FIG. 2F is a zymogram that shows MMP2 activity in the suprarenal aortas of ApoE$^{-/-}$ and ApoE$^{-/-}$/IDO$^{-/-}$ mice administered saline or AngII (1000 ng/min per kg) for 4 weeks. Beta-actin was used as a loading control.

N is 6-10 in each group. Data are expressed by mean ± s.e.m.
*P < 0.05 compared to saline Apoe-/- mice MMPs play a key role in the initiation and progression of AAA. See Hellenthal F A, et al., Biomarkers of AAA progression. Part 1: extracellular matrix degeneration. Nature reviews Cardiology. (2009) 6:464-74. In particular, VSMC-derived MMP2 (Airhart N, et al., Smooth muscle cells from abdominal aortic aneurysms are unique and can independently and synergistically degrade insoluble elastin. J Vasc Surg. (2014) 60:1033-41; discussion 1041-2; Dilme J F, et al., Influence of cardiovascular risk factors on levels of matrix metalloproteinases 2 and 9 in human abdominal aortic aneurysms. European journal of vascular and endovascular surgery: the official journal of the European Society for Vascular Surgery. (2014) 48:374-81), and macrophage-derived MMP9 (Gong Y, et al., Inflammatory macrophage migration requires MMP-9 activation by plasminogen in mice. J Clin Invest. (2008) 118:3012-24) are critical for AAA development. Thus, IDO deletion effects on the levels of MMP2 and MMP9 in AngII-induced AAA formation was determined. MMP2 expression (FIGS. 2A, 2B, and 2E) and activity (FIG. 2F) were substantially increased in AngII-infused ApoE$^{-/-}$ mice. In contrast, the increases in MMP2 expression and activity were dramatically abrogated in the aortas of AngII-infused IDO-mice (FIGS. 2A, 2B, 2E, and 2F). However, IDO deletion did not alter the AngII-induced increase in MMP9 activity (FIG. 2F). Therefore, MMP2 seems to be the most predominant MMP inhibited by IDO deletion in AngII-induced AAA formation.

Example 3. Vascular IDO Deletion Inhibits AAA Formation

Figure 3A:
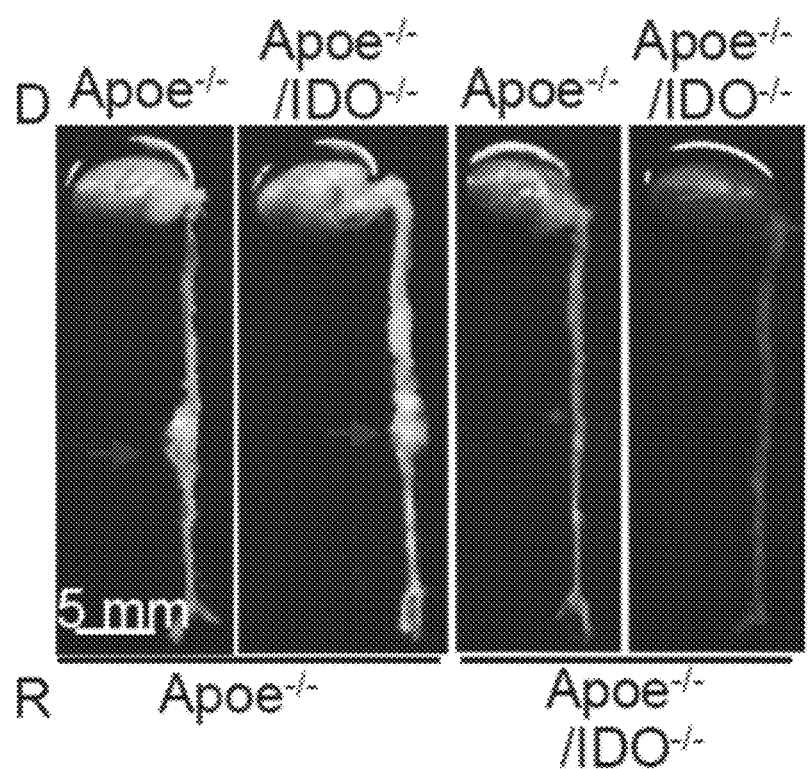
FIG. 3A depicts representative photographs of the macroscopic features of AngII-induced aneurysms in ApoE$^{-/-}$ and ApoE$^{-/-}$/IDO$^{-/-}$ mice reconstituted with ApoE$^{-/-}$ or ApoE$^{-/-}$/IDO$^{+/+}$ bone marrow cells, followed by 4 weeks of saline or AngII infusion (1000 ng/min per kg). Arrows indicate typical abdominal aortic aneurysm (AAA).
Figure 3B:
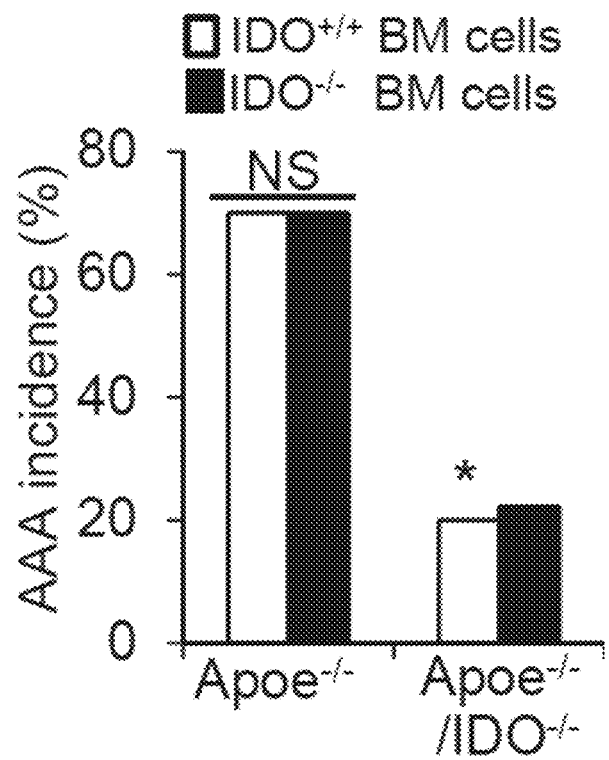
FIG. 3B is a bar graph that shows the incidence of AngII-induced AAA in ApoE$^{-/-}$ and ApoE$^{-/-}$/IDO$^{-/-}$ mice reconstituted with ApoE$^{-/-}$ or ApoE$^{-/-}$/IDO$^{+/+}$ bone marrow cells, followed by 4 weeks of saline or AngII infusion (1000 ng/min per kg). The x-axis shows the mouse genotype, and the y-axis shows the AAA incidence in percent. N=10-15 per group. BM, bone marrow; NS, not significant. *P<0.01 vs. AngII-infused ApoE$^{-/-}$ mice reconstituted with ApoE$^{-/-}$/IDO$^{+/+}$ bone marrow cells.

Based on the above-mentioned data, we postulated that the activation of the Kyn pathway in VSMCs promotes AAA formation. To test this hypothesis, reciprocal bone marrow transplants between ApoE$^{-/-}$ and ApoE$^{-/-}$/IDO$^{-/-}$ mice were performed, in which bone marrow cells were transplanted into irradiated mice. After 6 weeks of engraftment, transplanted mice were treated with AngII (1000 ng/min per kg) for 4 weeks. This led to the formation of AAAs in ApoE$^{-/-}$ mice transplanted with either IDO$^{-/-}$ or IDO$^{+/+}$ bone marrow cells, with a similar incidence of approximately 70% (FIGS. 3A and 3B). In contrast, an inhibition of AAA formation (20% incidence) was observed in ApoE$^{-/-}$/IDO$^{-/-}$ mice transplanted with either IDO$^{-/-}$ or IDO$^{+/+}$ bone marrow cells (FIGS. 3A and 3B).

Figure 3C:
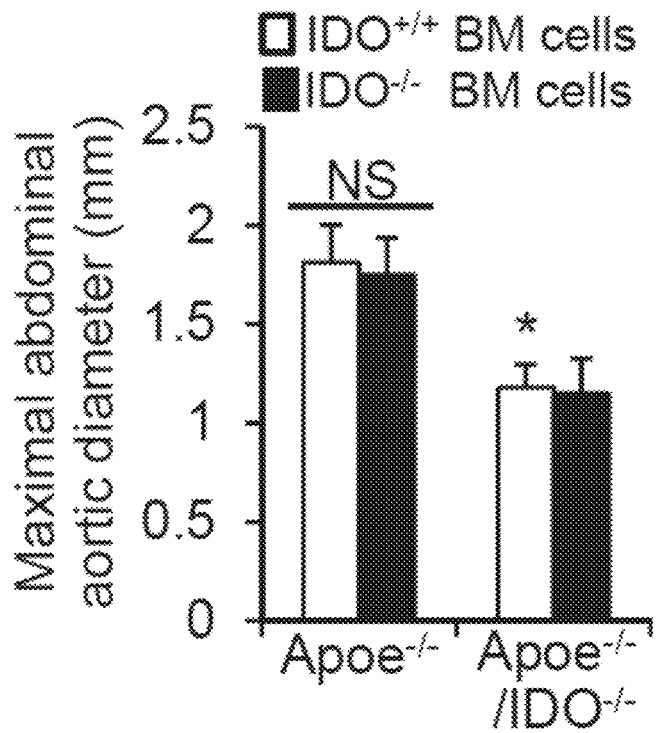
FIG. 3C is a bar graph that shows the maximal abdominal aortic diameter in ApoE$^{-/-}$ and ApoE$^{-/-}$/IDO$^{-/-}$ mice reconstituted with ApoE$^{-/-}$ or ApoE$^{-/-}$/IDO$^{+/+}$ bone marrow cells, followed by 4 weeks of saline or AngII infusion (1000 ng/min per kg). The x-axis shows the mouse genotype, and the y-axis shows the maximal abdominal aortic diameter in millimeters. N=10-15 per group. BM, bone marrow; NS, not significant. *P<0.01 vs. AngII-infused ApoE$^{-/-}$ mice reconstituted with ApoE$^{-/-}$/IDO$^{+/+}$ bone marrow cells. P values were obtained by a $\chi^2$ test in band by a one-way ANOVA with a post hoc analysis using Bonferroni's multiple comparisons test. The error bars are standard error of the mean.
Figure 3D:
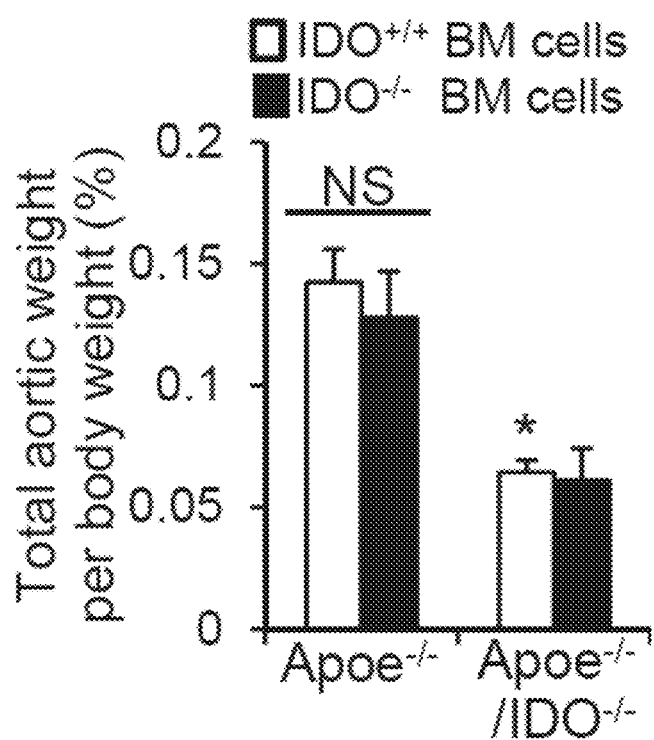
FIG. 3D is a bar graph that shows the total aortic weight in ApoE$^{-/-}$ and ApoE$^{-/-}$/IDO$^{-/-}$ mice reconstituted with ApoE$^{-/-}$ or ApoE$^{-/-}$/IDO$^{+/+}$ bone marrow cells, followed by 4 weeks of saline or AngII infusion (1000 ng/min per kg). The x-axis shows the mouse genotype, and the y-axis shows the total aortic weight per body weight in percent. N=10-15 per group. BM, bone marrow; NS, not significant. *P<0.01 vs. AngII-infused ApoE$^{-/-}$ mice reconstituted with ApoE$^{-/-}$/IDO$^{+/+}$ bone marrow cells. P values were obtained by a $\chi^2$ test in band by a one-way ANOVA with a post hoc analysis using Bonferroni's multiple comparisons test. The error bars are standard error of the mean.

No differences in the maximal abdominal aortic diameter (FIG. 3C) and total aortic weight (FIG. 3D) were observed between mice transplanted with IDO$^{-/-}$ bone marrow cells and mice transplanted with IDO$^{+/+}$ bone marrow cells. These data suggest that IDO deficiency in vascular cells, rather than bone marrow-derived cells, is crucial for the development of AAA.

Figure 9A:
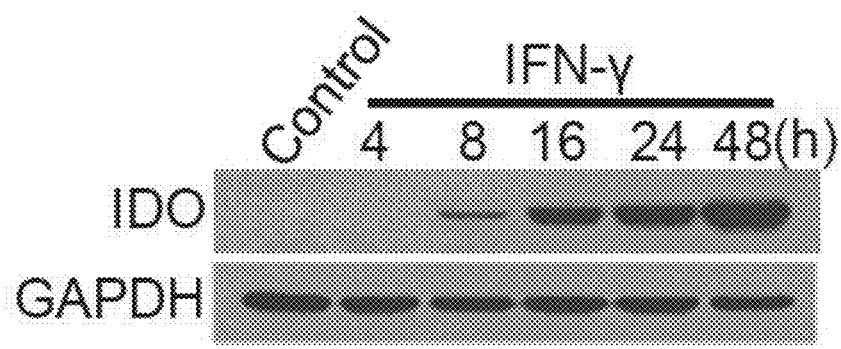
FIG. 9A is an immunoblot that shows detection of IDO and GAPDH proteins in cultured HASMC that were incubated with 100 μM IFN-γ for the indicated time. 3 independent experiments were performed for all data.
Figure 9B:
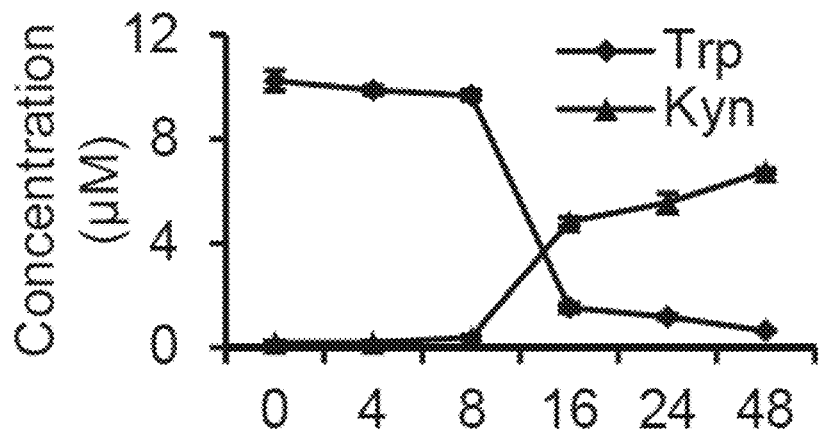
FIG. 9B is a line graph that shows the Trp and Kyn levels as detected by HPLC in cultured HASMC that were incubated with 100 μM IFN-γ for the indicated time. The x-axis shows time in hours, and the y-axis shows micromolar concentration. 3 independent experiments were performed for all data. The P values were obtained by a one-way ANOVA plus a post hoc analysis using Bonferroni's multiple comparisons test. The error bars are standard error of the mean.
Figure 9C:
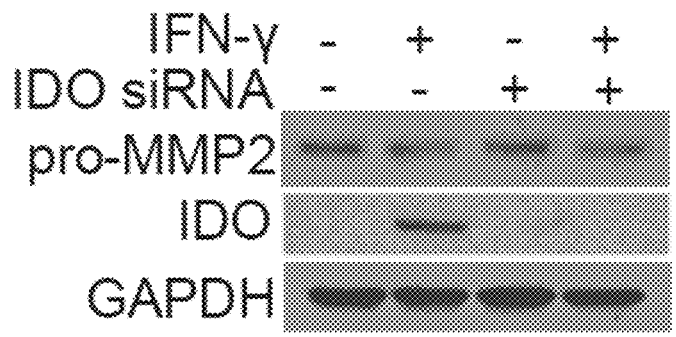
FIG. 9C is an immunoblot that shows detected of Pro-MMP2, Trp, and Kyn proteins in cultured HASMC transfected with control siRNA or IDO siRNA treated with or without IFN-γ for 48 hours. 3 independent experiments were performed for all data.
Figure 9D:
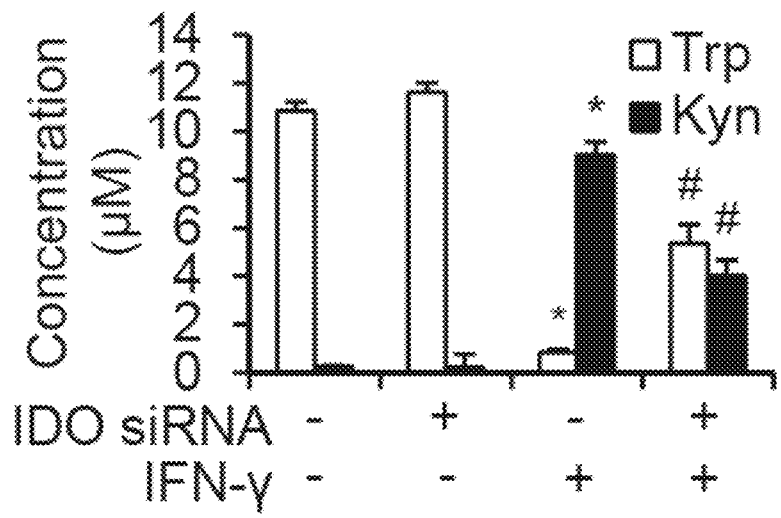
FIG. 9D is a bar graph that shows Trp and Kyn levels as detected by HPLC in cultured HASMC transfected with control siRNA or IDO siRNA treated with or without IFN-γ for 48 hours. The x-axis shows administration of IDO siRNA and IFN-γ, and the y-axis shows micromolar concentration. 3 independent experiments were performed for all data. *P<0.01 vs control siRNA without IFN-γ treatment, #P<0.01 vs control siRNA with IFN-γ treatment. The P values were obtained by a one-way ANOVA plus a post hoc analysis using Bonferroni's multiple comparisons test. The error bars are standard error of the mean.
Figure 10A:
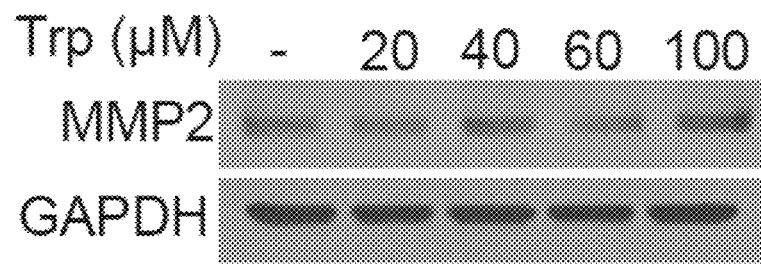
FIG. 10A is an immunoblot that shows detection of Pro-MMP2 and GAPDH in cultured HASMC that were incubated with the indicated concentrations of Trp for 48 hours.
Figure 10B:
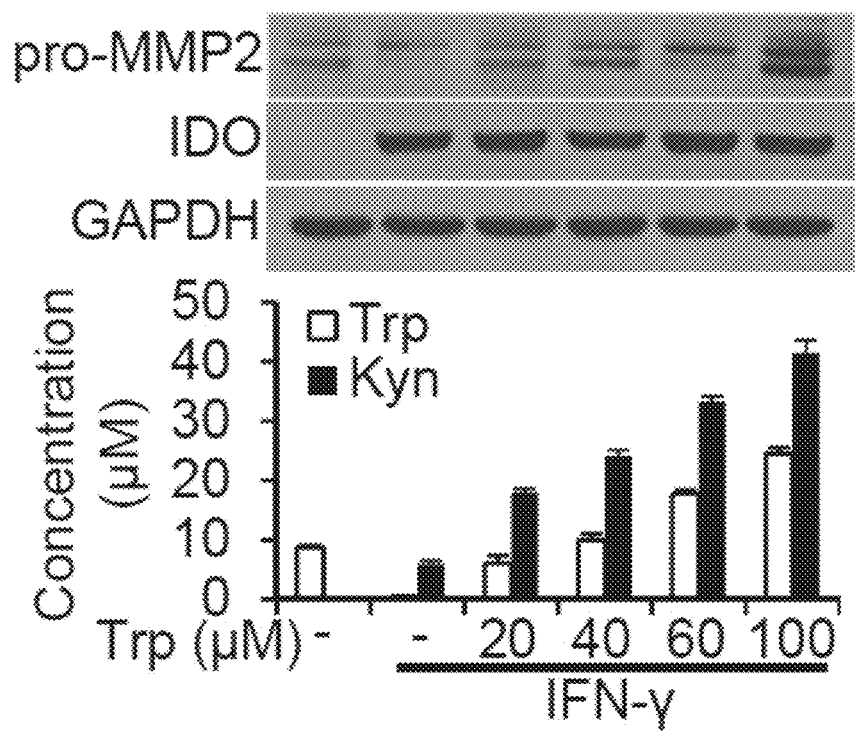
FIG. 10B is an immunoblot that shows detection of Pro-MMP2, IDO, and GAPDH proteins in cultured HASMC that were either untreated (control) or treated with IFN-γ combined with the indicated concentrations of exogenous Trp for 48 hours, and a bar graph that shows the Trp and Kyn levels in the culture medium as detected by HPLC. The x-axis of the bar graph shows the micromolar concentration of Trp administered with or with IFN-γ, and the y-axis of the bar graph shows the micromolar concentration of Trp and Kyn. The error bars are standard error of the mean.
Figure 10C:
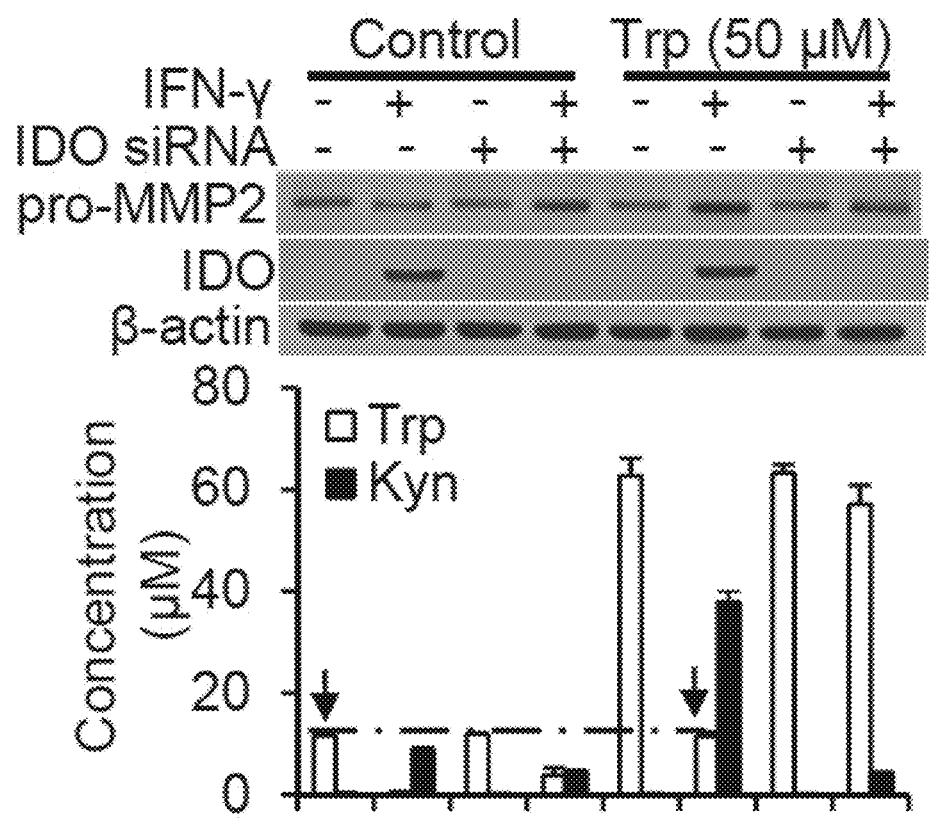
FIG. 10C is an immunoblot that shows detected of Pro-MMP2, IDO, and beta-actin in cultured HASMC transfected with control siRNA or IDO siRNA that were treated with vehicle (control) or IFN-γ with or without addition of 50 μM Trp for 48 hours, and a bar graph that shows the Trp and Kyn levels in the culture medium as detected by HPLC. The x-axis of the bar graph shows administration of IFN-γ, IDO siRNA, and Trp, and the y-axis of the bar graph shows micromolar concentration of Trp and Kyn. The error bars are standard error of the mean.
Figure 10D:
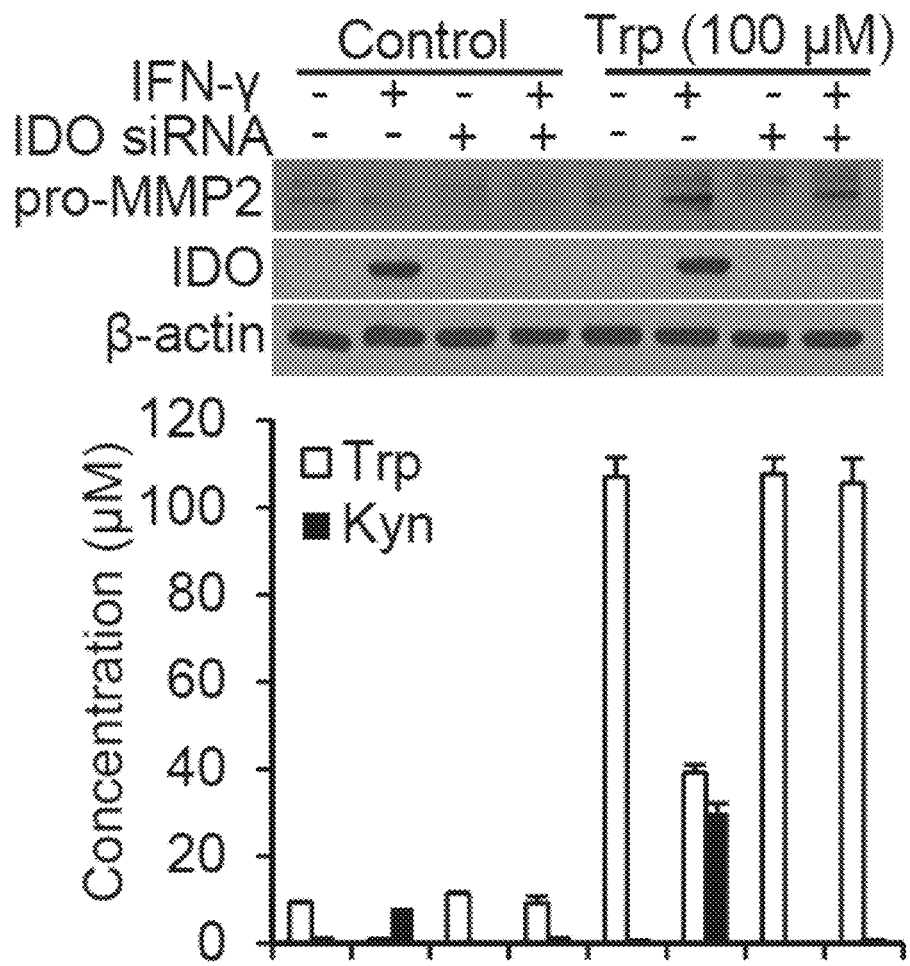
FIG. 10D is an immunoblot that shows detected Pro-MMPS, IDO, and beta-actin in cultured HASMC transfected with control siRNA or IDO siRNA that were treated with vehicle (control) or IFN-γ with or without addition of 100 μM Trp for 48 hours, and a bar graph that shows the Trp and Kyn levels in the culture medium as detected by HPLC. The x-axis of the bar graph shows administration of IFN-γ, IDO siRNA, and Trp, and the y-axis shows micromolar concentration of Trp and Kyn. The error bars are standard error of the mean.

Example 4. IFN-γ-Induced MMP2 Expression with Additional Trp in Human Aortic Smooth Muscle Cells (HASMCs) is IDO Dependent Next, we determined if Kyn pathway activation regulates MMP2 expression in HASMCs. As depicted in FIG. 9A, IFN-γ (100 nM) powerfully induces IDO expression in HASMCs in a time-dependent manner. IFN-γ also induced the formation of Kyn and the consumption of Trp in the supernatant as a time dependent manner (FIG. 9B). Interestingly, Trp was almost used up by the cells after 48 hours of treatment. HASMCs were then transfected with or without IDO siRNA for 48 hours and treated with IFN-γ (100 nM). Unexpectedly, MMP2 protein expression was decreased, along with IDO induction (FIG. 9C), whereas the increase in Kyn in the culture medium was accompanied by Trp depletion (FIG. 9D). Trp depletion has been shown to inhibit MMP expression in human fibroblasts (Varga J, et al., Control of extracellular matrix degradation by interferon-gamma. The tryptophan connection. Adv Exp Med Biol. (1996) 398:143-8) and to halt cell cycle progression in T cells (Munn D H, et al., Inhibition of T cell proliferation by macrophage tryptophan catabolism. J Exp Med. (1999) 189:1363-72). However, no reductions in Trp were observed in AngII-infused ApoE$^{-/-}$ mice (FIG. 2D). Therefore, different concentrations of exogenous Trp were supplemented in the culture medium of HASMCs with IFN-γ treatment for 48 hours to mimic the in vivo environment. MMP2 expression was markedly upregulated in HASMCs exposed to IFN-γ and >40 μM Trp (FIG. 10B), whereas Trp addition did not alter MMP2 expression in HASMCs without IFN-γ (FIG. 10A). Meanwhile, Kyn formation was intensely amplified in the presence of excessive Trp in the culture medium of IFN-γ-treated HASMCs (FIG. 10B). Three-fold increases in Kyn were detected in the supernatant of IFN-γ-treated, Trp-supplemented (100 μM) HASMCs, compared with that in IFN-γ-treated HASMCs. When 50 μM Trp was added to the culture medium of IFN-γ-treated HASMCs, Trp levels were restored to control levels, and MMP2 expression was increased along with IDO induction (FIG. 10C). These results suggest that IFN-γ induces MMP2 expression in vitro when sufficient amounts of Trp are present. As expected, IDO knockdown significantly inhibited IFN-γ-induced MMP2 expression, even in the presence of additional Trp (FIG. 10C). This was further confirmed in IFN-γ-treated HASMCs with the addition of 100 μM Trp (FIG. 10D).

Figure 4A:
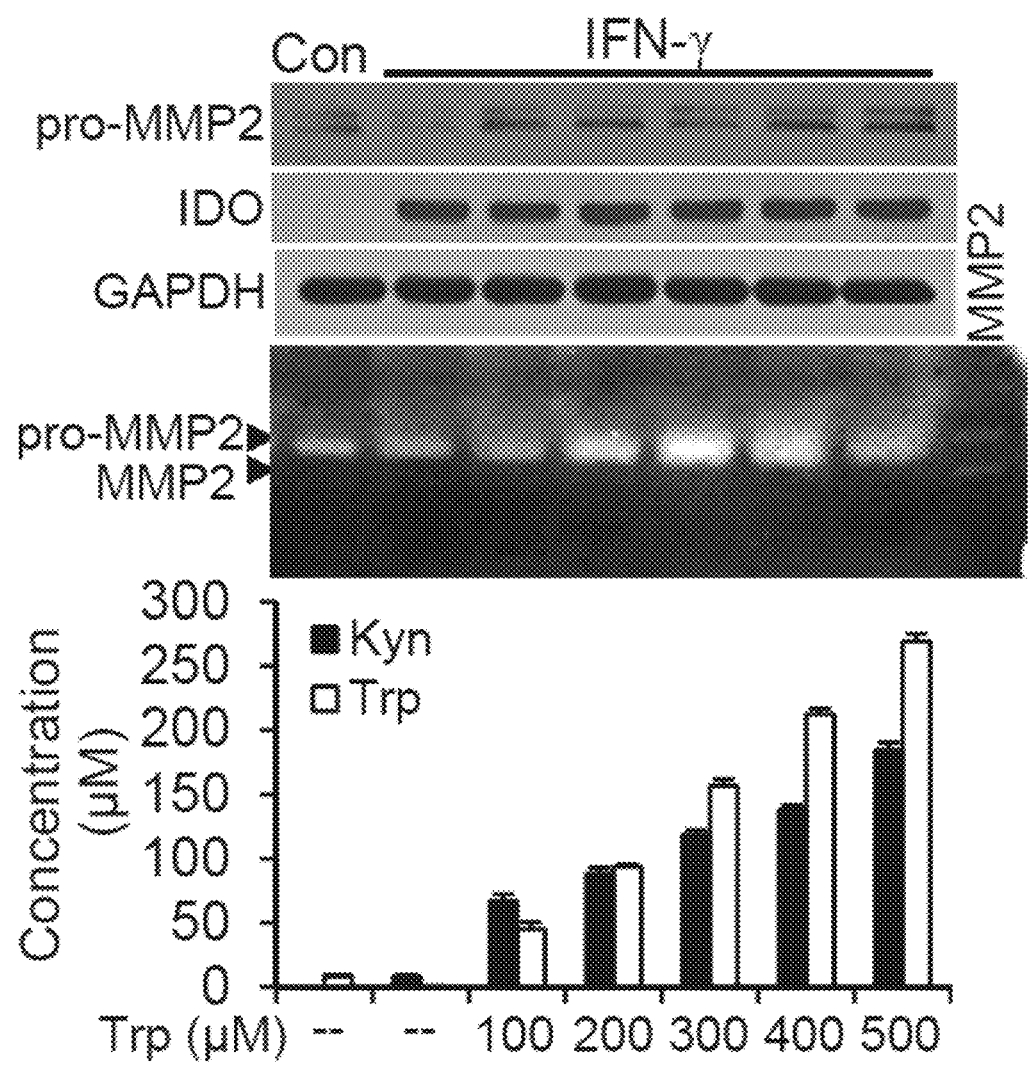
FIG. 4A is an immunoblot, zymogram, and bar graph for cultured HASMCs that were either untreated (control; Con) or treated with IFN-γ combined with the indicated concentrations of exogenous Trp for 48 hours. Pro-MMP2, IDO, and glyceraldehyde-3-phosphate dehydrogenase (GAPDH) proteins were detected by immunoblotting. MMP2 activities in the culture medium were detected by zymography. Trp and Kyn levels in the culture medium were detected by high-performance liquid chromatography (HPLC). Three independent experiments were performed for all quantitative data. The error bars are standard error of the mean.
Figure 4B:
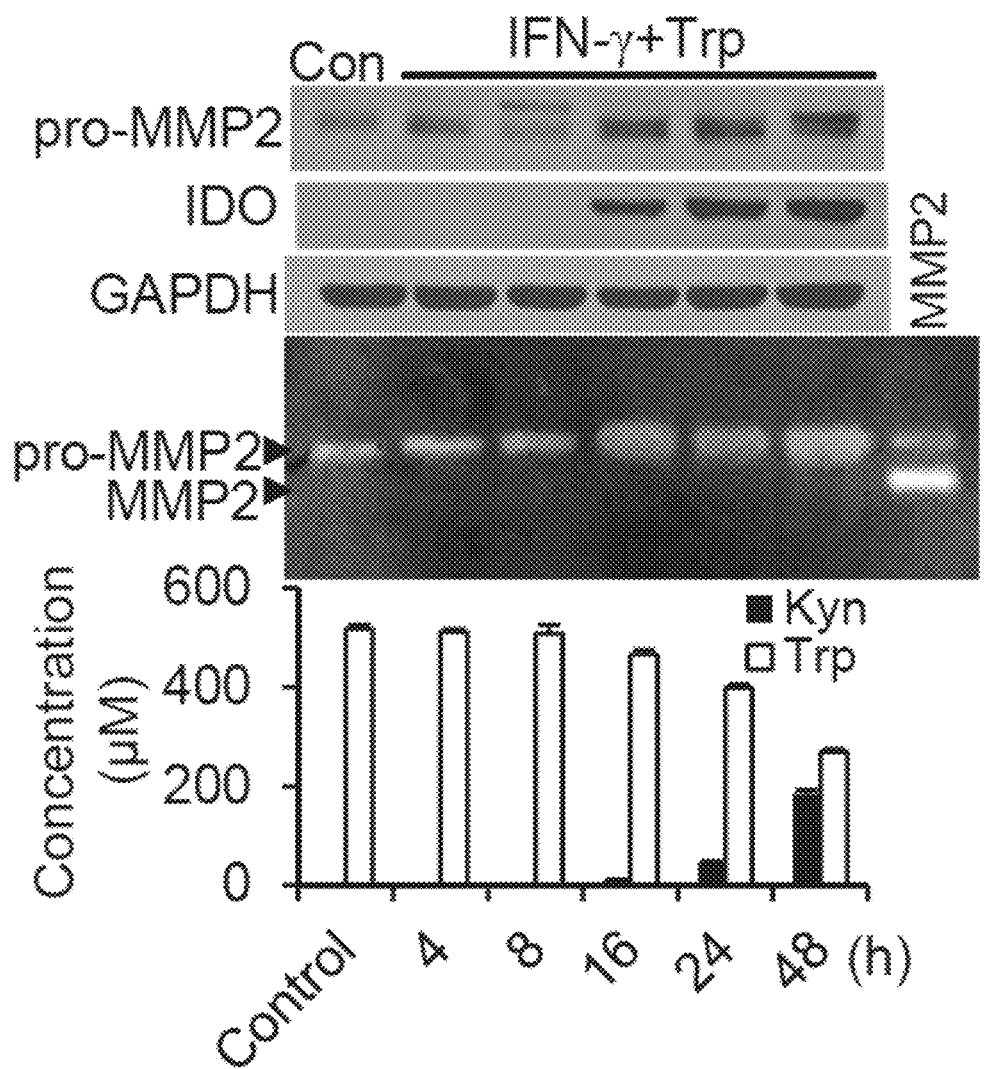
FIG. 4B is an immunoblot, zymogram, and bar graph for cultured HASMCs that were either untreated (control; Con) or treated with IFN-γ and 500 μM Trp for 48 hours. Pro-MMP2, IDO, and glyceraldehyde-3-phosphate dehydrogenase (GAPDH) proteins were detected by immunoblotting. MMP2 activities in the culture medium were detected by zymography. Trp and Kyn levels in the culture medium were detected by high-performance liquid chromatography (HPLC). Three independent experiments were performed for all quantitative data. The error bars are standard error of the mean.
Figure 4C:
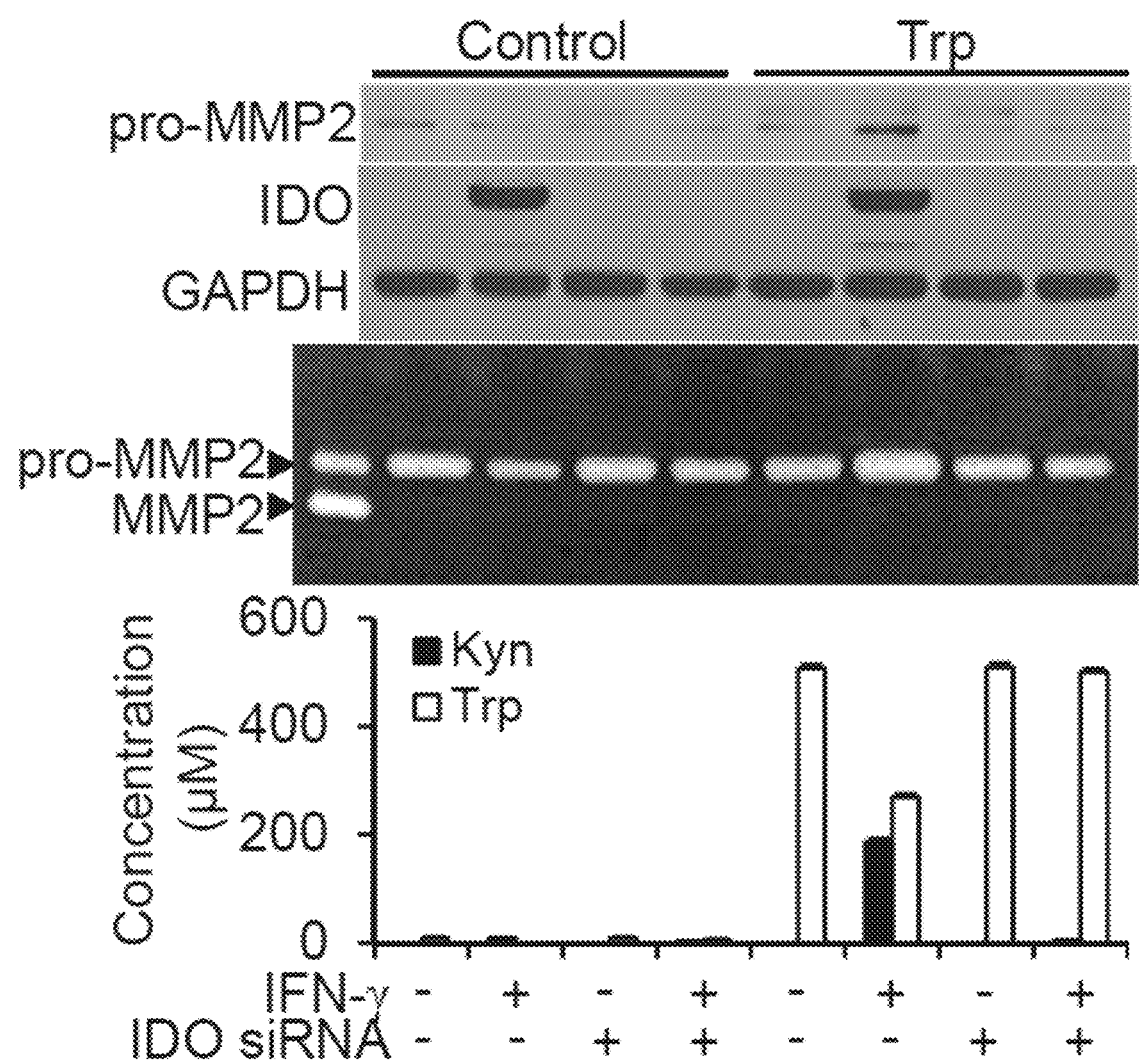
FIG. 4C is an immunblot, zymogram, and bar graph for HASMCs that were transfected with control siRNA or IDO siRNA and treated with DMSO (control) or IFN-γ in the presence of absence of 500 μM Trp for 48 hours. Pro-MMP2, IDO, and glyceraldehyde-3-phosphate dehydrogenase (GAPDH) proteins were detected by immunoblotting. MMP2 activities in the culture medium were detected by zymography. Trp and Kyn levels in the culture medium were detected by high-performance liquid chromatography (HPLC). Three independent experiments were performed for all quantitative data. The error bars are standard error of the mean.
Figure 10E:
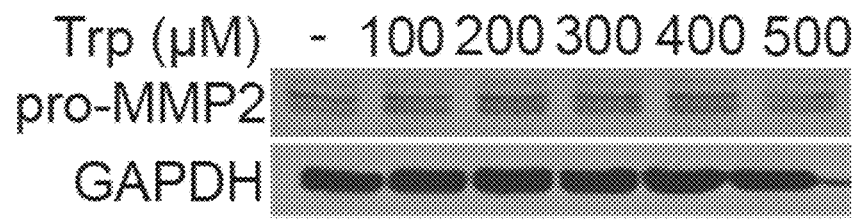
FIG. 10E is an immunoblot that shows detection of Pro-MMP2 and GAPDH in cultured HASMC that were incubated with the indicated concentrations of Trp for 48 hours.

Hypertryptophanemia (Martin J R, et al., Familial hypertryptophanemia in two siblings. Clin Genet. (1995) 47:180: Andrade V S, et al., Creatine and pyruvate prevent behavioral and oxidative stress alterations caused by hypertryptophanemia in rats. Molecular and cellular biochemistry. (2012) 362:225-32) is a rare autosomal recessive metabolic disorder that results in a massive buildup of Trp in the blood (Becerra A, et al., Increased activity of indoleamine 2,3-dioxygenase in serum from acutely infected dengue patients linked to gamma interferon antiviral function. J Gen Virol. (2009) 90:810-7; Kiank C, et al., Psychological stress-induced, IDO1-dependent tryptophan catabolism: implications on immunosuppression in mice and humans. PLoS One. (2010) 5: e11825). The addition of 500 μM Trp to HASMCs did not affect MMP2 expression (FIG. 10E). However, MMP2 expression, MMP2 activity, and Kyn formation in the supernatant were increased in IFN-γ-treated HASMCs supplemented with Trp in a concentration- and time-dependent manner (FIGS. 4A and 4B). In addition, no further increases in Kyn were detected in the supernatant of IFN-γ-treated HASMCs supplemented with >500 μM Trp (data not shown). Concomitantly, the upregulation of MMP2 by IFN-γ with 500 μM exogenous Trp was blocked by IDO deletion (FIG. 4C). These results suggest that Kyn pathway activation potently promotes MMP2 expression and activity in HASMCs in vitro, thus indicating that Trp-derived Kyns may directly induce a concentration- and time-dependent induction of MMP2.

Example 5. 3-HAA Promotes MMP2 Expression in HASMCs

Figure 5A:
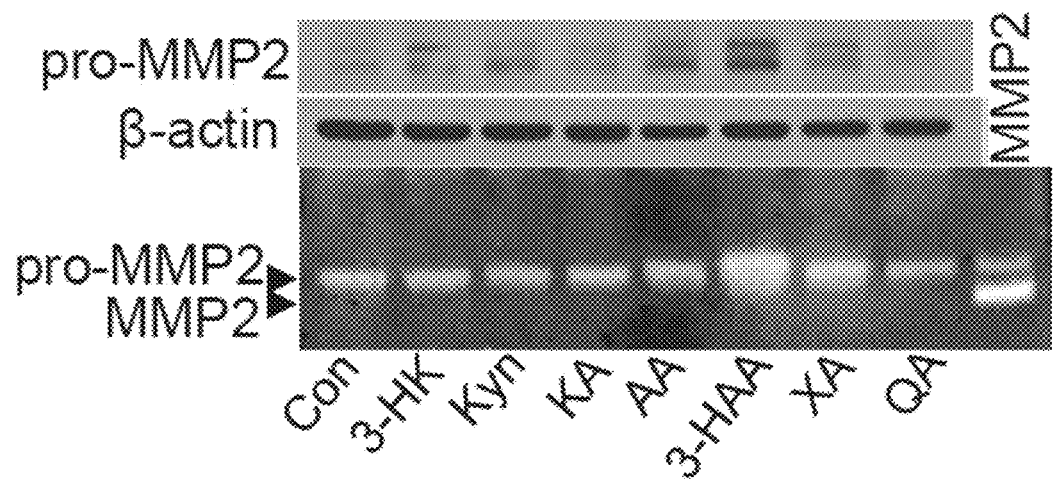
FIG. 5A is an immunoblot and zymogram for cultured HASMCs that were either untreated (control; Con) or treated with the indicated metabolites of Trp degradation (Kyn: 100 μM; 3-hydroxykynurenine [3-HK]: 100 M; kynurenic acid [KA]: 75 M; anthranilic acid [AA]: 100 M; 3-HAA: 200 M; xanthurenic acid [XA]: 200 M; quinolinic acid [QA]: 1 mM) for 48 hours. Pro-MMP2 was detected by immunoblotting. Beta-actin was used as a loading control, and MMP2 activities in the culture medium were detected by zymography. Representative data from three independent experiments are shown.
Figure 5B:
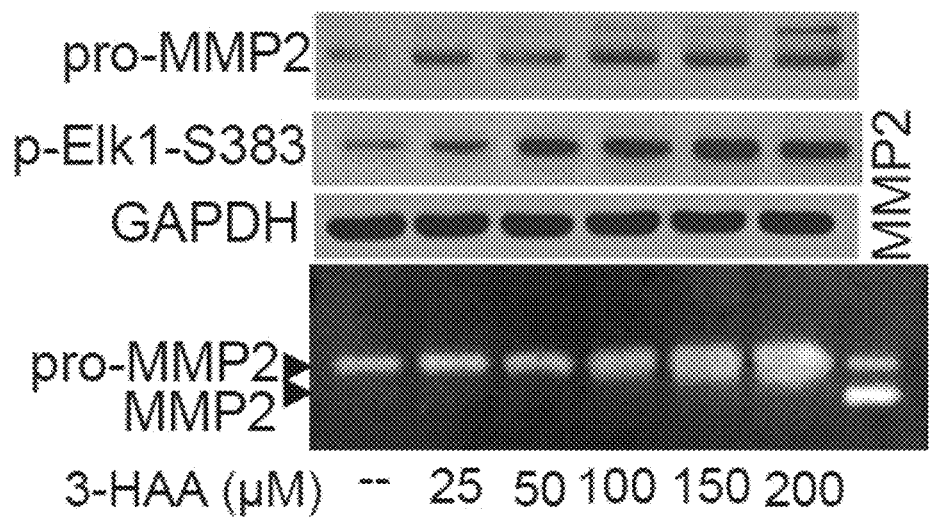
FIG. 5B is an immunoblot and zymogram for cultured HASMCs that were incubated with the indicated concentrations of 3-HAA for 48 hours. Pro-MMP2 and phosphorylated (p)-Elk1 were detected by immunoblotting. GAPDH was used as a loading control, and MMP2 activities in the culture medium were detected by zymography. Representative data from three independent experiments are shown.
Figure 5C:
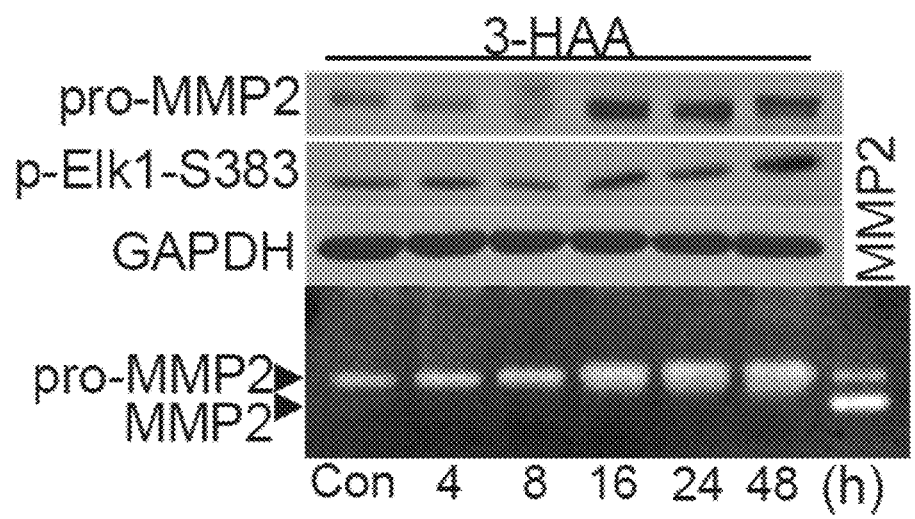
FIG. 5C is an immunoblot and zymogram for cultured HASMCs that were incubated with 200 μM 3-HAA for the indicated time points. Pro-MMP2 and p-Elk1 were detected by immunoblotting. GAPDH was used as a loading control, and MMP2 activities in the culture medium were detected by zymography. Representative data from three independent experiments are shown.

To identify Kyn pathway catabolites that upregulate MMP2, the expression and activity of MMP2 were detected in HASMCs incubated with major exogenous metabolites (Wang Q, et al., Tryptophan-kynurenine pathway is dysregulated in inflammation, and immune activation. Frontiers in bioscience (Landmark edition). (2015) 20:1116-43; Kiank C, et al., Psychological stress-induced, IDO1-dependent tryptophan catabolism: implications on immunosuppression in mice and humans. PLoS One. (2010) 5: e1182) of Trp degradation. A dramatic increase in MMP2 expression and activity was observed with 3-HAA (Polyzos K A, et al., Inhibition of indoleamine 2,3-dioxygenase promotes vascular inflammation and increases atherosclerosis in ApoE$^{-/-}$ mice. Cardiovasc Res. (2015) 106:295-302; Zhang L, et al., The tryptophan metabolite 3-hydroxyanthranilic acid lowers plasma lipids and decreases atherosclerosis in hypercholesterolaemic mice. Eur Heart J. (2012) 33:2025-34; Yan Y, et al., IDO upregulates regulatory T cells via tryptophan catabolite and suppresses encephalitogenic T cell responses in experimental autoimmune encephalomyelitis. J Immunol. (2010) 185:5953-61; Krause D, et al., The tryptophan metabolite 3-hydroxyanthranilic acid plays anti-inflammatory and neuroprotective roles during inflammation: role of hemeoxygenase-1. Am J Pathol. (2011) 179:1360-72), but not with Kyn (Wang Q, et al., Activation of NAD(P)H Oxidase by Tryptophan-Derived 3-Hydroxykynurenine Accelerates Endothelial Apoptosis and Dysfunction In Vivo. Circ Res. (2014) 114:480-92), 3-HK (Wang Q, et al., Activation of NAD(P)H Oxidase by Tryptophan-Derived 3-Hydroxykynurenine Accelerates Endothelial Apoptosis and Dysfunction In Vivo. Circ Res. (2014) 114:480-92), kynurenic acid (KA) (Klein C, et al., The neuroprotector kynurenic acid increases neuronal cell survival through neprilysin induction. Neuropharmacology. (2013) 70:254-60), AA (Terness P, et al., Inhibition of allogeneic T cell proliferation by indoleamine 2,3-dioxygenase-expressing dendritic cells: mediation of suppression by tryptophan metabolites. J Exp Med. (2002) 196:447-57), xanthurenic acid (XA) (Malina H Z, et al., Pathological apoptosis by xanthurenic acid, a tryptophan metabolite: activation of cell caspases but not cytoskeleton breakdown. BMC Physiol. (2001) 1:7), or quinolinic acid (QA) (Hayashi T, et al., 3-Hydroxyanthranilic acid inhibits PDK1 activation and suppresses experimental asthma by inducing T cell apoptosis. Proc Natl Acad Sci USA. (2007) 104:18619-24) (FIG. 5A). Furthermore, 3-HAA induced the expression and activity of MMP2, as well as the phosphorylation of Elk1 at Ser383, in a concentration- and time-dependent manner (FIGS. 5B and 5C). Elk1 is an important transcriptional factor for MMP2 expression (Mahmoodzadeh S, et al., 17beta-Estradiol inhibits matrix metalloproteinase-2 transcription via MAP kinase in fibroblasts. Cardiovasc Res. (2010) 85:719-28).

Example 6. Elimination of Endogenous 3-HAA Blocks MMP2 Induction in HASMCs

Following its synthesis by IDO in certain cell types, Kyn can be further metabolized by kynurenine-3-monooxygenase into 3-HK, which is catabolized by KNU to form 3-HAA (Wang Q, et al., Tryptophan-kynurenine pathway is dysregulated in inflammation, and immune activation. Frontiers in bioscience (Landmark edition). (2015) 20:1116-43).

Figure 5D:
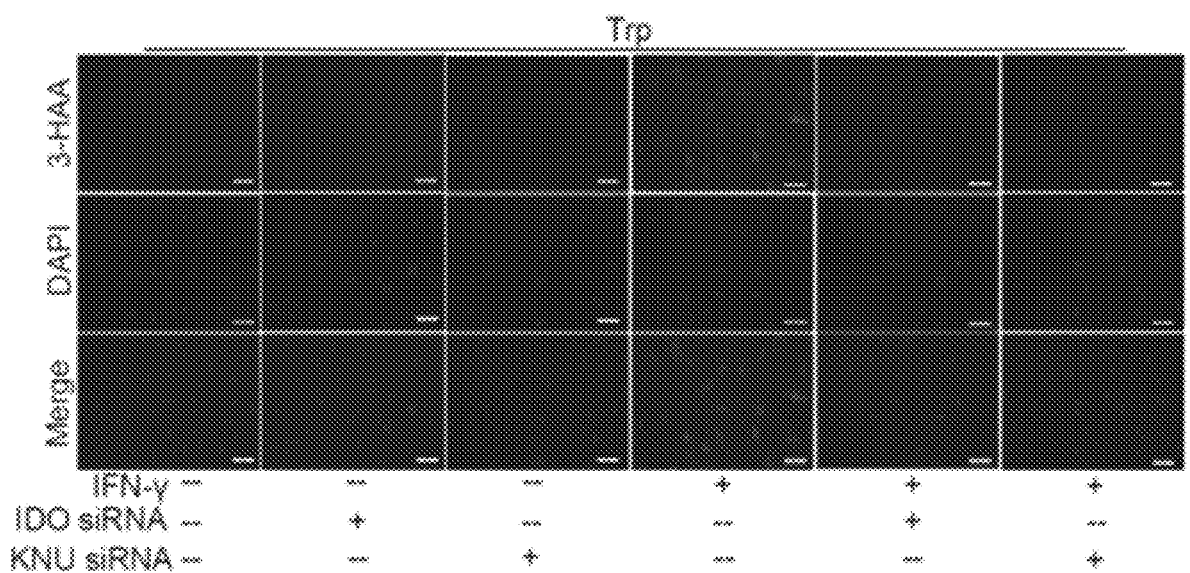
FIG. 5D shows cultured HASMCs that were transfected with control siRNA, IDO siRNA, or kynureninase (KYNU) siRNA and treated with vehicle (control) or IFN-γ with the addition of 500 μM Trp for 48 hours. A conjugated 3-HAA antibody was used to detected endogenous 3-HAA in HASMCs, and cells were counterstained with a nuclear stain (DAPI).
Figure 5E:
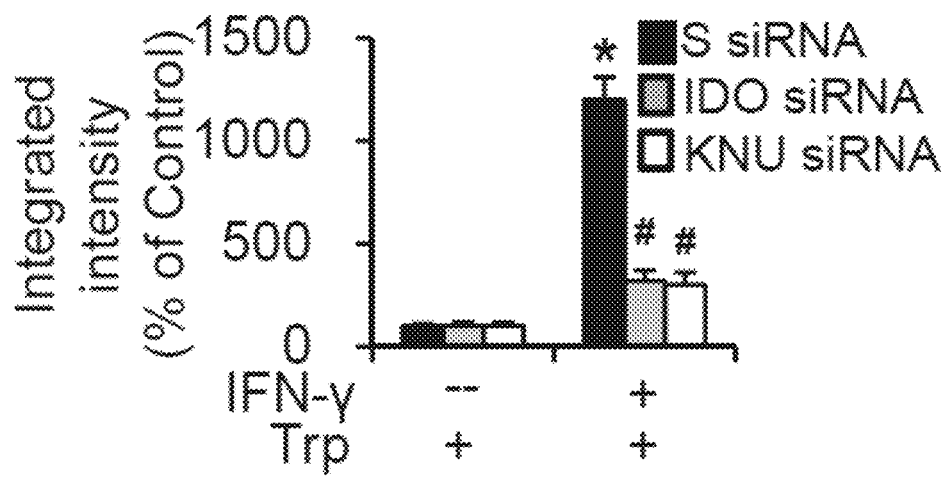
FIG. 5E is a bar graph that shows quantitative analysis of the fluorescence intensity of intracellular 3-HAA in cultured HASMCs that were transfected with control siRNA, IDO siRNA, or kyureninase (KYNU) siRNA and treated with vehicle (control) or IFN-γ with the addition of 500 μM Trp for 48 hours. A conjugated 3-HAA antibody was used to detected endogenous 3-HAA in HASMCs, and cells were counterstained with a nuclear stain (DAPI). The x-axis shows treatment with IFN-γ or Trp, and the y-axis shows integrated intensity as a percent of the control. *P<0.01 vs. scrambled siRNA without IFN-γ, #P<0.01 vs. scrambled siRNA with IFN-γ treatment. P values were obtained by a one-way ANOVA with a post hoc analysis using Bonferroni's multiple comparisons test. The error bars are standard error of the mean. Ser siRNA: scrambled siRNA.
Figure 5F:
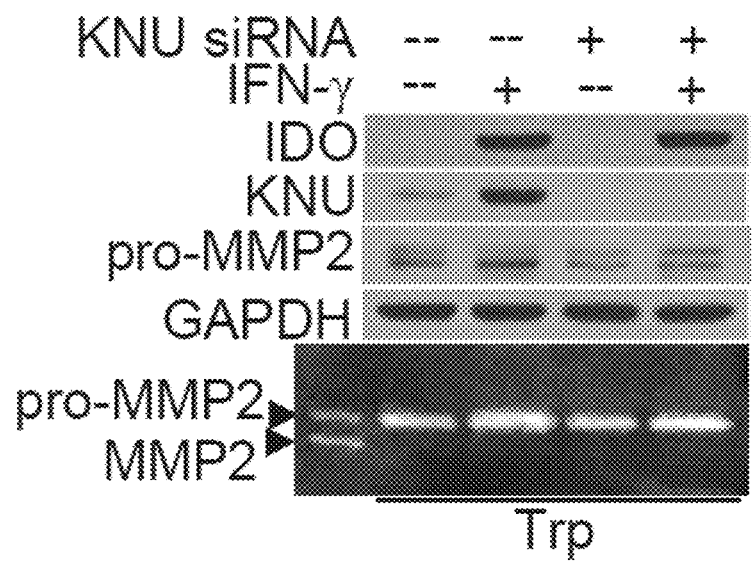
FIG. 5F is an immunoblot and zymogram for cultured HASMCs that were transfected with control siRNA, IDO siRNA, or kynureninase (KYNU) siRNA and treated with vehicle (control) or IFN-γ with the addition of 500 μM Trp for 48 hours. Pro-MMP2, IDO, and KNU proteins were detected by immunoblotting. GAPDH was used as a loading control, and MMP2 activities in the culture medium were detected b zymography. Representative data from three independent experiments are shown.

To further validate the effects of 3-HAA on MMP2 induction in VSMCs, we detected endogenous 3-HAA and the expression of KNU. KNU and intracellular 3-HAA expression emerged in IFN-γ-treated, Trp-supplemented HASMCs, along with MMP2 elevation (FIGS. 5D-F). Accordingly, IDO or KNU knockdown blocked endogenous 3-HAA formation (FIGS. 5D and 5E), which resulted in the inhibition of MMP2 expression and activity induced by IFN-γ with additional Trp (FIG. 5F). These results suggest that Trp-derived 3-HAA upregulates MMP2 expression in HASMCs in vitro.

Example 7. IDO Deletion Abolishes 3-HAA Generation in AAA Mice

Figure 6A:
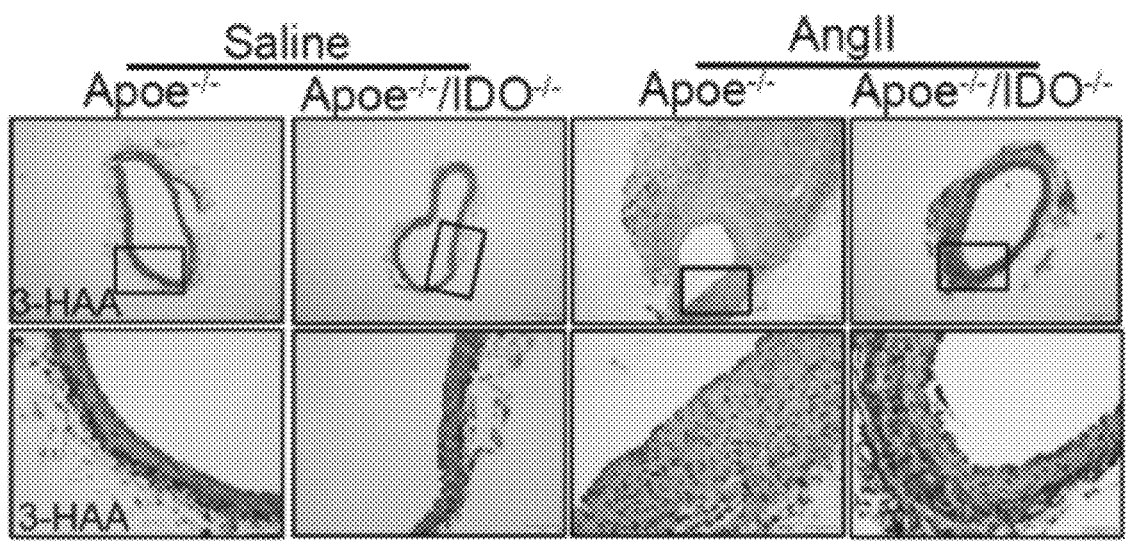
FIG. 6A shows representative immunohistochemical staining for 3-HAA in the suprarenal aortas of ApoE$^{-/-}$ and ApoE$^{-/-}$/IDO$^{-/-}$ mice administered saline or AngII (1000 ng/min per kg) for 4 weeks.
Figure 6B:
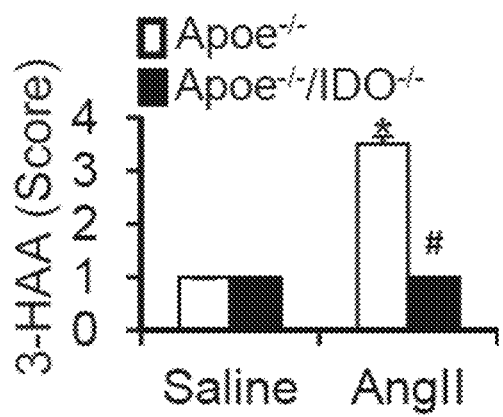
FIG. 6B is a bar graph that shows immunohistochemical staining quantification for 3-HAA in the suprarenal aortas of ApoE$^{-/-}$ and ApoE$^{-/-}$/IDO$^{-/-}$ mice administered saline or AngII (1000 ng/min per kg) for 4 weeks. *P<0.01 vs. saline-infused ApoE$^{-/-}$ mice, #P<0.01 vs. AngII-infused ApoE$^{-/-}$ mice. N=8-10 per group. P values were obtained by a one-way ANOVA with a post hoc analysis using Bonferroni's multiple comparisons test. The error bars are standard error of the mean.
Figure 6C:
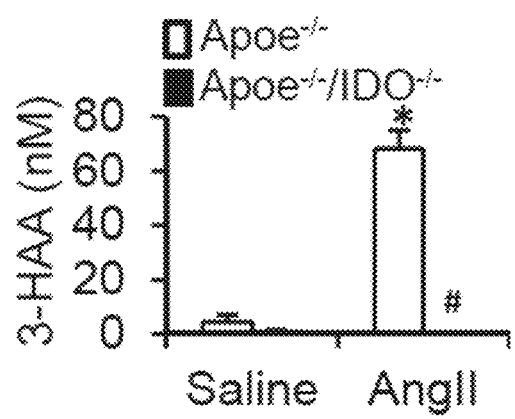
FIG. 6C is a bar graph that shows the serum levels of 3-HAA detected by HPLC in ApoE$^{-/-}$ and ApoE$^{-/-}$/IDO$^{-/-}$ mice after administration of saline or AngII (1000 ng/min per kg). *P<0.01 vs. saline-infused ApoE$^{-/-}$ mice, #P<0.01 vs. AngII-infused ApoE$^{-/-}$ mice. N=8-10 per group. P values were obtained by a one-way ANOVA with a post hoc analysis using Bonferroni's multiple comparisons test. The error bars are standard error of the mean.

Next, endogenous 3-HAA in vivo was detected. In line with the in vitro data, increased levels of 3-HAA were observed in the aortas of AngII-treated ApoE$^{-/-}$ mice, but not in those of IDO$^{-/-}$ mice (FIGS. 6A and 6B). Plasma levels were notably raised in AngII-treated ApoE$^{-/-}$ mice (FIG. 6C), suggesting that IDO deficiency suppresses MMP2 expression in aortas by inhibiting endogenous 3-HAA formation.

Example 8. 3-HAA Accelerates MMP2 Expression in Mouse Aortas

To ascertain the effect of 3-HAA in MMP2 expression in vivo, ApoE$^{-/-}$ and ApoE$^{-/-}$/IDO-mice were intra-peritoneally treated with vehicle or 3-HAA (200 mg/kg/d) for 6 weeks.

Figure 6D:
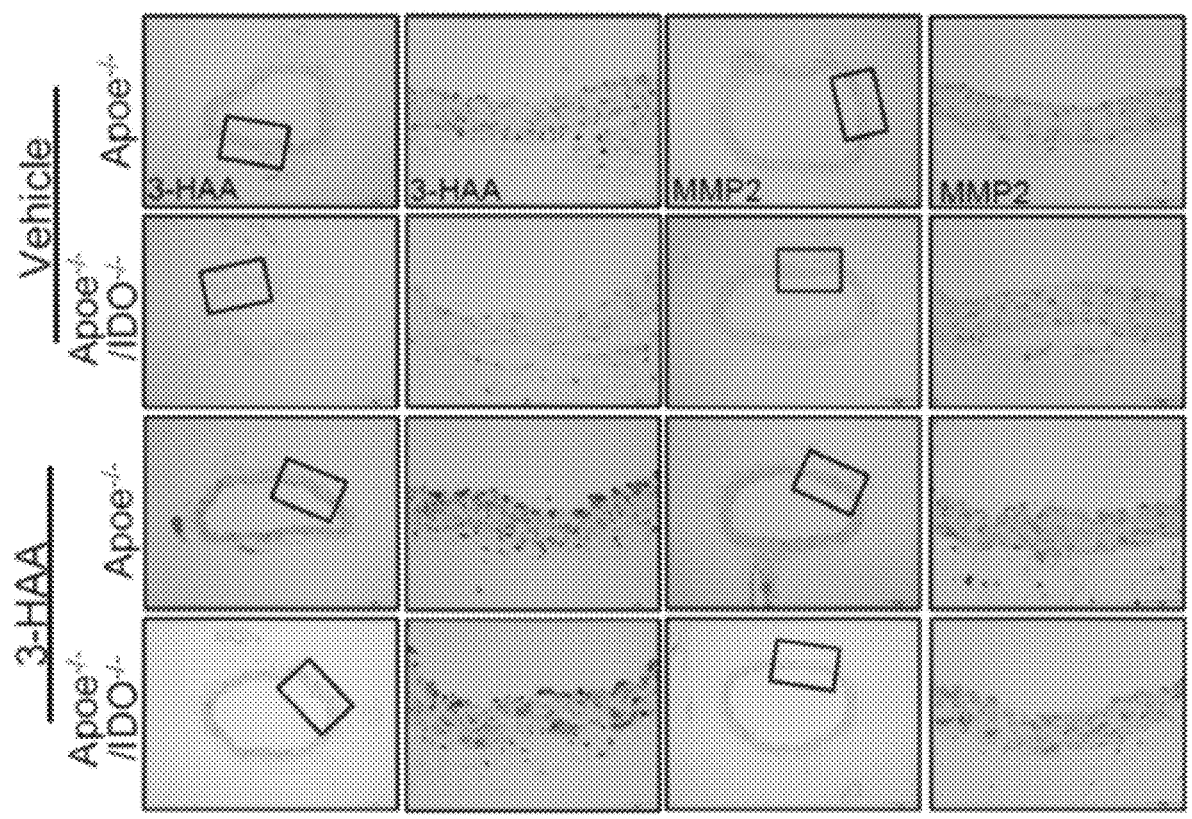
FIG. 6D shows representative immunohistochemical staining for 3-HAA and MMP2 in the aortas of ApoE$^{-/-}$ and ApoE$^{-/-}$/IDO$^{-/-}$ mice that were intra-peritoneally injected with vehicle (0 μL of 20% DMSO in Captisol) or 3-HAA (200 mg/kg/d) for 6 weeks. N=8-12 per group.
Figure 6E:
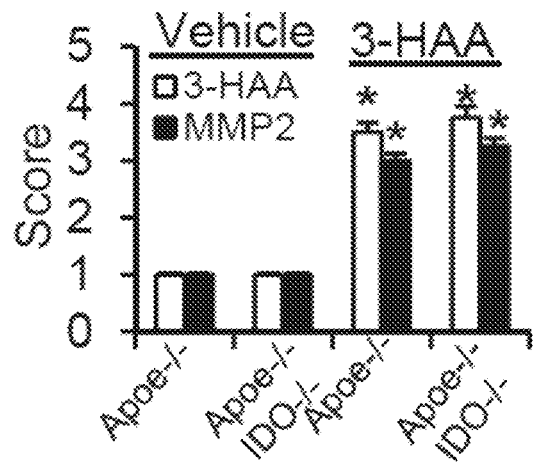
FIG. 6E is a bar graph that shows immunohistochemical staining quantification for 3-HAA in the aortas of ApoE$^{-/-}$ and ApoE$^{-/-}$/IDO$^{-/-}$ mice that were intra-peritoneally injected with vehicle (0 μL of 20% DMSO in Captisol) or 3-HAA (200 mg/kg/d) for 6 weeks. *P<0.01 vs. vehicle-injected ApoE$^{-/-}$ mice. N=8-12 per group. P values were obtained by a one-way ANOVA with a post hoc analysis using Bonferroni's multiple comparisons test. The error bars are standard error of the mean.
Figure 6F:
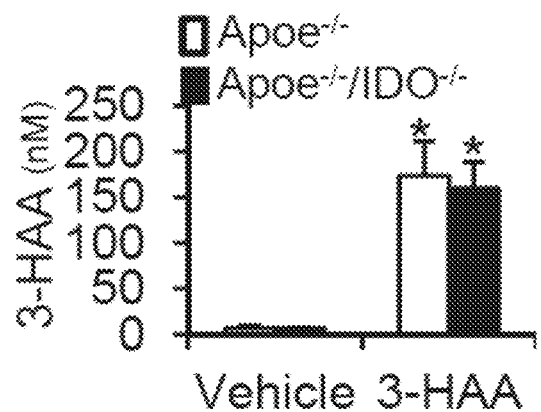
FIG. 6F is a bar graph that shows serum levels of 3-HAA that were detected by HPLC in ApoE$^{-/-}$ and ApoE$^{-/-}$/IDO$^{-/-}$ mice after administration of vehicle (0 μL of 20% DMSO in Captisol) or 3-HAA (200 mg/kg/d). *P<0.01 vs. vehicle-injected ApoE$^{-/-}$ mice. N=8-12 per group. P values were obtained by a one-way ANOVA with a post hoc analysis using Bonferroni's multiple comparisons test. The error bars are standard error of the mean.
Figure 6G:
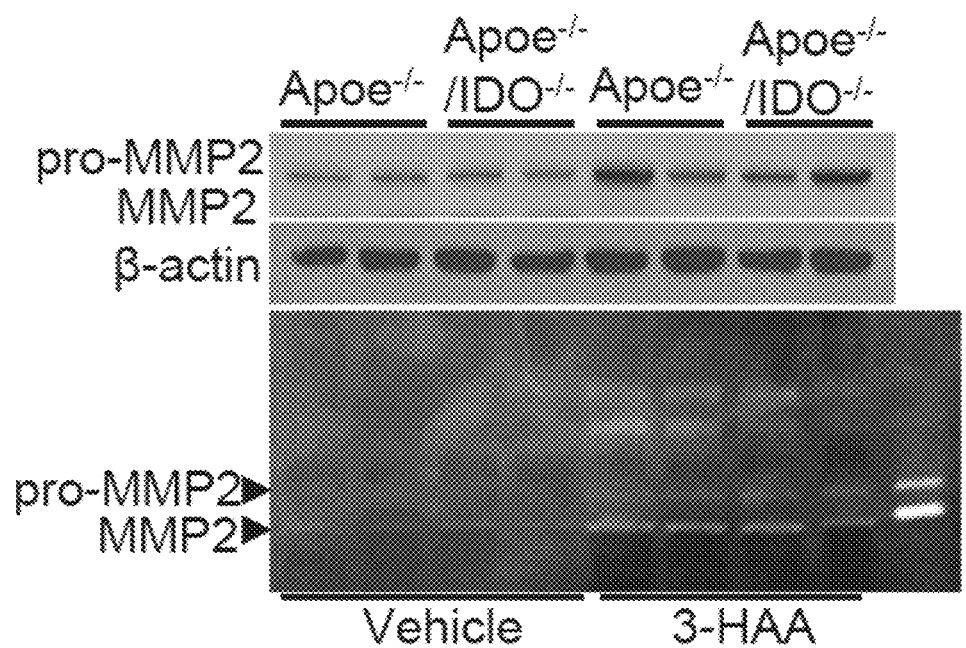
FIG. 6G is an immunoblot and zymogram showing the expression of MMP2 and β-actin (by immunblotting), and MMP2 activity (by zymography) in the aortas of ApoE$^{-/-}$ and ApoE$^{-/-}$/IDO$^{-/-}$ mice that were intra-peritoneally injected with vehicle (0 μL of 20% DMSO in Captisol) or 3-HAA (200 mg/kg/d) for 6 weeks. N=8-12 per group.
Figure 6H:
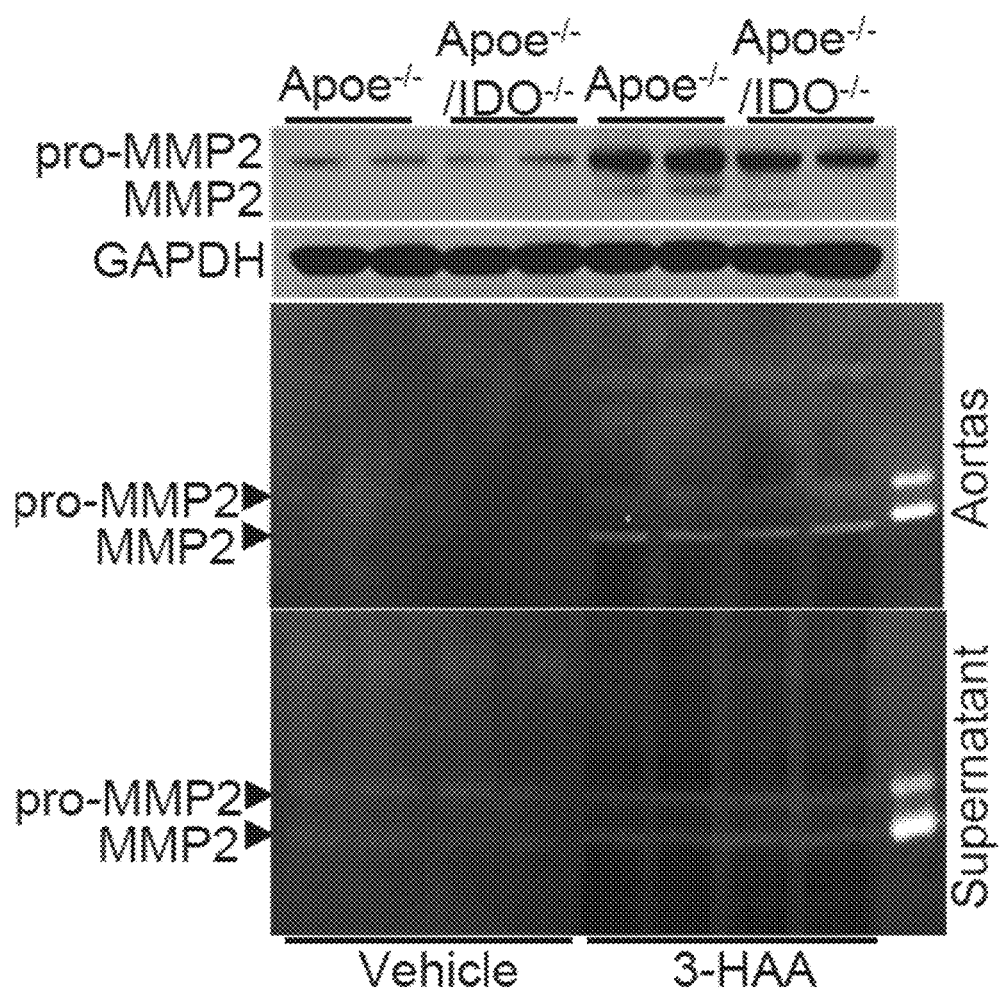
FIG. 6H is an immunoblot and zymogram for aortas isolated from ApoE$^{-/-}$ and ApoE$^{-/-}$/IDO$^{-/-}$ mice that were treated with vehicle or 400 μM 3-HAA for 38 hours ex vivo. MMP2, Pro-MMP2, and GAPDH protein expression in the aortas was detected by immunoblotting, and MMP2 activity in the aortas and supernatants were detected by zymography. N=8 per group.

Corresponding increases in 3-HAA were detected in the plasma (FIG. 6F) and aortas (FIGS. 6D and 6E) of 3-HAA-injected ApoE$^{-/-}$ and ApoE$^{-/-}$/IDO$^{-/-}$ mice. As depicted in Table 4, 3-HAA injection does not affect any metabolic parameters in ApoE$^{-/-}$ or ApoE$^{-/-}$/IDO$^{-/-}$ mice. Consequently, MMP2 expression (FIGS. 6D, 6E, and 6G) and activity (FIG. 6G) were remarkably increased in both 3-HAA-treated ApoE$^{-/-}$ and ApoE$^{-/-}$/IDO$^{-/-}$ mice, as compared with vehicle-treated mice. Aortas isolated from ApoE$^{-/-}$ and ApoE$^{-/-}$/IDO$^{-/-}$ mice were also incubated with or without 400 μM 3-HAA for 48 hours. In the aortas from both ApoE$^{-/-}$ and ApoE$^{-/-}$/IDO$^{-/-}$ mice, 3-HAA treatment significantly upregulated MMP2 expression and activity (FIG. 6H). A similar increase in MMP2 activity was observed in the culture medium of 3-HAA-treated aortas (FIG. 6H). These results suggest that exogenous 3-HAA upregulates MMP2 expression in mouse aortas in vivo and ex vivo. Furthermore, 3-HAA-mediated MMP2 induction was independent of IDO.

TABLE 4

| Serum lipid and glucose level in 3- HAA-injected mice. | | | | |
|---|---|---|---|---|
| | Vehicle | | 3-HAA | |
| Groups | Apoe−/− | Apoe−/−/IDO−/− | Apoe−/− | Apoe−/−/IDO−/− |
| Cholesterol (mg/dl) | 489.7 ± 26.6 | 492.5 ± 30.0 | 471 ± 26.6 | 470.8 ± 30.8 |
| Triglyceride (mg/dl) | 125.4 ± 4.8 | 135.8 ± 7.0 | 131.5 ± 5.5 | 123.4 ± 10.1 |
| BG (mg/dl) | 127 ± 29 | 142 ± 32 | 137 ± 24 | 132 ± 29 |

N is 6-10 in each group. Data are expressed by mean ± s.e.m.

Example 9. KNU Deficiency Attenuates AngII-Induced AAA Formation

Figure 7A:
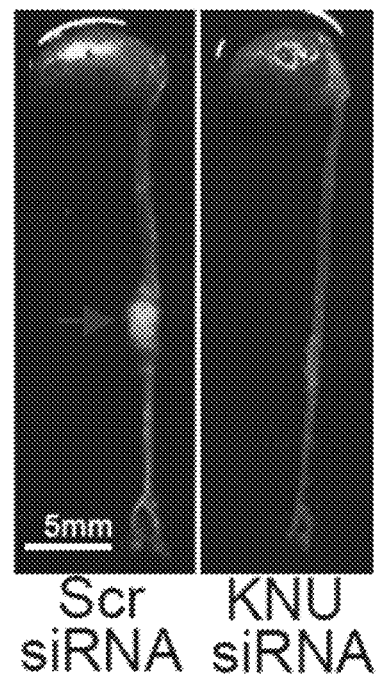
FIG. 7A depict representative photographs showing the macroscopic features of AngII induced aneurysms in ApoE$^{-/-}$ mice that were transfected with scrambled (Ser) siRNA or KNU siRNA followed by infusion with AngII (1000 ng/min per kg) for 4 weeks. The arrow indicated typical AAA. N=10-12 in each group.
Figure 7B:
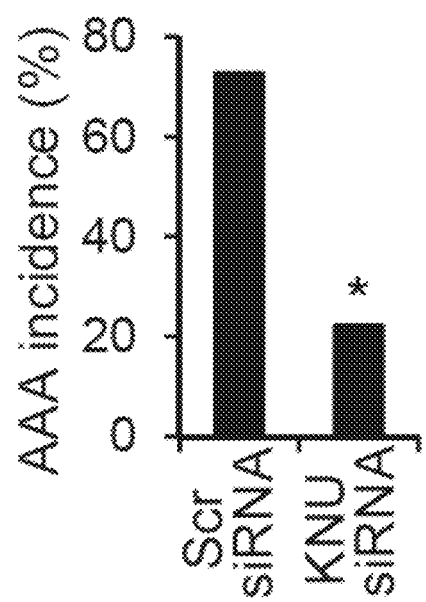
FIG. 7B is a bar graph that shows the incidence of AngII-induced AAA in ApoE$^{-/-}$ mice transfected with scrambled (Ser) siRNA or KNU siRNA followed by infusion with AngII (1000 ng/min per kg) for 4 weeks. The x-axis show the siRNA transfected, and the y-axis shows AAA incidence in percent. *P<0.01 vs. scrambled siRNA-transfected ApoE$^{-/-}$ mice. N=10-12 in each group.
Figure 7C:
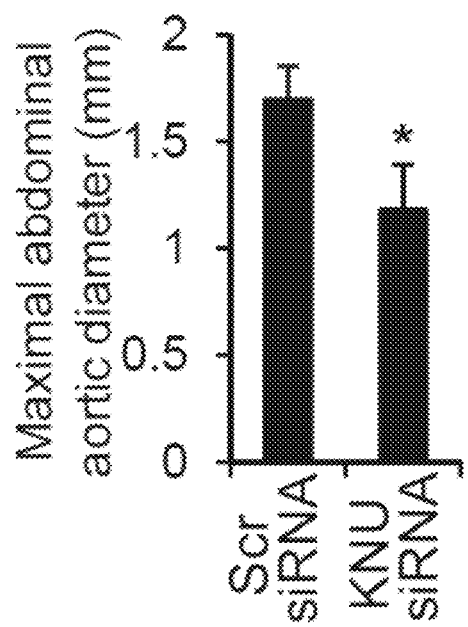
FIG. 7C is a bar graph that shows the maximal abdominal aortic diameter in ApoE$^{-/-}$ mice transfected with scrambled (Ser) siRNA or KNU siRNA followed by infusion with AngII (1000 ng/min per kg) for 4 weeks. The x-axis shows the siRNA transfected, and the y-axis shows the maximal abdominal aortic diameter in millimeters. *P<0.01 vs. scrambled siRNA-transfected ApoE$^{-/-}$ mice. N=10-12 in each group. P values were obtained by a $\chi^2$ test in band by a one-way ANOVA with a post hoc analysis using Bonferroni's multiple comparisons test. The error bars are standard error of the mean.
Figure 7D:
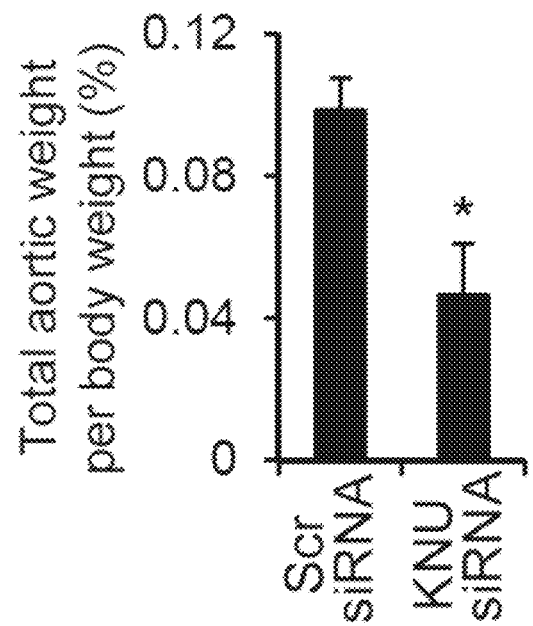
FIG. 7D is a bar graph that shows the total aortic weight in ApoE$^{-/-}$ mice transfected with scrambled (Ser) siRNA or KNU siRNA followed by infusion with AngII (1000 ng/min per kg) for 4 weeks. The x-axis shows the siRNA transfected, and the y-axis shows the total aortic weight per body weight in percent. *P<0.01 vs. scrambled siRNA-transfected ApoE$^{-/-}$ mice. N=10-12 in each group. P values were obtained by a $\chi^2$ test in band by a one-way ANOVA with a post hoc analysis using Bonferroni's multiple comparisons test. The error bars are standard error of the mean.
Figure 7E:
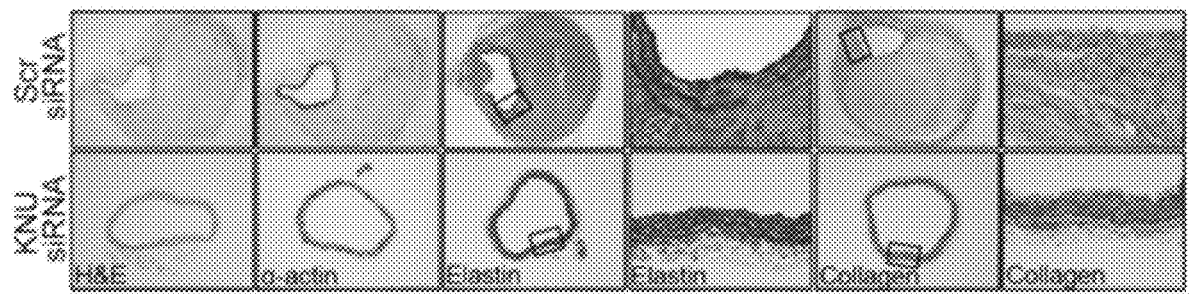
FIG. 7E shows representative immunoblotting and staining with H&E, α-actin, Van Gieson's, and Masson's Trichrome stain in the suprarenal aortas of ApoE$^{-/-}$ mice transfected with scrambled (Ser) siRNA or KNU siRNA followed by infusion with AngII (1000 ng/min per kg) for 4 weeks. N=10-12 in each group.
Figure 7F:
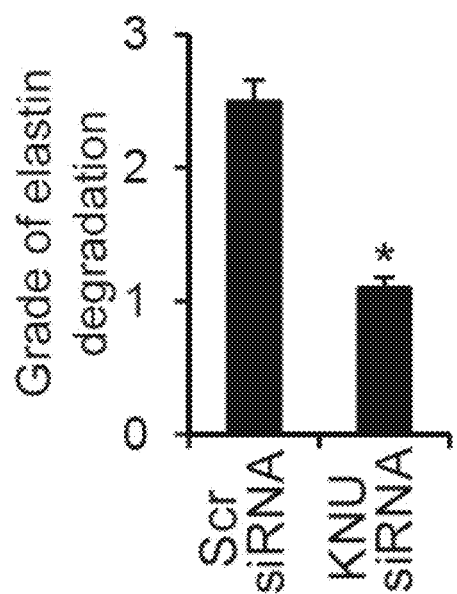
FIG. 7F is a bar graph that shows the grade of elastin degradation in the aortic wall of ApoE$^{-/-}$ mice transfected with scrambled (Ser) siRNA or KNU siRNA followed by infusion with AngII (1000 ng/min per kg) for 4 weeks. The x-axis shows the siRNA transfected, and the y-axis shows the grade of elastin degradation. *P<0.01 vs. scrambled siRNA-transfected ApoE$^{-/-}$ mice. N=10-12 in each group. P values were obtained by a $\chi^2$ test in band by a one-way ANOVA with a post hoc analysis using Bonferroni's multiple comparisons test. The error bars are standard error of the mean.
Figure 7G:
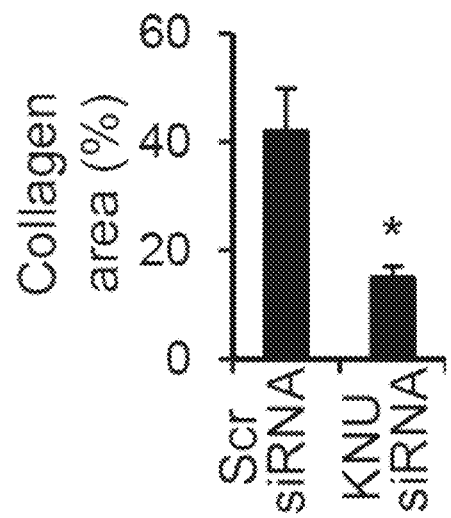
FIG. 7G is a bar graph that shows collagen deposition in the aortic wall of ApoE$^{-/-}$ mice transfected with scrambled (Ser) siRNA or KNU siRNA followed by infusion with AngII (1000 ng/min per kg) for 4 weeks. The x-axis is the siRNA transfected, and the y-axis is the area of collagen in percent. *P<0.01 vs. scrambled siRNA-transfected ApoE$^{-/-}$ mice. N=10-12 in each group. P values were obtained by a $\chi^2$ test in band by a one-way ANOVA with a post hoc analysis using Bonferroni's multiple comparisons test. The error bars are standard error of the mean.

To further identify the effects of endogenous 3-HAA on AAA development, AngII-infused ApoE$^{-/-}$ mice were treated with KNU siRNA. There were no differences in blood pressure or heart rate between scrambled siRNA- and KNU siRNA-transfected, AngII-infused mice (data not shown). Changes in metabolic parameters were also not observed (data not shown). Only 22% of AngII-infused, KNU siRNA-transfected ApoE$^{-/-}$ mice developed AAA compared with a 75% incidence of AAA in AngII-infused, scrambled siRNA-transfected ApoE$^{-/-}$ mice (FIGS. 7A and 7B). The maximal abdominal aortic diameter (FIG. 7C) and total aortic weight (FIG. 7D) were remarkably lower in mice with KNU knockdown. Moreover, AngII infusion did not cause significant elastic lamina degradation and aortic expansion in KNU siRNA-transfected ApoE-mice (FIGS. 7E and 7F). Collagen deposition was dramatically reduced in KNU siRNA-transfected mice compared with control mice (FIGS. 7E and 7G). These results suggest that KNU knockdown protects ApoE$^{-/-}$ mice from AngII-induced AAA formation in vivo.

Figure 8A:
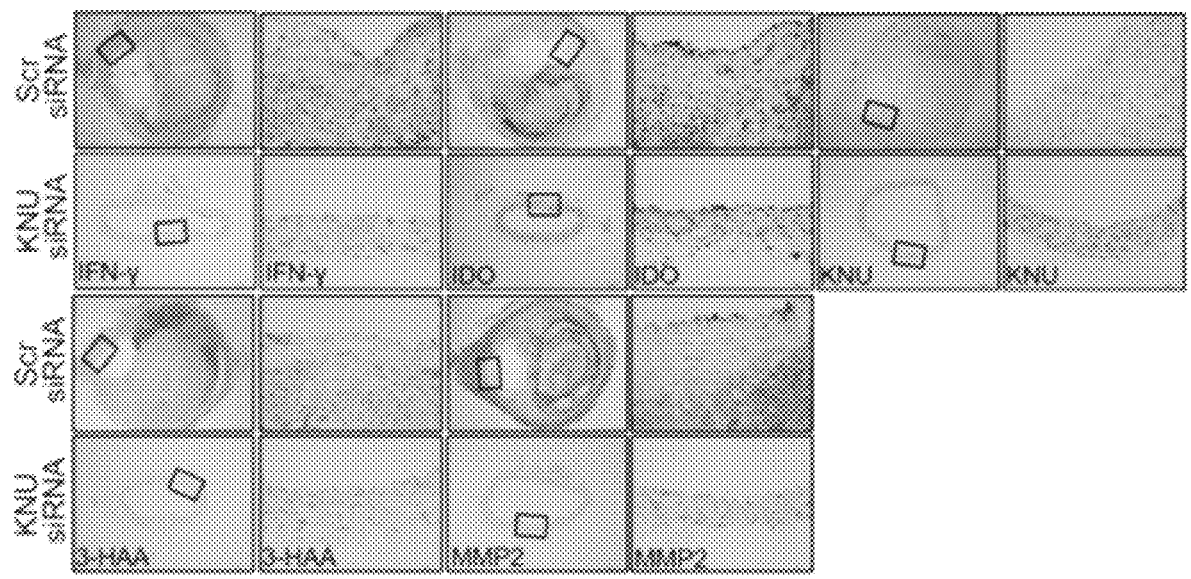
FIG. 8A shows representative immunochemical staining in the suprarenal aortas of ApoE$^{-/-}$ mice transfected with scrambled (Ser) siRNA or kynureninase (KYNU) siRNA followed by infusion with AngII (1000 ng/min per kg) for 4 weeks. N=6-10 in each group.
Figure 8B:
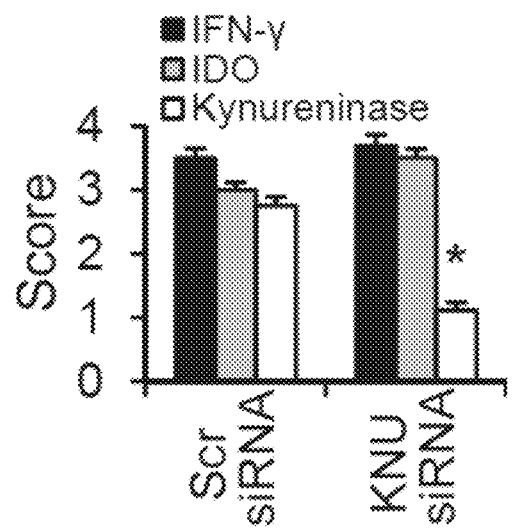
FIG. 8B is a bar graph that shows the quantification of IFN-γ, IDO, and KNU in the suprarenal aortas of ApoE$^{-/-}$ mice transfected with scrambled (Ser) siRNA or kynureninase (KYNU) siRNA followed by infusion with AngII (1000 ng/min per kg) for 4 weeks. The x-axis is the siRNA transfected, and the y=axis is the quantification score. N=6-10 in each group. *P<0.01 vs. scrambled siRNA-transfected ApoE$^{-/-}$ mice. P values were obtained by a one-way ANOVA with a post hoc analysis using Bonferroni's multiple comparisons test. The error bars are standard error of the mean.
Figure 8C:
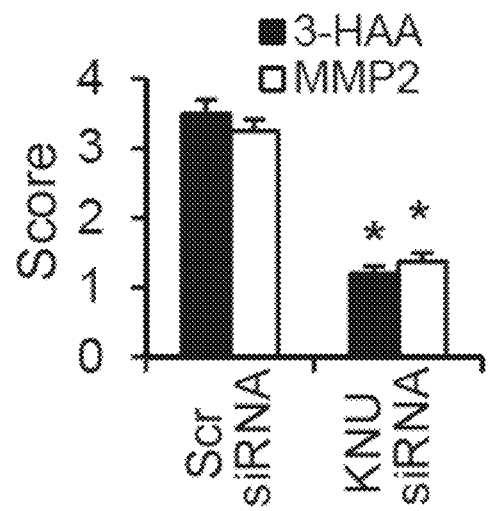
FIG. 8C is a bar graph that shows the quantification of 3-HAA and MMP2 in the suprarenal aorta of ApoE$^{-/-}$ mice transfected with scrambled (Ser) siRNA or kynureninase (KNU) siRNA followed by infusion with AngII (1000 ng/min per kg) for 4 weeks. The x-axis is the siRNA transfected, and the y-axis is the quantification score. N=6-10 in each group. *P<0.01 vs. scrambled siRNA-transfected ApoE$^{-/-}$ mice. P values were obtained by a one-way ANOVA with a post hoc analysis using Bonferroni's multiple comparisons test. The error bars are standard error of the mean.
Figure 8D:
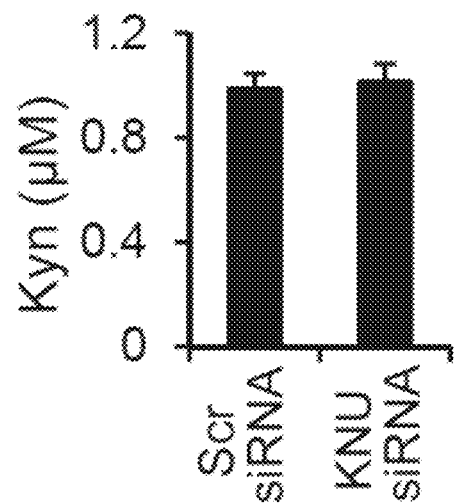
FIG. 8D is a bar graph that shows the serum concentration of Kyn detected by HPLC in ApoE$^{-/-}$ mice transfected with scrambled (Ser) siRNA or kynureninase (KNU) siRNA followed by infusion with AngII (1000 ng/min per kg) for 4 weeks. n=6-10 in each group. The x-axis is the siRNA transfected, and the y-axis is the micromolar serum concentration of Kyn. *P<0.01 vs. scrambled siRNA-transfected ApoE$^{-/-}$ mice. P values were obtained by a one-way ANOVA with a post hoc analysis using Bonferroni's multiple comparisons test. The error bars are standard error of the mean.
Figure 8E:
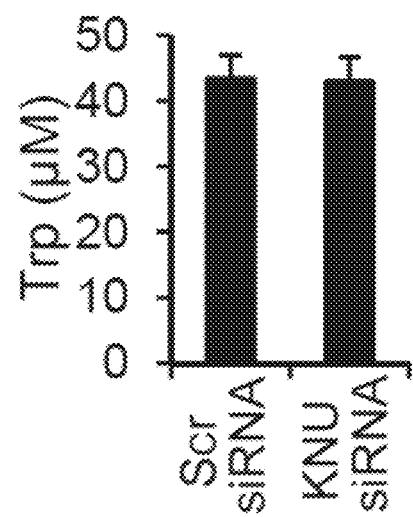
FIG. 8E is a bar graph that shows the serum concentration of Trp detected by HPLC in ApoE$^{-/-}$ mice transfected with scrambled (Ser) siRNA or kynureninase (KNU) siRNA followed by infusion with AngII (1000 ng/min per kg) for 4 weeks. The x-axis is the siRNA transfected, and the y-axis is the micromolar serum concentration of Trp. N=6-10 in each group. *P<0.01 vs. scrambled siRNA-transfected ApoE$^{-/-}$ mice. P values were obtained by a one-way ANOVA with a post hoc analysis using Bonferroni's multiple comparisons test. The error bars are standard error of the mean.
Figure 8F:
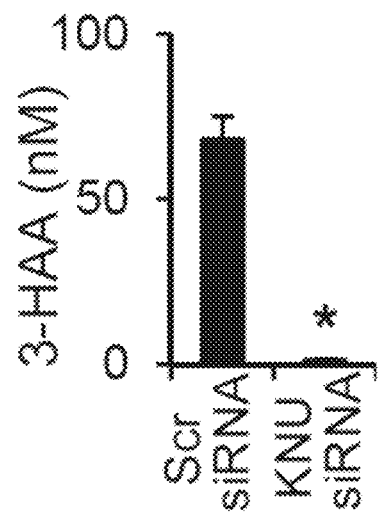
FIG. 8F is a bar graph that shows the serum concentration of 3-HAA detected by HPLC in ApoE$^{-/-}$ mice transfected with scrambled (Ser) siRNA or kynureninase (KNU) siRNA followed by infusion with AngII (1000 ng/min per kg) for 4 weeks. The x-axis is the siRNA transfected, and the y-axis is the micromolar serum concentration of 3-HAA. N=6-10 in each group. *P<0.01 vs. scrambled siRNA-transfected ApoE$^{-/-}$ mice. P values were obtained by a one-way ANOVA with a post hoc analysis using Bonferroni's multiple comparisons test. The error bars are standard error of the mean.
Figure 8G:
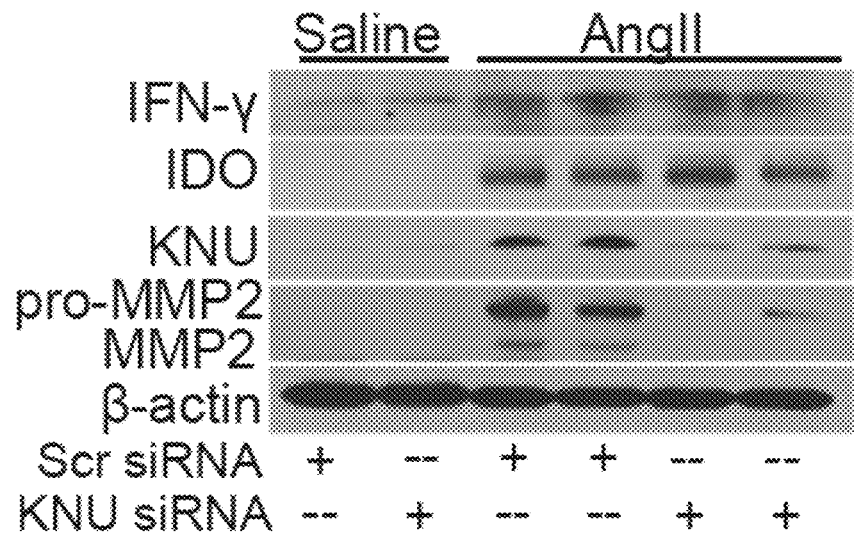
FIG. 8G shows the protein expression levels of IFN-γ, IDO, KNU, MMP2, and beta-actin in the suprarenal aortas of ApoE$^{-/-}$ mice transfected with scrambled (Ser) siRNA or kynureninase (KNU) siRNA followed by infusion with AngII (1000 ng/min per kg) for 4 weeks. N=6-10 in each group.

Example 10. Inhibition of Trp-Derived 3-HAA Abolishes MMP2 Upregulation in AAA Mice KNU silencing did not alter serum concentrations of inflammatory cytokines in AngII-infused ApoE$^{-/-}$ mice (data not shown). Accordingly, both IFN-γ and IDO expression levels were markedly enhanced in the aortas of AngII-treated ApoE$^{-/-}$ mice with or without KNU knockdown (FIGS. 8A, 8B, and 8G). As expected, AngII only increased KNU expression in ApoE$^{-/-}$ mice (FIGS. 8A, 8B, and 8G). In line with this, high plasma levels of Kyn were detected in both groups of mice (FIG. 8D), whereas high 3-HAA levels were only observed in the plasma (FIG. 8F) and aortas (FIGS. 8A and 8C) of AngII-treated ApoE$^{-/-}$ mice but not in KNU siRNA-transfected ApoE$^{-/-}$ mice. Because of compensatory Trp in the mouse diet, no differences in plasma Trp levels were found between scrambled siRNA- and KNU siRNA-transfected mice (FIG. 8E).

Figure 8H:
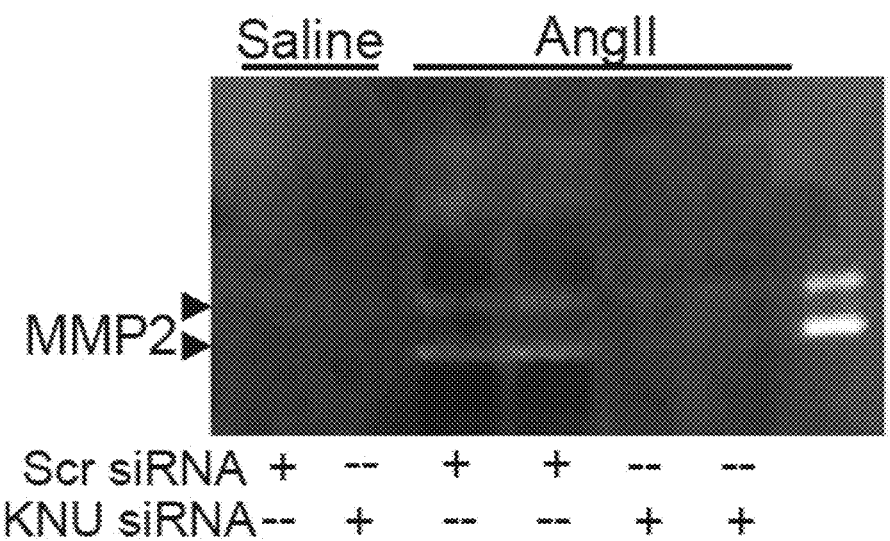
FIG. 8H is a zymogram that shows the MMP2 activity in the suprarenal aortas of ApoE$^{-/-}$ mice transfected with scrambled (Ser) siRNA or kynureninase (KNU) siRNA followed by infusion with AngII (1000 ng/min per kg) for 4 weeks. N=6-10 in each group.

Next, whether KNU silencing affects MMP2 levels in AngII-induced AAA formation was determined. Compared with AngII-infused ApoE$^{-/-}$ mice, MMP2 expression (FIGS. 8A, 8C, and 8G) and activity (FIG. 8H) were significantly reduced in AngII-infused, KNU siRNA-transfected ApoE$^{-/-}$ mice, indicating that endogenous 3-HAA reduction lowers MMP2 expression to inhibit AAA formation.

Figure 11:
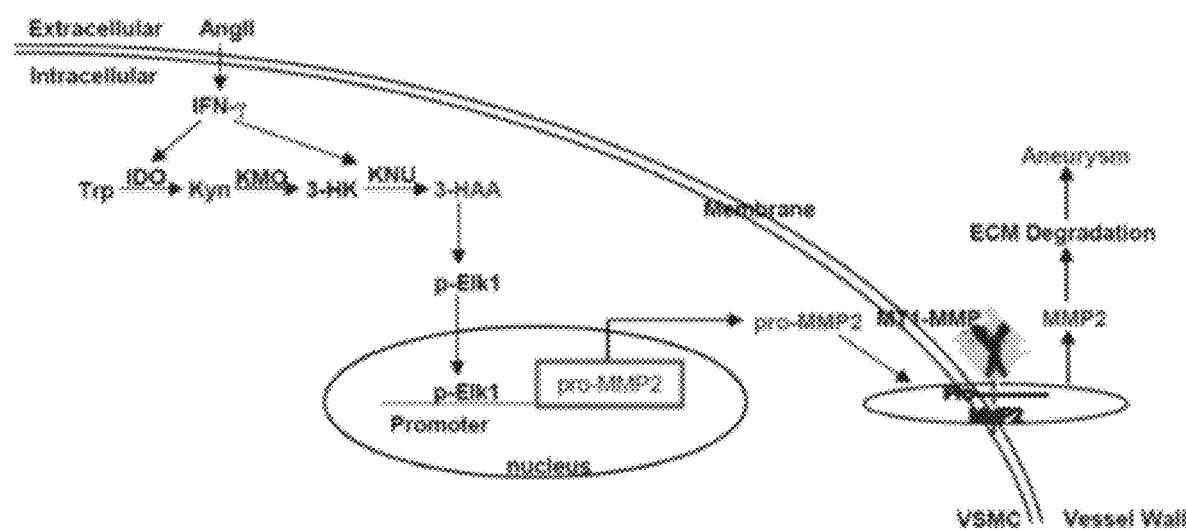
FIG. 11 is a proposed scheme for AngII-induced AAA formation via 3-hydroxyanthranilic acid (3-HAA) elevation in mice. AngII binds to its receptor in vascular smooth muscle cells to promote secretion of IFN-γ, which powerfully activates the kynurenine (Kyn) pathway of tryptophan (Trp) metabolism. Highly-induced indoleamine-2,3-dioxygenase (IDO) initially catalyzes Trp to Kyn, which is further metabolized to 3-HAA by intensely upregulated kynureninase (KYNU) expression. Trp-derived 3-HAA induces the phosphorylation of the main MMP2 transcriptional factor Elk1, which triggers MMP2 overexpression and subsequent MMP2 secretion to outside of cells and cleavage to activated MMP2 by MT1-MMP. In vascular walls, active MMP2 degrades extracellular matrix resulting in the loss of the resistance of the vascular wall to blood flow and consequent formation of an aortic aneurysm.

This study is the first to show that IDO deletion or KNU knockdown in vivo restrained AngII-induced AAA in ApoE$^{-/-}$ mice. In VSMCs, AngII-mediated IFN-γ induced the expression of IDO and KNU, which are two key enzymes that regulate 3-HAA formation in the kynurenine pathway of Trp metabolism. Elevated 3-HAA upregulated Elk1 phosphorylation at Ser383, resulting in the aberrant expression and activation of MMP2 and consequent extracellular matrix degradation (FIG. 11). This mechanism not only provides an evident link between the Trp-Kyn pathway and AAA but also identifies a specific Trp metabolite (3-HAA) that promotes AAA formation.

Example 11. Kynurenine Pathway Activation in Human AAA Formation

Figure 12:
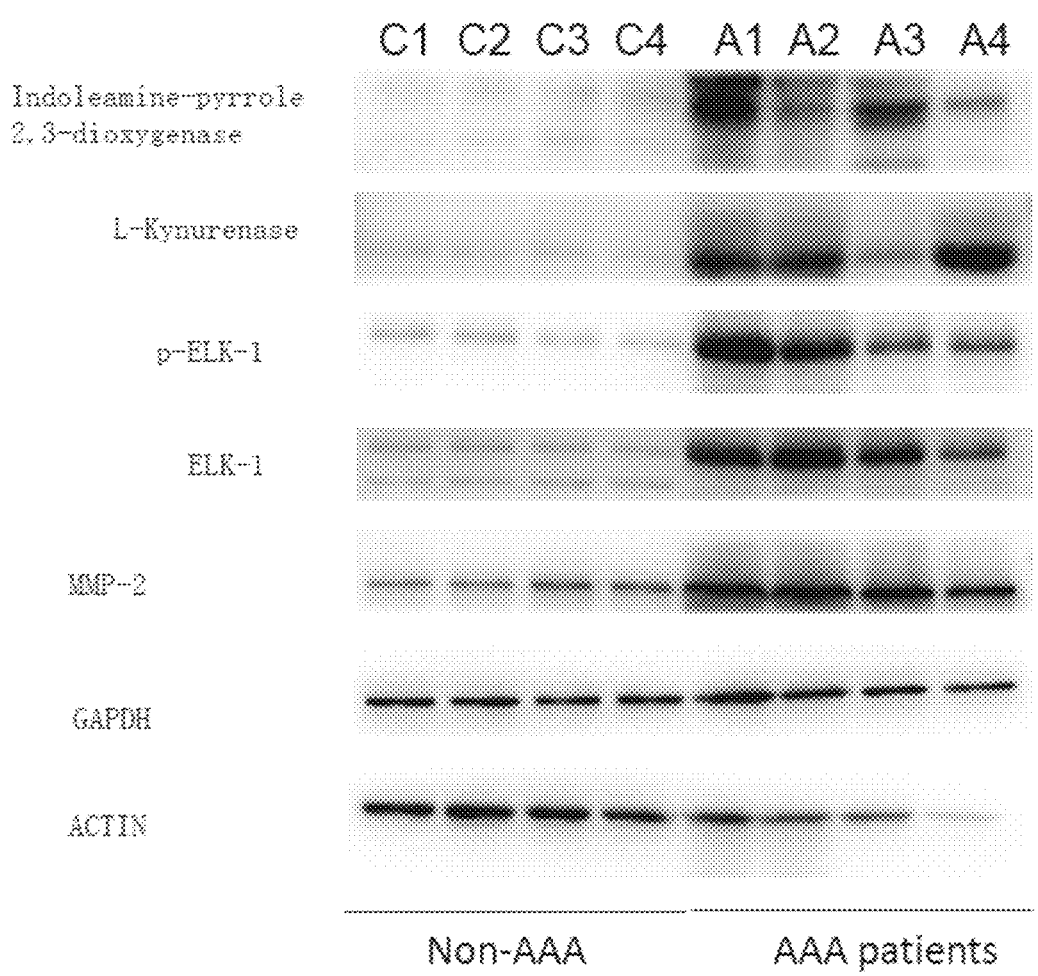
FIG. 12 is a western blot that shows detection of indoleamine-pyrrole 2,3-dioxygenase, L-kynurenase, p-ELK-1, ELK-1, MMP2, GAPDH, and actin in human AAA tissues and their control adjacent aortic section without an aneurysm that were obtained from patients undergoing open surgery.
Figure 13A:
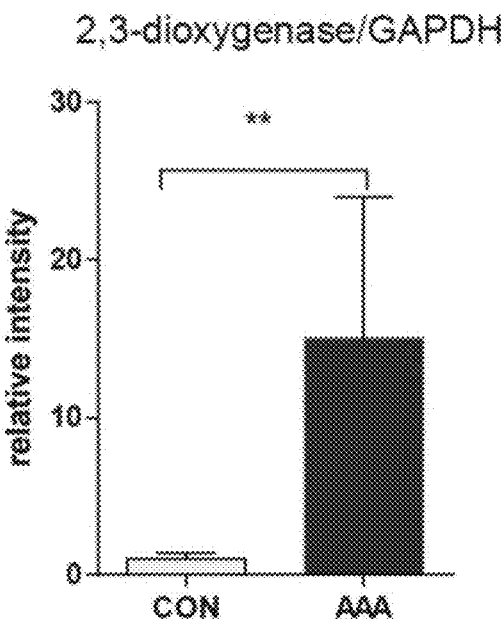
FIG. 13A is a bar graph that shows densitometric analysis of the western blot shown in FIG. 12 of 2,3-dioxygenase in relation to GAPDH in control tissue and AAA tissue obtained from patients undergoing open surgery. The x-axis shows the sampled tissue, and the y-axis shows the relative intensity. *p<0.01. The error bars are standard error of the mean.
Figure 13B:
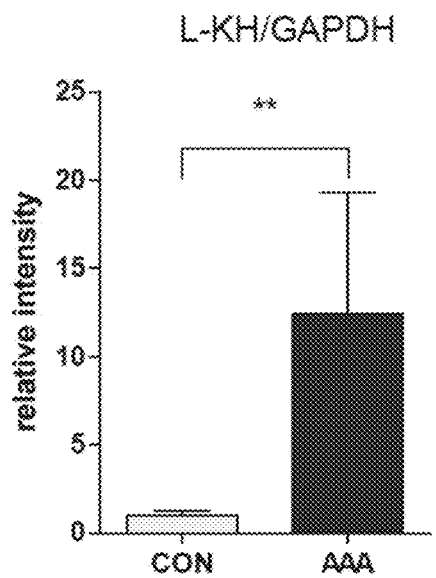
FIG. 13B is a bar graph that shows densitometric analysis of the western blot shown in FIG. 12 of L-Kyn in relation to GAPDH in control tissue and AAA tissue obtained from patients undergoing open surgery. The x-axis shows the sampled tissue, and the y-axis shows the relative intensity. *p<0.01. The error bars are standard error of the mean.
Figure 13C:
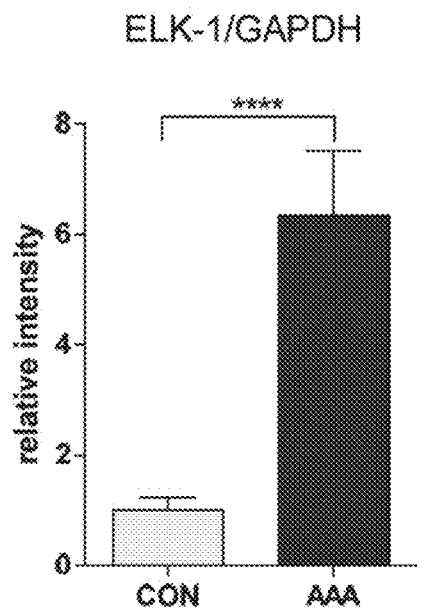
FIG. 13C is a bar graph that shows densitometric analysis of the western blot shown in FIG. 12 of ELK-1 in relation to GAPDH in control tissue and AAA tissue obtained from patients undergoing open surgery. The x-axis shows the sampled tissue, and the y-axis shows the relative intensity. *p<0.01. The error bars are standard error of the mean.
Figure 13D:
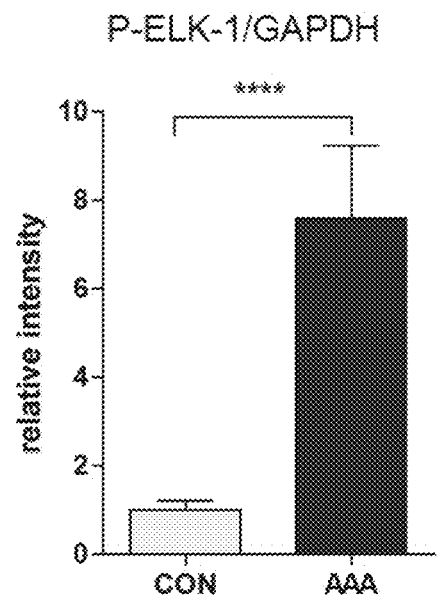
FIG. 13D is a bar graph that shows densitometric analysis of the western blot shown in FIG. 12 of P-ELK-1 in relation to GAPDH in control tissue and AAA tissue obtained from patients undergoing open surgery. The x-axis shows the sampled tissue, and the y-axis shows the relative intensity. *p<0.01. The error bars are the standard error of the mean.
Figure 13E:
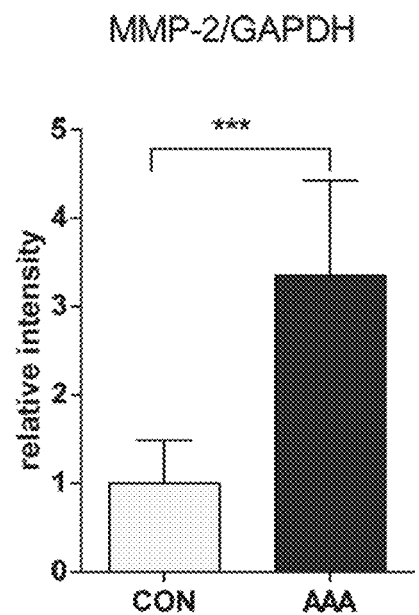
FIG. 13E is a bar graph that shows densitometric analysis of the western blot shown in FIG. 12 of MMP-2 in relation to GAPDH in control tissue and AAA tissue obtained from patients undergoing open surgery. The x-axis shows the sampled tissue, and the y-axis shows the relative intensity. *p<0.01. The error bars are the standard error of the mean.
Figure 14:
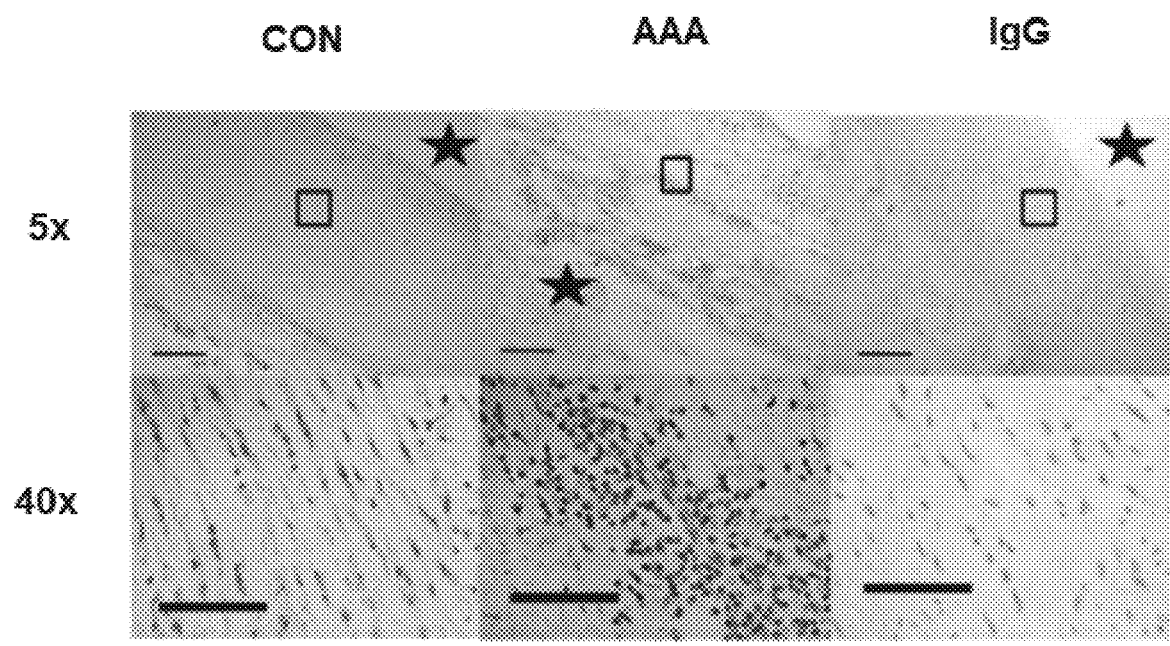
FIG. 14 shows representative immunohistochemical staining of kyureninase in human aortic sections with or without AAA.
Figure 15:
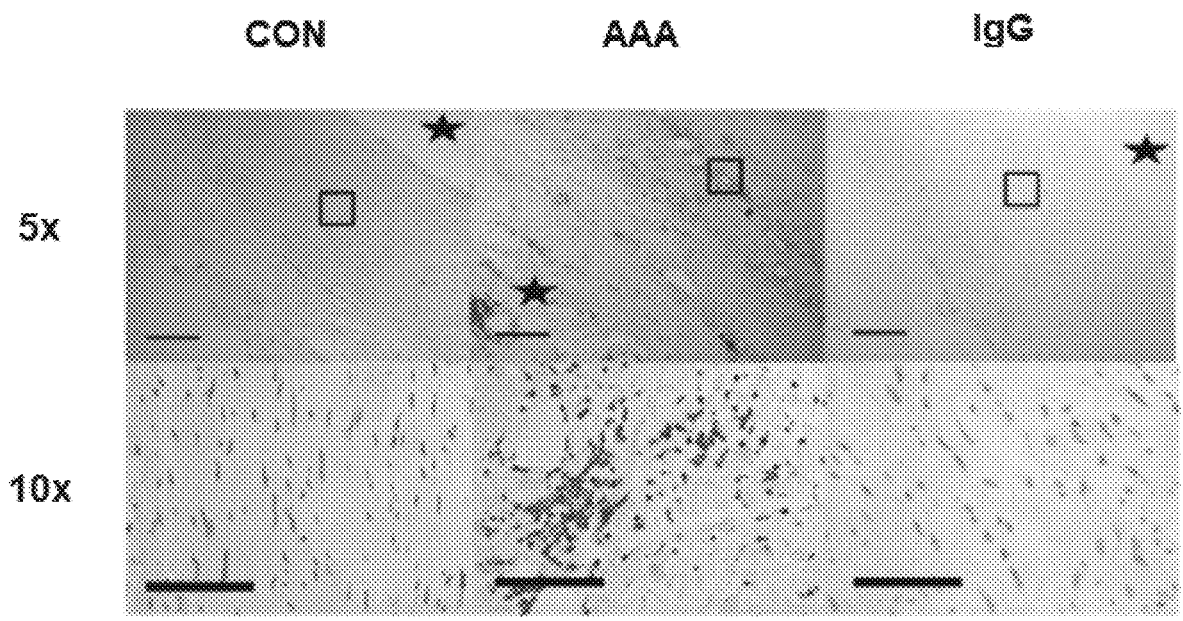
FIG. 15 shows representative immunohistochemical staining of indoleamine-pyrrole 2,3-dioxygenase (IDO) in human aortic sections with or without AAA.
Figure 16:
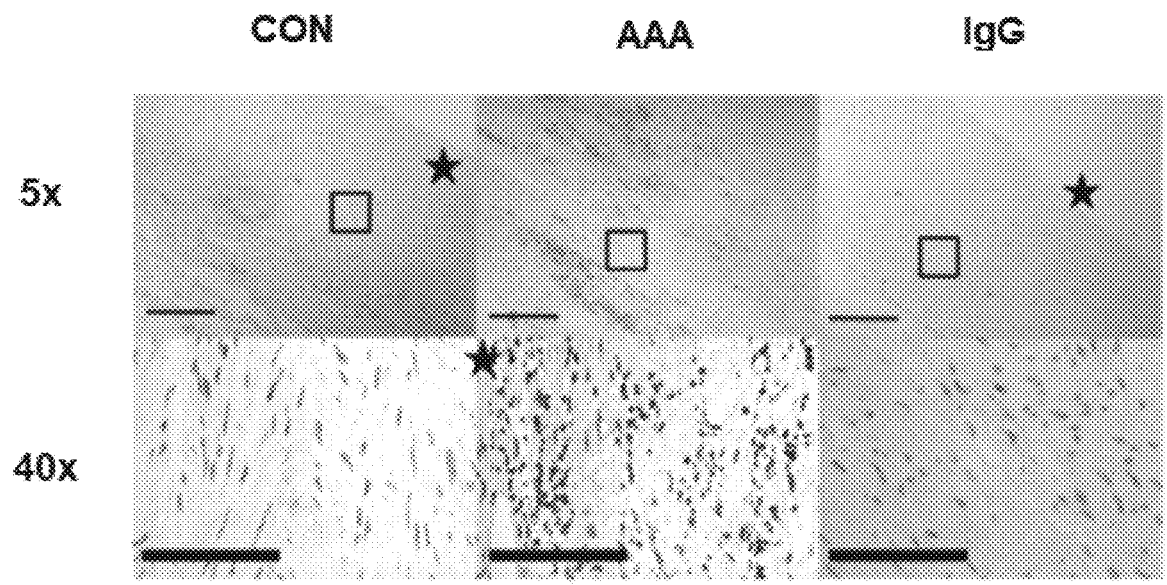
FIG. 16 show representative immunohistochemical staining of 2-hydroxyanthranilic acid (3-HAA) in human aortic sections with or without AAA. Human AAA samples had stronger anti-3-HAA staining than adjacent nonaneurysmal aortic sections.
Figure 28:
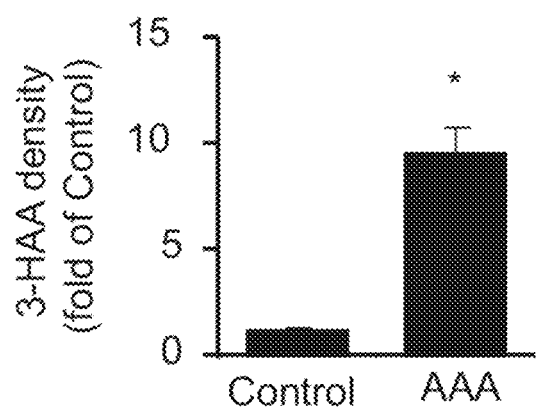
FIG. 28 is a bar graph that shows the density of 3-HAA as determined by immunohistochemical staining of human aortic sections with or without AAA. The x-axis shows the patient group, and the y-axis shows the 3-HAA density as the fold of the control group. *P<0.01 versus the control. The error bars are standard error of the mean.

To establish the clinical relevance of the Kynurenine Pathway and AAA formation, the expression of Kyn pathways key enzymes IDO1 and KYNU in human AAA samples was examined. Human AAA tissues and their control adjacent aortic sections without an aneurysm were obtained from patients undergoing open surgery. Pro-aneurysmal molecules, such as the expression of IDO, KYNU, MMP2, etc., was dramatically elevated in human AAA sections compared with adjacent nonaneurysmal aortic sections (FIG. 12 and FIG. 13). Importantly, both IDO1 and KYNU were significantly upregulated in human AAA samples (from FIG. 12 to FIG. 16). Moreover, human AAA samples had stronger anti-3-HAA staining than adjacent nonaneurysmal aortic sections (FIG. 16). 3-HAA concentration is significantly increased in subjects with AAA (FIG. 17) and AAA-associated aortic dissections. Finally, 3-HAA density was found to be higher in the aortic sections obtained from subjects with AAA (FIG. 28).

Example 12. Effect of Acipimox on Preventing AngII-Induced Abdominal Aortic Aneurysm To evaluate whether acipimox has inhibitory effects on AngII-induced AAA formation, male ApoE$^{-/-}$ mice at age eight weeks were administrated either 1) acipimox (0.1% wt) or 2) vehicle control (water) by drinking water. After four weeks, Alzet osmotic mini pumps (Model 2004) were implanted into each group. Pumps were filled either with 1) saline vehicle or 2) solutions of Ang II (Sigma Chemical Co., St. Louis, Mo., USA) that delivered (subcutaneously) 1.44 mg/kg/day of Ang II for 28 days. Pumps were placed into the subcutaneous space of isoflurane anesthetized mice through a small incision in the back of the neck that was closed with surgical glue. All incision sites healed rapidly without the need for any medication.

To quantify AAA incidence and size, the maximum width of abdominal aorta was measured with Image Pro Plus software (Media Cybernetics). Aneurysm incidence was quantified based on a definition of aneurysm as an external width of the suprarenal aorta that was increased by 50% or greater compared with aortas from saline-infused mice. The average diameter of the normal suprarenal aorta in control mice is 0.8 mm. Therefore, a threshold of 1.22 mm as evidence of aneurysm formation was set.

Figure 18:
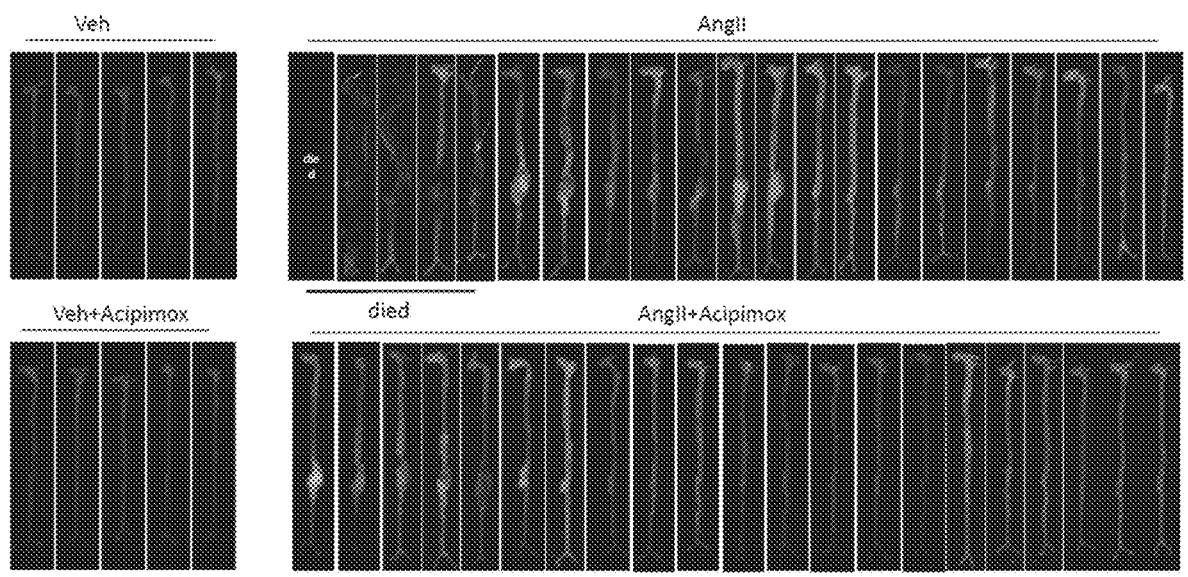
FIG. 18 are representative photographs showing the macroscopic features of Ang-II induced aneurysms in four groups of ApoE$^{-/-}$ mice: vehicle treated; vehicle+acipimox treated; AngII treated; and AngII+acipimox treated.
Figure 19A:
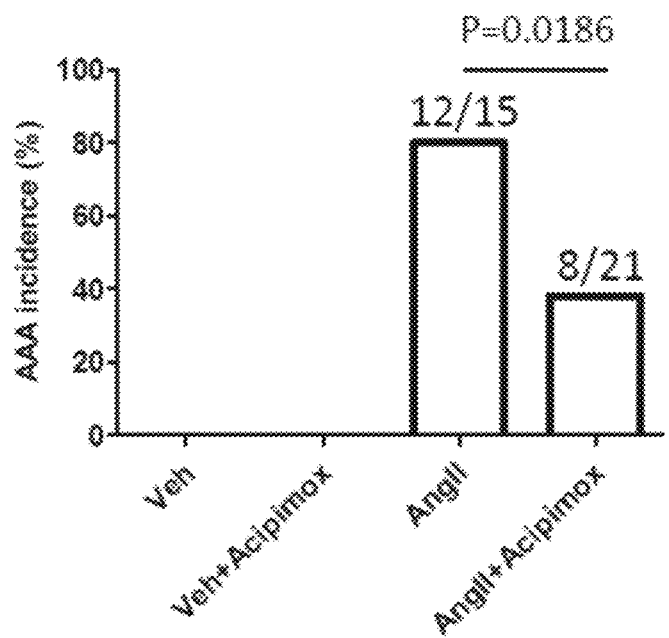
FIG. 19A is a bar graph that shows AAA incidence in four groups of ApoE$^{-/-}$ mice: vehicle treated; vehicle+acipimox treated; AngII treated; and AngII+acipimox treated. The x-axis shows the group of mice, and the y-axis shows the AAA incidence in percent.
Figure 19B:
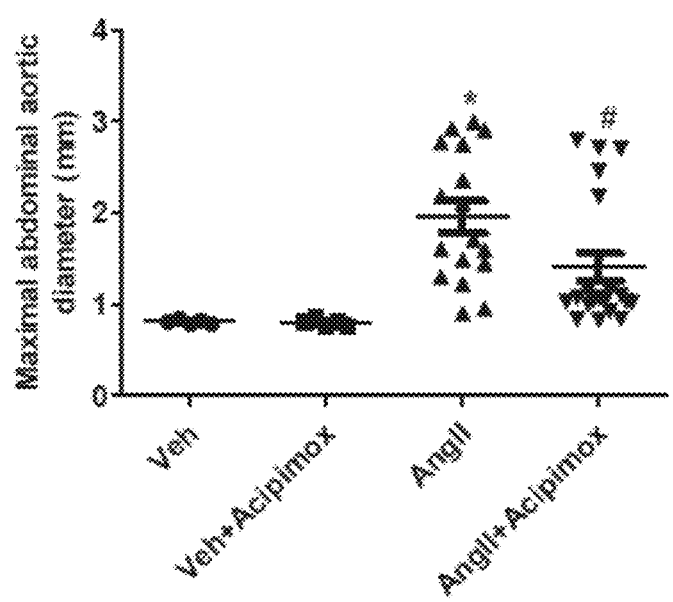
FIG. 19B is a scatter plot that shows maximal abdominal aortic diameter in four groups of ApoE$^{-/-}$ mice: vehicle treated; vehicle+acipimox treated; AngII treated; and AngII+acipimox treated. The x-axis shows the group of mice, and y-axis shows the maximal abdominal aortic diameter in millimeters. *P<0.05 versus vehicle. #P<0.05 versus AngII. The error bars are standard error of the mean.
Figure 19C:
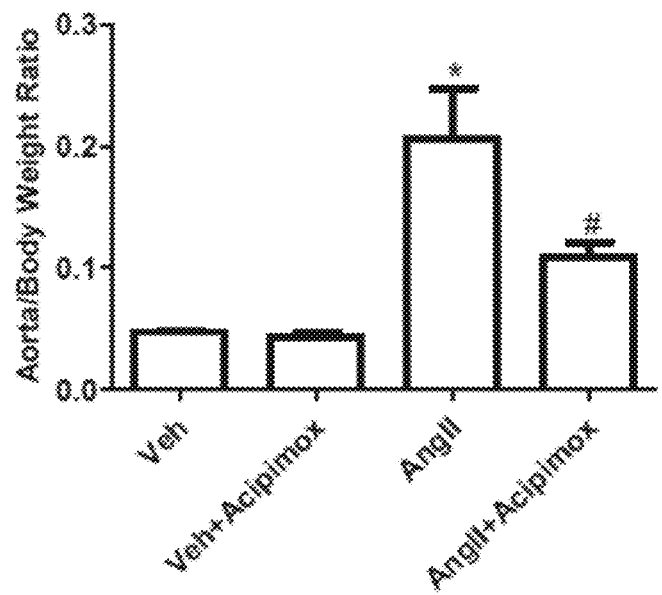
FIG. 19C is a bar graph that shows the aorta weight to body weight ratio in four groups of ApoE$^{-/-}$ mice: vehicle treated; vehicle+acipimox treated; AngII treated; and AngII+acipimox treated. The x-axis shows the group of mice, and the y-axis shows the aorta weight to body weight ration. *P<0.05 versus vehicle. #P<0.05 versus AngII. The error bars are standard error of the mean.
Figure 20:
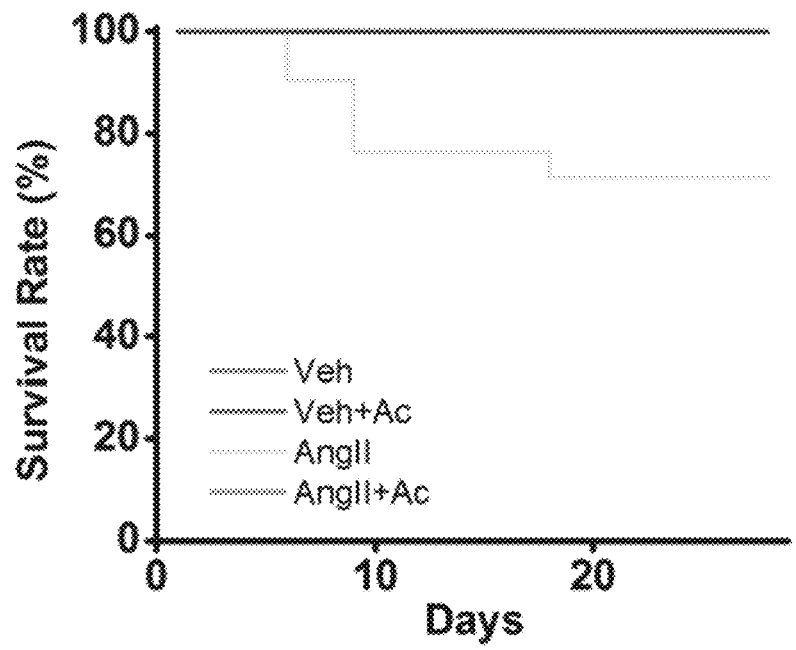
FIG. 20 is a graph that shows the survival rate in days in four groups of ApoE$^{-/-}$ mice: vehicle treated; vehicle+acipimox treated; AngII treated; and AngII+acipimox treated. The x-axis is treatment time in days, and the y-axis is survival rate in percent.

No AAA formation was observed in ApoE$^{-/-}$ mice receiving vehicle alone or acipimox+vehicle (see. FIGS. 18 and 19A/19B). Eighty percent of ApoE$^{-/-}$ mice receiving AngII+vehicle developed AAA (see FIGS. 18 and 19A). Comparatively, only 38% of ApoE$^{-/-}$ mice receiving AngII+acipimox developed AAA (see FIGS. 18 and 19). In addition, acipimox+AngII mice showed dramatically decreased maximal abdominal aortic diameter and total aortic weight compared with AngII-treated mice (FIG. 19). Furthermore, AngII+vehicle mice experienced a 28.6% mortality rate, compared to a mortality rate of 0% for AngII+acipimox mice (FIG. 20).

Figure 21:
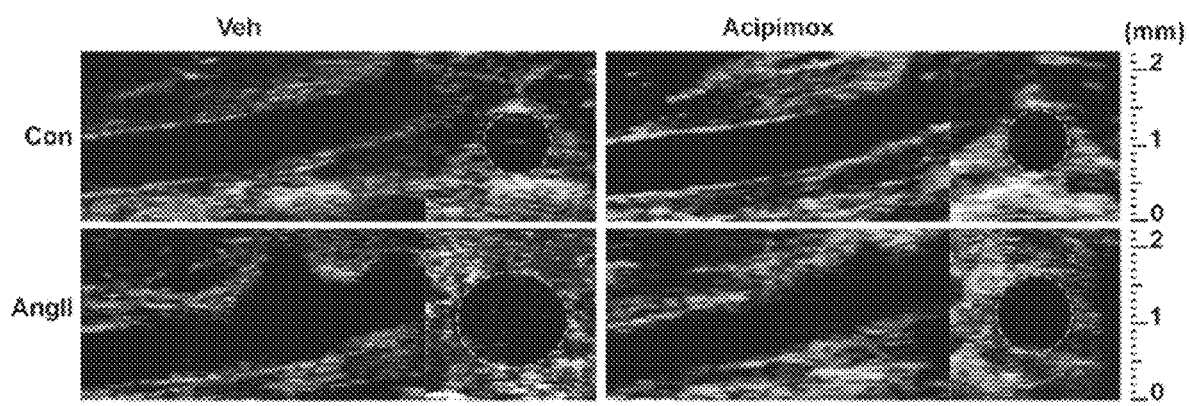
FIG. 21 depicts representative images of the mice abdominal aorta from four groups of ApoE$^{-/-}$ mice: vehicle treated; vehicle+acipimox treated; AngII treated; and AngII+acipimox treated.
Figure 22A:
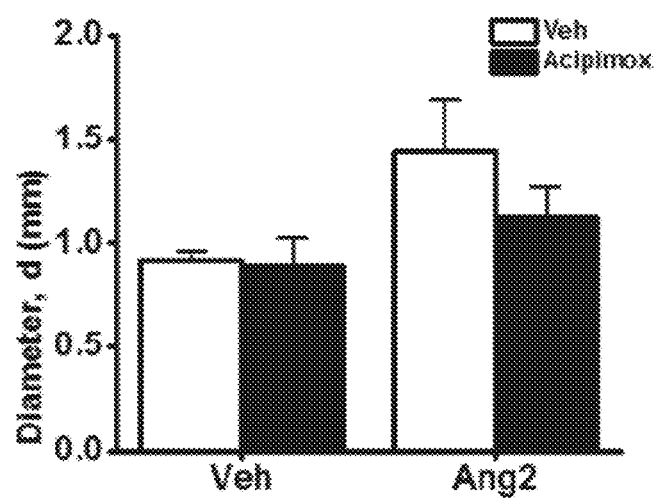
FIG. 22A is a bar graph that shows the abdominal diastolic aortic diameter as measured by ultrasound in four groups of ApoE$^{-/-}$ mice: vehicle treated; vehicle+acipimox treated; AngII treated; and AngII+acipimox treated. The x-axis is the group of mice, and the y-axis is the diastolic diameter in millimeters. N=4 for each group. The error bars are standard error of the mean.
Figure 22B:
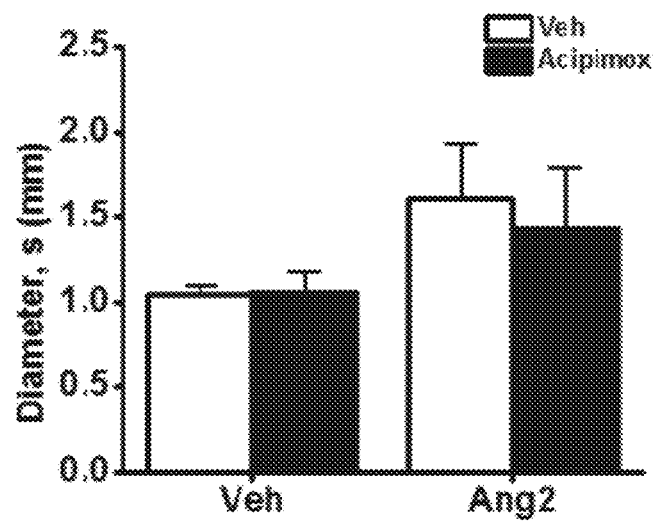
FIG. 22B is a bar graph that shows the abdominal systolic aortic diameter as measured by ultrasound in four groups of ApoE$^{-/-}$ mice: vehicle treated; vehicle+acipimox treated; AngII treated; and AngII+acipimox treated. The x-axis is the group of mice, and the y-axis is the systolic diameter in millimeters. N=4 for each group. The error bars are standard error of the mean.

Abdominal aorta dimeter was measured by ultrasound as described above. As shown in FIGS. 21, 22A and 22B, acipimox treatment inhibited AngII-induced abdominal aorta dilation, while AngII significantly increase the diastolic diameter and systolic diameter compared with vehicle and acipimox treated mice.

Figure 23A:
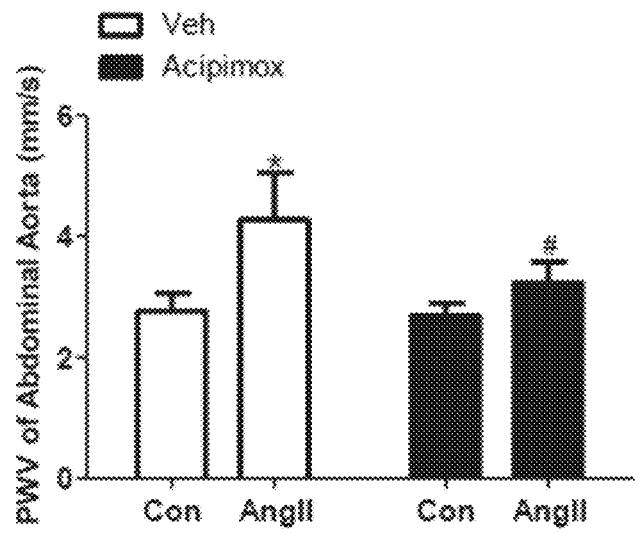
FIG. 23A is a bar graph that shows the speed of propagation (PWV) in the abdominal aorta (mm/s) as measured in four groups of ApoE$^{-/-}$ mice: vehicle treated; vehicle+ acipimox treated; AngII treated; and AngII+acipimox treated. The x-axis shows the group of mice, and the y-axis shows the PWV of the abdominal aorta in millimeters per second. *P<0.05 versus vehicle. #P<0.05 versus AngII treated. The error bars are standard error of the mean.
Figure 23B:
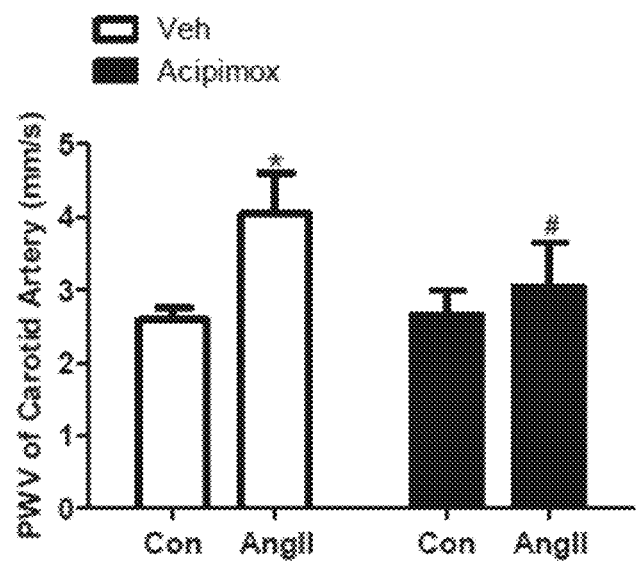
FIG. 23B is a bar graph that shows the speed of propagation (PWV) in the carotid artery (mm/s) as measured in four groups of ApoE$^{-/-}$ mice: vehicle treated; vehicle+ acipimox treated; AngII treated; AngII+acipimox treated. The x-axis shows the group of mice, and the y-axis shows the PWV of the carotid artery in millimeters per second. *P<0.05 versus vehicle. #P<0.05 versus AngII treated. The error bars are standard error of the mean.
Figure 24A:
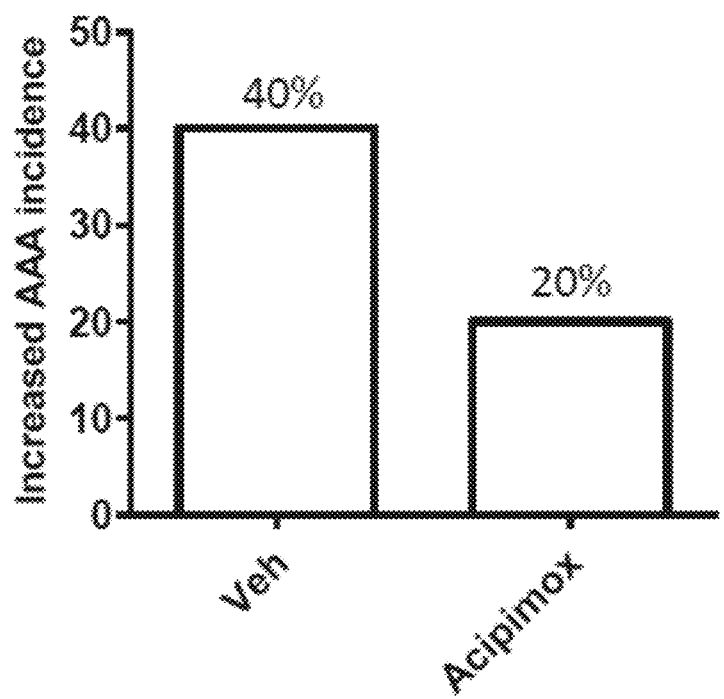
FIG. 24A is a bar graph that shows the increase in the development of AAA formation in two groups of ApoE$^{-/-}$ mice infused with AngII for four weeks and then treated with either vehicle or acipimox for six weeks. The x-axis is the treatment, and the y-axis is the increase in AAA incidence in percent.
Figure 24B:
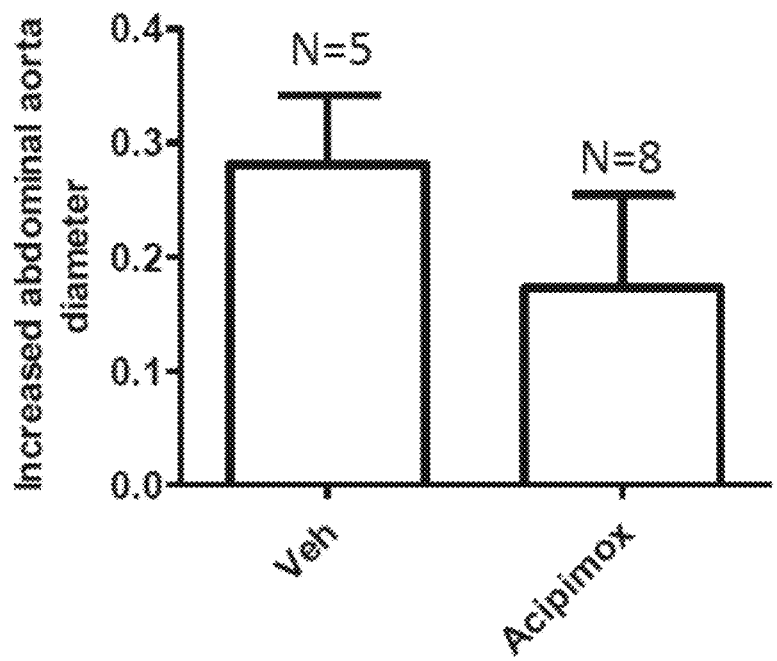
FIG. 24B is a bar graph that shows the increase in abdominal diastolic aorta diameter in mice without AAA formation after four weeks of AngII infusion treatment with either vehicle (N=5) or acipimox (N=8) for six weeks. The x-axis shows the treatment, and the y-axis shows the increase in abdominal aorta diameter.

The effect of acipimox on the speed of propagation (i.e. PWV), which is parameter for arterial stiffness, was analyzed. AngII treatment significantly increased the PWV of the carotid artery and abdominal aorta, while acipimox treatment inhibited the effect of AngII. The results of the analysis are provided in FIGS. 23A and 23B.

Example 13. Effect of Acipimox on Treating Ang-II-Induced Abdominal Aortic Aneurysm To test the effect of acipimox on treating AngII-induced abdominal aortic aneurysm, male ApoE$^{-/-}$ mice at age 8 weeks were infused with AngII (1,000 ng/kg/min) or saline (0.9% sodium chloride) by Alzet osmotic pumps for four weeks. Four weeks later, mice were treated with acipimox (0.1% wt) or vehicle control (water) by drinking water for 6 weeks. AAA incidence, maximal abdominal aorta diameter and aorta/body weight ratio were examined to evaluate the therapeutic effect of acipimox on AngII-induced AAA.

To quantify AAA incidence and size, the maximum width of abdominal aorta was measured with Image Pro Plus software (Media Cybernetics). Aneurysm incidence was quantified based on a definition of aneurysm as an external width of the suprarenal aorta that was increased by 50% or greater compared with aortas from saline-infused mice. The average diameter of the normal suprarenal aorta in control mice is 0.8 mm. Therefore, a threshold of 1.22 mm as evidence of aneurysm formation was set. Vehicle control mice did not develop AAA. After 4-weeks of AngII-infusion, mice where divided into two groups vehicle treated (n=10) or acipimox treated (n=15). Before treatment, the AAA incidence was 50% and 46.7%, respectively. After six weeks of treatment with vehicle or acipimox, AAA incidence increased to 90% and 66.7%, respectively.

The incidence of AAA formation was analyzed for mice who did not develop AAA following four weeks of AngII infusion and then treated with either vehicle or acipimox for six weeks. Mice treated with vehicle experienced a 40% increase in the formation of AAA during the six weeks following AngII infusion. Comparatively, acipimox treated mice experienced a 20% increase in AAA incidence. Furthermore, the abdominal diastolic aorta diameter in vehicle treated mice six weeks following AngII infusion was significantly increased compared to acipimox treated mice. Results are shown in FIGS. 24A, 24B, 26A and 26B.

Figure 29:
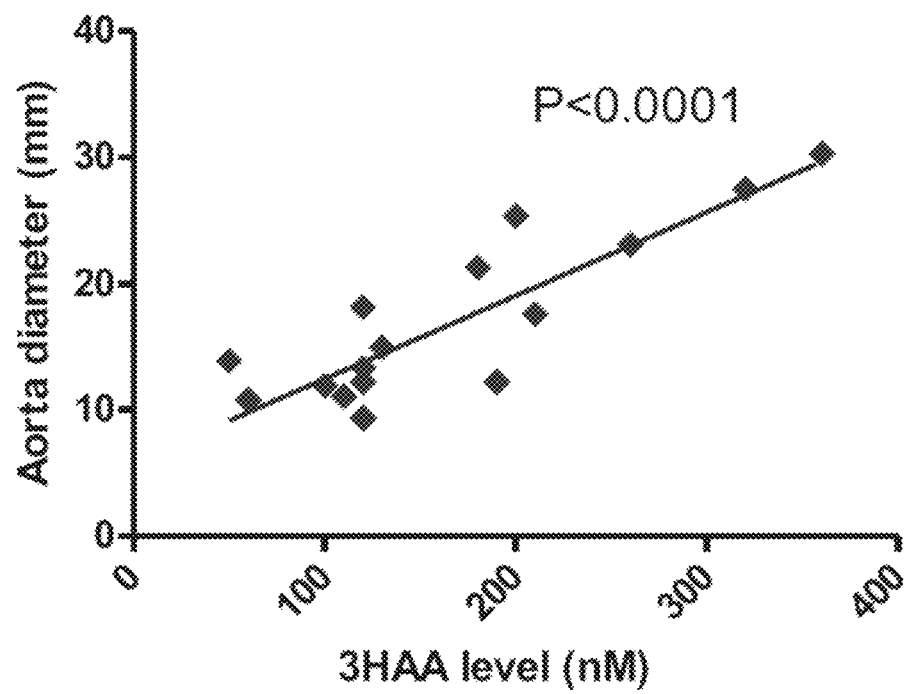
FIG. 29 is a scatter plot that shows the relationship between aorta diameter and 3-HAA level in aneurysm positive mice. The x-axis shows the nanomolar 3-HAA level. The y-axis shows the aorta diameter in millimeters. P<0.001. $R^2$=0.7355.

Example 14. Plasma 3-HAA Levels are Strongly Associated with Aortic Diameter in AAA-Positive Mice As shown in FIG. 29, there is a strong correlation found between aortal diameter and plasma 3-HAA level in mice. 3-HAA levels in aneurysm-positive mice are typically between 120-300 nM, while the range in aneurysm-free mice is 70-100 nM.

Example 15. Effect of OMBA, NBA, and 1MT on Treating AngII-Induced Abdominal Aortic Aneurysm To test the effect of other Kynurenine pathway inhibitors on treating AngII-induced abdominal aortic aneurysm, male ApoE$^{-/-}$ mice at age 8 weeks were infused with AngII (1,000 ng/kg/min) or saline (0.9% sodium chloride) by Alzet osmotic pumps for four weeks. Four weeks later, Ang-II treated mice were divided into five groups of 18 and administered o-methoxybenzoylalanine (OMB), (m-nitrobenzoyl)alanine (NBA), 1-methyltryptophan (1MT) or vehicle control (water) by drinking water for 6 weeks.

Figure 30:
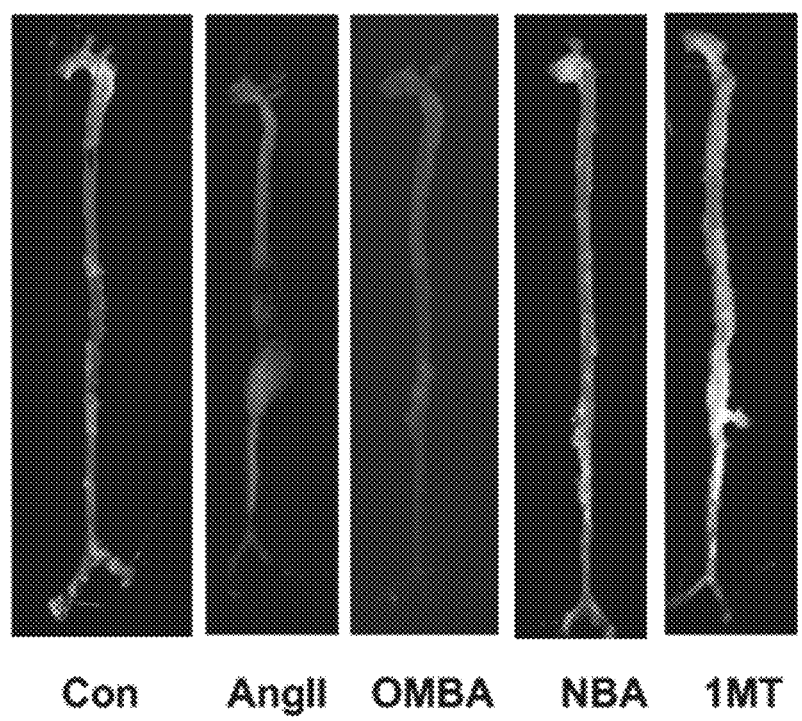
FIG. 30 depicts representative images of abdominal aorta from five groups of ApoE$^{-/-}$ mice: vehicle (saline) treated; AngII treated; AngII+OMBA treated; AngII+NBA treated; and AngII+1MT treated.
Figure 31A:
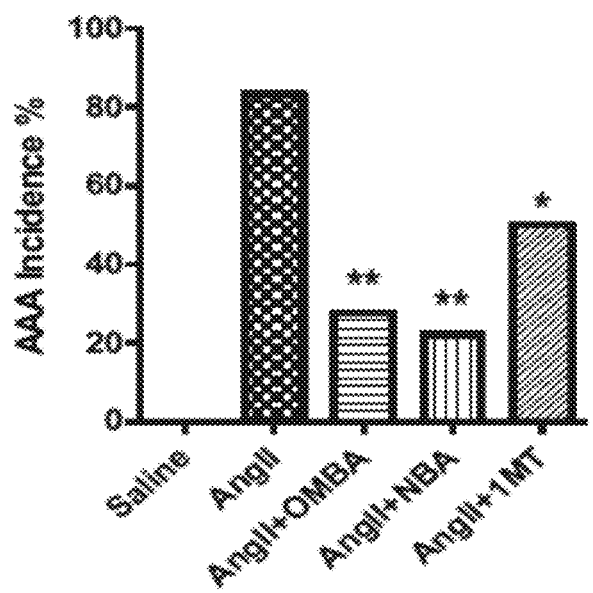
FIG. 31A is a bar graph that shows the incidence of AAA in five groups of ApoE$^{-/-}$ mice: vehicle (saline) treated; AngII treated; AngII+OMBA treated; AngII+NBA treated; and AngII+1MT treated. The x-axis shows the group of mice, and the y-axis shows AAA incidence in percent. P values were obtained using the chi-square test.

To quantify AAA incidence and size, the maximum width of abdominal aorta was measured with Image Pro Plus software (Media Cybernetics). Aneurysm incidence was quantified based on a definition of aneurysm as an external width of the suprarenal aorta that was increased by 50% or greater compared with aortas from saline-infused mice. The average diameter of the normal suprarenal aorta in control mice is 0.8 mm. Therefore, a threshold of 1.22 mm as evidence of aneurysm formation was set. Vehicle control mice did not develop AAA. Representative aortas from all groups are shown in FIG. 30. Incidence of AAA among the various groups of mice is outlined in FIG. 31A and Table 5 below.

TABLE 5

| Incidence of AAA Among Various Treatment Groups | | | | |
|---|---|---|---|---|
| Saline | AngII | AngII + OMBA | AngII + NBA | AngII + 1MT |
| 0 | 15/18 | 5/18 | 4/18 | 9/18 |

Figure 31B:
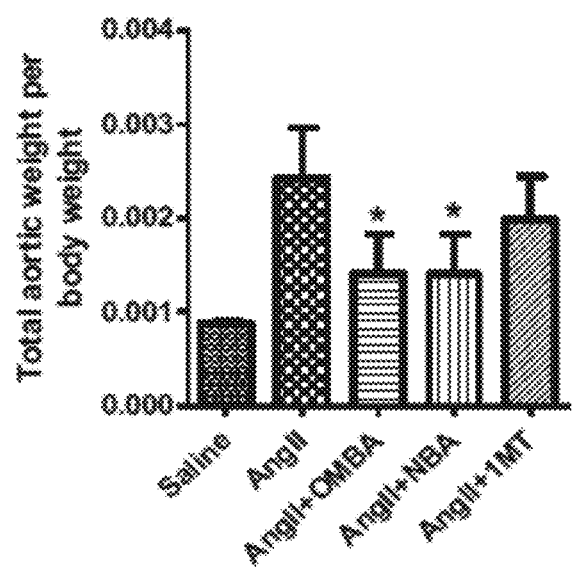
FIG. 31B is a bar graph that shows the aortic weight to body weight ratio in five groups of ApoE$^{-/-}$ mice: vehicle (saline) treated; AngII treated; AngII+OMBA treated; AngII+NBA treated; and AngII+1MT treated. The x-axis shows the group of mice, and the y-axis shows the aortic weight to body weight ratio. P values were obtained using one-way ANOVA with a post-hoc analysis using Bonferroni's multiple comparison's test. Error bars represent standard error of the mean.
Figure 31C:
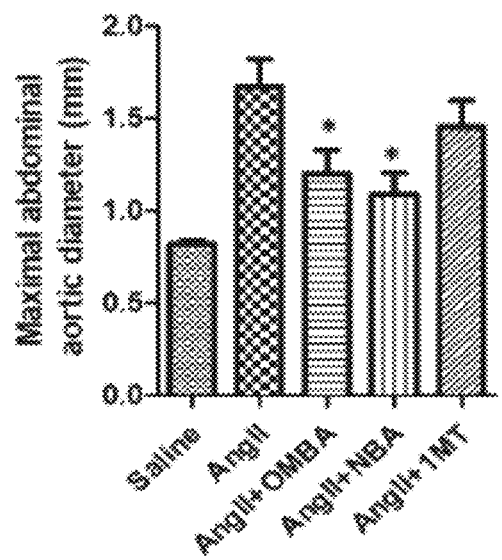
FIG. 31C is a bar graph that shows the maximal abdominal aortic diameter in five groups of ApoE$^{-/-}$ mice: vehicle (saline treated); AngII treated; AngII+OMBA treated; AngII+NBA treated; and AngII+1MT treated. The x-axis shows the group of mice, and the y-axis shows the maximal abdominal aortic diameter in millimeters. P values were obtained using one-way ANOVA with a post-hoc analysis using Bonferroni's multiple comparison's test. Error bars represent standard error of the mean.

As shown in FIGS. 31B and 31C, a lower aortic weight to body weight ratio and maximal abdominal aortic diameter was observed in AngII-administered mice treated with OMBA and NBA.

Figure 32A:
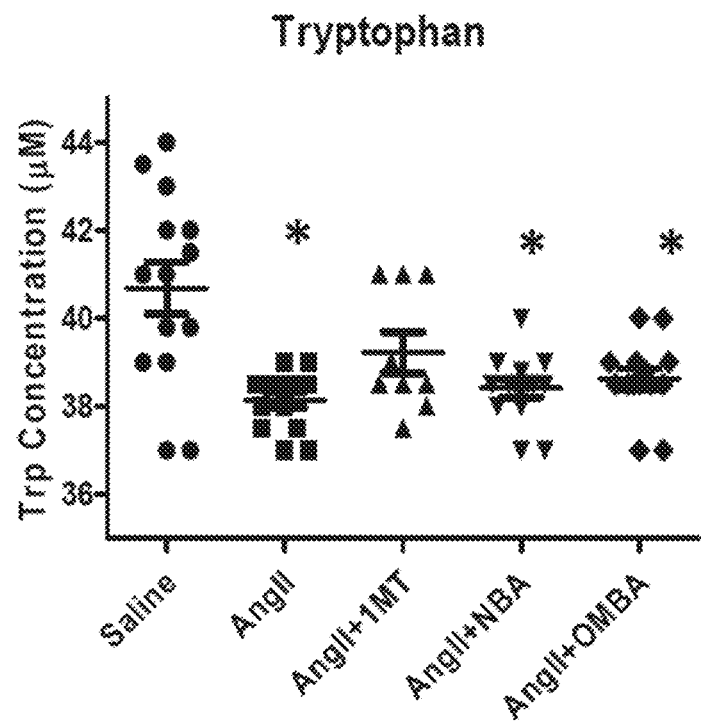
FIG. 32A is a scatter plot that shows the serum tryptophan concentration in five groups of ApoE$^{-/-}$ mice: vehicle (saline treated); AngII treated; AngII+OMBA treated; AngII+NBA treated; and AngII+1MT treated. The x-axis shows the group of mice, and the y-axis shows micromolar serum tryptophan concentration. N=10 in saline group and N=17 in AngII infused groups. P values were obtained by a one-way ANOVA with a post-hoc analysis using Bonferroni's multiple comparisons test. *P<0.01 for saline vs. Ang. II infused mice, #P<0.01 for AngII vs. AngII-infused inhibitor treated mice.
Figure 32B:
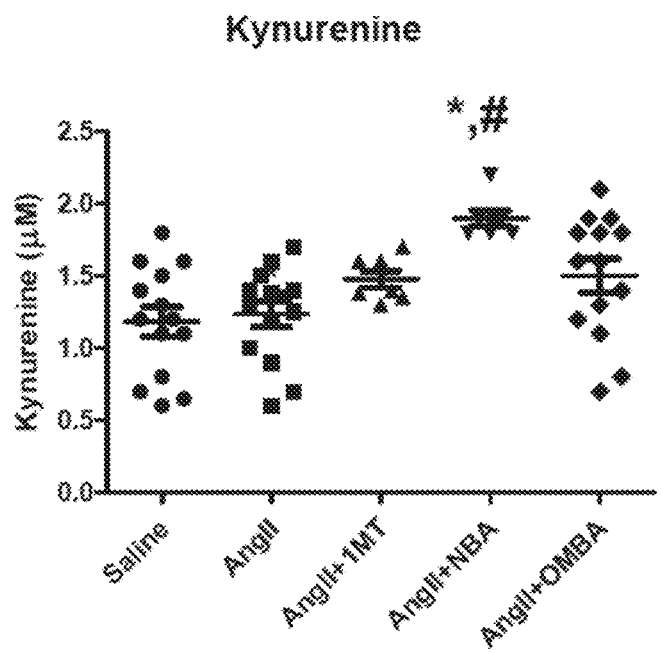
FIG. 32B is a scatter plot that shows the serum kynurenine concentration in five groups of ApoE$^{-/-}$ mice: vehicle (saline treated); AngII treated; AngII+OMBA treated; AngII+NBA treated; and AngII+1MT treated. The x-axis shows the group of mice, and the y-axis shows micromolar serum kynurenine concentration. N=10 in saline group and N=17 in AngII infused groups. P values were obtained by a one-way ANOVA with a post-hoc analysis using Bonferroni's multiple comparisons test. *P<0.01 for saline vs. Ang. II infused mice, #P<0.01 for AngII vs. AngII-infused inhibitor treated mice.
Figure 32C:
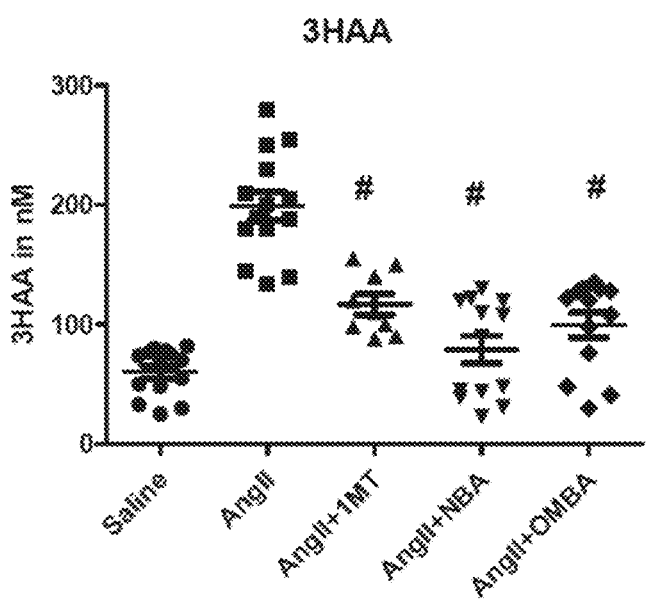
FIG. 32C is a scatter plot that shows the serum 3HAA concentration in five groups of ApoE$^{-/-}$ mice: vehicle (saline treated); AngII treated; AngII+OMBA treated; AngII+NBA treated; and AngII+1MT treated. The x-axis shows the group of mice, and the y-axis shows micromolar serum 3HAA concentration. N=10 in saline group and N=17 in AngII infused groups. P values were obtained by a one-way ANOVA with a post-hoc analysis using Bonferroni's multiple comparisons test. *P<0.01 for saline vs. Ang. II infused mice, #P<0.01 for AngII vs. AngII-infused inhibitor treated mice.
Figure 32D:
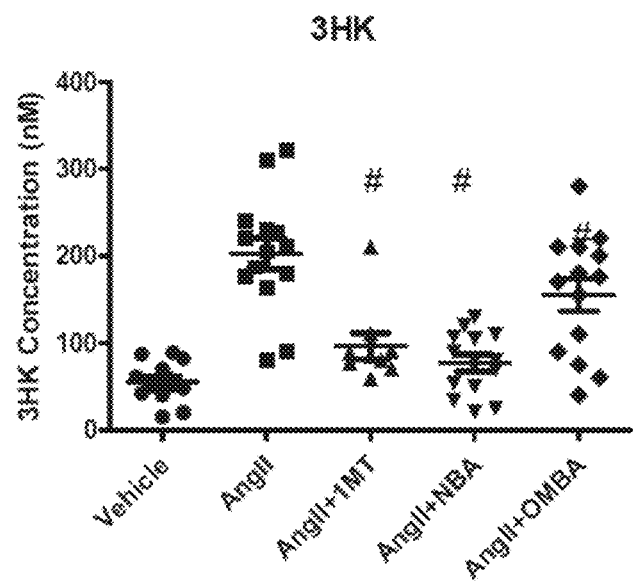
FIG. 32D is a scatter plot that shows the serum 3HK concentration in five groups of ApoE$^{-/-}$ mice: vehicle (saline treated); AngII treated; AngII+OMBA treated; AngII+NBA treated; and AngII+1MT treated. The x-axis shows the group of mice, and the y-axis shows micromolar serum 3HK concentration. N=10 in saline group and N=17 in AngII infused groups. P values were obtained by a one-way ANOVA with a post-hoc analysis using Bonferroni's multiple comparisons test. *P<0.01 for saline vs. Ang. II infused mice, #P<0.01 for AngII vs. AngII-infused inhibitor treated mice.
Figure 32E:
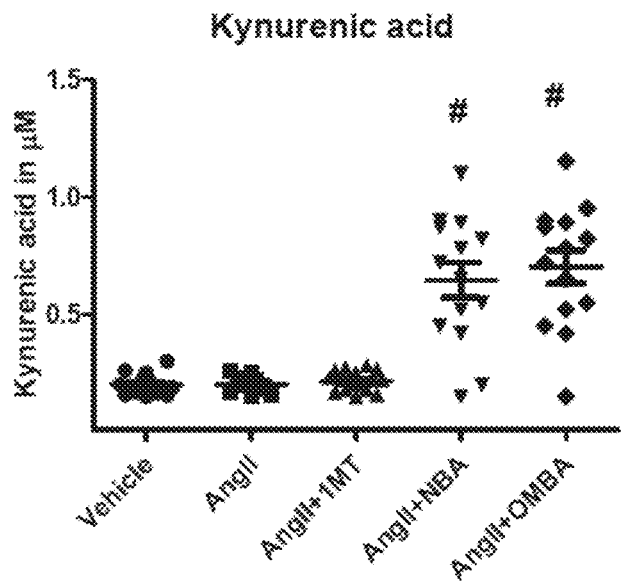
FIG. 32E is a scatter plot that shows the serum kynurenic acid concentration in five groups of ApoE$^{-/-}$ mice: vehicle (saline treated); AngII treated; AngII+OMBA treated; AngII+NBA treated; and AngII+1MT treated. The x-axis shows the group of mice, and the y-axis shows micromolar serum kynurenic concentration. N=10 in saline group and N=17 in AngII infused groups. P values were obtained by a one-way ANOVA with a post-hoc analysis using Bonferroni's multiple comparisons test. *P<0.01 for saline vs. Ang. II infused mice, #P<0.01 for AngII vs. AngII-infused inhibitor treated mice.
Figure 32F:
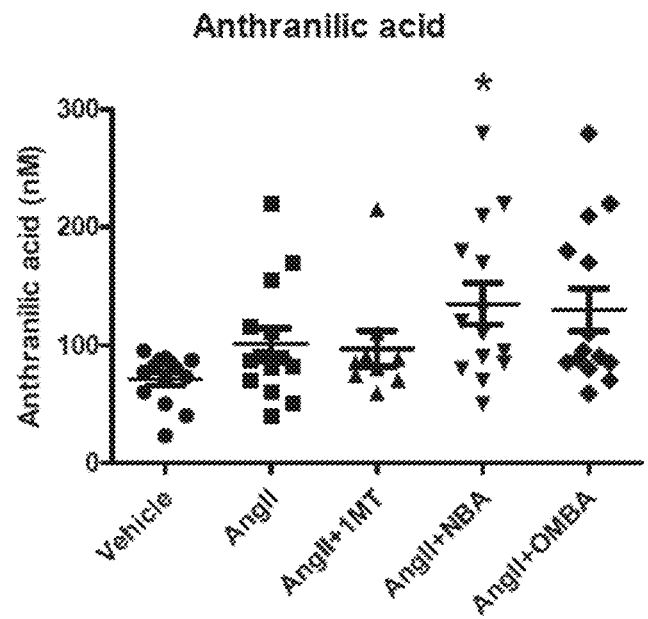
FIG. 32F is a scatter plot that shows the serum anthranilic acid concentration in five groups of ApoE$^{-/-}$ mice: vehicle (saline treated); AngII treated; AngII+OMBA treated; AngII+NBA treated; and AngII+1MT treated. The x-axis shows the group of mice, and the y-axis shows micromolar serum kynurenic concentration. N=10 in saline group and N=17 in AngII infused groups. P values were obtained by a one-way ANOVA with a post-hoc analysis using Bonferroni's multiple comparisons test. *P<0.01 for saline vs. Ang. II infused mice, #P<0.01 for AngII vs. AngII-infused inhibitor treated mice.
Figure 33A:
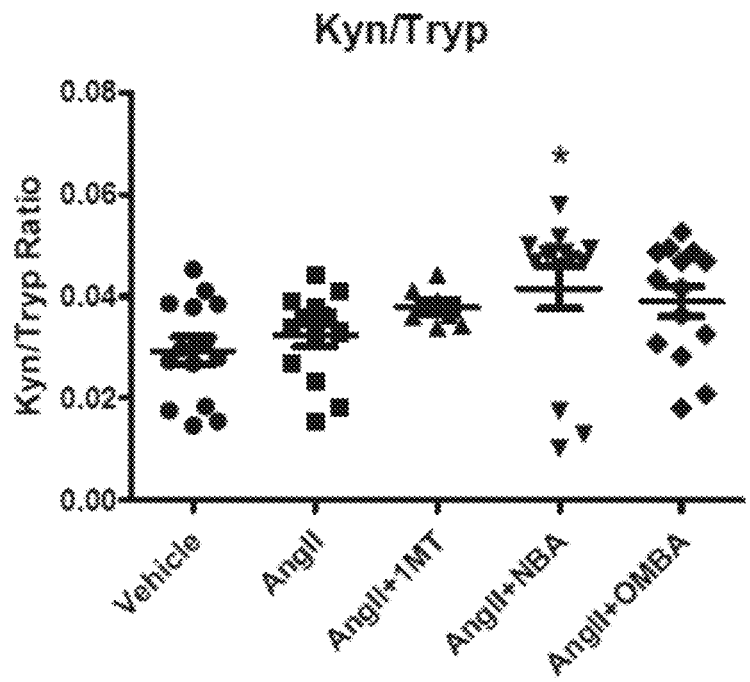
FIG. 33A is a scatter plot that shows the serum kynurenine/tryptophan ratio in five groups of ApoE$^{-/-}$ mice: vehicle (saline treated); AngII treated; AngII+OMBA treated; AngII+NBA treated; and AngII+1MT treated. The x-axis shows the group of mice, and the y-axis shows the serum kynurenine/tryptophan ratio. N=10 in saline group and N=17 in AngII infused groups. P values were obtained by a one-way ANOVA with a post-hoc analysis using Bonferroni's multiple comparisons test. *P<0.01 for saline vs. Ang. II infused mice, #P<0.01 for AngII vs. AngII-infused inhibitor treated mice.
Figure 33B:
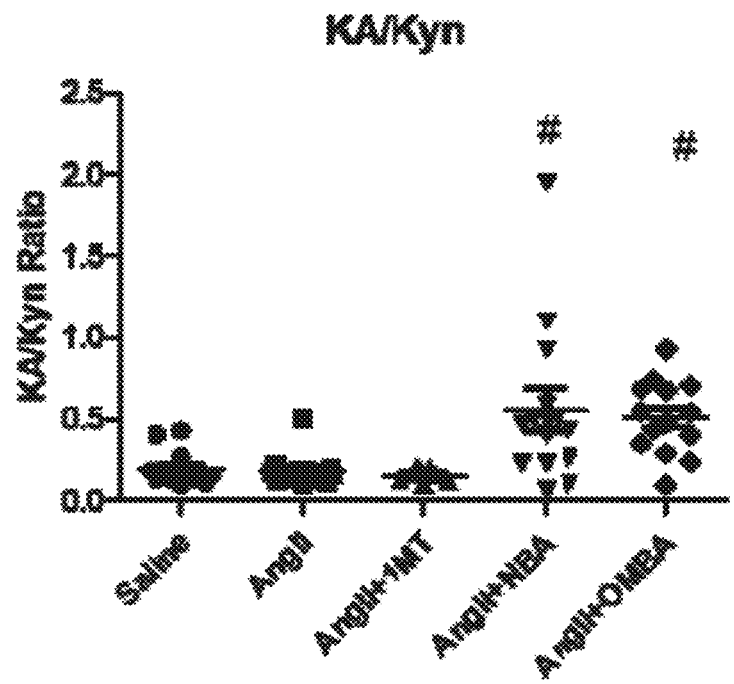
FIG. 33B is a scatter plot that shows the serum kynurenic acid/tryptophan ratio in five groups of ApoE$^{-/-}$ mice: vehicle (saline treated); AngII treated; AngII+OMBA treated; AngII+NBA treated; and AngII+1MT treated. The x-axis shows the group of mice, and the y-axis shows the serum kynurenic acid/tryptophan ratio. N=10 in saline group and N=17 in AngII infused groups. P values were obtained by a one-way ANOVA with a post-hoc analysis using Bonferroni's multiple comparisons test. *P<0.01 for saline vs. Ang. II infused mice, #P<0.01 for AngII vs. AngII-infused inhibitor treated mice.
Figure 33C:
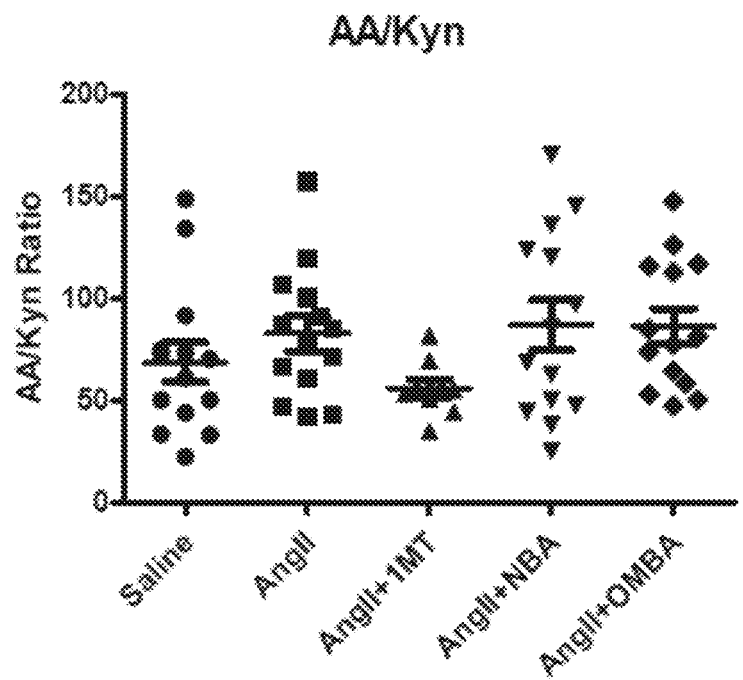
FIG. 33C is a scatter plot that shows the serum anthranilic acid/tryptophan ratio in five groups of ApoE$^{-/-}$ mice: vehicle (saline treated); AngII treated; AngII+OMBA treated; AngII+NBA treated; and AngII+1MT treated. The x-axis shows the group of mice, and the y-axis shows the serum anthranilic acid/tryptophan ratio. N=10 in saline group and N=17 in AngII infused groups. P values were obtained by a one-way ANOVA with a post-hoc analysis using Bonferroni's multiple comparisons test. *P<0.01 for saline vs. Ang. II infused mice, #P<0.01 for AngII vs. AngII-infused inhibitor treated mice.
Figure 33D:
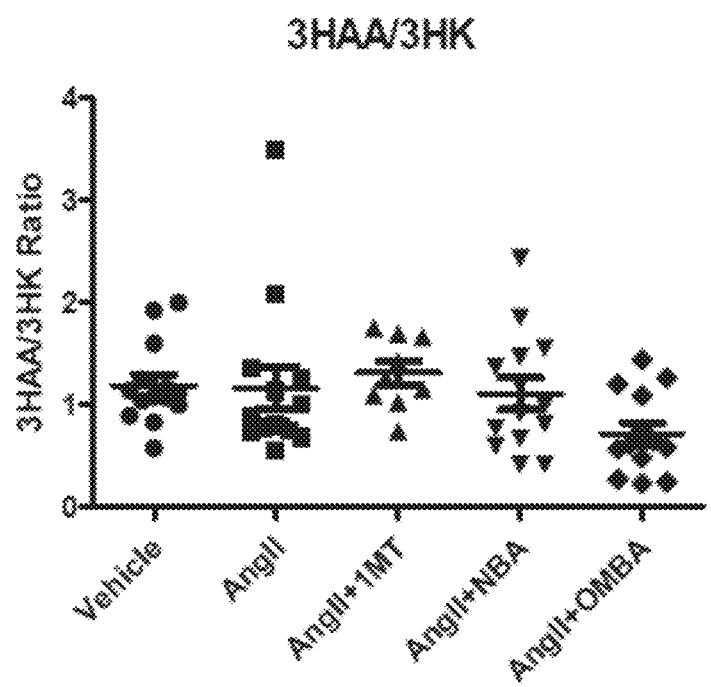
FIG. 33D is a scatter plot that shows the serum 3HAA/tryptophan ratio in five groups of ApoE$^{-/-}$ mice: vehicle (saline treated); AngII treated; AngII+OMBA treated; AngII+NBA treated; and AngII+1MT treated. The x-axis shows the group of mice, and the y-axis shows the serum 3HAA/tryptophan ratio. N=10 in saline group and N=17 in AngII infused groups. P values were obtained by a one-way ANOVA with a post-hoc analysis using Bonferroni's multiple comparisons test. *P<0.01 for saline vs. Ang. II infused mice, #P<0.01 for AngII vs. AngII-infused inhibitor treated mice.
Figure 34A:
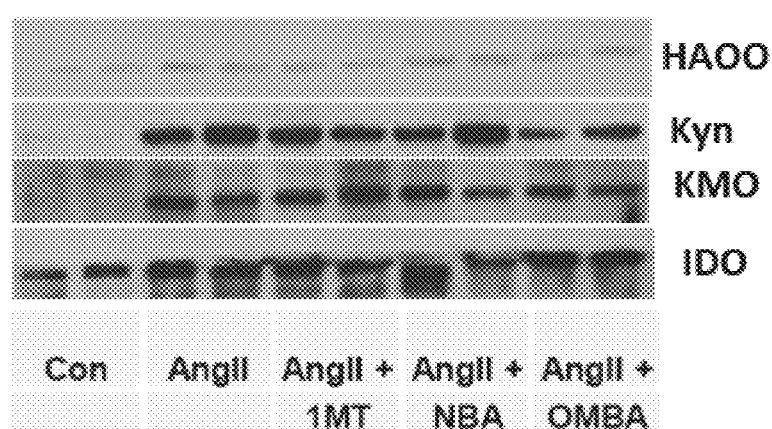
FIG. 34A is an immunoblot showing the expression of HAOO, Kynureninase, KMO, and IDO in five groups of ApoE$^{-/-}$ mice: vehicle (saline treated); AngII treated; AngII+OMBA treated; AngII+NBA treated; and AngII+1MT treated.
Figure 34B:
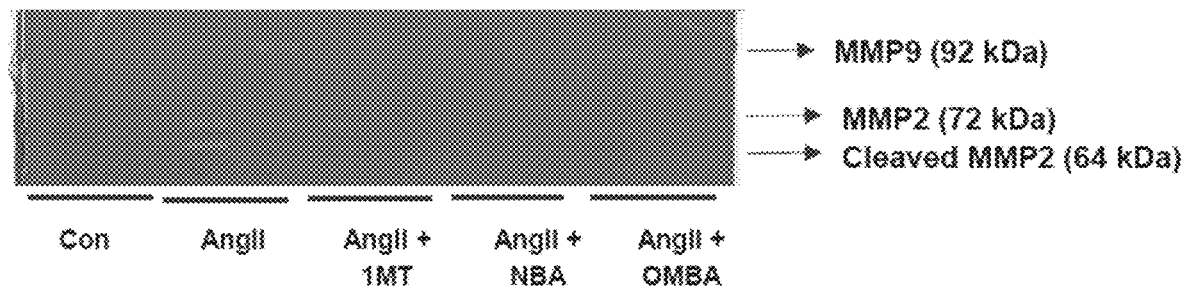
FIG. 34B is a zymogram that shows the levels of MMP9, MMP2, and cleaved MMP2 in five groups of ApoE$^{-/-}$ mice: vehicle (saline treated); AngII treated; AngII+OMBA treated; AngII+NBA treated; and AngII+1MT treated.
Figure 35:
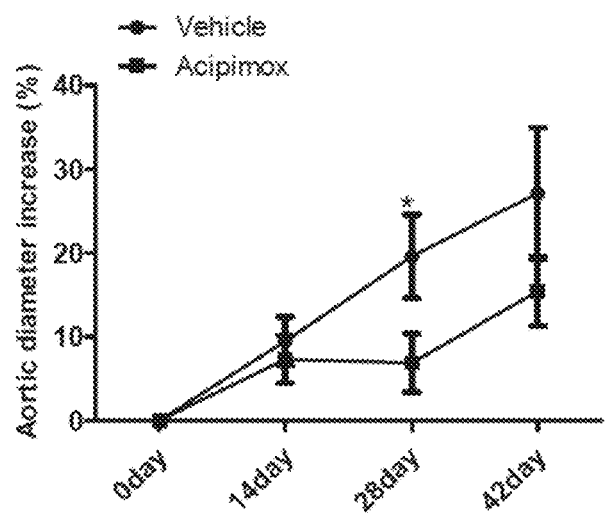
FIG. 35 is a line graph that shows the percentage increase over time in abdominal aortic diameter in mice treated with AngII (1.44 mg/kg/day) for 14 days, followed by infusion with vehicle or 0.1% acipimox for 6 weeks. The x-axis shows time in days, and the y-axis shows the aortic diameter increase in percent. The error bars are standard error of the mean.

Serum levels of tryptophan, kynurenine, 3-HAA, 3-HK, kynurenic acid, and anthranilic acid were also measured for all groups of mice to be treated. Serum levels of tryptophan were found to be decreased in AngII-administered mice treated with OMBA and NBA compared to control mice as shown in FIG. 32A. No significant changes in kynurenine levels were seen across the treatment groups (see FIG. 32B). As shown in FIGS. 32C and 32D, levels of 3-HK and 3-HAA were reduced for all drug treatment groups compared to AngII treated mice. Levels of kynurenic acid and anthranilic were elevated in AngII-administered mice treated with OMBA and NBA compared to those treated with AngII alone as shown in FIGS. 32E and 32F.

As shown in FIGS. 33A to 33D, no change in the ratio between metabolites was observed for the different treatment groups except for the kynurenic acid/kynurenine ratio for NBA and OMBA treated mice.

Example 16. Effect of Acipimox on Preventing Ang-II-Induced Abdominal Aortic Aneurysm in Aged Mice To compare the effect of acipimox on treating AngII-induced abdominal aortic aneurysm in young (3 months old) or old (24 months old) mice, male ApoE$^{-/-}$ mice in the aged mice group were treated with acipimox (0.1% wt) or vehicle control (water) by drinking water for 6 weeks. Four weeks later, mice in both age groups were infused with AngII (1,000 ng/kg/min) or saline (0.9% sodium chloride) by Alzet osmotic pumps for four weeks. AAA incidence and maximal abdominal aorta diameter were examined to evaluate the therapeutic effect of acipimox on AngII-induced AAA in old mice.

Figure 36A:
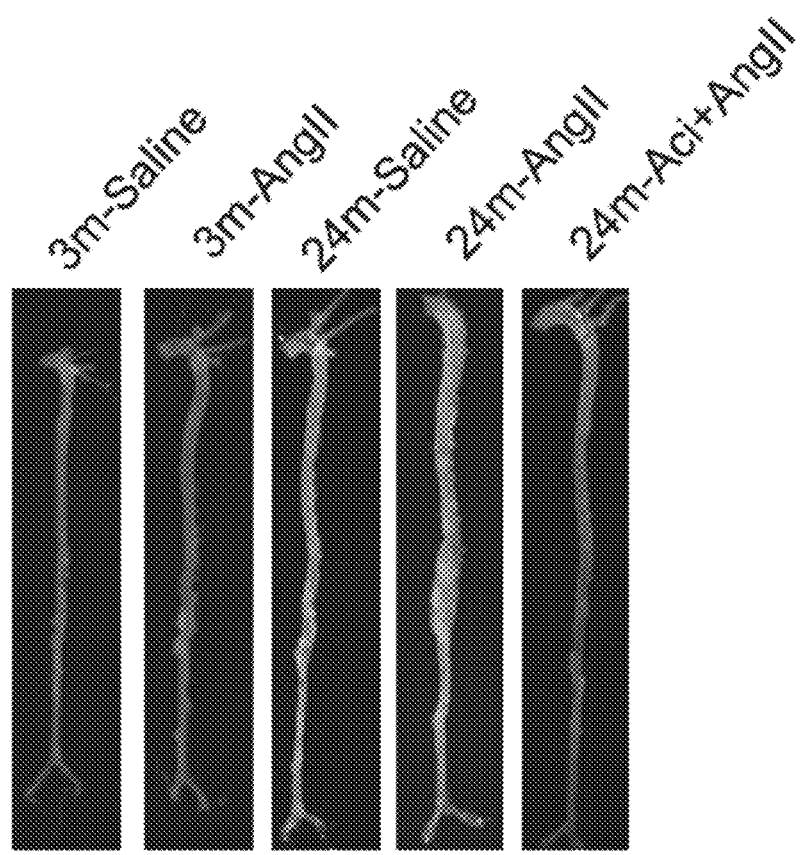
FIG. 36A shows representative images of abdominal aorta from five groups of ApoE$^{-/-}$ mice: 3 month old mice infused with saline (N=14); 3 month old mice infused with AngII (28); 24 month old mice infused with saline (N=9); 24 month old infused with AngII (N=18); and 24 month old infused with AngII+acipimox (Aci) (N=4).
Figure 36B:
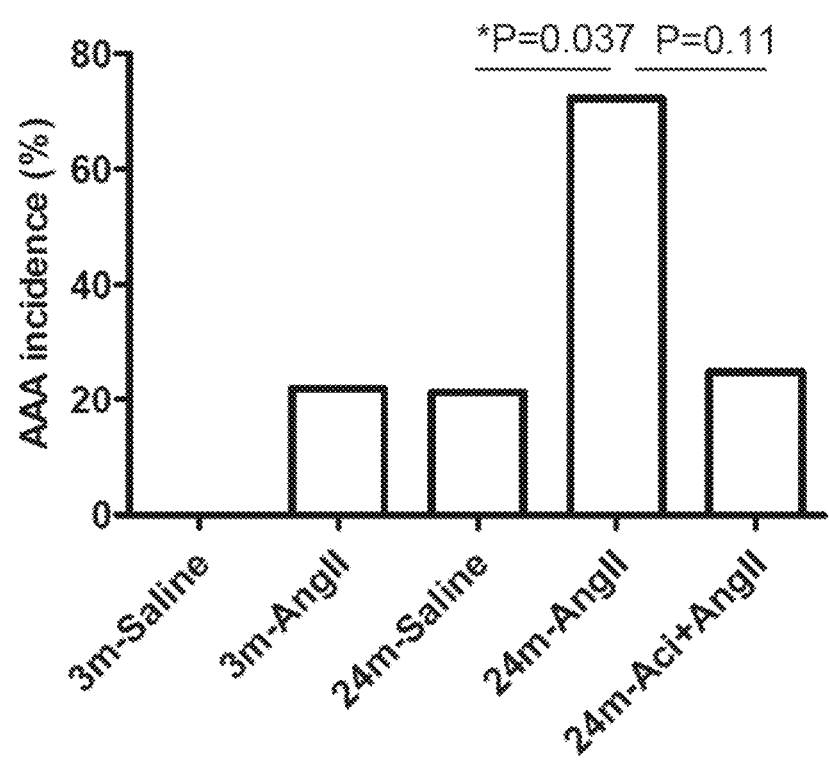
FIG. 36B is a bar graph that shows AAA incidence in five groups of ApoE$^{-/-}$ mice: 3 month old mice infused with saline (N=14); 3 month old mice infused with AngII (28); 24 month old mice infused with saline (N=9); 24 month old infused with AngII (N=18); and 24 month old infused with AngII+acipimox (Aci) (N=4). The x-axis is the group of mice, and the y-axis is AAA incidence in percent.
Figure 36C:
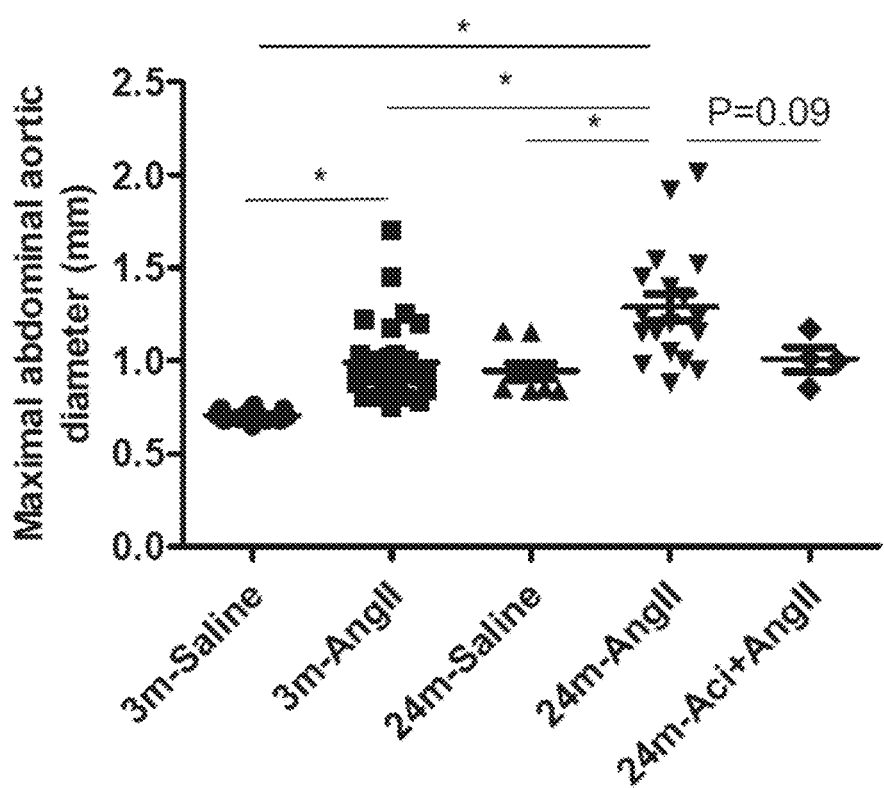
FIG. 36C is a scatter plot that shows maximal abdominal aortic diameter in five groups of ApoE$^{-/-}$ mice: 3 month old mice infused with saline (N=14); 3 month old mice infused with AngII (28); 24 month old mice infused with saline (N=9); 24 month old infused with AngII (N=18); and 24 month old infused with AngII+acipimox (Aci) (N=4). The x-axis is the group of mice, and the y-axis is maximal abdominal aortic diameter in millimeters.
Figure 37A:
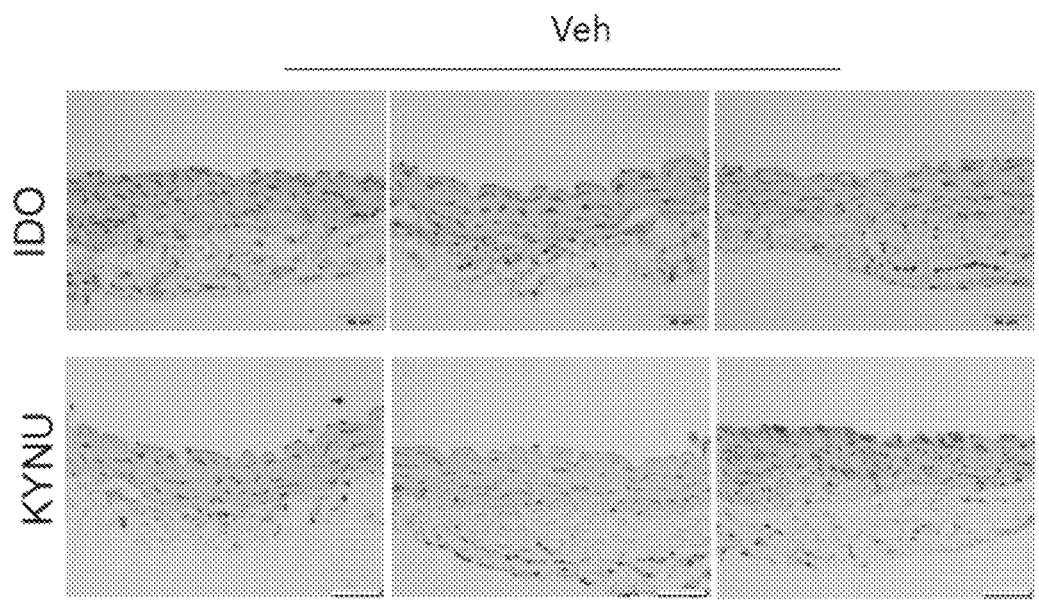
FIG. 37A shows representative immunohistochemical staining for IDO and KYNU in aortic cross sections of vehicle (saline) treated ApoE$^{-/-}$ mice.
Figure 37B:
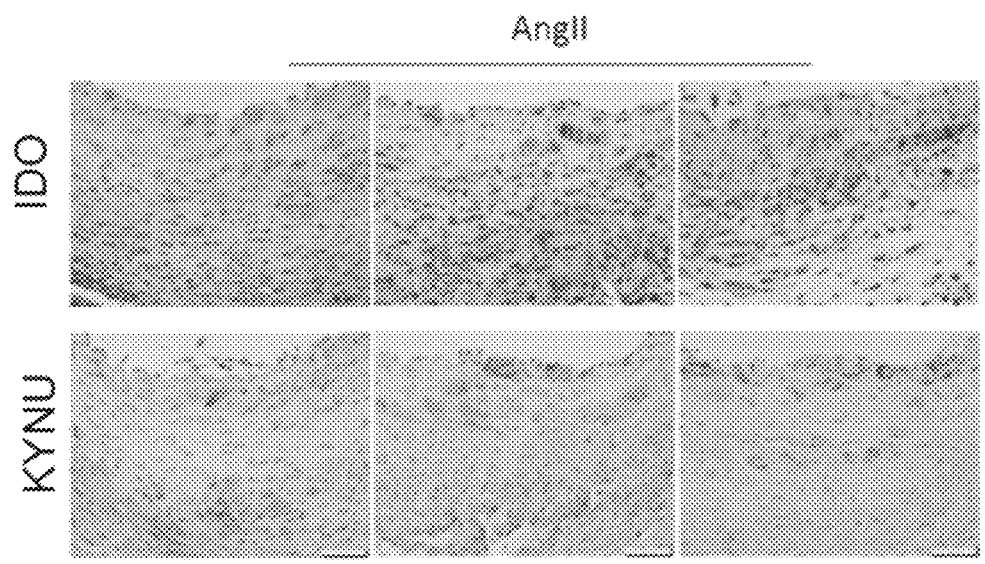
FIG. 37B shows representative immunohistochemical staining for IDO and KYNU in aortic cross sections of AngII treated ApoE$^{-/-}$ mice.
Figure 37C:
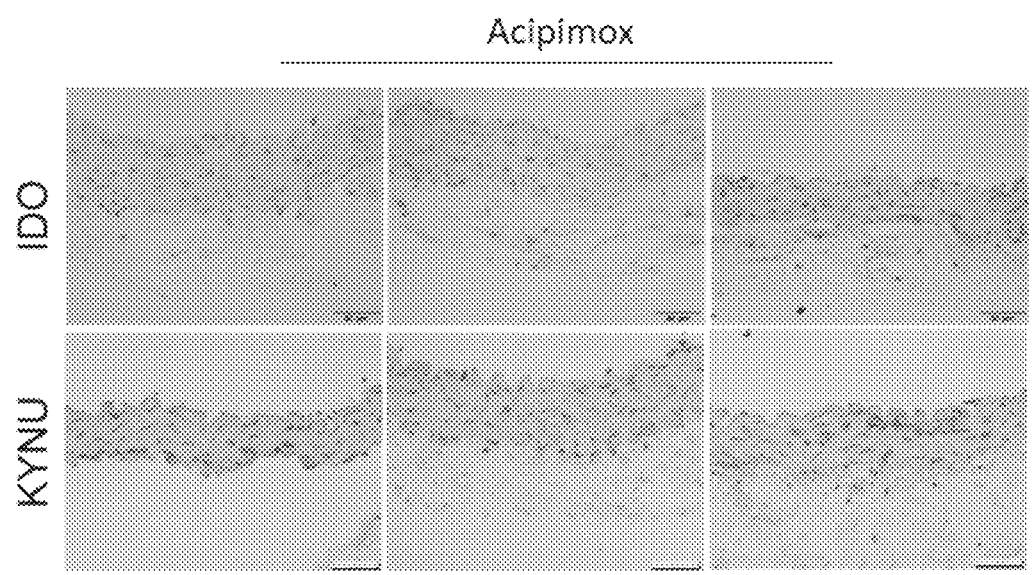
FIG. 37C shows representative immunohistochemical staining for IDO and KYNU in aortic cross sections of acipimox treated ApoE$^{-/-}$ mice.
Figure 37D:
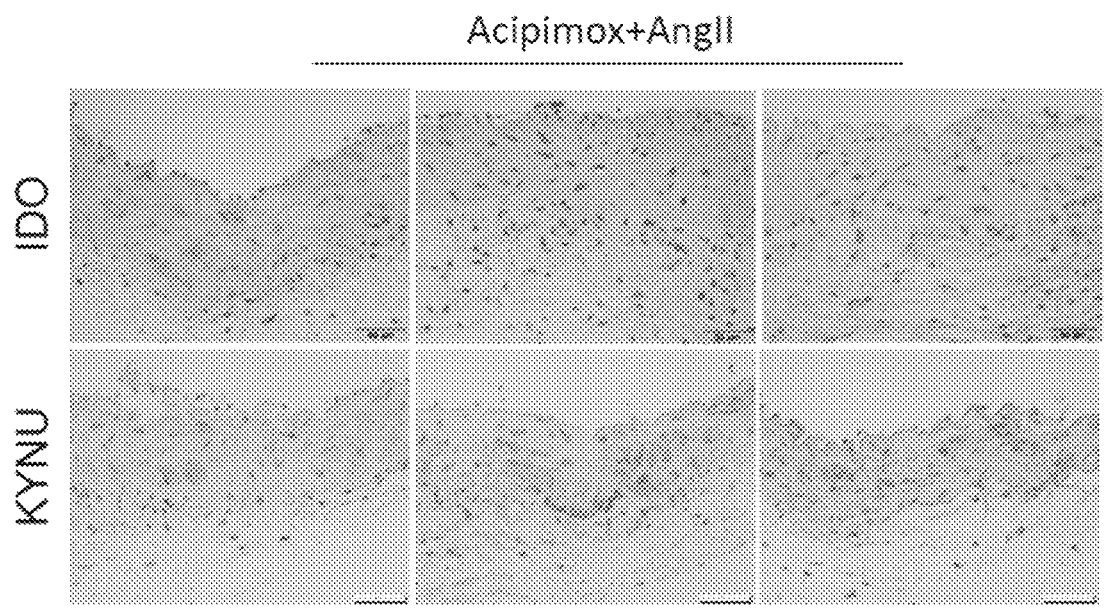
FIG. 37D shows representative immunohistochemical staining for IDO and KYNU in aortic cross sections of AngII+acipimox treated ApoE$^{-/-}$ mice.

To quantify AAA incidence and size, the maximum width of abdominal aorta was measured with Image Pro Plus software (Media Cybernetics). Aneurysm incidence was quantified based on a definition of aneurysm as an external width of the suprarenal aorta that was increased by 50% or greater compared with aortas from saline-infused mice. The average diameter of the normal suprarenal aorta in control mice is 0.705 mm. Therefore, a threshold of 1.06 mm as evidence of aneurysm formation was set. Young vehicle control mice did not develop AAA, while the AA incidence was 20% in old mice. After 4-weeks of AngII-infusion, mice where divided into two groups vehicle treated (n=10) or acipimox treated (n=15). Before treatment, the AAA incidence was 20% and 70% in young and old mice, respectively. After six weeks of treatment acipimox, AAA incidence decreased to 25% in the old mice group. Representative aortic dissections among the various treatment groups can be found in FIG. 36A. The treatment results are shown in FIGS. 36B and 36C.

Figure 38:
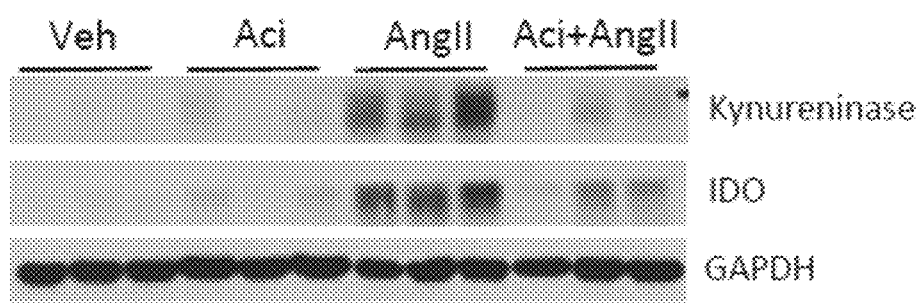
FIG. 38 is an immunoblot showing the expression of Kynureninase and IDO in five groups of ApoE$^{-/-}$ mice: vehicle (saline) treated; acipimox treated; AngII treated; and AngII+acipimox treated. GAPDH was used as a standard.

Example 17. Acipimox Inhibits the AngII-Induced Kynurenine Pathway in the Abdominal Aorta To test the effect of acipimox on the kynurenine pathway in the abdominal aorta of mice, male ApoE$^{-/-}$ mice at age 8 weeks were infused with AngII (1,000 ng/kg/min) or saline (0.9% sodium chloride) by Alzet osmotic pumps for four weeks. Four weeks later, mice were treated with acipimox (0.1% wt) or vehicle control (water) by drinking water for 6 weeks. Aortic sections of the sacrificed mice were stained using immunohistochemistry to determine levels of KYNU and IDO. The results are shown in FIGS. 37A-37D. As shown in FIG. 38, western blot analysis of expression of KYNU and IDO in the abdominal aorta of all treatment groups showed elevated levels of IDO and KYNU in AngII-treated mice, while levels were reduced in AngII-treated mice administered acimipox.

Figure 27A:
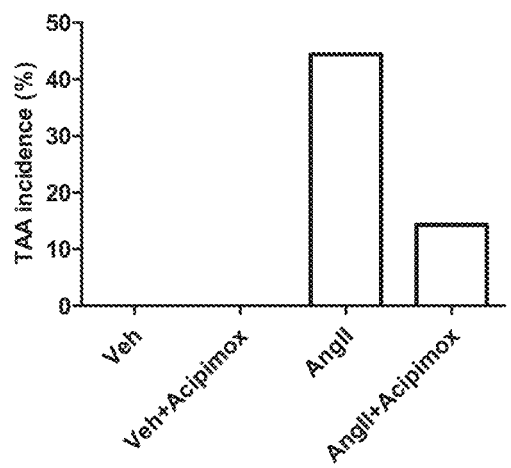
FIG. 27A is a bar graph that shows the incidence of TAA in one of four groups of ApoE$^{-/-}$ mice: vehicle treated; vehicle+acipimox treated; AngII treated; and AngII+acipimox treated. The x-axis show the group of mice, and the y-axis shows the incidence of TAA in percent.
Figure 27B:
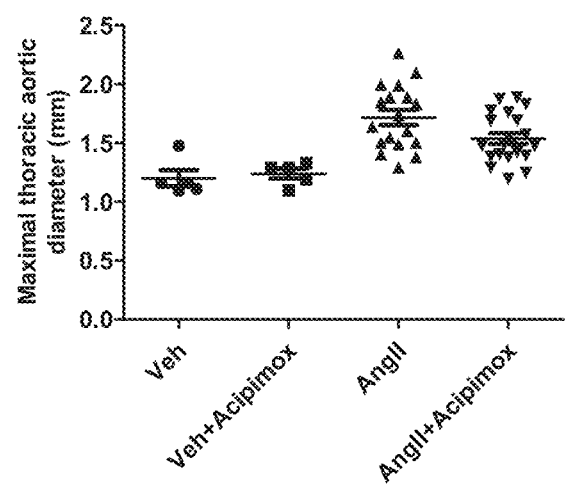
FIG. 27B is a scatter plot that shows the maximal thoracic aortic diameter in one of four groups of ApoE$^{-/-}$ mice: vehicle treated; vehicle+acipimox treated; AngII treated; and AngII+acipimox treated. The x-axis shows the group of mice, and the y-axis shows the maximal thoracic aortic diameter in millimeters. *P<0.05 versus vehicle. #P<0.05 versus AngII. The error bars are standard error of the mean.

Example 18. Acipimox Inhibits AngII-Induced Formation of Thoracic Aortal Aneurysms Use a similar procedure as described above for abdominal aortic aneurysms, the effect of acipimox on the formation of aneurysms in four groups of male ApoE$^{-/-}$ mice: treated with vehicle (saline); treated with vehicle+acipimox; treated with AngII; and treated with AngII+acipimox. As shown in FIGS. 27A and 27B, there was a marked reduction in the incidence of TAA in the AngII+acipimox group compared to the AngII group.

This specification has been described with reference to embodiments of the invention. However, one of ordinary skill in the art will appreciate that various modifications and changes can be made without departing from the scope of the invention as set forth in the claims below. While only certain representative materials, methods, and aspects of these materials and methods are specifically described, other materials and methods and combinations of various features of the materials and methods are intended to fall within the scope of the appended claims, as if specifically recited. Accordingly, the specification is to be regarded in an illustrative rather than a restrictive sense, and all such modifications are intended to be included within the scope of the invention.

I claim:

1. A method of treating a subject with an aneurysm comprising administering to the subject an effective amount of a KYNU inhibitor, a KMO inhibitor, a 3-HAO upregulator, or acipimox, wherein the aneurysm is an abdominal aortic aneurysm (AAA).

2. The method of claim 1, wherein the inhibitor is a KYNU inhibitor.

3. The method of claim 2, wherein the KYNU inhibitor is selected from 2-Amino-4-[3'-hydroxyphenyl]-4-hydroxybutanoic acid,

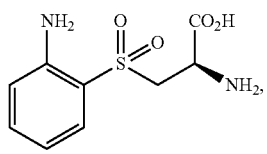 [SMILES: Nc1ccccc1S(=O)(=O)C[C@H](N)C(=O)O]

(4R)-dihydro-L-kynurenine, (4S)-dihydro-L-kynurenine,

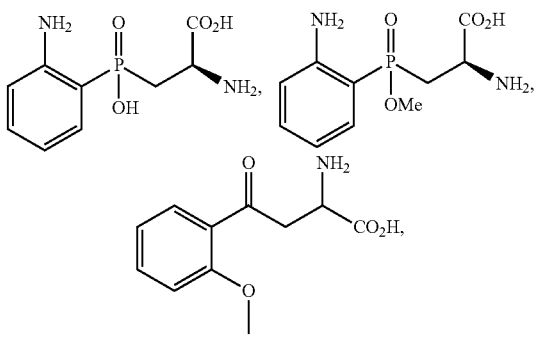

benserazide, o-Methoxybenzoylalanine (OMBA), and (m-Nitrobenzoyl)alanine (NBA), or a pharmaceutically acceptable salt thereof.

4. The method of claim 1, wherein the inhibitor is a KMO inhibitor.

5. The method of claim 4, wherein the KMO inhibitor is selected from GSK180, (R)-3-(5-chloro-6-(1-phenylethoxy)benzo[d]isoxazol-3-yl)propanoic acid, CHDI-340246, desamino FCE 28833, UPF 648, and Ro-61-8048, or a pharmaceutically acceptable salt thereof.

6. The method of claim 1, wherein the compound is acipimox, or a pharmaceutically acceptable salt thereof.

7. A method of reducing the risk of an aortic dissection in a subject having an underlying medical condition which predisposes the subject to the sudden dissection of an artery comprising administering to the subject an effective amount a KYNU inhibitor, a KMO inhibitor, a 3-HAO upregulator, or acipimox.

8. The method of claim 2, wherein the subject has an underlying medical disorder selected from Marfan syndrome, Loeys-Dietz syndrome, aneurysms-osteoarthritis syndrome, Ehlers-Danlos syndrome, familial thoracic aortic aneurysm/dissection, Shprintzen-Goldberg syndrome, cutis laxa syndrome, aortic valve disease, arterial tortuosity syndrome, X-linked Alport syndrome, Turner syndrome, a congenital heart malformation, a mutation in the gene COL1A1, a mutation in the gene COL1A2, a mutation in the gene MED12, a mutation in the gene SMAD4, a mutation in the gen PLOD3, a mutation in the gene ENG, a mutation in the gene ACVRL1, and a mutation in the gene NF1.

9. The method of claim 7, wherein the inhibitor is a KYNU inhibitor.

10. The method of claim 9, wherein the KYNU inhibitor is selected from 2-Amino-4-[3'-hydroxyphenyl]-4-hydroxybutanoic acid,

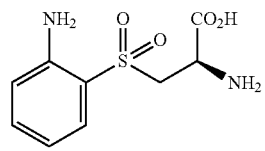 [SMILES: Nc1ccccc1S(=O)(=O)C[C@H](N)C(=O)O]

(4R)-dihydro-L-kynurenine, (4S)-dihydro-L-kynurenine,

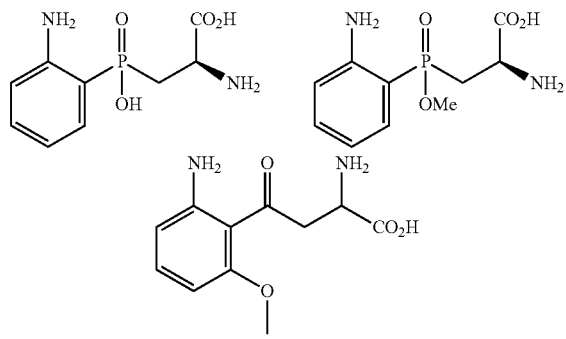

benserazide, o-Methoxybenzoylalanine (OMBA), and (m-Nitrobenzoyl)alanine (NBA), or a pharmaceutically acceptable salt thereof.

11. The method of claim 7, wherein the inhibitor is a KMO inhibitor.

12. The method of claim 11, wherein the KMO inhibitor is selected from GSK180, (R)-3-(5-chloro-6-(1-phenylethoxy)benzo[d]isoxazol-3-yl)propanoic acid, CHDI-340246, des-amino FCE 28833, UPF 648, and Ro-61-8048, or a pharmaceutically acceptable salt thereof.

13. The method of claim 7, wherein the compound is acipimox, or a pharmaceutically acceptable salt thereof.

14. A method of treating an aneurysm in a subject comprising: i. determining the level of 3-HAA present in a sample from the subject; ii. comparing the subject's level of 3-HAA to a range of standardized levels of 3-HAA derived from individuals with an aneurysm ("aneurysmal range"); and, iii. performing a medical intervention on the subject if the subject's levels of 3-HAA falls within the aneurysmal range, wherein the medical intervention comprises administering to the subject an effective amount of a KYNU inhibitor, a KMO inhibitor, a 3-HAO upregulator, or acipimox, or a pharmaceutically acceptable salt thereof.

15. The method of claim 14, wherein the aneurysmal range is an abdominal aortic aneurysmal range ("AAA aneurysmal range").

16. The method of claim 14, wherein the aneurysmal range is a thoracic aortic aneurysmal range ("TAA aneurysmal range").

17. The method of claim 14, wherein the aneurysmal range is a cerebral aneurysmal range ("CA aneurysmal range").

18. The method of claim 14, wherein the medical intervention comprises administering to the subject an effective amount of acipimox, or a pharmaceutically acceptable salt thereof.

19. A method of treating a subject with an aneurysm consisting of administering to the subject an effective amount of a KYNU inhibitor, a KMO inhibitor, a 3-HAO upregulator, or acipimox.

* * * * *

UNITED STATES PATENT AND TRADEMARK OFFICE
CERTIFICATE OF CORRECTION

PATENT NO. : 11,376,248 B2
APPLICATION NO. : 16/723304
DATED : July 5, 2022
INVENTOR(S) : Zou It is certified that error appears in the above-identified patent and that said Letters Patent is hereby corrected as shown below:

In the Specification

Column 1, Lines 16-19, should read:
--This invention was made with government support under grant numbers HL089220, HL079584, HL080499, HL110488, HL128014, HL132500, AG047776, and CA213022 awarded by the National Institute of Health. The government has certain rights in the invention.--

Signed and Sealed this
Thirtieth Day of August, 2022

Katherine Kelly Vidal
*Director of the United States Patent and Trademark Office*